(12) United States Patent
Gomez et al.

(10) Patent No.: US 11,267,803 B2
(45) Date of Patent: *Mar. 8, 2022

(54) CARBOCYCLIC PROLINAMIDE DERIVATIVES

(71) Applicant: ORION OPHTHALMOLOGY LLC, New York, NY (US)

(72) Inventors: Robert Gomez, North Vancouver (CA); Jinyue Ding, Burnaby (CA); Renata Marcella Oballa, Coquitlam (CA); David Andrew Powell, Vancouver (CA)

(73) Assignee: ORION OPHTHALMOLOGY LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/734,740

(22) Filed: Jan. 6, 2020

(65) Prior Publication Data

US 2020/0385362 A1 Dec. 10, 2020

Related U.S. Application Data

(63) Continuation of application No. 16/312,211, filed as application No. PCT/US2017/037766 on Jun. 15, 2017, now Pat. No. 10,526,315.

(60) Provisional application No. 62/352,959, filed on Jun. 21, 2016.

(51) Int. Cl.
| | |
|---|---|
| C07D 403/04 | (2006.01) |
| C07D 207/50 | (2006.01) |
| C07D 405/14 | (2006.01) |
| C07D 471/04 | (2006.01) |
| C07D 401/14 | (2006.01) |
| C07D 401/04 | (2006.01) |
| C07D 403/14 | (2006.01) |

(52) U.S. Cl.
CPC ......... *C07D 403/04* (2013.01); *C07D 207/50* (2013.01); *C07D 401/04* (2013.01); *C07D 401/14* (2013.01); *C07D 403/14* (2013.01); *C07D 405/14* (2013.01); *C07D 471/04* (2013.01)

(58) Field of Classification Search
CPC .. C07D 403/04; C07D 207/50; C07D 405/14; C07D 471/04; C07D 401/14
USPC ...................................................... 548/530
See application file for complete search history.

(56) References Cited

U.S. PATENT DOCUMENTS

| | | | |
|---|---|---|---|
| 4,562,197 A | 12/1985 | Snarey | |
| 5,169,841 A | 12/1992 | Kleeman et al. | |
| 5,225,402 A | 7/1993 | Ogawa et al. | |
| 5,436,254 A | 7/1995 | Ogawa et al. | |
| 5,652,247 A | 7/1997 | Ogawa et al. | |
| 5,866,564 A | 2/1999 | Kawamoto et al. | |
| 6,083,903 A | 7/2000 | Adams et al. | |
| 7,172,874 B2 | 2/2007 | Hollyfield et al. | |
| 7,273,851 B2 | 9/2007 | Miao et al. | |
| 7,341,839 B2 | 3/2008 | Hollyfield et al. | |
| 7,560,257 B2 | 7/2009 | Hollyfield et al. | |
| 7,820,671 B2 | 10/2010 | Babine et al. | |
| 7,825,152 B2 | 11/2010 | Brandl et al. | |
| 7,972,787 B2 | 7/2011 | Deangelis | |
| 8,137,991 B2 | 3/2012 | Crabb et al. | |
| 8,211,932 B2 | 7/2012 | Patane et al. | |
| 8,232,056 B2 | 7/2012 | Deangelis | |

(Continued)

FOREIGN PATENT DOCUMENTS

| | | |
|---|---|---|
| CA | 2 851 462 | 7/2004 |
| CN | 102807607 | 12/2012 |

(Continued)

OTHER PUBLICATIONS

Bachovchin, D. A. et al., "A high-throughput, multiplexed assay for superfamily-wide profiling of enzyme activity", Nature Chemical Biology, 2014, vol. 10, No. 8, pp. 656-663.

(Continued)

*Primary Examiner* — Niloofar Rahmani

(74) *Attorney, Agent, or Firm* — Jon E. Gordon; Haug Partners LLP

(57) ABSTRACT

This invention is directed to novel carbocyclic prolinamide derivatives of Formula (I), and pharmaceutically acceptable salts, solvates, solvates of the salt and prodrugs thereof, useful in the prevention (e.g., delaying the onset of or reducing the risk of developing) and treatment (e.g., controlling, alleviating, or slowing the progression of) of age-related macular degeneration (AMD) and related diseases of the eye. These diseases include dry-AMD, wet-AMD, geographic atrophy, diabetic retinopathy, retinopathy of prematurity, polypoidal choroidal vasculopathy, and degeneration of retinal or photoreceptor cells. The invention disclosed herein is further directed to methods of prevention, slowing the progress of, and treatment of dry-AMD, wet-AMD, and geographic atrophy, diabetic retinopathy, retinopathy of prematurity, polypoidal choroidal vasculopathy, and degeneration of retinal or photoreceptor cells, comprising: administration of a therapeutically effective amount of compound of the invention. The compounds of the invention are inhibitors of HTRA1. Thus, the compounds of the invention are useful in the prevention and treatment of a wide range of diseases mediated (in whole or in part) by HTRA1. The compounds of the invention are also useful for inhibiting HTRA1 protease activity in an eye or locus of an arthritis or related condition.

19 Claims, No Drawings

(56) References Cited

U.S. PATENT DOCUMENTS

| | | | |
|---|---|---|---|
| 8,252,923 B2 | 8/2012 | Babine et al. | |
| 8,445,527 B2 | 5/2013 | Patane et al. | |
| 8,529,882 B2 | 9/2013 | Babine et al. | |
| 10,526,315 B2* | 1/2020 | Gomez | A61P 43/00 |
| 2002/0177725 A1 | 11/2002 | Priestley | |
| 2003/0216325 A1 | 11/2003 | Saksena et al. | |
| 2004/0048802 A1 | 3/2004 | Ripka et al. | |
| 2005/0027101 A1 | 2/2005 | Gutheil | |
| 2005/0119226 A1 | 6/2005 | Walter et al. | |
| 2005/0176651 A1 | 8/2005 | Madge et al. | |
| 2005/0282757 A1 | 12/2005 | Combe-Marzelle et al. | |
| 2006/0014700 A1 | 1/2006 | Cohen et al. | |
| 2006/0025327 A1 | 2/2006 | Sanchez et al. | |
| 2010/0330097 A1 | 12/2010 | Hageman | |
| 2011/0003880 A1 | 1/2011 | Bhattacharya et al. | |
| 2011/0052602 A1 | 3/2011 | Hoh et al. | |
| 2012/0003641 A1 | 1/2012 | Graham et al. | |
| 2012/0142608 A1 | 6/2012 | Hageman | |
| 2013/0122016 A1 | 5/2013 | Deangelis | |

FOREIGN PATENT DOCUMENTS

| | | |
|---|---|---|
| EP | 0 354 522 | 2/1990 |
| EP | 0 471 651 | 2/1992 |
| EP | 2 368 901 | 9/2011 |
| EP | 2 518 079 | 10/2012 |
| EP | 2 007 789 | 5/2015 |
| JP | 2015-120685 | 7/2015 |
| WO | WO 89/09612 | 10/1989 |
| WO | WO 91/13904 | 9/1991 |
| WO | WO 92/07869 | 5/1992 |
| WO | WO 93/25574 | 12/1993 |
| WO | WO 94/02526 | 9/1994 |
| WO | WO 94/25049 | 11/1994 |
| WO | WO 94/25051 | 11/1994 |
| WO | WO 95/09634 | 4/1995 |
| WO | WO 95/09838 | 4/1995 |
| WO | WO 95/09858 | 4/1995 |
| WO | WO 95/09838 | 5/1995 |
| WO | WO 95/20603 | 8/1995 |
| WO | WO 96/11697 | 4/1996 |
| WO | WO 96/12499 | 5/1996 |
| WO | WO 96/13266 | 5/1996 |
| WO | WO 96/16079 | 5/1996 |
| WO | WO 96/40743 | 12/1996 |
| WO | WO 97/31939 | 8/1997 |
| WO | WO 97/31937 | 9/1997 |
| WO | WO 98/17679 | 4/1998 |
| WO | WO 98/22496 | 5/1998 |
| WO | WO 99/07734 | 2/1999 |
| WO | WO 99/20230 | 10/1999 |
| WO | WO 00/08134 | 2/2000 |
| WO | WO 02/06280 | 1/2002 |
| WO | WO 02/08187 | 1/2002 |
| WO | WO 02/08256 | 1/2002 |
| WO | WO 02/18369 | 3/2002 |
| WO | WO 02/181335 | 3/2002 |
| WO | WO 02/40016 | 5/2002 |
| WO | WO 02/094857 | 11/2002 |
| WO | WO 02/096933 | 12/2002 |
| WO | WO 03/062265 | 7/2003 |
| WO | WO 03/087092 | 10/2003 |
| WO | WO 2004/004658 | 1/2004 |
| WO | WO 2004/022070 | 3/2004 |
| WO | WO 2004/062601 | 7/2004 |
| WO | WO 2004/089297 | 10/2004 |
| WO | WO 2004/092161 | 10/2004 |
| WO | WO 2004/092162 | 10/2004 |
| WO | WO 2004/113365 | 12/2004 |
| WO | WO 2004-113365 A2 | 12/2004 |
| WO | WO 2005/007681 | 1/2005 |
| WO | WO 2005/028502 | 3/2005 |
| WO | WO 2005/035525 | 4/2005 |
| WO | WO 2005/077969 | 5/2005 |
| WO | WO 2005/074904 | 8/2005 |
| WO | WO 2005/082348 | 9/2005 |
| WO | WO 2005/084685 | 9/2005 |
| WO | WO 2005/084686 | 9/2005 |
| WO | WO 2005/084687 | 9/2005 |
| WO | WO 2005/105829 | 11/2005 |
| WO | WO 2005/0325525 | 12/2005 |
| WO | WO 2006/021409 | 3/2006 |
| WO | WO 2006/021413 | 3/2006 |
| WO | WO 2006/113942 | 3/2006 |
| WO | WO 2006/059082 | 6/2006 |
| WO | WO 2006/059083 | 6/2006 |
| WO | WO 2006/130552 | 12/2006 |
| WO | WO 2006/130553 | 12/2006 |
| WO | WO 2006/130554 | 12/2006 |
| WO | WO 2006/130627 | 12/2006 |
| WO | WO 2007/016476 | 2/2007 |
| WO | WO 2007/089618 | 8/2007 |
| WO | WO 2007/120595 | 10/2007 |
| WO | WO 2007/120959 | 10/2007 |
| WO | WO 2007/005838 | 11/2007 |
| WO | WO 2007/133865 | 11/2007 |
| WO | WO 2007/139585 | 12/2007 |
| WO | WO 2007/146695 | 12/2007 |
| WO | WO 2007/146831 | 12/2007 |
| WO | WO 2008/13893 | 1/2008 |
| WO | WO 2008/014236 | 1/2008 |
| WO | WO 2008/067040 | 6/2008 |
| WO | WO 2008/086053 | 7/2008 |
| WO | WO 2008/089485 | 7/2008 |
| WO | WO 2008/094370 | 8/2008 |
| WO | WO 2008/103299 | 8/2008 |
| WO | WO 2008/106130 | 9/2008 |
| WO | WO 2008/112798 | 9/2008 |
| WO | WO 2008/112801 | 9/2008 |
| WO | WO 2008/118848 | 10/2008 |
| WO | WO 2008/141227 | 11/2008 |
| WO | WO 2009/006460 | 1/2009 |
| WO | WO 2009/006473 | 1/2009 |
| WO | WO 2009/008913 | 1/2009 |
| WO | WO 2009/020448 | 2/2009 |
| WO | WO 2009/046405 | 4/2009 |
| WO | WO 2009/055355 | 4/2009 |
| WO | WO 2009/0518581 | 4/2009 |
| WO | WO 2009/059317 | 5/2009 |
| WO | WO 2009/071601 | 6/2009 |
| WO | WO 2009/073780 | 6/2009 |
| WO | WO 2009/100225 | 8/2009 |
| WO | WO 2009/109860 | 9/2009 |
| WO | WO 2010/012222 | 2/2010 |
| WO | WO 2010/019210 | 2/2010 |
| WO | WO 2010/036357 | 4/2010 |
| WO | WO 2010/054110 | 5/2010 |
| WO | WO 2011/094426 | 8/2010 |
| WO | WO 2010/132459 | 11/2010 |
| WO | WO 2010/145376 | 12/2010 |
| WO | WO 01/02424 | 1/2011 |
| WO | WO 2011/053774 | 5/2011 |
| WO | WO 2011/075607 | 6/2011 |
| WO | WO 2011-075607 A1 | 6/2011 |
| WO | WO 2011/094426 | 8/2011 |
| WO | WO 2011/109355 | 9/2011 |
| WO | WO 2011/146401 | 11/2011 |
| WO | WO 2011/156632 | 12/2011 |
| WO | WO 2012/040242 | 3/2012 |
| WO | WO 2012/078540 | 6/2012 |
| WO | WO 2012-078540 A1 | 6/2012 |
| WO | WO 2012/088411 | 6/2012 |
| WO | WO 2012/125869 | 9/2012 |
| WO | WO 2013/033396 | 3/2013 |
| WO | WO 2013/055998 | 4/2013 |
| WO | WO 2013/059287 | 4/2013 |
| WO | WO 2013/123456 | 8/2013 |
| WO | WO 2013/149306 | 10/2013 |
| WO | WO 2013/123456 | 12/2013 |
| WO | WO 2014/043558 | 3/2014 |
| WO | WO 2014/179446 | 11/2014 |
| WO | WO 2015/042297 | 3/2015 |
| WO | WO 2015/042447 | 3/2015 |
| WO | WO 2015/091939 | 6/2016 |

(56) References Cited

FOREIGN PATENT DOCUMENTS

| WO | WO 2016/100555 | 6/2016 |
| --- | --- | --- |
| WO | WO 2016/135070 | 9/2016 |
| WO | WO 2016/162345 | 10/2016 |
| WO | WO 2016/180751 | 11/2016 |
| WO | WO 2017/075212 | 5/2017 |
| WO | WO 2017/148964 | 9/2017 |
| WO | WO 2017/148967 | 9/2017 |
| WO | WO 2017/222914 | 12/2017 |
| WO | WO 2017/222915 | 12/2017 |
| WO | WO 2017/222917 | 12/2017 |
| WO | WO 2018/002105 | 1/2018 |
| WO | WO 2018/015240 | 1/2018 |
| WO | WO 2018/036942 | 3/2018 |
| WO | WO 2018/036957 | 3/2018 |
| WO | WO 2018/206816 | 11/2018 |

OTHER PUBLICATIONS

International Search Report and Written Opinion dated Sep. 25, 2017 in corresponding International Application No. PCT/US2017/037766.
Brian L. Ellis et al., A survey of ex vivo/in vitro transduction efficiency of mammalian primary cells and cell lines with Nine natural adeno-associated virus (AAC1-9) and one engineered adeno-associated virus serotype, Virology Journal 2013, 10:74, pp. 1-10.
Material Information Sheet, AAV Vectors: General Information, Perelman School of Medicine, University of Pennsylvania, Penn Vector Core, Gene Therapy Program, Department of Pathology and Laboratory Medicine.
P. Pechan et al., Novel anti-VEGF chimeric molecules delivered by AAV vectors for inhibition of retinal neovascularization, Gene Therapy (2009) 16, pp. 10-16.
Working with Viral Vectors (2013), Stanford University.
ARVO 2014 Annual Meeting Abstracts by Scientific Section/Group—Retina.
Lin Chen et al., Light damage induced changes in mouse retinal gene expression, Experimental Eye Research 79 (2004), pp. 239-247.
Yu Chen et al., Autophagy protects the retina from light-induced degeneration, J. Biol. Chem., published online Jan. 22, 2013.
Jiang Wu et al., Light-Evoked Responses of the Mouse Retinal Pigment Epithelium, J. Neurophysiol 91: 1134-1142, 2004. First published Nov. 12, 2003; doi: 10.1152/jn.00958.2003.
Abeer M. Al-Ghananeem et al., Phase I and Phase II Ocular Metabolic Activities and the Role of Metabolism in Ophthalmic Prodrug and Codrug Design and Delivery, Molecules 2007, 12, pp. 373-388.
Bruce I. Gaynes et al., Biotransformation in Review: Applications in Ocular Disease and Drug Design, Journal of Ocular Pharmacology and Therapeutics, vol. 12, No. 4, 1996, pp. 527-539.
Tao Zhang et al., Drug Transporter and Cytochrome P450 mRNA Expression in Human Ocular Barriers: Implications for Ocular Drug Disposition, Drug Metabolism and Disposition, DMD 36, 2008, pp. 1300-1307.
Aqeela Afzal et al., Targeting retinal and choroid neovascularization using the small molecule inhibitor carboxyamidotriazole, Brain Research Bulletin 81 (2010) 26, pp. 320-326.
W. Amoaku et al., Action on AMD. Optimising patient management: act not to ensure current and continual delivery of best possible patient care, Eye (2012) 26, pp. S2-S21
Santosh Aryal et al., Polymeric Nanoparticles with Precise Ratiometric Control over Drug Loading for Combination Therapy, *Mol Pharm.* Aug. 1, 2011; 8(4): 1401-1407.
Feng Cao et al., Advances in research of PepT1-targeted prodrug, Asian Journal of Pharmaceutical Sciences 2012, 7(2): pp. 110-122.
Hao Chen et al., Different Intravitreal Properties of Three Triamcinolone Formulations and Their Possible Impact on Retina Practice, Investigate Ophthalmology & Visual Science, Mar. 2013, vol. 54, No. 3, pp. 2178-85.
Narayan P. S. Cheruvu et al., Effect of Eye Pigmentation on Transscleral Drug Delivery, Investigative Ophthalmology & Visual Science, Jan. 2008, vol. 49, No. 1, pp. 333-341.
John B. Christoforidis et al., Intravitreal Devices for the Treatment of Vitreous Inflammation, Hindawi Publishing Corporation, Mediators of Inflammation, vol. 2012, Article ID 126463, 8 pages.
Corbin Clawson et al., Synthesis and Characterization of Lipin-Polymer Hybrid Nanoparticles with pH Triggered PEG Shedding, Langmuir. Sep. 6, 2011; 27(17): 10556-10561.
Frank Cloutier et al., Antiangiogenic Activity of Aganirsen in Nonhuman Primate and Rodent Models of Retinal Neovascular Disease after Tropical Administration, Investigative Ophthalmology & Visual Science, Mar. 2012, vol. 53, No. 3, pp. 1195-1203.
Eva M. del Amo et al., Current and future ophthalmic drug delivery systems. A shift to the posterior segment, Drug Discovery Today, vol. 13, Nos. 3/4, Feb. 2008, pp. 135-143.
John Doukas et al., Topical Administration of a Multi-Targeted Kinase Inhibitor Suppresses Choroidal Neovascularization and Retinal Edema, *J Cell Physiol*. Jul. 2008; 2016(1): 29-37.
Rocio Herrero-Vanrell, Microparticles as Drug Delivery Systems for the back of the Eye, Chapter 10, pp. 230-259.
Jithan Aukunnuru et al., Drug Suspension Development for the Back of the Eye, Chapter 18, pp. 448-469.
Clive G. Wilson et al., Principles of Retinal Drug Delivery from Within the Vitreous, Chapter 6, pp. 124-159.
Gauri P. Misra et al., Hydrogels for Ocular Posterior Segment Drug Delivery, Chapter 12, pp. 290-305.
Uday B. Kompella et al., Drug Product Development for the Back of the Eye, Advances in the Pharmaceutical Sciences Series 2.
Wennan Du et al., The Effect of Ocular Pigmentation of Transscleral Delivery of Triamcinolone Acetonide, Journal of Ocualr Pharmacology and Therapeutics, vol. 29, No. 7, 2013, pp. 633-638.
Chandrasekar Durairaj et al., Influence of Dosage Form on the Intravitreal Pharmacokinetics of Diclofenac, Investigative Ophthalmology & Visual Science, Oct. 2009, vol. 50, No. 10, pp. 4887-4897.
Henry F. Edelhausser et al., Ophthalmic Drug Delivery Systems for the Treatment of Retinal Diseases: Basic Research to Clinical Applications, Investigative Ophthalmology & Visual Science, Nov. 2010, vol. 51, No. 11, pp. 5403-5420.
Ronnie H. Fang et al., Large-Scale Synthesis of Lipid-Polymer Hybrid Nanoparticles Using a Multi-Inlet Vortex Reactor, Langmuir 2012, 28, pp. 13824-13829.
Ronnie H. Fang et al., Quick Synthesis of Lipid-Polymer Hybrid Nanoparticles with Low Polydispersity Using a Single-Step Sonication Method, Langmuir 2010, 26(22), pp. 16958-16962.
Esther Furrer et al., Pharmacokinetics and Posterior Segment Biodistribution of ESBA 105, an Anti-TNF-α Single-Chain Antibody, upon Topical Administration to the Rabbit Eye, Investigative Ophthalmology & Visual Science, Feb. 2009, vol. 50, No. 2, pp. 771-777
Ripal Gaudana et al., Ocular Drug Delivery, The AAPS Journal, vol. 12, No. 3, Sep. 2010, pp. 348-360.
Bruce Gaynes et al., Topical ophthalmic NSAIDs: a discussion with focus on nepafenac ophthalmic suspension, Clinical Ophthalmology 2008;2(2), pp. 355-368.
Nahid Heghjou et al., Sustained Release Intraocular Drug Delivery Devices for Treatment of Uveitis, Journal of Ophthalmic and Vision Research 2011; vol. 6, No. 4, pp. 317-329.
Jose R. Hombebueno et al., Intravitreal Injection of Normal Saline Induces Retinal Degeneration in the C57BL/6J Mouse, TVST, 2014, vol. 3, No. 2, Article 3.
Takeshi Iwase et al., Topical Pazopanib Blocks VEGF-Induced Vascular Leakage and Neovascular in the Mouse Retina but is Ineffective in the Rabbit, Investigative Ophthalmology & Visual Science, Jan. 2013, vol. 54, No. 1, pp. 503-511.
Rajendra S. Kadam et al., Selera-Choroid-RPE Transport or Eight β-Blockers in Human, Bovine, Porcine, Rabbit, and Rat Models, Investigative Ophthalmology & Visual Science, Jul. 2011, vol. 52, No. 8, pp. 5387-5399.
Stefanie Kaempf et al., Novel organotypic culture model of adult mammalian neurosensory retina in co-culture with retinal pigment epithelium, Journal of Neuroscience Methods 173 (2008) pp. 45-58.

(56) References Cited

OTHER PUBLICATIONS

Brian G. Kennedy et al., P-glycoprotein expression in human retinal pigment epithelium, Molecular Vision 2002; 8, pp. 422-430.
Heidi Kidron et al., Prediction of the Vitreal Half-Life of Small Molecular Drug-Like Compounds, Pharm Res (2012) 29, pp. 3302-3311.
Hyuncheol Kim et al., Safety and Pharmacokinetics of a Preservative-Free Triamcinolone Acetonide Formulation for Intravitreal Administration, Retina 26, 2006, pp. 523-530.
Jae Suk Kim et al., A novel cytarabine crystalline lipid prodrug: Hexadecyloxypropyl cytarabine 3', 5'-cyclic monophosphate for proliferative vitreoretinopathy, Molecular Vision 2012; 18, pp. 1907-1917.
Steven B. Koevary, Pharmacokinetics of Topical Ocular Drug Delivery: Potential Uses for the Treatment of Diseases of the Posterior Segment and Beyond, Current Drug Metabolism, 2003, 4, pp. 213-222.
Uday B. Kompelia et al., Recent advances in ophthalmic drug delivery, *The Deliv.* 2010 Sep. 1; (3), pp. 435-456.
R. Koshes et al., Comparison of vitreous replacement with Healon® and with HPMC in rabbits' eyes, Documenta Ophthalmologica 61, 1986, pp. 247-253.
Noriyuki Kuno et al., Recent Advances in Ocular Drug Delivery Systems, *Polymers* 2011, 3, pp. 193-221.
E. Lavik et al., Novel drug delivery systems for glaucoma, Eye (2011) 25, pp. 578-586.
Teodosio Libondi et al., Topical napafenac for treatment of exudative age-related macular degeneration, ACTA Ophthalmologica 2010, pp. e32-e33.
Lucentis, Drugs and Health Products.
Michelle T. Mara et al., Solution Formulation Devlopment of a VEGF Inhibitor for Intravitreal Injection, AAPS PharmSciTech, vol. 12, No. 1, Mar. 2011, pp. 362-371.
Damia Mawad et al., Advances in Hydrogels Applied to Degenerative Diseases, Current Pharmaceutical Design, 2012, 18, pp. 2558-2575.
Ripal Guadana et al., Ocular Drug Delivery, The AAPS Journal, vol. 12, No. 3, Sep. 2010, pp. 348-360.
Yoki Miura et al., Change of Morphological and Functional Characteristics of Retinal Pigment Epithelium Cells during Cultivation of Retinal Pigment Epithelium-Choroid Perfusion Tissue Culture, Ophthalmic Res 2010; 43, pp. 122-133.
Sri Mudumba et al., Tolerability and Pharmacokineitcs of Intravitreal Sirolimus, Journal of Ocular Pharmacology and Therapeutics, vol. 28, No. 5, 2012, pp. 507-514.
Moorthy S. et al., Development of Prodrug 4-Chloro-3-(5-methyl-3{[4-(2-pyrrolidin-1-ylethoxy)phenyl]amino)-1,2,4-benzotriazin-7-yl)phenyl Benzoate (TG100801): A Topically Administed Therapeutic Candidate in Clinical Trials for the Treatment of Age-Related Macular Degeneration, J. Med. Chem. 2008, 51, pp. 1546-1559.
Leena Pitkänen et al., Permeability of Retinal Pigment Epithelium: Effects of Permeant Molecular Weight and Lipophilicity, Investigative Ophthalmology & Visual Science, Feb. 2005, vol. 46, No. 2, pp. 641-646.
Scott J. Robbie et al., Assessing a novel depot delivery strategy for non-invasive administration of VEGF/PDGF RTK inhibitors for ocular neovascular disease, IOVS Papers in Press. Published on Feb. 5, 2013 as Manuscript IOVS. 12-10169.
Candice Ann Robinson, Efficacy of Topical Delivery of Potentially Therapeutic Peptides and Monoclonal Antibodies to the Posteror Segment of the Rat Eye in Eye Drops versus PharmaLight Technology, May 2008.
Xiangfang Rong et al., Effects of Erythropoietin-Dextran Microparticle-Based PLGA/PLA Microspheres on RGCs, Investigative Ophthalmology & Visual Science, Sep. 2012, vol. 53, No. 10, pp. 6025-6034.
Namdev B. Shelke et al., Intravitreal Poly(L-Lactide) Microparticles Sustain Retinal and Choroidal Delivery of TG-0054, A Hydrophilic Drug Intended for Neovascular Diseases, *Drug Deliv Transl Res.* Feb. 2011; 1(1): 76-90.

Shwu-Jiuan et al., inhibition of choroidal neovascularization by topical application of aniogenesis inhibitor vasostatin, Molecular Vision 2000; 15, pp. 1897-1905.
Brian G. Short, Safety Evaluation of Ocular Drug Delivery Formulations: Techniques and Practical Condsiderations, Toxicologic Pathology, 36:49-62, 2008.
Jianfeng Xu et al., Inhibitory Efficacy of Intravitreal Dexamethasone Acetate-Loaded PLGA Nanoparticles on Choroidal Neovascularization in a Laser-Induced Rat Model, Journal of Ocular Pharmacology and Therapeutics, vol. 23, No. 6, 2007, pp. 527-539.
Y. Sultana et al., Nanotechnology in Ocular Delivery: Current and Future Directions, Drugs of Today 2011, 47(6), pp. 441-455.
Kyoichi Takahashi et al., Topical Nepafenac Inhibits Ocular Neovascularization, Investigative Ophthalmology & Visual Science, Jan. 2003, vol. 44, No. 1, pp. 409-415.
Thilini Rasika et al., Drug delivery to the posterior segment of the eye, Drug Discovery Today, vol. 16, Nos. 5/6, Mar. 2011, pp. 270-277.
Arto Urtti, Challenges and obstacles of ocular pharmacokinetics and drug delivery, Advances Drug Delivery Reviews, 58 (2006), pp. 1131-1135.
Wai T. Wong et al., Treatment of Geographic Atrophy by the Topical Administration of OT-551: Results of a Phase II Clinical Trial, Investigative Ophthalmology & Visual Science, Dec. 2010, vol. 51, No. 12, pp. 6131-6139.
Yousef Yafai et al., Anti-angiogenic effects of the receptor tyrosine kinase inhibitor, pazopanib, on choroidal neovascularization in rats, European Journal of Pharmacology, 666 (2011), pp. 12-18.
Tsutomu Yasukawa et al.
Tsutomu Yasukawa et al., Recent Advances in Intraocular Drug Delivery Systems, Recent Patents on Drug Delivery & Formulation 2011, 5, 1-10.
Liangfang Zhang et al., Self-Assembled Lipid-Polymer Hybrid Nanoparticles: A Robust Drug Delivery Platform, ACS Nano, vol. 2, No. 8, pp. 1696-1702.
L. Zhang et al., Nanoparticles in Medicine: Therapeutic Applications and Developments, Clinical Pharmacology & Therapeutics, vol. 83, No. 5, May 2008, pp. 761-769.
Pharmacology Review(s), Center for Drug Evaluation and Research, Application No. 125387Orig1s000.
Summary Review, Center for Drug Evaluation and Research, Application No. 22-315.
Pharmacology Review(s), Center for Drug Evaluation and Research, Application No. 22-315.
Pharmacology Review, Center for Drug Evaluation and Research, Application No. 22-048/22-223.
Pharmacology Review(s), Center for Drug Evaluation and Research, Application No. NDA 22-220.
Daniel A. Bachovin et al., Superfamily-wide portrait of serine hydrolase inhibition achieved by library-versus-library screening, PNAS, Dec. 7, 2010, vol. 107, No. 49, 20941-20946.
Daniel A. Bachovchin et al., The pharmacological landscape and therapeutic potential of serine hydrolases, Jan. 2012, vol. 11, 52-68.
Jae Won Chang et al., Proteome-Wide Reactivity Profiling Identifies Diverse Carbamate Chemotypes Tuned for Serine Hydrolase Inhibition, ACS Chem. Biol.
Ludovic C. J. Gillett et al., In-Cell Selectivity Profiling of Serine Protease Inhibitors by Activity-based Proteomics, Molecular & Cellular Proteomics 7.7, 1241-1253.
Nadim Jessani et al., The development and application of methods for activity-based protein profiling, Current Opinion in Chemical Biology, 2004, 8:54-59.
Douglas S. Johnson et al., Strategies for discovering and derisking covalent, irreversible enzyme inhibitors, Future Medd Chem. Jun. 1, 2010; 2(6): 949-964.
Yongsheng Liu et al., Activity-based protein profiling: The serine hydrolases, 14694-14699, PNAS, Dec. 21, 1999, vol. 96, No. 26.
Xiaodan Liu et al., Rapid Development of a Potent Photo-triggered Inhibitor of the Serine Hydrolase RBBP9, ChemBioChem 2012, 13, 2082-2093.
James C. Powers et al., Irreversible Inhibitors of Serine, Cystein, and Threonine Protease, Chem. Rev. 2002, 102, 4639-4750.

(56) References Cited

OTHER PUBLICATIONS

Anette von Matt et al., Selective Boron-Containing Thrombin Inhibitors-X-ray Analysis Reveals Surprising Binding Mode, Bioorganic & Medicinal Chemistry 8(2000) 2291-2303.
Abbenante et al., Protease Inhibitors in the Clinic, Medicinal Chemistry, 2005, 1, 71-104.
Adibekian et al., Click-generated triazole ureas as ultrapotent, in vivo-active serine hydrolase inhibitors, Nat Chem Biol.; 7(7): 469-478.
Adibekian et al., Click-generated triazole ureas as ultrapotent, in vivo-active serine hydrolase inhibitors, Nat Chem Biol. 7, 469-478.
Adibekian et al., Confirming Target Engagement for Reversible Inhibitors in Vivo by Kinetically Tuned Activity-Based Probes, J. Am. Chem. Soc. 2012, 134, 10345-10348.
Albers et al., Discovery and Optimization of Boronic Acid Based Inhibitors of Autotaxin, J. Med. Chem. 2010, 53, 4958-4967.
Anselm et al., Discovery of a factor Xa inhibitor (3R,4R)-1-(2,2-difluoro-ethyl)-pyrrolidine-3,4-dicarboxylic acid 3-[(5-chloro-pyridin-2-yl)-amide] 4-{[2-flouor-4-(2-oxo-2H-pyridin-1-yl)-phenyl]-amide} as a clinical candidate, Bioorganic & Medicinal Chemistry Letters 20 (2010) 5313-5319.
Aratsu-Kapur Luciferase Movie.Avi.
Aratsu-Kapur, 2011, Clin Cancer Res, Proteosome inhibitor target engagement, SI.
Aratsu-Kapur et al., Nonproteasomal Targets of the Proteasome Inhibitors Bortezomib and Carfilzomib: a Clinical Adverse Events, Clin Cancer Res 2011;17:2734-2743. Published Online First, Mar. 1, 2011.
Bachovin et al., Superfamily-wide portrait of serine hydrolase inhibition achieved by library-versus-library screening, PNAS, Dec. 7, 2010, vol. 107, No. 49, 20941-20946.
Bachovchin et al., The pharmacological landscape and therapeutic potential of serine hydrolases, Jan. 2012, vol. 11, 52-68.
Baker et al., Therapeutic potential of boron-containing compounds, Future Med. Chem. (2009) 1(7), 1275-1288.
Bertrand et al., Inhibition of Trypsin and Thrombin by Amino(4-amidinophenyl)methanephosphonate Diphenyl Ester Derivatives: X-ray Structures and Molecular Models, Bioochemistry 1996, 35, 3147-3155.
Blackburn et al., Characterization of a new series of non-covalent proteasome inhibitors with exquisite potency and selectivity for the 20S B5-subunit, Biochem. J. (2010) 430, 461-476.
Brak et al., Identification of a new Class of Nonpeptide Inhibitors of Cruzain, J Am Chem Soc. May 21, 2008; 130(20): 6404-6410.
Brown et al., Peptide Length and Leaving-Group Sterics Influeunce Potency of Peptide Phosphonate Protease Inhibitors, Chemistry & Biology 18, 48-57, Jan. 28, 2011.
Chang et al., Proteome-Wide Reactivity Profiling Identifies Diverse Carbanate Chemotypes Tunes for Serine Hydrolase Inhibition.
Choe et al., Substrate Profiling of Cysteine Protease Using a Combinatorial Peptide Library Identifies Functionally Unique Specificities, Journal of Biological Chemistry, vol. 281, No. 18, May 5, 2006.
The Career of Benjamin F. Cravatt.
Drag et al., Emerging principles in protease-based drug discovery, Nat. Rev Drug Discov. Sep. 2010; 9(9): 690-701.
Edwards et al., Peptidyl α-Ketoheterocyclic Inhibitors of Human Neutrophil Eleatase. 3. In Vitro and in Vivo Potency of a Series of Peptidyl α-Ketobenzoxazoles, J. Med. Chem. 1995, 38.
Edwards et al., Peptidyl α-Ketoheterocyclic Inhibitors of Human Neutrophil Eleatase. 3. In Vitro and in Vivo Potency of a Series of Peptidyl α-Ketobenzoxazoles, J. Med. Chem. 1995, 38, 3972-3982.
Lucas et al., Targeting COPD: Advances on Low-Molecular-Weight Inhibitors of Human Neutrophil Elastase.
Ema.europe Velcade Tox data 2004.
Farr-Jones et al., Crystal versus solution structure of enzymes: NMR spectroscopy of a peptide boronic acid-serine protease complex in the crystalline state, Proc. Natl. Acad. Sci. USA, vol. 86, pp. 6922-6924, Sep. 1989. Biochemistry.

Flentze et al., Inhibition of dipeptidyl aminopeptidase IV (DP-IV) by Xaa-boroPro dipeptides and use of these inhibitors to examine the role of DP-IV in T-cell function, Proc. Natl. Acad. Sci. USA, vol. 88, pp. 1556-1559, Feb. 1991. Biochemistry.
Gál et al., Chapter, Inhibition of the Serine Protease of the Complement Sydtem.
Proteases, General Protease Presentation.
Gillet et al., Supplementary Data, In-cell Selectivity Profiling of Serine Protease Inhibitors by Activity-based Proteomics. Molecular & Cellular Proteomics 7.7.
Gillet et al., In-cell Selectivity Profiling of Serine Protease Inhibitors by Activity-based Proteomics. Molecular & Cellular Proteomics 7.7.
Godinat et al., Supplementary Information for: A Bioorthogonal In Vivo Ligation Reaction and its Application for Non-Invasive Bioluminescent Imaging of Protease Activity in Living Mice.
Godinat et al., A Biocompatible in Vivo Ligation Reaction and its Application for Non-Invasive Bioluminescent Imaging of Protease Activity in Living Mice.
Gohara et al., Allostery in trypsin-like protease suggests new theraputic strategiesm Trends in Biotechnology, Nov. 2011, vol. 29, No. 11, 577-585.
Hagel et al., Selective irreversible inhibition of a protease by targeting a noncatalytic cysteine, Nature Chemical Biology, vol. 7, Jan. 2011.
Harris et al., Rapid and general profiling of protease specificity by using combinatorial fluorogenic substrate libraries, PNAS, Jul. 5, 2000, vol. 97, No. 14, 7754-7759.
Inagaki et al., Characterization and Optimization of Selective, Nonpeptidic Inhibitors of Cathepsin S with an Unprecedented Binding mode, J. Med. Chem. 2007, 50, 2693-2699.
Jessani et al., The development and application of methods for activity-based protein profiling, Current Opinion in Chemical Biology 2004, 8:54-59.
Johnson et al., Strategies for discovering and derisking covalent, irreversible enzyme inhibitors, Future Med Chem. Jun. 1, 2010; 2(6): 949-964.
Joossens et al., Diphenyl Phosphate Inhibitors for the Urokinase-Type Plasminogen Activator: Optimization of the P4 Position, J. Med. Chem. 206, 49, 5785-5793.
Kettner et al., Inhibition of the Serine Proteases Leukocyte Elastase, Pancreatic Elastase, Cathepsin G, and Chymotrypsin by Peptide Boronic Acids, vol. 259, No. 24, issue of Dec. 25, pp. 15106-15114, 1984.
Keyomarsi et al., Semi-high throughput method of measuring proteasome inhibition in vitro and in cultured cells, Cell Biol Toxicol (2011) 27:123-131.
Knight, Active-Site Titration of Peptidase, Methods in Enzymology, vol. 248.
LeBeau et al., Potent and Selective Peptidyl Boronic Acid Inhibitors of the Serine Protease Prostate-Specific Antigen, Chemistry & Biology 15, 665-674, Jul. 21, 2008.
Liu et al., Activity-based protein profiling: The serine hydrolases, 14694-14699, PNAS, Dec. 21, 1999, vol. 96, No. 26.
Liu et al., Rapid Development of a potent Photo-triggered Inhibitor of the Serine Hydrolase RBBP9, ChemBioChem 2012, 12, 2082-2093
Liu et al., Intraocular hemorrhage causes retinal vascular dysfuntion via plasma kallikrein, IOVS Papers in Press. Published on Jan. 8, 2013 as manuscript iovs. 12-10537.
Marinaro et al., Physical and Chemical Properties of Boronic Acids: Formulation Implications.
Marnett et al., Papa's got a brand new tag: advances in identification of protease and their substrates, Trends in Biotechnology, vol. 23, No. 2, Feb. 2005.
Maynard et al., Discovery of a Potent Boronic Acid Derived Inhibitor of the HCV RNA-Dependent RNA Polymerase, Hournal of Medicinal Chemistry.
Micale et al., Development of peptidomimetic boronates as proteasome inhibitors, European Journal of Medicinal Chemistry 64 (2013) 23-24.
Moellering et al., How Chemoproteomics Can Enable Drug Discovery and Development, Chemistry & Biology 19, Jan. 27, 2012.

(56) References Cited

OTHER PUBLICATIONS

Moffitt et al., Accepted Manuscript. Chymotrypsin-like serine proteinase are involved in the maintenance of cell viability.
Nar, The role of structural information in the discovery of direct thrombin and factor Xa inhibitors, Trends in Pharmacological Sciences, May 2012, vol. 33, No. 5, pp. 279-288.
Nilsson et al., Purification and Functional Characterization of Factor I. Chapter 15.
O'Donoghue et al., Global identification of peptidase specificity by multiplex substrate profiling. Nature Methods. Advance Online Publication.
Patterson et al., Identification of Selective, Nonpeptide Nitrile Inhibitors of Cathepsin S Using the Substrate Activity Screening Method, J. Med. Chem. 2006, 49, 6298-6307.
Patterson et al., Substrate activity screening (SAS): a general procedure for the preparation and screening of a fragment-based non-peptide protease substrate library for inhibitor discovery, Nature Protocols, vol. 2, No. 2, 2007, pp. 424-433.
Pekol et al., Human Metabolism of the Proteasome Inhibitor Bortezomib: Identification of Circulating metabolites, vol. 33, No. 6, pp. 771-777.
Poplawski et al., Pro-Soft Val-boroPro: A Strategy for Enhancing in Vivo Performance of Boronic Acid Inhibitors of Serine Proteases, J. Med. Chem. 2011, 54, 2022-2028.
Powers et al., Irreversible Inhibitors of Serine, Cysteine, and Threonine Protease, Chem. Rev. 2002, 102, 4639-4750.
Robertson, Mechanistic Basis of Enzyme0Targeted Drugs, Biochemistry, vol. 44, No. 15, 2005, 5561-5571.
Sabidó et al., Supporting Information. Towards the identification of unknown neuropeptide precursor-processing enzymes: Design and synthesis of a new family of dipeptidyl phosphonate activity probes for substrate-based protease identification.
Sabidé et al., Towards the identification of unknown neuropeptide precursor-processing enzymes: Design and synthesis of a new family of dipeptidyl phosphonate activity probes for substrate-based protease identification, Bioorganic & Medicinal Chemistry 18 (2010) 8350-8355.
Salisbury et al., Supporting Information. Rapid Identification of Potent Nonpeptidic Serine Protease Inhibitors.
Salisbury et al., Rapid Identification pf Potent Nonpeptidic Serine Protease Inhibitors., ChemBioChem 2006, 7, 1034-1037.
Simon et al., Determining target engagement in living systems, Nature Chemical Biology, vol. 9, Apr. 2013, pp. 200-2005.
Singh, Supplementary Information. Nature Rev. Drug discovery, Covalent Drugs SI, Apr. 2011.
Singh et al., The resurgence of covalent drugs, vol. 10, Apr. 2011, pp. 307-317.
Small et al., Substrate specificity and anzymatic characteristic of MarP, a periplasmic protease required for resistance to acid and oxidative stress in *Mycobacterium tuberculosis*\*.
Small (O'Donoghue) 2012 MarP Figures.
Soellner et al., Fragment-Based Substrate Activity Screening method for the Identification of Potent Inhibitors of the *Mycobacterium tuberculosis* Phosphatase PtpB, J. Am. Chem. Soc. 2007, 129, 9613-9615.
Tapparelli et al., In Vitro and In Vivo Characterization of a Neutral Boron-containing Thrombin Inhibitor, vol. 268, No. 7, issue of Mar. 5, pp. 4734-4741, 1993.
Tully et al., Supporting Information. Activity-Based Probes that Target Functional Subclasses of Phospholipases in Proteomes.
Tulley et al., Activity-Based Probes that Target Functional Subclasses of Phospholipases in Proteomes, J. Am. Chem. Soc. 2010, 132, 4364-3265.Turk, Targeting proteases: successes, failures and future prospects, vol. 5, Sep. 2006, pp. 785-799.
Van Doren, Matrix metalloproteinase interactions with collagen and elastin, Matrix Biol. (2015).
von Matt et al., Selective Boron-Containing Thrombin Inhibitors-X-ray Analysis Reveals Surprising Binding Mode, Bioorganic & Medicinal Chemistry 8 (2000) 2291-2303.

Webb, The Kallikrein/Kinin System in Ocular Function, Journal of Ocular Pharmacology and Therapeutics, vol. 27, No. 6, 2011, pp. 539-543.
Weerapana et al., Disparate proteome reactivity profiles of carbon electrophiles, Nature Chemical Biology, vol. No. 7, Jul. 2008, pp. 405-407.
Wood et al., Susbtrate Activity Screening: A Fragment-Based Method for the Rapid Identification of Nonpeptidic Protease Inhibitors, J. Am. Chem. Soc. 2005, 127, 15521-15527.
Xu et al., An improved synthesis of a fluorophosphate-poly-ethylene glycol-biotin probe and its use against competitive substrates, Beilstein J. Org. Chem. 2013, 9, 89-96.
Zuhl et al., Competitive Activity-Based Protein Profiling Identifies Aza-$\beta$Lactams ad a Versatile Chemotype for Serine Hydrolase Inhibition, J. Am. Chem. Soc. 2012, 134, 5068-5071.
Hauske et al., Selectivity profiling of DegP substrates and inhibitors, Bioorganic & Medicinal Chemistry 17 (2009) 2920-2924.
Lipinska et al., The HtrA (DegP) Protein, Essential for *Escherichia coli* Survival at High Temperatures, Is an Endopeptidase, Journal of Bacteriology, vol. 172, No. 4, Apr. 1990, pp. 1791-1797.
Löwer et al., Inhibitors of Helicobacter pylori Protease HtrA Found by "Virtual Ligand" Screening Combat Bacterial Invasion of Epithelia, Mar. 2011, vol. 6, issue 3, e17986.
Table S6 from Lower, 2011, PLOS one—structures and activities of Helicobacter pylori HtrA inhibitors.
Lamden et al., Aminoalkylphosphonofluoridate derivatives: Rapid and Potentially Elective Inactivators of Serine Peptidase, Biochemical and Biophysical Research Communications, vol. 112, No. 3, 1085-1090.
Bartlett et al., Inhibition of Chymotrypsin by Phosphonate and Phosphonamidate Peptide Analogs, Bioorganic Chemistry 14, 356-377 (1986), pp. 356-377.
Ni et al., Synthesis and Kinetic Studies of an Amidine-containing Phosphonofluoridate: a Novel Potent Inhibitor of Trypsin-like Enzymes, Bioorganic & Medicinal Chemistry 6 (1998) 1767-1773.
Milroy et al., Selective Chemical Imaging of Static Actin in live Cells, J. Am. Chem. Soc. 2012, 134, 8480-8486.
Milroy et al., Supporting Material. Selective Chemical Imaging of Static Actin in live Cells.
Tully et al., Supporting Information. Activity-based Probes that Target Functional Subclasses of Phospolipases in Proteomes.
Tully et al., Activity-Based Probes That Target Functional Subclasses of Phospholipases in Proteomes, J. Am. Chem. Soc. 2010. 132, 3264-3265.
Tuin et al., Activity-Based Protein Profiling Reveals Broad Reactivity of the Nerve Agent Sarin, Chem. Res. Toxicol. 2009, 22, 683-689.
Huang et al., Qualitative analysis of the fluorophosphonate-based chemical probes using the serine hydrolasas from mouse liver and poly-3-hydroxybutyrate depolymerase (PhaZ) from *Bacillus thuringiensis*, Anal Bioanal Chem (2012) 404:2387-2396, Kidd et al., Profiling Serine Hydrolase Activities in Complex Proteomes, Biochemistry 2001, 40, 5005-4015.
Niu, Advanced water soluble BODIPY dyes: Synthesis and application, Jul. 2011.
de Rezende et al., A Review of the Synthetic Strategies for the Development of BODIPY Dyes for Conjugate with Proteins. Orbital: The electronic Journal of Chemistry, vol. 5, No. 1, Jan.-Mar. 2013, 62-83.
Liu et al., Activity-based protein profiling: The serine hydrolases, PNAS, vol. 96, No. 26, Dec. 21, 1991, 14694-14699.
Preparation of a Fluoro Phosphonate-BIODIPY Probe, Ref: Org. Lett., 2013, 15(6), pp. 1338-1341.
ActivX® Serine Hydrolase Probes, Thermo Scientific.
Digenis et al., Peptidyl Carbamates Incorporating Amino Acid Isosteres as Novel Elastase Inhibitors, J. Med. Chem. 1986, 29, 1468-1476.
Rypacek et al., Synthetic Macromolecular Inhibitors of Human Leukocyte Elastase. 1. Synthesis of Peptidyl Carbamates Bound to Water-Soluble Polymers: Poly-$\alpha,\beta$-[N-(2-hydroxyethyl)-D,L-aspartammide] and Poly-$\alpha$-[N$^5$-(2-hydroxyethyl)-L-Glutamine], J. Med. Chem. 1994, 37, 1850-1856.

(56) References Cited

OTHER PUBLICATIONS

Potashman et al., Covalent Modifiers: An Orthogonal Approach to Drug Design, Journal of Medicinal Chemistry, vol. 52, No. 5, Mar. 12, 2009, pp. 1231-1246.
Classes of Irreversible Protease Warheads, Powers Chem. Rev. 2002, 102, 4639-4750.
Brouwater et al., Peptido Sulfonyl Fluorides as New Powerful Proteasome Inhibitors, J. Med. Chem. 2012, 55, 10995-11003.
Bialas et al., Exploring the Sn Binding Pockets in Gingipains by newly Developed Inhibitors: Structure-Based Design, Chemistry, and Activity, J. Med. Chem. 2006, 49, 1744-1753, Powers et al., Irreversible Inhibitors of Serine, Cysteine, and Threonine Proteases, Chem. Rev. 2002, 102, 4639-4750.
Sieburth et al., Silanediol Protease Inhibitors: From Conception to Validation, Eur. J. Org. Chem. 2006, 311-322.
Brouower et al., Synthesis and biological evaluationof novel irreversible serine protease inhibitors using amino acid based sulfonyl fluorides as an electrophilic trap, Bioorganic & Medicinal Chemistry 19 (2011) 2397-2406.
Brouwer et al., Synthesis of β-aminoethanesulfonyl fluorides of 2-substituted taurine sulfonyl fluorides as potential protease inhibitors, Tetreahedron Letters 50 (2009) 3391-3393.
Hall, Structure, Properties, and Preparation of Boronic Acid Derivatives.
Carmès et al., A new Access to α-Hydroxy Boronic Esters from α-Alkoxyorganolithium Reagents, Tetrahedron Letters 39, (1998) 555-556.
Putty et al., Supplemental Material For: Characterization of D-boroAla as a Novel Broad Spectrum Antibacterial Agent Targeting D-Ala-D-Ala ligase.
Hong et al., Catalytic Enantioselective One-pot Aminoborylation of Aldehydes: A Strategy for Construction of Nonracemic α-Amino Boronates, J. Am. Chem. Soc.
Katz et al., Episelection: Novel $K_i$—Nanomolar Inhibitors of Serine Proteases Selected by Binding or Chemistry on an Enzyme Surface, Biochemistry 1995, 34, 8264-8280.
Lu et al., Synthesis and structural characterization of carboxyethylpyrrole-modified proteins: mediators of age-related macular degeneration, Bioorganic & Medicinal Chemistry 17 (2009) 7548-7561.
Matteson, Boronic Esters in Stereodirected Synthesis, Tetrahedron Report No. 250, Tetrahedron, vol. 45, No. 7, pp. 1859-1885, 1989.
Matteson, Boronic Esters in Asymmetric Synthesis, The Journal or Organic Chemistry.
Metteson, α-Amido Boronic Acids: A Synthetic Challenge and Their Properties as Serine Protease Inhibitors, Medicinal Research Reviews, vol. 28, No. 2, 233-246, 2008.
Putty et al., Characterization of D-boroAla as a novel Broad-Spectrum Antibacterial Agent Targeting D-Ala-D-Ala Ligase, Chem Biol Drug Des 2011, 78: 757-763.
Rönn et al., Exploration of acyl sulfonamides as carboxylic acid replacements in protease inhibitors of the hepatitis C virus full-length NS3, Bioorganic & Medicinal Chemistry 14 (2006) 54-559.
von Matt er al., Selective Boron-Containing Thrombin Inhibitors—X-ray Analysis Reveals Surprising Binding Mode, Bioorganic & Medicinal Chemistry 8 (2000) 2291-2303.
von Matt er al., Selective Boron-Containing Thrombin Inhibitors—X-ray Analysis Reveals Surprising Binding Mode, Bioorganic & Medicinal Chemistry 8 (2000) 2291-2203.
Wagner et al., Rational Design, Synthesis, and X-ray Structure of Selective Noncovalent Thrombin Inhibitors, J. Med. Chem. 1998, 41, 3664-3674.
Weski et al., Chemical Biology Approaches Reveal Conserved Features of a C-Terminal Processing PDZ Protease, ChemBioChem 2012, 13, 402-408.
Weski et al., Supporting Information. Chemical Biology Approaches Reveal Conserved Features of a C-Terminal Processing PDZ Protease, ChemBioChem 2012, 12, 402-408.
Wienand et al., Design Synthesis and Biological Evaluation of Selective Boron-containing Thrombin Inhibitors, Bioorganic & Medicinal Chemistry 7 (1999) 1295-1307.
Zajdlik et al., α-Boryl Isocyanides Enable Facile Preparation of Bioactive Boropeptides, Angew. Chem. Int. Ed. 2013, 52. 8411-8415.
Bishop et al., Hyperexcitable Substantia Nigra Dopamine Neurons in Pink1—and *HtrA2/Omi*- Deficient Mice, J. Neurophysiol 104: 3009-320, 2010.
Cilenti et al., Characterization of a Novel and Specific Inhibitor for the Pro-apoptotic Protease Omi/HtrA2* The Journal of Biological Chemistry, vol. 278, No. 13, issue of Mar. 28, pp. 11489-11494, 2003.
Dagda et al., Mitochondrial quality control: insights on how Parkinson's disease related genes Pink1, parkin, and Omi/HtrA2 interact to maintain mitochondrial homeostasis, J. Bioenerg Biomembr (2009) 41:473-479.
Desideri et al., Review Article, Mitochondrial Stress Signalling: HTRA2 and Parkinson's Disease, International Journal of Cell Biology, vol. 2012, article ID 607929, 6 pages.
Ding et al., Enhanced HtrA2/Omi Expression in Oxidative Injury to Retinal Pigment Epithelial Cells and Murine Models of Neurodegeneration, Investigative Ophthalmology & Visual Science, Oct. 2009, vol. 50, No. 10, pp. 4957-7966.
Fitzgerald et al., Phosphorylation of HtrA2 by Cyclin Dependent Kinase 5 is important for mitochondrial function, Cell Death Differ. Feb. 2012; 19(2): 257-266.
Gerhardt et al., Idebenone and Resveratrol Extend Lifespan and Improve Motor Function of HtrA2 Knockout Mice, Dec. 2011, vol. 5, issue 12, e28855.
Hartkamp et al., HtrA2, taming the oncogenic activities of WT1, Cell Cycle 9:13, 2508-2514; Jul. 1, 2010.
Huttunen et al., HtrA2 Regulates β-Amyloid Precursor Protein (APP) Metabolism through Endoplasmic Reticulum-associated Degradation, Journal of Biological Chemistry, vol. 282, No. 38, pp. 28285-28295, Sep. 21, 2007.
Kim et al., Omi/HtrA2 protease is associated with tubular cell apoptosis and fibrosis induced by unilateral ureteral obstruction, Am J Physiol Renal Physiol 298: F1332-F1340, 2010.
Li et al., Structural insights into the pro-apoptotic function of mitochondrial serine protease HtrA2/Omi, Nature Structural Biology, vol. 9, No. 6, Jun. 2002, pp. 436-441.
Li et al., Omi/HtrAs is a positive regulator of autophagy that facilities the degradiation of mutant proteins involved in neurodegenerative diseases, Cell Death and Differentiation (2010) 17, 1773-1784.
Lin et al., Novel variant Pro 143Ala in HTRA2 contributes to Parkinson's disease by inducing hyperphosphorylation of HTRA2 protein in mitochondria, Hum Gener (2011) 130:817-827.
Liu et al., Role of Omi/HtrA2 in Apoptotic Cell Death after Myocardial Ischemia and Reperfusion, Circulation. 2005;111:90-96; originally published online Dec. 20, 2004.
Plun-Favreau et al., HtrA2 deficiency causes mitochondrial uncoupling through the $F_1F_0$-ATP synthase and consequent ATP depletion, Citation: Cell Death and Disease (2012) 3, e335.
Ross et al., Genetic variation of *Omi/HtrA2* and Parkinson's disease, Parkinsonism Relat Disord. Nov. 2008; 14(7): 543.
Savopoulos et al., Expression, Purification, and Functional Analysis of the Human Serine Protease HtrA2, Protein Expression and Purification 19, 227-234 (2000).
Seong et al., N-terminal truncation circumvent proteolytic degradation of the human HtrA2/Omi serine protease in *Escherichia coli*: rapid purification of a proteolytically active HtrA2/Omi, Protein Expression and Purification 33 (2004) 200-208.
Su et al., UCF-101, A Novel Omi/HtrA2 Inhibitor, Protects Against Cerebral Ischemia/Reperfusion Injury in Rats, The Anatomical Record, 292:854-861 (2009).
Verhagen et al., HtrA2 Promotes Cell Death through it's Serine Protease Activity and it's Ability to Antagonize Inhibitor of Apoptosis Proteins, The Journal of Biological Chemistry, vol. 277, No. 1, issue of Jan. 4, pp. 445-454, 2002.
Walle et al., The mitochondrial serine protease HtrA2/Omi: an overview. Cell Death and Differentiation (2008) 15, 453-460.
Westerlund et al., Altered enzymtic activity and allele frequency of OMI/HTRAA in Alzheimer's disease; FASEB J. Apr. 2011. 25(4): 1345-1352.

(56) References Cited

OTHER PUBLICATIONS

Yun et al., Loss-of-Function Analysis Suggests that OMI/HtrA2 is not an Essential Component of the *pink1/parkin* Pathway *In Vivo*, The Journal of Neuroscience, Dec. 31, 2008, 28(53):14500-14510.
Zhang et al., Structural and functional analysis of the ligand specificity of the HtrA2/Omi PDZ domain, Protein Science (2007), 16:1738-1750.
Beleford et al., High Temperature Requirement A3 (HtrA3) Promotes Etoposide- and Cisplatin-induced Cytotoxicity in Lung Cancer Cell Lines* The Journal of Biological Chemistry, vol. 285, No. 16, pp. 12011-12027, Apr. 16, 2010.
Bowden et al., HTRA3 expression in non-pregnant rhesus monkey ovary and endometrium, and at the maternal-fetal interface during early pregnancy, Reproductive Biology and Endocrinology 2008, 6:22.
Dynon et al., HtrA3 as an Early Marker for Preeclampia: Specific Monoclonal Antibodies and Sensitive High-Throughput Assays for Serum Screening, PLOS One, Sep. 2012, vol. 7, issue 9, e45956.
Nie et al., Identification and cloning of two isoforms of human high-temperature requirement factor A3 (htrA3), characterization of its genomic structure and comparison of its tissue distribution with HtrA1 and HtrA2, Biochem J. (2003) 371, 39-48.
Runyon et al., Structural and functional analysis of the PDZ domains of human HtrA1 and HtrA 3, Protein Science (2007), 16:2454-2471.
Singh et al., Activity-Modulating Monoclonal Antibodies to the Human Serine Protease HtrA3 Provide Novel Insights into Regulating HtrA Proteolytic Activities, PLOS One, Sep. 2014, vol. 9, issue 9, e108235.
Brandi L. Williams et al., Chromosome 10q26-driven age-related macular degeneration is associated with reduced levels of *HTRA1* in human retinal pigment epithelium, PNAS 2021, vol. 118, No. 30 e2103617118, pp. 1-9.
Tuli et al., Stress measurements in mice after transportation, *Department of Biomedical Science and Ethics, Lab Anim* 1995 29: 132, DOI: 10.1258/002367795780740249, The online version of this article can be found at: http://lan.sagepub.com/content/29/2/132.
Capdevila et al., Acclimatization of rats after ground transportation to a new aminal facility' *Lab Anim* 2007 41L 255, DOI: 10.125/002367707780378096, The online version of this article can be found at: http://lan.sagepub.com/content/21/2/255, Apr. 1, 2007.
Baek et al., *Fundus autofluorescence (FAF) non-invasively identifies chlorioretinal toxicity in a rat model of retinal pigment epithelium (RPE) damage*. Aug. 12, 2014.
Nagai et al. *Novel CCR3 Antagonists Are Effective Mono—and Combination Inhibitors of Choroidal Neovascular Growth and Vascular Permeability*, The American Journal of Pathology, vol. 185, No. 9, Sep. 2015.
Abedi et al., Genetic Influences on the Outcome of Anti-Vascular Endothelial Growth Factor Treatment in Neovascular Age-related Macular Degeneration, 2013 by the Amercan Academy of Ophthalmology ISSN 0161-6420.
Alkhatib et al., Chondroadherin fragmentation mediated by the protease HTRA1 distinguishes human intervertebral disc degeneration from normal aging, published online May 14, 2013.
Altobellie et al., *HtrA1: Its future potential as a novel biomarker for cancer*, Received Jan. 19, 2015; Accepted Mar. 16, 2015, DOI: 10.3892/or.2015.4016.
Ambati et al., *Mechanisms of Age-Related Macular Degeneration*, University of Kentucky, Lexington, KY 40506, USA, Correspondence: jamba2@email.uky.edu http://dx.doi.org/10.1016/j.neuron.2012.006.018.
Ambati et al., *Immunology of age-related macular degeneration*, www.nature.com/reviews/immunol, Jun. 2013.
Prof. Bandello. AMD Book—AMD Age-Related Macular Degeneration, 1st Edition—Jun. 2010, ISBN: 978-989-96792-0-7.
The AMD Gene Consortium 2013, *Seven New Loci Associated with Age-Related Macular Degeneration*, Nature Genetics:doi:10.1038/ng.2578.
The AMD Gene Consortium 2013, Seven new loci associated with age-related macular degeneration Nature Genetics Advances Online Publication.
An, et al., *Identification of Novel Substrates for the Serine Protease HTRA1 in the Human RPE Secretome, IOVS*Jul. 2010, vol. 51, No. 7.
Andreoli et al., *Comprehensive Analysis of CFH and LOC387715/ARRMS2/HTRA1 Variants with respect to Phenotype in Advanced Age Related* Macular Degeneration, NIH Public Access, Am J Ophthalmol. Dec. 2009; 148(6): 869-874, doi:10.1016/j.ajo.2009.07.002.
Angi et al., *Proteomic Analyses of the Vitreous Humour, Hindawi Publishing Corporation Mediators of Inflammation* vol. 2012, Article ID 148039, 7 pages doi:10.1155/2012/148039, Received Jul. 7, 2012; Accepted Aug. 3, 2012.
Aredo et al, *Differences in the distribution, phenotype and gene expression of subretinal microglia/macrophages in C57BL/6N (Crb 1 rd8/rd8) versus C57BL6/J (Crb 1 wt/wt) mice*, Journal of Neuroinflammation (2015) 12:6 DOI 10.1186/s12974-014-0221-4.
Bastiaans et al., *Factor Xa and thrombin stimulate proinflammatory and profibrotic mediator production by retinal pigment epothelial cells: a role in vitreoretinal disorders?*, Received: Nov. 30, 2012/Revised: Mar. 14, 2013/ Accepted: Mar. 19, 2013/Published online: Apr. 20, 2013.
Beaufort et al., 2014 HTRA1 carasil murine Ko and TGFb binding protein supp, Supporting Information, PNAS, 10.1073/pnas.1418087111.
Beaufort et al—*Cerebral small vessel disease-related protease HtrA1 processes latent TGF-β binding protein 1 and facilitates TGF-β signaling*, PNAS, Contributed by Robert Huber, Sep. 27, 2014 (sent for review Jul. 27, 2014).
Bianchi et al, *Two Novel HTRA1 Mutations in a European Carasil Patient*, Mar. 11, 2014, Clinical/Scientific Notes, American Academy of Neurology.
Bird, *Therapeutic targets in age-related macular disease*, The Journal of Clinical Investigation, vol. 120 No. 9 Sep. 2010.
Black et al., *Age-related macular degeneration: genome-wide association studies to translation*, Genetics in medicine, Submitted Dec. 16, 2014; accepted Apr. 20, 2015; advance online publication May 28, 2015. doi:10.1038/gim.2015.70.
Ding, et al., *Anti-amyloid therapy protects against retinal pigmented epithelium damage and vision loss in a model of age-related macular degeneration*, Edited by Alan Bird, University of London, London, United Kingdom, and accepted by the Editorial Baord May 24, 2011 (received for review Jan. 17, 2011).
Bradley et al. Complement in age-related macular degeneration: a focus on function., Eye (2011) 25, 683-693; doi:10.1038/eye.2011.37; published online Mar. 11, 2011.
Bressler., *Defining the Prevalence of AMD and Investigation Racial Differences*, Prevalence rates and racial differences in AMD can help guide the development of screening and treatment policies, Cover Story Genetics and AMD, Jan./Feb. 2007.
Toomey et al., Regulation of age-related macular degeneration-like pathology by complement factor H, Edited by Jeremy Nathans, John Hopkins University, Baltimore, MD, and approved Apr. 28, 2015 (received for review Dec. 19, 2014).
Cabrera et al., Preprint—*HrtA1 activation is driven by an allosteric mechanism of intermonomer communication*, http://dx.doi.org/10.1101/163717 doi: bioRxiv preprint first posted online Jul. 14, 2017.
Cabrera et al., 2017 Supplemental Material (excel Spreadsheet).
Cabrera et al., *HrtA1 activation is driven by an allosteric mechanism of intermonomer communication*, Scientific Reports, Supplemental Material 2017.
Cabrera et al.,—*HrtA1 activation is driven by an allosteric mechanism of intermonomer communication*, Scientific Reports, Nov. 1, 2017—Scientific Reports, DOI:10.1038/s41598-017-14208-z.
Cameron et al., *HTRA1 Variant Confers Similar Risks to Geography Atrophy and Neovascular Age-Related Macular Degeneration*, [Cell Cycle 6:9, 1122-1125, May 1, 2007]; ©2007 Landes Bioscience.
Campioni et al., Molecular Cancer Research, *The Serine Protease HtrA1 Specifically Interacts and Degrades the Tuberous Sclerosis Complex 2 Protein, Mol Cancer Res* 2010;8:1248-1260. Published Online First Jul. 29, 2010.

(56) References Cited

OTHER PUBLICATIONS

Cao et al., *A Subretinal Matrigel Rat Chorodial Neovascularization (CNV) Model and Inhibition of CNV and Associated Inflammation and Fibrosis vy VEGF Trap*, Investigate Ophthalmology & Visual Science, Nov. 2010, vol. 51, No. 11, Association for Research in Vision and Ophthalmology.

Catchpole et al., *Systemic Administration of Abeta mAb Reduces Retinal Deposition of Abeta and Activated Complement C2 in Age-Related Macular Degeneration Mouse Model*, PLOS, www.plosone.org, Jun. 2013 |, vol. 8, Issue 6.

Ranibizumab and Bevacizumab for Neovascular Age-Related Macular Degeneration, The CATT Research Group, The New England Journal of Medicine, May 19, 2011 vol. 364 No. 20.

Chamberland, et al., *Identification of a Novel HtrA1-susceptible Cleavage Site in Human Aggrecan Evidence for the Involvement of HtrA1 in Aggrecan Proteolysis In Vivo*, Received for publication, Jun. 23, 2009, and in revised form, Jul. 31, 2009 Published, JBC Papers in Press, Aug. 5, 2009, DOI 10.1074/jbc.M109.037051.

Chan et al., *Human HtrA1 In The Archived Eyes With Age-Related Macular Degeneration*, Trans Am Ophthalmol Soc/ vol. 105/2007.

Chang et al., *Survey of Common Eye Diseases in Laboratory Mouse Strains*, Genetics, Submitted: Apr. 24, 2013, Accepted: Jun. 20, 2013, The Association for Research in Vision and Ophthalmology, Inc.

Chang, Mouse Models for Studies of Retinal Degeneration and Diseases, chapter 2, Bernhard H. F. Weber and Thomas Langmann (eds.), *Retinal Degeneration: Methods and Protocols, Methods in Molecular Biology*, vol. 935, DOI 10.1007/978-1-62703-080-9 2, © Springer Science+Business Media, LLC 2013.

Chen et al., *Assessing Susceptibility to Age-Related Macular Degeneration With Genetic Markers and Environment Factors*, Ophthalmic Molecular Genetics, Arch Ophthalmol/vol. 129 (No. 3), Mar. 2011.

Chen et al., *No association of age-related maculopathy susceptibility protein 2/HtrA serine peptidase I or complement factor H polymorphisms with early age-related maculopathy in a Chinese cohort*, Molecular Vision Published May 1, 2013; 19:944-954 http://movis.org/molvis/v19/994 Published May 1, 2013.

Chen et al., *Age- and Light-Dependent Development of Localised Retinal Atrophy in $CCL2^{-/-}2CX3CR1^{GFP/GFP}$ Mice*, PLOS, Apr. 2013, vol. 8, Issue 4, www.plosone.org.

Chen et al., *N-Terminomics identifies HtrA1 cleavage of thrombospondin-1 with generation of a proangiogenic fragment in the polarized retinal pigment epithelial cell model of age-related macular degeneration*, Matrix Biology, https://doi.org/10.1016/j.matbio.2018.03.013.

Cherepanoff et al., *Bruch's membrane and choroidal macrophages in early and advanced age-related macular degeneration*, Br J Ophthalmol 2010;94:918e925. doi:10.1136/bjo.2009.165563, Downloaded from http://bjo.bmj.com/ on Apr. 27, 2015—Published by group.bmj.com.

Chien, et al., *Identification of Tubulins as Substrates of Serine Protease HtrA1 by Mixture-Based Oriented Peptide Library Screening*, Journal of Cellular Biochemistry, Published online Mar. 19, 2009 in Wiley InterScience (www.interscience.wiley.com).

Chong et al. *Decreased Thickness and Intergrity of the Macular Elastic Layer of Bruch's Membrane Correspond to the Distribution of Lesions Associated with Age-Related Macular Degeneration*, Molecular Pathogenesis of Genetic and Inherited Diseases, American Journal of Pathology.

Chong et al. *Age-Related Macular Degeneration Phenotypes Associated With Mutually Exclusive Homozygous Risk Variants In CFH and Htra1 Genes*, Retina, The Journal of Retinal and Vitreous Diseases 2015 vol. 35 No. 5.

Cilenti et al., *Characterization of a Novel and Specific Inhibitor for the Pro-apoptotic Protease Omi/HtrA2\**, vol. 278, No. 13, Issue of Mar. 28, 2013, pp. 11489-11494, 2003, The Journal of Biological Chemistry.

Clausen et al., *HTRA protease: regulated protealysis in protein quality control*, Reviews, www.nature.com/reviews/molcellbio Mar. 2011 vol. 12.

Clausen et al., *The HtrA Family of Protease: Impications for Protein Composition and Cell Fate*, Review, Molecular Cell, vol. 10, 443-455, Sep. 2002.

Coakwell et al., *Contribution of growth differentiation factor 6-dependent cell survival to early-onset retinal dystrophies*, Human Molecular Genetics, 2013, vol. 22, No. 7, doi:10.1093/hmgdds560, Advance Access published on Jan. 9, 2013.

Curcio, et al., *Structure, Function, and Pathology of Bruch's Membrane*, Anatomy and Physiology, Section I, Chapter 20, 2013.

De Luca, et al., *Distribution of the Serine Protease HtrA1 in Normal Human Tissues*, vol. 51(10): 1279-1284, May 2003, The Journal of Histochemistry & Cytochemistry, http://www.jhc.org.

De Luca, et al., *Pattern of Expression of HtrA1 During Mouse Development*, vol. 52(12): 1609-1617, 2004, Journal of Histochemistry & Cytochemistry, http://www.jhc.org, Downloaded from jhc.sagepub.com by guest on Dec. 17, 2012.

DeAngelis et al., *Alleles in the HrtA1 Serine Peptidase 1 Gene Alter the Risk of Neovascular Age-Related Macular Degeneration*, doi:10.1016/j.ophtha.2007.10.032, 2008 by the American Academy of Ophthalmology.

DaAngelis et al., *Genetics of Age-Related Macular Degeneration: Current Concepts, Future Directions*, Received Jun. 21, 2010; revised Mar. 15, 2011; accepted Mar. 29, 2011, ISSN: 0882-0538, DOI: 10.3109/08820538.2011.577129, Informa Healthcare.

DeWan et al., Supporting Online Material for *HTRA1* Promoter Polymorphism in Wet Age-Related Macular www.sciencemag.org/cgi/content/full/1133807/DCI.

Ding et al., PNAS ApoE b-amyloid AMD Supporting Information, 0.1073-pnas.1100901108, www.pnas.org/cgi/content/short/1100901108, 2011 PNAS.

Ding et al., *Anti-amyloid therapy protects against retinal pigmented epithelium damage and vision loss in a model of age-related macular degeneration*, PNAS, ApoE b-amyloid AMD, Jul. 12, 2011, vol. 108 | No. 28, www.pnas.org/cgi/doi/10.1073/pnas.1100901108, http://www.pnas.org/lookup/suppl/doi:10.1073/pnas.1100901108/-/DCSupplemental.

Ding et al., Anti-amyloid therapy protects against retinal pigmented epithelium damage and vision loss in a model of age-related macular degeneration, A-beta Ab ApoE model, PNAS Jul. 12, 2011, vol. 108, No. 28, http://www.pnas.org/lookup.suppl/doi:10.1073/pnas.1100901108/-/DCSupplemental.

Do et al. *Choroidal Neovascularization Regression on Fluorescein Angiography after VEGF BlockadeCase Report in Ophthalmology*, The Wilmer Eye Institute, Published online: Nov. 7, 2012.

Duvvuri et al., *Role of Metabolism in Ocular Drug Delivery*, Current Drug Metabolism, 2004, 5, 507-515, *1Division of Pharmaceutoical Sciences, University of Missouri-Kansas City*, 2004 Bentham Science Publishers Ltd.

Eigenbrot et al., Structural and Functional Analysis of HrtA1 and Its Subdomains, Supplemental Information, Structure, vol. 20, 2012.

Eigenbrot et al., *Structural and Functional Analysis of HrtA1 and Its Subdomains*, Cell Press, Structure 20, 1040-1050, Jun. 6, 2012, DOI 10.1016/j.str.2012.03.021.

Heidmann, et al., *Quantitative enumeration of vascular smooth muscle call and endothelial cells derived from bone marrow precursors in experimental choroidal neovascularization*, Received Jul. 16, 2004; accepted in revised form Oct. 5, 2004, http://www.elsevier.com/locate/yexer.

Evans et al., *New hope for dry AMD?*, From The Analyst's Couch, News & Analysis, vol. 12, Jul. 2013.

Vierkotten et al., *Overexpression of HTRA1 Leads to Ultrastructural Changes in the Elastic Layer of Bruch's Membrane via Cleavage of Extracellular Matrix Components*, PLOS, Center of Ophthalmology, University of Cologne, Aug. 2011, vol. 6, Issue 8.

Feehan et al., *Identifying subtypes of patients with neovascular age-related macular degeneration by genotypic and cardiovascular risk characteristics*, BMC Medical Genetics. Feehan et al. BMC Medical Genetics 2011, http://www.biomedcentral.com/1471-2350/12/83.

(56) References Cited

OTHER PUBLICATIONS

Finger et al., *Predictors of anti-VEGF treatment response in neovascular-age-related macular degeneration*, Article history: Received Jul. 13, 2012, Received in revised form, Mar. 14, 2013, Accepted Mar. 19, 2013, www.sciencedirect.com/science/journal/00396257.
Friedrich et al. *Risk- and non-risk-associated variants at the 10q26 AMD locus influence ARMS2 mRNA expression but exclude pathogenic effects due to protein deficiency*, Human Molecular Genetics, 2011, vol. 20, No. 7 1387-1399, doi:10.1093/hmg/ddr020 Advance Access published on Jan. 20, 2011.
Frochaux et al., *Alpha-1-Antitrypsin: A Novel Human High Temperature Requirement Protease A1 (HTRA1) Substrate in Human Placental Tissue, (HTRA1) Substrate in Human Placental Tissue.* PLoS ONE 9(10): e109483. doi:10.1371/journal.pone.0109483, published Oct. 20, 2014.
Fukutake, *Cerebral Autosomal Recessive Arteriopathy with Subcortical Infarcts and Leukoencephalopathy (CARASIL): From Discovery to Gene Identification*, Journal of Stroke and Cerebrovascular Diseases, vol. 20, No. 2 (Mar.-Apr.), 2011: pp. 85-93.
Yaspan et al., A Common SNP at the CFI Locus is Associated with Rapid Progression of Geographic Atrophy, May 2014, Genentech Inc—Poster.
Glanz et al., *Loss-of-Function of HtrA1 Abrogates All-Trans Retinoic Acid-Induced Osteogenic Differentiation of Mouse Adipose-Derived Stromal Cells Through Deficiencies in p70S6K Activation*, Center for Applied Biotechnology and Molecular Medicine, 2016.
Godinat et al., *A Biocampatible in Vivo Ligation Reaction and Its Application for Noninvasive Bioluminescent Imaging of Protease Activity in Living Mice*, pubs.acs.org/acschemicalbiology, Mar. 6, 2013, dx.doi.org/10.1021/cb3007314, ACS Publications.
Gohara et al., *Allostery in trypsin-like protease suggests new therapeutic strategies*, Department of Biochemistry and Molecular Biology, Nov. 2011, vol. 29, No. 11.
Gorin, *Genetic insights into age-related macular degeneration: Controversies addressing risk, causality, and therapeutics*, http://dx.doi.org/10.1016/j.mam.2012.04.004, Available online Apr. 27, 2012.
Graham et al., *Serine Protease HTRA1 Antagonizes Transforming Growrh Factor-b Signaling by Cleaving Its Receptors and Loss of HTRA1 In Vivo Enhances Bone Formation*, Sep. 2013, vol. 8, Issue 9, PLOS ONE, www.plosone.org.
Grassman et al., *The genetics of age-related macular degeneration (AMD)—Novel target for designing treatment options?*, http://dx.doi.org/10.1016/j.ejpb.2015.04.039, Wuropen Journal of Pharmaceuticals and Biopharmaceuticals, May 16, 2015.
Grassman et al., *Recombinant Haplotypes Narrow the ARMS2/HTRA1 Association Signal for Age-Related Macular Degeneration*, orcid.org/0000-0002-8808-7723, Genetics, vol. 205, 919-924 Feb. 2017.
Grassmann et al., *Clinical and Genetic Factors Associated with Progression of Geographic Atrophy Lesions in Age-Related Macular Degeneration*, PLOS ONE, DOI:10.1371/jounral.pone.0126636 May 11, 2015.
Grau et al., *Implications of the serine protease HtrA1 in amyloid precursor protein processing*, www.pnas.org_cgi_doi_10.1073 pnas.0501823102.
Grau et al., *The Role of Human HtrA1 in Arthritic Disease\**, Journal of Biological Chemistry, vol. 281 No. 10, Mar. 10, 2006, DOI 10.1074/jbc.M500361200.
Grunwald et al., *Risk of Geographic Atrophy in the Comparison of Age-Related Macular Degeneration Treatments Trials*, 2013 by the American Academy of Ophthalmology, ISSN 0161-6420/13, http://dx.doi.org/10.1016/j.ophtha.2013.08.015.
Grunwald et al., Growth of Geographic Atrophy in the Comparison of Age-related Macular Degeneration Treatments Trials, http://dx/doi.org/10.1016/j.ophtha.2014.11.007, ISSN 0161-6420/14, 2015 by the American Academy of Ophthalmology.
Gu et al., *Proteomic and Genomic Biomarkers for Age-Related Macular Degeneration*, R.E., Chapter 47 Anderson et al. (eds.), Retinal Degenerative Diseases, Advances in Experimental 411 Medicine and Biology 664, DOI 10.1007/978-1-4419-1399-9_47, Springer Science+Business Media, LLC 2010.
Hadfield et al., *HtrA1 Inhibits Mineral Deposition by Osteoblasts Requirement for the Protease and PDZ Domains\** Received for publication, Nov. 13, 2007 Published, JBC Papers in Press, Dec. 22, 2007, DOI 10.1074/jbc.M709299200.
Hadziahmetovic et al., *Microarray Analysis of Murine Retinal Light Damage Reveals Changes in Iron Regulatory, Complement, and Antioxidant Genes in the Neurosensory Retina and Isolated RPE*, Investigative Ophthalmology & Visual Science, Aug. 2012, vol. 53, No. 9, The Association for Research in Vision and Ophthalmology, Inc.
Hageman et al, *Clinical validation of a genetic model to estimate the risk of developing choroidal neovascular age-related macular degeneration*, Primary Research, Henry Stewart Publications 1479-7364.
Hagstrom et al., *Pharmacogenetics fro Genes Associated with Age-Related Macular Degeneration in the Comparison of AMD Treatments Trials (CATT)*, ISSN 0161-6420, http://dx.doi.org/10.1016/j.ophtha.2012.11.037, Mar. 2013 by the *American Academy of Ophthamology*.
Hanheart et al, Continuing Medical Education: *Fellow eye effect of unilateral intravitreal Bevacizumab injection in eyes with diabetic macular edema*, Medscape Education, Published online: May 23, 2014, http://www.nature.com/eye.
Hanhart et al, Eye 2015_Fellow eye effect correspondence, Eye (2015) 29,293; doi:10.1038/eye.2014.274; published online Nov. 14, 2014.
Hara, et al., The New England Journal of Medicine, Supplementary Appendix, Supplementary Methods, Association of HTRA1 mutations and familial ischemic cerebral small-vessel disease. N Engl J Med 2009;360:1729-39.
Hara, et al., *Association of HTRA1 Mutations and Familial Ischemic Cerebral Small-Vessel Disease, The New England Journal of Medicine* 360; 17 nejm.org Apr. 23, 2009, N Engl J Med 2009;360:1729-39.
Hasan et al., *Abnormal developmentofplacentainHrtA1-deficient mice*, http://dx.doi.org/10.1016/j.ydbio.2014.10.015, Developmental Biology, journal homepage: www.elsevier.com/locate/developmentalbiology, Oct. 2014.
Hayashi et al., CFH and ARMS2 Variations in Age-Related Macular Degeneration, Polypoidal Choroidal Vasculopathy, and Retinal Angiomatous Proliferation, Investigative Ophthalmology & Visual Science, Nov. 2010, vol. 51, No. 11, Association for Research in Vision and Ophthalmology.
He et al., *HtrA1 sensitizes ovarian cancer cells to cisplatin-induced cytotoxicity by targeting XIAP for degradation*, International Journal of Cancer, Cancer: 130, 1029-1035 (2012), DOI: 10.1002/ijc.26044, Received Dec. 16, 2010; Accepted Feb. 22, 2011; Online Mar. 8, 2011.
Holliday et al., *Insights into the Genetic Architecture of Early Stage Age-Related Macualr Degeneration: A Genome-Wide Assoication Study Meta-Analysis*, Jan. 2013, vol. 8, Issue 1, www.plosone.org.
Hollyfield et al., *Oxidative damage-induced inflammation initiates age-related macular degeneration*, Published in final edited form as: *Nat Med.* Feb. 2008; 14(2): 194-198. doi:10.1038/nml709. NIH Public Access.
Hollyfield et al., *A Hapten Generated From An Oxidation Fragment of Docosahexaenoic Acid is Sufficient to Initiate Agerelated Macular Degeneration*, Published in final edited form as: Mol Neurobiol. Jun. 2010; 41(0): doi:10.1007/s12035-010-8110-z.
Holz et al., *Recent developments in the treatment of age-related macular degeneration*, Review, The Journal of Clinical Investigation http://www.jci.org vol. 124, No. 4, Apr. 2014.
Holz et al., *Geographic Atrophy Clinical Features and Potential Therapeutic Approaches*, Translational Science Review, ISSN 0161-6420, http://dx.doi.org/10.1016/j.ophtha.2013.11.023, The American Academy of Ophthalmology, May 2014.
Holz Ophthalmology 2014 GA clinical features and potential therapeutic approaches_ summary table of clinical development status.
Holz et al., *Progression of Geographic Atrophy and Impact of Fundus Autofluorescence Patterns in Age-related Macular Degeneration*, www.ajo.com, doi:10.1016/j.ajo.2006.11.041. Mar. 2017.

(56) References Cited

OTHER PUBLICATIONS

Holz et al., *Recent developments in the treatment of age-related macular degeneration*, The Journal of Clinical Investigation http://www.jci.org vol. 124 No. 4 Apr. 2014.
Hou, *LPS increases the incidence of collagen-induced arthritis in mice through induction of protease HTRA1 expression*, Arthritis & Rheumatism DOI 10.1002/art.38124, 2013 American College of Rheumatology Received: Nov. 25, 2012; Revised; Jul. 11, 2013; Accepted: Aug. 1, 2013.
Hou et al., *The Inhibitory Effect of IFN-g on Protease HTRA1 Expression in Rheumatoid Arthritis*, J Immunol published online Jun. 6, 2014, http://http//www.jimmunol.org/content/early/2014/06/06/jimmunol.1302700.
Housset et al., *Thrombospondin-1 and Pathogenesis of Age-Related Macular Degeneration*, Journal of Ocular Pharmacology and Therapeutics, vol 31, No. 7, 2015, Mary Ann Liebert, Inc., DOI: 10.1089/jop.2015.0023.
HtrA1 search on Thomson Pharma, Oct. 13, 2012.
Huang et al., Blockade of VEGFR1 and 2 Suppresses Pathological Angiogenesis and Vascular Leakage in the Eye, Jun. 2011, vol. 6, Issue 6, www.plosone.org.
Huang et al., VEGF Receptor Blockade Markedly Reduces Retinal Microglia/Macrophage Infiltration into Laser-Induced CNV, Aug. 2013, vol. 8, Issue 8, www.plosone.org.
Huang et al., Inhibition of Choroidal Neovascularization (CNV) by X-82 in a Subretinal Matrigel CNV Model, Meeting Abstract, Apr. 2009.
Iejima et al., Molecular Bases of Disease: *High-Temperature Requirement A Serine Peptidase 1 Gene is Transcriptionally Regulated by Insertion/Deletion Nucleotides Located at the 3 Prime End of Age-Related Maculopathy Susceptibility 2 Gene in Patients with Age-Related Macular Degeneration*,. Biol. Chem. published online Dec. 17, 2014, http://www/jbc.org/lookup/doi/10.1074.jbc.M114.593384.
Iejima et al., HTRA1 (Hight Temperature Requirement A Serine Peptidase 1) Gene Is Transcriptionally Regulated by Insertion/Deletion Nucleotides Located at the 3_End of the ARMS2 (Age-related Maculopathy Susceptibility 2) Gene in Patients with Age-related Macualr Degeneration, Doi: 10.1074/jbc.M114.593384 originally published online Dec. 17, 2014, doi: 1.1074/jbc.M114.593384.
Immuno-oncology at the crossroads: where are we headed after PD-1 blockade?, Smartanalust, 2015.
Jacobo et al., *AMD-associated silent polymorphisms in HtrA1 impair its ability to antagonize IGF-1, MCB Accepts*, published online ahead of print on Mar. 11, 2013, Mol. Cell. Biol. doi:10.1128/MCB.01283-12, 2013, American Society for Microbiology.
Jacobo et al., *Age-Related Macular Degeneration-Associated Silent Polymorphisms in HtrA1 Impair Its Ability To Antagonize Insulin-Like Growth Factor 1*, http://mcb.asm.org/, Molecular and Cellular Biology pp. 1976-1990, May 2013 vol. 33 No. 10.
Jacobo et al., *Focus on Molecules: HrtA1 and neovascular AMD*, http://dx.doi.org/10.1016/j.exer.2010.07.006,/ Experimental Eye Research, Jan. 4-5, 2012.
Jax CNV Mouse model JR5558 Abstracts, Mar. 7, 2013, http://www.abstractsonline.com/plan/AbstractPrintView.aspx?mID=2684&sKey=94b35del.
Jiang et al., *Overexpression of HTRA1 Leads to Down-Regulation of Fibronectin and Functional Changes in RF/6A Cells and HUVECs*, www.plosone.org, Oct. 2012, vol. 7, Issue 10.
Joachim et al., *Incidence and Progression of Geographic Atrophy, Observations from a Population-based Cohort*, The American Academy of Ophthalmology, http://dx.doi.org/10.1016/j.ophtha.2013.03.029, Mar. 2013, Article in Press.
Jonas, *Intravitreal Injection of Triamcinolone, Chapter 9*, Medical Retina, 2005. pp. 143-163.
Jones et al., SI Appendix for Increase Expression of HTRA1 in Retinal Pigment Epithelium Induces Polypoidal Choroidal Vasculopathy in Mice, 2011, PNAS Supplemental Material.
Jones et al., *Increased expression of multifunctional serine protease, HTRA1, in retinal pigment epithelium induces polypoidal choroidal vasculopathy in mice*, PNAS, Aug. 30, 2011, vol. 108, No. 35, www.pnas.org/cgi/doi/10.1073/pnas.1102853108.
JR558 Mice Abstracts—http://www.abstractsonline.com/plan/AbstractPrintView.aspx?mID=2684&sKey=94b35del . . . , Mar. 7, 2013.
Kamppeter et al., *Intraocular Concentration of Triamcinolone Acetonide after Intravitreal Injection in the Rabbit Eye*, doi:10.1016/j.ophtha.2008.01.019 Available online: Mar. 20, 2008, American Academy of Ophthalmology, Manuscript No. 2007-1071.
Kanda et al., *A variant of mitochondrial protein LOC387715/ARMS2, not HTRA1, is strongly associated with age-related macular degeneration*, PNAS, Oct. 9, 2007, vol. 104, No. 41, www.pnas.org/cgi/doi/10.1073/pnas.0703933104.
Katschke, et al., Protein Structure and Folding: *Inhibiting Alternative Pathway Complement Activation by Targeting the Factor D Exosite*, J. Biol. Chem. 2012, 287:12886-12892., doi:10.1074/jbc.M112.345082, The Journal of Biological Chemistry vol. 287, No. 16, pp. 12886-12892, Apr. 13, 2012.
Katta et al., *The molecular genetic basis of age-related macular degeneration: an overview*, Review Article, Journal of Genetics, vol. 88, No. 4, Dec. 2009.
Keenan et al., *Mapping the Differential Distribution of Proteoglycan Core Proteins in the Adult Human Retina, Choroid, and Sclera*, Investigative Ophthalmology & Visual Science, Nov. 2012, vol. 53, No. 12, The Association for Research in Vision and Ophthalmology, Inc.
Kennedy et al., *Lipofuscin of the Retinal Pigment Epithelium: A Review*, Eye (1995) 9, 763-771 © 1995 Royal College of Ophthalmologists, Nov. 1, 1995.
Kim et al., Mol Cell Biol, HtrA1 is a novel antagonist controlling FGF signaling via cleavage of FGF8 Accepts, published online ahead of print on Sep. 4, 2012, Mol. Cell. Biol. doi:10.1128/MCB.00872-12, 2012, American Society for Microbiology.
Kim et al., HtrA1 Is a Novel Antagonist Controlling Fibroblast Growth Factor (FGF) Signaling via Cleavage of FGF8, Molecular and Cellular Biology pp. 4482-4492, Nov. 2012 vol. 32 No. 21, 2012, http://mcb.asm.org.
Kitaoka et al., Axonal protection by Nmnat3 overexpression with involvement of autophagy in optic nerve degeneration, published online Oct. 17, 2013.
Klein et al., *Progression of Geographic Atrophy and Genotype in Age-Related Macular Degeneration, Ophthalmology*. Aug. 2010; 117(8): 1554-1559.e1. doi:10.1016/j.ophtha.2009.12.012, NIH Public Access, Author Manuscript.
Kloeckener-Gruissem et al., *Genetic Association with Response to Intravitreal Ranibizumab in Patients with Neovascular AMD*, Genetics, Investigative Ophthalmology & Visual Science, Jun. 2011, vol. 52, No. 7.
Koenekoop et al., *Mutations in NMNATI casue Leber congenital amaurosis and identify a new disease pathway for retinal degeneration*, NIH Public Access Author Manuscript, Nat Genet. Sep. 2012; 44(9): 10335-1039. doi:10.1038/ng.2356.
Kortvely et al., Retinal Degenerative Diseases Mechanisms and Experimental Therapy, Advances in Experimental Medicine and Biology vol. 854, Advances in Experimental Medicine and Biology ISBN 978-3-319-17120-3 ISBN 978-3-319-17121-0 (eBook) DOI 10.1007/978-3-319-17121-0, Springer International Publishing Switzerland 2016.
Kortvely et al., Chapter 4 Gene Structure of the 10q26 Locus: A Clue to Cracking the ARSM2/HTRA1 Riddle?, Springer International Publishing Switzerland 2015 (Author's proof)—Dispatch Date: Oct. 6, 2015 Proof No. 1.
Kumar et al, Proteolytic Degradation and Inflammation Play Critical Roles in Polypoidal Choroidal Vasculopathy, Molecular Pathogenesis of Genetic and Inherited Diseases, The American Journal of Pathology, vol. 187, No. 12, Dec. 2017.
Kumar et al., *Angiographic features of transgenic mice with increased expression of human serine protease HTRA1 in retinal pigment epithelium*, IOVS Papers in Press. Published on May 22, 2014 as Manuscript iovs. 13-13111, The Association for Research in Vision and Ophthalmology, Inc.
Kumar 2017 AJP HTRA1 inhibitor and PCV Fig 1.
Kumar 2017 AJP HTRA1 inhibitor and PCV Supp Material.

(56) References Cited

OTHER PUBLICATIONS

Kumar et al., Proteolytic Degradation and Inflammation Play Critical Roles in Polypodial Choroidal Vasculopathy, Accepted Manuscript, https://doi.org/10.1016/j.ajpath.2017.08.025, *The American Journal of Pathology*, Accepted Date: Aug. 17, 2017.

Kumar et al., Inflammation plays an important role in the pathogenesis of Polypoidal Choroidal Vasculopathy—2015 Poster.

Kumar et al., *Angiographic Features of Transgenic Mice WIrh Increased Expression of Human Serine Protease HTRA1 in Retinal Pigment Epithelium*, IOVS, Jun. 2014, vol. 55, No. 6, Downloaded From: http://iovs.arvojournals.org/pdfaccess.ashx?url=/data/Journals/IOVS/932990/ on May 11, 2015 Terms of Use.

Kumaramanickavel, *Age-Related Macular Degeneration: Genetics and Biology*, Asia-Pacific Journal of Ophthalmology, vol. 5, No. 4, Jul./Aug. 2016, http://www.apjo.org, Review Article.

Roche's lampalizumab phase II data shows benefit in patients with the advanced form of dry age-related macular degeneration, Investor Update, Basel, Aug. 27, 2013.

Lambert et al, MMP-2 and MMP-9 synergized in promoting choroidal neovascularization, *The FASEB Journal* express article 10.1096/fj.03-0113fje. Puublished online October 16, 2003.

Launay, *HtrA1-dependent proteolysis of TGF-b controls both neuronal maturation and developmental survival*, published online 13.6.08, Cell Death and Differentiation.

Leveziel et al., *Genotypic Influences on Serverity of Exudative Age-Related Macular Degeneration*, Retina, Investigative Ophthalmology & Visual Science, May 2010, vol. 51, No. 5.

Li et al., *Overexpression of Fibulin-5 in Retinal Pigment Epithelial Cells Inhibits Cell Proliferation and Migration and Downregulates VEGF, CXCR4, and TGFB I Expression on Cocultured Choroidal Endothelial Cells*, DOI: I OJ I 09/02713683.2012.665561, Received Oct. 31, 2011; revised Jan. 22, 2012; accepted Feb. 6, 2012, Informa Healthcare.

Liao et al., *Specific correlation between the major chromosome 10q26 haplotype conferrinf risk for age-related macular degeneration and the expression of HTRA1*, Molecular Vision, http://www.molvis.org/molvis/v23/318, Published Jun. 14, 2017.

Lin et al, 2018 Aging Cell HTRA1 an AMD protease processes extracellular matrix proteins EFEMP1 and TSP1 Supp Material.

Lin et al., *HTRA1, an age-related macular degeneration protease, processes extracellular matrix proteins EFEMP1 and TSP1*, DOI: 10.1111/acel.12710, Accepted: Nov. 7, 2017, Wiley Aging Cell.

Losonczy et al., *Effect of the Gas6 c.834+7G.A Polymorphism and the Interaction of Known Risk Factors on AMD Pathogenesis in Hungarian Patients*, www.plosone.org, Nov. 2012, vol. 7, Issue 11.

Loyet et al—Sep. 2012 IOVS Activation of the Alternative Complement Pathway in Vitreous is Controlled by Genetics in Age-related Macular Degeneration Supplement 1.

Loyet et al—Sep. 2012 IOVS Activation of the Alternative Complement Pathway in Vitreous is Controlled by Genetics in Age-related Macular Degeneration Supplement 2.

Loyet et al., *Activation of the Alternative Complement Pathway in Vitreous is Controlled by Genetics in Age-related Macular Degeneration*, Retina, Complement Activation in AMD, IOVS, Sep. 2012, vol. 53, No. 10.

Lu et al., Synthesis and structural characterization of carboxyethylpyrrole-modified proteins:mediators of age-related macular degeneration, Bioorganic & Medicinal Chemistry, Bioorganic & Medicinal Chemistry 17 (2009) 7548-7561, Available online Sep. 13, 2009.

Luhmann et al., Cc12, Cx3cr1 and Cc12/Cx3cr1 chemokine deficiencies are not sufficient to cause age-related reinal degeneration, Experimental Eye Research, http://dx.doi.org/10.1016/j.exer.2012.11.015, Experimental Eye Research 107 (2013), Available online Dec. 8, 2012.

Ly et al., Mitotic Misregulation and Human Aging; DOI: 10.1126/science.287.5462.2486, Mar. 31, 2000, vol. 287, Science www.sciencemag.org.

Lyzogubov et al., *Immunology: Polyethylene Glycol (PEG)-induced Mouse Model of Choroidal Neovascularization*, J. Biol. Chem. 2011, 286:16229-16237, doi: 10.1074/jbc.M110.204701 originally published online Mar. 23, 2011.

Lyzogubov et al—2014 Exp Eye Res Peg induced mouse murine Dry AMD supplemental Material.

Lyzogubov et al., *Polyethylene glycol induced mouse model of retinal degeneration*, Experimental Eye Research (2014) 1e10, Aug. 2, 2014, http://dx.doi.org/10.1016/j.exer.2014.07.021.

Ma et al., Microglia in the Mouse Retina Alter the Structure and Function of Retinal Pigmented Epithelial Cells: A Potential Cellular Interaction Relevent to AMD, www.plosone.org, Nov. 2009, vol. 4, Issue 11, www.plosone.org.

Maguire et al., Incidence of Choroidal Neovascularization in the Fellow Eye in the Comparison of Age-Related Macualr Degeneration Treatment Trials, http://dx.doi.org/10.1016/j.ophtha.2013.03.017, Accepted: Mar. 8, 2013, Article in Press, Ophthalmology.

Martins et al., *Binding Specificity and Regulation of the Serine Protease and PDZ Domains of HtrA2.Omi\**, Received for publication, Aug. 6, 2003, and in revised form, Sep. 24, 2003 Published, JBC Papers in Press, Sep. 25, 2003, DOI 10.1074/jbc.M308659200, The Journal of Biological Chemistry.

Matibo 2017 Revision—Chen et al., N-Terminomics Identifies HtrA1 Cleavage of Thrombospondin-1 with Generation of a Proangiogenic Fragment in the Polarized Retinal Pigment Epithelial Cell Model of Age-related Macular Degeneration.

McCarthy et al., *Predictive Model of Choroidal Neovascularization and Geographic Atrophy Incidence Applied to Clinical* Trial Design, http://dx.doi.org/10.1016/j.ajo.2012.03.021, Accepted for publication Mar. 16, 2012, vol. 154, No. 3, Elsevier Inc.

McKibbin et al., CFH, VEGF and HTRA1 promoter genotype may influence the response to intravitreal ranibizumab therapy for neovascular age-related macular degeneration, Published Online First May 10, 2011, http://group.bmj.com/ on Sep. 30, 2012—Published by group.bmj.com Melo et al., *HtrA1 Mediated Intracellular Effects on Tubulin Using a Polarized RPE Disease Model*, EBioMedicine, https://doi.org/10.1016/j.ebiom.2017.12.011, Available online Dec. 13, 2017, www.ebiomedicine.com.

*Melo et al., 2017 Roche EBioMedicine(2)—HtrA1 Mediated Intracellular Effects on Tubulin Using a Polarized RPE Disease Model*, EBioMedicine, https://doi.org/10.1016/j.ebiom.2017.12.011, Available online Dec. 13, 2017, www.ebiomedicine.com.

Melo Roche, EBIOM-D-2017—Elsevier Editorial System(tm) for Manuscript Draft, Manuscript Number: EBIOM-D-17-00153R1, Title: HtrA1 mediated intracellular effects on tubulin using a polarized RPE disease model.

Melo, HtrA1 mediated intracellular effects on tubulin using a polarized RPE disease model supplementary Nov. 3, 2017 reduced.

Mendioroz et al., *Amissensehtral mutation expands carasil Syndrome to the Caucasian population*, Neurology 75, Nov. 30, 2010, Clinical/Scientific Notes.

Mettu et al., Retinal pigment epithelium response to oxidant injury in the pathogenesis of early age-related macular degeneration, Molecular Aspects of Medicine, Available online May 3, 2012, http://dx.doi.org/10.1016/j.mam.2012.04.006.

Micklisch et al., Age-related macular degeneration associated polymorphism rs10490924 in ARMS2 results in deficiency of a complement activator, Micklisch et al. Journal of Neuroinflammation (2017), DOI 10.1186/s12974-016-0776-3, Jan. 5, 2017.

Mo et al., Interferon—Inductible Protein-10 (IP-10) and Eotaxin as Biomarkers in Age-Related Macular Degeneration, Retina, Investigative Ophthalmology & Visual Science, Aug. 2010, vol. 51, No. 8.

Mullany et al., *Expression and Functional Significance of HtrA1 Loss in Endometrial Cancer*, Published Online First Nov. 23, 2010; DOI:10.1158/1078-0432.CCR-09-3069, Clinical Cancer Research, www.aacrjournals.org, Clin Cancer Res; 17(3) Feb. 1, 2011.

Muratoglu et al., LRP1 Protects the Vasculature by Regulating Levels of Connective Tissue Growth Factor and HtrA1, http://atvb.ahajournals.org/content/early/2013/07/18/ATVBAHA.113.301893, Downloaded from http://atvb.ahajournals.org/ at University of Wash-

(56) References Cited

OTHER PUBLICATIONS ington on Jul. 23, 2013, DOI: 10.1161/ATVBAHA.113.301893, Arteriosclerosis Thrombosis, and Vascular Biology.
Murwantoko et al., Binding of proteins to the PDZ domain regulates proteolytic activity of HtrA1 serine protease, Biochem. J. (2004) 381, 895-904 (Printed in Great Britain), Aug, 2004.
Nagai, Spontaneous CNV in a Novel Mutant Mouse Is Assoicated With Early CEGF-A-Driven Angiogenesis and Late-Stage Focal Edema, Neural Cell Loss, and Dysfunction, IOVS Jun. 2014, vol. 55, No. 6, The Association for Research in Vision and Ophthalmology, Inc. www.iovs.org, ISSN: 1552-5783.
Nagai et al., IOVS Papers in Press. Published on May 20, 2014 ad Manuscript iovs.14-13989, 2014 by The Association for Research om Vision and Ophthalmology, Inc.
*Nagai et al.*, Spontaneous CNV in a Novel Mutant Mouse Is Associated With Early VEGF-A-Driven Angiogenesis and Late-Stage Focal Edema, Neural Cell Loss, and Dysfunction, IOVS, Jun. 2014, vol. 55 No. 6, DOI:10.1167/ iovs.14-13989.
Nagai et al., Novel CCR3 Antagonists Are Effective Mono- and Combination Inhibitors of Choroidal Neovascular Growth and Vascular Permeability, The American Journal of Pathology—ajp.amjpathol.org, Jul. 25, 2015.
Nakayama et al., IOVS Papers in Press. Published on Sep. 9, 2014 as Manuscript iovs.14-14453—2014 IVOS whole body over expression of HTRA1 and cigarette smoke CNV.
Nakayama et al., Overexpression of HtrA1 and Exposure to Mainstream Cigarette Smoke Leads to Choroidal Neovascularization and Subretinal Deposits in Aged Mice, 2014 The Association for Research in Vision and Ophthalmology, Inc. IOVS, Oct. 2014, vol. 55, No. 10.
Newman et al., Systems-level analysis of age-related macular degeneration reveals global biomarkers and phenotype-specific functional networks, http://www.biomedical.com/1741-7015/10/21/abstract, Genmore Medicine 2012, doi: 10.1186/PREACCEPT-1418491035586234.
Ng et al., *HTRA1* promoter variant differentiates polypoidal choroidal vasculopathy from exudative-related macular degeneration, Scientific Reoports, Published: Jun. 24, 2016, DOI: 10.1038/srep28639.
Ng et al., Interactive Expressions of HtrA1 and VEGF in Human Vitreous Humors and Fetal RPE Cells, Investigative Ophthalmology & Visual Science, May 2011, vol. 52, No. 6, *IOVS*.
Milton, The development of biologics for ocular diseases: Using PKPD to understand what we cannot see, Oct. 10, 2011.
Nowak et al., Age-related macular degeneration (AMD): pathogenesis and therapy, Feb. 21, 2006, Pharmacological Reports.
Nowak-Sliwainska et al., Photodynamic therapy for polypoidal choroidal vasculopathy, Progress in Retinal and Eye Research, therapy for polypoidal choroidal vasculopathy, Progress in Retinal and Eye Research (2013), http://dx.doi.org/10.1016/j.preteyeres.2013.09.003, JPRR535 proof Oct. 16, 2013.
Ohkuma et al., Retinal angiomatous proliferation associated with risk alleles of *ARMS2/HTRA1* gene polymorphisms in Japanese patients, Clinical Ophthalmology 2014:8 143-148, Published with Dove Pre Journal Dec. 27, 2013.
Oka et al., HtrA1 serine protease inhibits signaling mediated by Tgfβ family proteins, Development 131, 1041-1053, Published by The Company of Biologists 2004, doi:10.12/dev.00999, Accepted Nov. 21, 2003.
Orlin et al., Association Between High-Risk Disease Loci and Response to Anti-Vascular Endothelial Growth Factor Treatment for Wet Agerelated Macular Degeneration, Retina, The Journal of Retinal and Vitreous Diseases, 2012, vol. 32, No. 1.
Pahl et al., Characterization of the 10q26-orthologue in rhesus n1onkeys corroborates a functional connection between *ARMS2* and *HTRA1*, Experinlental Eye Research, Available online Mar. 21, 2012, doi:10.1016/j.exer.2012.03.007.
Patel et al., Review of Ranibizumab Trials for Neovascular Age-Related Macular Degeneration, Informa Healthcare, DOI, I 0.3109/08820538.200.570815, Received Nov. 6, 2010; revised Feb. 6, 2011; accepted Feb. 18, 2011.

Pennesi et al., Animal models of age related macular degeneration, Molecular Aspects of Medicine, Available online Jun. 15, 2012. http://dx.doi.org/10.1016/j.mam.2012.06.003.
Pinto et al., Interpretation of the mouse electroretinogram, Doc Ophthalmol. Nov. 2007; 115(3): 127-136. doi:10.1007/s10633-007-9064-y., NIH Public Access.
Punzo et al., Cellular Responses to Photoreceptor Death in the *rdl* Mouse Model of Retinal Degeneration, Investigative Ophthalmology & Visual Science, Feb. 2007, vol. 48, No. 2.
Querques et al., Treatment of Dry Age-Related Macular Degeneration, Published online: Sep. 11, 2014, DOI: 10.1159/000363187, Ophthalmic Res 2014;52:107-115.
Rakoczy, et al., Detection and Possible Functions of a Cysteine Protease Involved in Digestion of Rod Outer Segments by Retinal Pigment Epithelial Cells, Investigative Ophthalmology & Visual Science, Nov. 1994, vol. 35, No. 12.
Reynolds et al., Dietary Omega-3 Fatty Acids, Other Fat Intake, Genetic Susceptibility, and Progression to Incident Geographic Atrophy, ISSN 0161-6420, http://dx.doi.org/10.1016/j.ophtha.2012.10.020, 2013 by the American Academy of Ophthalmology.
Rickman et al., Dry Age-Related Macular Degeneration: Mechanisms, Therapeutic Targets, and Imaging, IOVS, Dec. 2013, vol. 54, No. 14.
Rimpelä et al., Ocular Melanin Binding of Drugs: *In Vitro* Binding Studies Combined to a Pharmacokinetic Model, Feb. 2014, Division of Pharmaceutical Biosciences.
Risør et al., The autolysis of human HtrA1 is governed by the redox state of its N-terminal domain, *Biochemistry*, Accepted Manuscript • Publication Date (Web): May 20, 2014, Downloaded from http://pubs.acs.org on May 23, 2014.
Robbie, The role of innate immune cells in ocular ageing and pathological neovascularization, A thesis submitted for the degree of Doctor of Philosophy, 2012, Department of Genetics Institute of Ophthalmology University College London.
Rosenfeld, Characteristics of Patients Losing Vision after 2 Years of Monthly Dosing in the Phase III Ranibizumab Clinical Trials, Ohpthalmology *vol. 188, No. 3, Mar. 2011*, doi:10.1016/j.ophtha.2010.07.011.
Runyon et al., Strucutral and functional analysis of the PDZ domains of human HtrA1 and HtrA3, (Received Jun. 3, 2007; Final Revision Jul. 20, 2007; Accepted Jul. 27, 2007), www.proteinscience.org.
Hombrebueno, J., et al. *Intravitreal Injection of Normal Saline Induces Retinal Degeneration in the C57BL/6J Mouse*, TVST, vol. 3, No. 2, 2014.
Salmoon, R., et al., *Discovery of Carboxyethylpyrroles (CEPs): Critical Insights into AMD, Autism, Cancer, and Wound Healing from Basic Research on the Chemistry of Oxidized Phospholipids*, Chem. Res. Toxicol. vol. 24, 1803-1816, 2011.
Seddon, J., et al. *Validation of a Prediction Algorithm for Progression to Advanced Macular Degeneration Subtypes*, JAMA Ophthalmol, vol. 131 No. 4, 448-455, Apr. 2013.
Seddon, J., et al., *Association of CFH Y402H and LOC387715 A69S With Progression of Age-Related Macular Degeneration*, JAMA, vol. 297, No. 16, 1793-1800, Apr. 25, 2007.
Sennlaub, F. et al., *CCR2β monocytes infiltrate atrophic lesions in age-related macular disaese and mediate photorecptor degeneration inn experimental subretinal inflammation in Cx3crl deficient mice*, EMBO Mol Med., vol. 5, 1775-1793, (2013).
Liao, S., et al., *Specific correlation between the major chromosome 10q26 haplotype conferring risk for age-related macular degeneration and the expression of HtTRA1*, Molecular Vision, 23:218-333, Jun. 14, 2017.
Sharma, NS, et al., Correspondence *Fellow Eye Effect of Unilateral Intravitreal bevacizumab injection in eyes with diabetic macular edema*, EYE, vol. 29, 290-291, doi:10.1038/eye.2014.249; published online Nov. 21, 2014.
Sharma, et al., *New Biomarker for Neovascular Age-Related Macular Degeneration: Eotaxin-2*, DOI: 10.1089/dna.2012.1786, DNA and Cell Biology vol. 31, No. 11, 2012.
Sharp et al., *Helicobacter* Infection Decreases Reproductive Performance of IL10-deficient Mice, vol. 58, No. 5 Oct. 2008 pp. 447-453, Comparative Medicine.

(56) References Cited

OTHER PUBLICATIONS

Shiga et al., Cerebral small-vessel disease protein HTRA1 controls the amount of TGF-β 1 via cleavage of proTGF-β 1, Human Molecular Genetics, 2011, vol. 20, No. 9, pp. 1800-1810 doi:10.1093/hmg/ddr063 Advance Access published on Feb. 14, 2011.
Singh et al., Increased Expression of CD200 on Circulating CD11b+ Monocytes in Patients with Neovascualr Age-related Macular Degeneration, http://dx.doi.org/10.1016/j.ophtha.2012.11.002, *2013 by the American Academy of Ophthalmology*.
Skorko-Glonek et al., HtrA Protease Family as Therapeutic Targets, *Current Pharmaceutical Design*, 2013, Department of Biochemistry, University of Gdansk.
Sobrin et al., Nature and nuture—genes and environment—predict onset and progression of macular degeneration, Progress in Retinal and Eye Research, http://dx.doi.org/10.1016/j.preteyeres.2013.12.004, Available online Dec. 27, 2013, Progress in Retinal and Eye Research 40 (2014) 1-15.
Sobrin, et al., *ARMS2/HTRA1* Locus Can Confer Differential Susceptibility to the Advanced Subtypes of Age-Related Macular Degeneration, doi:10.1016/j.ajo.2010.08.015, Feb. 2011, http://ajo.com/.
Stanton et al., Chapter 47, The Chromosome 10q26 Susceptibility Locus in Age-Related Macular Degeneration, 2012, *Retinal Degenerative Diseases*, Advances in Experimental Medicine and Biology 723, DOI 10.1007/978-1-4614-0631-0_47.
Stanton et al., Chapter 32 Inflammatory Biomarkers for AMD, 2014, *Retinal Degenerative Diseases*, Advances in Experimental Medicine and Biology 801, DOI 10.1007/978-1-4614-3209-8_32.
Stanton et al., Evidence That the HTRA1 Interactome Influences Susceptibility to Age-Related Macular Degeneration, ARVO Annual Meeting Abstract, Apr. 2011, Investigative Ophthalmology & Visual Science Apr. 2011, vol. 52, 3913.
Stewart et al., Pharmacokinetics, pharmacokinamics and preclinical characteristics of ophthalmic drugs that bind VEGF, Expert Rev. Clin. Pharmacol. 7(2), 167-180 (2014), ISSN 1751-2433.
Stewart et al. Clinical and differential utility of VEGF inhibitors in wet age-related macular degeneration: focus on aflibercept, Clinical Ophthalmology 2012:6 1175-1186, Jul. 25, 2012, Dove Press.
*Supanji et al.—Experimental Eye Research 2013 HtrA1 senescence Supp Material*.
Supanji et al., HtrA1 is induced by oxidative stess and enhances cell senescence through p38 MAPK pathway, Experimental Eye Research, Available online Apr. 24, 2013, http://dx.doi.org/10.1016/j.exer.2013.04.013.
Swenson et al. Limitations of Green Fluorescent Protein as a Cell Lineage Marker, Stem Cells Technology Development 2007;25:2593-2600, *Express* Jul. 5, 2007.
Takeda et al., CCR3 is a therapeutic and diagnostic target for neovascular agerelated macular degeneration, Nature. Jun. 9, 2009; 460(7252): 225-230. doi:10.1038/nature08151, NIH Public Access Author Manuscript.
Tanaka et al., Analysis of candidate genes for age-related macular degeneration subtypes in the Japanese population, *Molecular Vision* 2011; 17:2751-2758 http://www.molvis.org/molvis/y17/a297 Received Jan. 11, 2011, Accepted Oct. 19, 2011, Published Oct. 22, 2011.
Tateoka et al, Unusual case of cerebral small vessel disease with a heterozygous nonsense mutation in HTRA1, Letter to the Editor, Journal of the Neurological Sciences, Journal of the Neurological Sciences 362 (2016) 144-146, http://dx.doi.org/10.1016/j.jns.2016.01.037, Mar. 7, 2016.
Tennstaedt et al., Human High Temperature Requirement Serine Protease A1(HTRA1) Degrades Tau Protein Aggregates, The Journal of Biological Chemistry, Jun. 15, 2012•vol. 287•No. 25.
Tennstaedt et al., Protein Synthesis and Degradation: Human High Temperature Requirement Serine Protease A1 (HTRA1) Degrades Tau Protein Aggregates, Published on Apr. 25, 2012 as Manuscript M111.316232, doi: 10.1074/jbc.M111.316232, JBC Papers.
Teper et al., Involvement of genetic factors in the response to a variable-dosing ranibizumab treatment regimen for age-related macular degeneration, *Molecular Vision* 2010; 16:2598-2604 http://www.molvis.org/molvis/v16/a278 Received May 20, 2010 | Accepted Dec. 2, 2010 | Published Dec. 7, 2010.
Tiaden et al., Molecular Bases of Disease: Detrimental Role for Human High Temperature Requirement Serine Protease A1 (HTRA1) in the Pathogenesis of Intervertebral Disc (IVD) Degeneration*, *J. Biol. Chem. 2012, 287:21335-21345., doi: 10.1074/jbc.M112.341032 originally published online May 3, 2012*.
Tiaden et al., The Emerging Roles of HTRA1 in Musculoskeletal Disease, http://dx.doi.org/10.1016/j.ajpath.2013.02.003, Mar. 8, 2013, Min-Review.
Tian et al., Association of genetic polymorphism with response to bevacizumab for neovascular age-related macular degeneration in the Chinese population, Research Article, *Pharmacogenomics* (2012) 13(7), 779-787, Mar. 15, 2012.
Tocharus et al., Developmentally regulated expression of mouse HtrA3 and its role an inhibitor of TGF-β signaling, Received Jan. 13, 2004; revised Mar. 1, 2004; accepted Mar. 4, 2004.
Tolentino et al., Drugs in Phase II clinical trials for the treatment of age-related macular degeneration, 10.1517/13543784.2015.961601, Review, 2015 Informa UK, Ltd. ISSN 1354-3784.
Tong et al., *LOC387715/HTRA1* gene polymorphisms and susceptibility to agerelated macular degeneration: A Huge review and meta-analysis, *Molecular Vision* 2010; 16:195☐-198☐http://www.molvis.org/molvis/v16/a213 Received Nov. 9, 2009 | Accepted Sep. 30, 2010, Published Oct. 5, 2010.
Tosi et al., HTRA1 and TGF-β Concentrations in the Aqueous Humor of Patients With Neovascular Age-Related Macular Degeneration, DOI:10.1167/iovs.16-20922, iovs.16-20922, Jan. 2017, vol. 58, No. 1.
Truebestein et al., Substrate-induced remodeling of the active site regulates human HTRA1 activity, vol. 18, No. 3 Mar. 2011, Brief Communications, nature structural & molecular biology.
Truebestein, Structural and Biochemical Characterization of the Human Serine Protease HtrA1, Inaugural-Dissertation, Jun. 18, 2020.
Tsiftsoglou et al., Human Complement Factor I Does Not Require Cofactors for Cleavage of Synthetic Substrates, *The Journal of Immunology, J Immunol* 2004; 173:367-375; http://http//www.jinumunol.org/content/173/1/367.
Tsuchiya et al., Expression of mouse HtrA1 serine protease in normal bone and cartilage and its upregulation in joint cartilage damaged by experimental arthritis, Received Dec. 2, 2004; accepted Mar. 21, 2005, Available online Jul. 1, 2005, doi:10.1016/j.bone.2005.03.015.
Tuo et al., The *HtrA1* promotor polymorphism, smoking, and age-related macular degeneration in multiple case-control samples, *Ophthalmology*. Nov. 2008; 115(11): 1891-1898. doi:10.1016/j.ophtha.2008.05.021., NIH Public Access.
Tuo et al., Genetics of Immunological and Inflammatory Components in Age-related Macular Degeneration, Ocul Immunol Inflamm. Feb. 2012; 20(1): 27-36. doi:10.3109/09273948.2011.628432, NIH:Public Access.
Uno et al., Impaired expression of thrombospondin-1 in eyes with age related macular degeneration, Br J Ophthalmol 2006;90:48-54. doi: 10.1136/bjo.2005.074005.
van Asten et al., A Deep Phenotype Association Study Reveals Specific Phenotype Associations with Genetic Variants in Age-related Macular Degeneration, https://doi.org/10.1016/j.ophtha.2017.09.023, Ophthalmology.
van Lookeren et al., Mechanisms of age-related macular degeneration and therapeutic opportunities, *J Pathol* 2014; 232: 151-164, Sep. 2013, DOI: 10.1002/path.4266.
Vendura et al. Heterozygous HTRA1 mutations are associated with autosomal dominant cerebral small vessel disease, Brain, (2015). Published by Oxford University Press.
Vierkotten (Fauser), 2011, Fig S2.
Vierkotten et al., Overexpression of HTRA1 Leads to Ultrastructual Changes in the Elastic Layer of Bruch's Membrane via Cleavage of Extracellular Matrix Components, Aug. 2011, vol. 6, Issue 8, www.plosone.org.

(56) References Cited

OTHER PUBLICATIONS

Wang et al., Lack of Thrombospondin-1 and Exacerbation of Choroidal Neovascularization, NIH Public Access, Arch Ophthalmol. May 1, 2012; 130(5): 615-620. doi:10.1001/archopthalmol.2011.1892.
Wang, Chromosome 10q26 locus and age-related macular degeneration: A progress update, Accepted Manuscript, *Experimental Eye Research*, DOI: 10.1016/j.exer.2013.11.009, Nov. 18, 2013.
Wang et al., Direct Effect of Sodium Iodate on Neurosensory Retina, IOVS, Mar. 2014, vol. 55, No. 3, DOI:10.1167/iovs.13-13075.
Wang et al., CFH Y402H polymorphism is associated with elevated vitreal GM-CSF and choroidal macrophages in the postmortem human eye, *Molecular Vision* 2015; 21:264-272 http://www.molvis.org/molvis/v21/264, Received Sep. 2, 2014 | Accepted Mar. 11, 2015 | Published Mar. 13, 2015.
Wang et al., Down-Regulation of HrtA1 Activates the Epithelial-Mesenchymal Transition and ATM DNA Damage Response Pathways.
Whitcup et al., The Role of the Immune Response in Age-Related Macular Degeneration, http://dx.doi.org/10.1155/2013/348092., Accepted Apr. 9, 2013, International Journal of Inflammation.
Whitmore, et al., Altered gene expression in dry age-related macular degeneration suggests early loss of choroidal endothelial cells, *Molecular Vision* 2013; 19:2274-2297 http://www.molvis.org/molvis/v19/2274, Received Jul. 3, 2013 | Accepted Nov. 14, 2013 | Published Nov. 16, 2013.
Wu et al., HtrA1 is upregulated during RANKL-induced osteoclastogenesis, and negatively regulates osteoblast differentiation and BMP2-innduced Smad1/5/8, ERK and p38 phosphorylation, Nov. 23, 2013, FEBS Letters.
Jones, A., et al., *Increased expression of multifunctional serine protease, HTRA1, in retinal pigment epithelium induces polypoidal choroidal vasculopathy in mice*, PNAS, vol. 108, No. 35, 14578-14583 Aug. 30, 2011.
Zhang, K., et al., *Ophthalmic drug discovery: novel targets and mechanisms for retinal diseases and glaucoma*, Nature Reviews Drug Discovery, vol. 11, 541-559 Jul. 2012.
Zhang, et al., *High Temperature Requirement Factor A1 (HTRA1) Gene Regulates Angiogenesis through Transforming Growth Factor-_ Family Member Growth Differentiation Factor 6\**, Journal of Biological Chemistry, vol. 287, No. 2, Jan. 6, 2012.
Zeiss, C. J., *Reveiw Paper: Animals as Models of Age-Related Macular Degeneration: An Imperfect Measure of the Truth*, Veterinary Pathology, vol. 47(3) 396-314 2010.
Ziess, C.J., *Translational models of ocular disease*, Veterinary Ophthalmology 16, Supplement 1, 15-33, 2013.
Zahn, et al., *Preclinical Evaluation of the Novel Small-Molecule Integrin α5β1 Inhibitor JSM6427 in Monkey and Rabbit Models of Chloroidal Neovascularization*, Arch Opthalmol, vol. 127, No. 10 1329-1335, Oct. 2009.
Yuan et al., *Genetic Association with Response to Intravitreal Ranizumab for Neovascular Age-Related Macular Degeneration in the Han Chinese Population*, Ophthalmologica, DOI: 10.1159/000355068, received Jun. 19, 2013, accepted Jul. 19, 2013, published online Sep. 25, 2013.
Yuan et al., *Quantitative Proteomics: Comparison of the Macular Bruch Membrane/Choroid Complex from Age-related Macular Degeneration and Normal Eyes\**, Molecular & Cellular Proteomics 9.6, American Society for Biochemistry and Molecular Biology, Inc., 1031-1046, 2010.
Yu, Y., et al., *Prospective Assessment of Genetic Effects on Progression to Different Stages of Age-Related Macular Degeneration Using Multistate Markov Models*, Investigative Ophthalmology & Visual Science, vol. 53, No. 3, 1548-1556, Mar. 2012.
Yu, W., et al., *Cumulative association between age-related macular degeneration and less studied genetic variants in PLEKHA1/ARMS2/HTRA1: a meta and gene-cluster analysis*, Mol Biol Rep, DOI 10.1007/s11033-013-2656-6, Received Feb. 13, 2013, Accepted Aug. 22, 2013.

Yu, T., et al., *Inhibition of cell proliferation, migration and apoptosis in blue-light illuminated human retinal pigment epithelium cells by down-regulation of HtrA1*, Int. J. Ophthalmol, vol. 10, No. 4 DOI:10.18240/ijo.2017.04.04, Apr. 18, 2017.
Yee, et al., *Fibrotic-like changes in degenerate human intervertebral discs revealed by quantitative proteomic analysis*, Osteoarthritis and Cartilage, DOI: 10.1016/j.joca.2015.09.020, Received Mar. 10, 2015, Revised Date Aug. 13, 2015, Accepted Sep. 19, 2015.
Lapaire et al., *Miccroarray Screening for Novel Preeclampsia Biomarker Candidates*, Published online: Mar. 29, 2012, DOI: 10.1159/000337325, Department of Obstetrics and Gynecology University Hospital Basel.
Hou et al., *Lipopolysaccharide Increases the Incidence of Collagen-Induced Arthritis in Mice Through Induction of Protease HTRA-1 Expression*, col. 65. No. 11, Nov. 2013, pp. 2835-2846, DOI: 10.1002/art.38124, American College of Rhuematology.
Hasan et al., *Protein-base Open Sandwich Immuno-PCR for Sensitive Detection of Small Biomarkers*, Analytical Sciences, Sep. 10, 2013, vol. 29.
Kasai et al., *Soluble heparin-binding EGF-like growth factor (HB-EGF) detected by newly developed immuno-PCR method is a clear-cut serological biomarkers for ovarian cancer*, Published Oct. 30, 2012, Am J Trans Res 2012;4(4):415-421, www.ajtr.org/ISSN:1943-8141/JTR1208002.
Nakano et al., *Development of a Highly Sensitive Immuno-PCR Assay for the Measurement of a-Galactosidase A Protein Levels in Serum and Plasma*, www.plosone.org, Nov. 2013, vol. 8, Issue 11.
Zhang et al., *Real-time immuno-polymerase chain reaction in a 384-well format: Detection of vascular endothelial growth factor and epidermal growth factor-like domain 7*, Analytical Biochemistry, Available online Jul. 8, 2014, journal homepage: www.elsevier.com/locate/yabio.
Nagai 2015-Supplemental Figure 1. Chemical structures of GW766994X and GW782415X.
Nagai 2015-Supplemental Table S1. Plasma concentration of drug in cynomoglus monkeys at day 28 following oral administration of GW782415X.
Nagai 2015-Supplemental Table S2. Calculations of drug release from in-dwelling implants.
JR5558 Mice Data Jax Labs Sep. 18, 2015.
Allensworth et al., Investigation of the differential potentials of TLR agonists to elicit uveitis in mice, Accepted Sep. 4, 2011. DOI: 10.1189/jlb.0511249, *Journal of Leukocyte Biology*, vol. 90, Dec. 2011.
Bosmann et al., *Fingerprinting of the TLR4-induced acute inflammatory Response*, Published in final edited form as: Exp Mol Pathol. Dec. 2012; 93(3): 319-323. doi:10.1016/j.yexmp.2012.08.006., NIH Public Access.
Couturier et al., Anti-vascular endothelial growth factor acts on retinal microglia/macrophage activation in a rat model of ocular inflammation, http://www.molvis.org/molvis/v20/908, Published Jun. 23, 2014.
Byron, et al., Defining the extracellular matrix using proteomics, International Journal of Experimental Pathology, Accepted for publication: Nov. 16, 2012, Int. J. Exp. Path. (2013), 94, 75-92.
Decaris, et al., *Proteomic Analysis of Altered Extracellular Matrix Turnover in Bleomycin-induced Pulmonary Fibrosis*, Apr. 2014, The American Society for Biochemistry and Molecular Biology, Inc.
Karwatowski et al., *Preparation of Bruch's membrane and analysis of the age-related changes in the structural collagens*, British Journal of Ophthalmology 1995; 79: 944-952, Accepted for publication Jun. 15, 1995.
Naba et al., The Matrisome: *In Silico* Definition and *In Vivo* Characterization by Proteomics of Normal and Tumor Extracellular Matrices*, *Molecular & Cellular Proteomics* 11.4, Apr. 2012, DOI 10.1074/mcp.M111.014647.
Naba et al., 2012, Supplemental Data, Extended Experimental Procedures.
Nita et al., Age-related macular degeneration and changes in the extracellular matrix, Medical Science Monitor, Published: Jun. 18, 2014, Review Articles, DOI: 10.12659/MSM.889887, http://www.medscimonit.com.download/index/idArt/889887.

(56) References Cited

OTHER PUBLICATIONS

Sivaprasad et al., Serum Elastin-Derived Peptides in Age-Related Macular Degeneration, Investigative Ophthalmology & Visual Science, Sep. 2005, vol. 46, No. 9.
Cheruvu et al., Effect of Eye Pigmentation on Transscleral, Drug Delivery: *IOVS*, Jan. 2008, vol. 49, No. 1.
Hong et al., Current Understanding of the Binding Sites, Capacity, Affinity, and Biological Significance of Metals in Melanin, *J Phys Chem B*. Jul. 19, 2007, 111(28): 7938-7947. doi:10.1021/jp071439h, NIH Public Access Author Manuscript.
Kadam et al., Sclera-Choroid-RPE Transport of Eight_—Blockers in Human, Bovine, Porcine, Rabbit, and Rat Models, Retina, *IOVS*, Jul. 2011, vol. 52, No. 8.
Schmidt et al., Melanin Concentration in Normal Human Retinal Pigment Epithelium, *Regional Variation and Age-Related Reduction*, Investigative Ophthalmology & Visual Science/ Jul. 1986.
Su et al, Catechol Polymers for pH-Responsive, Targeted Drug Delivery to Cancer Cells, Jul. 13, 2011, JACS, dx.doi.org/10.1021/ja203077x | J. Am. Chem. Soc. 2011, 133, 11850-11853.
Pescina et al., Ex vivo models to evaluate the role of ocular melanin in trans-scleral drug delivery, European Journal of Pharmaceutical Sciences, Available online Mar. 30, 2012.
Enzmann et al., Behavioral and anatomical abnormalities in a sodium iodate-induced model of retinal pigment epithelium degeneration, Experimental Eye Research, Available online Sep. 19, 2005, Research 82 (2006) 441-448, http://www.elsevier.com/locate/yexer.
Franco, et al., Decreased Visual Function after Patchy Loss of Retinal Pigment Epithelium Induced by Low-Dose Sodium Iodate, *IOVS*, Aug. 2009, vol. 50, No. 8.
Jiang et al., Effects of hydralazine on NaIO3-induced rat retinal pigment epithelium degeneration, Int J Ophthalmol col. 2. No. 2, Jun. 18, ww.ijo.com.
Machalinska et al., Endogenous regeneration of damaged retinal pigment epithelium following low dose sodium iodate administration: An insight into the role of glial cells in retinal repair, Experimental Eye Research 112 (2013) 68e78, Available online Apr. 25, 2013, Experimental Eye Research.
Machalinska et al., Sodium Iodate Selectivity Injuries the Posterior Pole of the Retina in a Dose-Dependent Manner: Morphological and Electrophysiological Study, DOI 10.1007/s110644-010-0248-6, Accepted: Aug. 10, 2010/ Published online: Aug. 20, 2010.
Qin et al., Resveratrol protects RPE cells from sodium iodate by modulating PPARα and PPARδ, Available online Dec. 3, 2013, Experimental Eye Research 118 (2014) 100e108.
Wang et al., Direct Effect of Sodium Iodate on Neurosensory Retina, 2014;55:1941-1952. DOI:10.1167/iovs.13-13075, IOVS j Mar. 2014 j vol. 55 j No. 3 j 1942.
Zhang et al., A modified histoimmunochemistry-assisted method for *in situ* RPE evaluation, [Frontiers in Bioscience E4, 1571-1581, Jan. 1, 2012].
Alkhatib et al., Glycobiology and Extracellular Matrices: Chondroadherin fragmentation mediated by the protease HTRA1 distinguishes human intervertebral disc degeneration from normal aging, *published online May 14, 2013. Biol. Chem.*, 10.1074/jbc.M112.443010.
C, Ramachandran—Cartilage protection, Oct. 11, 2012.
Holt et al., Osteoarthritis-like changes in the heterozygous sedc mouse associated with the HtrA1eDdr2eMmp-13 degradative pathway: a new model of osteoarthritis, Accepted Nov. 21, 2011, http://dx.doi.org/10.1016/j.joca.2011.11.008, Osteoarthritis and Cartilage 20 (2012) 430e439.
Jefferies et al., Genome-Wide DNA Methylation Study Identifies Significant Epigenomic Changes in Osteoarthritic Cartilage, Arthritis & Rheumatology vol. 66, No. 10, Oct. 2014, pp. 2804-2815, DOI 10.1002/art.38762.
Martel-Pelletier et al., Future therapeutics for osteoarthritis, Bone, doi:10.1016/j.bone.2011.10.008, Available inline Oct. 17, 2011, Bone 51 (2012) 297-311.
Matthews, Disease Modification Promising Targets and Impediments to Success, http://dx.doi.org/10.1016/j.rdc.2012.10.006, 2013 Elsevier Inc., http://rheumatic.theclinics.com/.
P Mitchell—Expression of HtrA1 in Chondrocytes Lilly poster.
Polur et al., Role of HTRA1, a serine protease, in the progression of articular cartilage degeneration, Published in final edited form as: *Histol Histopathol.* May 2010; 25(5): 599-608, NIH Public Access Author Manuscript.
Reginster et al., Efficacy and safety of strontium ranelate in the treatment of knee osteoarthritis: results of a double-blind, randomised placebo-controlled trial, Published Online First Nov. 1, 2012, Ann Rheum Dis 2013;72:179-186. doi:10.1136/annrheumdis-2012-202231, downloaded from ard.bmj.com on Mar. 20, 2013— Published by group.bmj.com.
Tiaden et al., The Emerging Roles of HTRA1 in Musculoskeletal Disease, Mini-Review, Accepted for publication Feb. 1, 2013. http://ajp.amipathol.org/, AJPA1265 proof, Mar. 8, 2013.
Tsuchiya et al., Expression of mouse HtrA1 serine protease in normal bone and cartilage and its upregulation in joint cartilage damaged by experimental arthritis, Bone 37 (2005) 323-336, Received Dec. 2, 2004; accepted Mar. 21, 2005, Available online Jul. 1, 2005, doi:10.1016/j.bone.2005.03.015.
Urano et al., Association of HTRA1 promoter polymorphism with spinal disc degeneration in Japanese women, J Bone Miner Metab (2010) 28:220-226 DOI 10.1007/s00774-009-0124-0, Published online: Oct. 2, 2009.
Wu et al., Comparative Proteomic Characterization of Articular Cartilage Tissue From Normal Donors and Patients With Osteoarthritis, Arthritis & Rheumatism, vol. 56, No. 11, Nov. 2007, pp. 3675-3684 DOI 10.1002/art.22876, 2007.
Zack et al., Identification of Fibronectin Neoepitopes Present in Human Osteoarthritic Cartilage, Arthritis & Rheumatism, vol. 54, No. 9, Sep. 2006, pp. 2912-2922 DOI 10.1002/art.22045, 2006, American College of Rheumatology.
Overall Lab Protocols Nov. 2016, Bench Protocol to Perform TAILS v5.
Kleifield et al., Identifying and quantifying proteolytic events and the natural N terminome by terminal amine isotopic labeling of substrates, vol. 6, No. 10, 2011, nature protocols.
Chien et t al, Identification of Tubulins as Substrates of Serine Protease HtrA1 by Mixture-Based Oriented Peptide Library Screening, Article, Journal of Cellular Biochemistry 107:253-263 (2009), Published online Mar. 19, 2009 in Wiley InterScience (www.interscience.wiley.com).
Doucet et al., Broad Cleavage Identification of Multiple Proteolytic Cleavage Site Sequences in Complex High Molecular Weight Proteins Using a Quantitative Proteomics as a Complement to Edman Sequencing*, *Molecular & Cellular Proteomics 10.5,* DOI 10.1074/mcp.M110.003533.
Doucet et al., Amino-Terminal Oriented Mass Spectrometry of Substrates (ATOMS): N-Terminal Sequencing of Proteins and Proteolytic Cleavage Sites by Quantitative Mass Spectrometry, Chapter 13, ISSN 0076-6879, DOI: 10.1016/B978-0-12-385950-1.0013-4, Methods in Enzymology, vol. 501, 2011 Elsevier Inc.
Tholen et al., Deletion of Cysteine Cathespins B or L Yields Differential Impacts on Murine Skin Proteome and Degradome*, *Molecular & Cellular Proteomics* 12.3, DOI 10.1074/mcp.M112.017962, 2013 by The American Society for Biochemistry and Molecular Biology, Inc.
Gibbs et al, Isolation and Culture of Primary Mouse Retinal Pigmented Epithelial Cells, *Retinal Degenerations: Mechanisms and Experimental Therapy* Edited by LaVail et al., Kluwer Academic/Plenum Publishers, 2003.
Austins et al., Biologically Active Fibronectin Fragments Stimulate Release of MCP-1 and Catabolic Cytokines from Murine Retinal Pigment Epithelium, Investigative Ophthalmology & Visual Science, Jun. 2009, vol. 50, No. 6, *IOVS*, Jun. 2009, vol. 50, No. 6.
Hadfield, et al., Genomics, Proteomics, and Bioinformatics: HtrA1 Inhibits Mineral Deposition by Osteoblasts: Requirement for the Protease and PDZ Domains, doi: 10.1074/jbc.M709299200, *published online Dec. 22, 2007, J. Biol. Chem.* 2008, 283:5928-5938, The Journal of Biological Chemistry vol. 283, No. 9, pp. 5928-5938, Feb. 29, 2008.

(56) References Cited

OTHER PUBLICATIONS

Jiang et al., Overexpression of HTRA1 Leads to Down-Regualtion of Fibronectin and Functional Changes in RF/6A Cells and HUVECs, Oct. 2012, vol. 7, Issue 10, www.plosone.org.

Kim et al., Protective Effect of Clusterin from Oxidative Stess—Induced Apoptosis in Human Retinal Pigment Epithelial Cells, Retinal. Cell Biology, IOVS, Jan. 2010, vol. 51, No. 1.

Ng et al., Interactive Expressions of HtrA1 and VEGF in Human Vitreous Humors and Fetal RPE Cells, Investigative Ophthalmology & Visual Science, May 2011, vol. 52, No. 6, IOVS, Biochemistry and Molecular Biology.

Ortwerth et al., A comparison of the inhibition of porcine pancreatic elastase and human neutrophil elastase by alpha-crystallin, accepted on May 12, 1994, Current Eye Research.

Ruel, et al., Fibronectin Fragments and the Cleaving Enzyme ADAM-8 in the Degenerative Human Intervertebral Disc, SPINE vol. 39, No. 16, pp. 1274-1279, 2014, Lippincott Williams & Wilkins.

Sharma et al., The Binding and Inhibition of Trypsin by α-Crystallin, Mar. 27, 987, Mason Institute of Ophthalmology and Department of Biochemistry.

Taiden et al., A detrimental role fot human high temperature requirement serine protease A1 (HTRA1) in the pathogenesis of intervertebral disc (IVD) degeneration *, doi: 10.1074/jbc.M112.341032, J. Biol. Chem. published online May 3, 2012.

Vidmar et al., Latent fibronectin-degrading serine proteinase activity in N-terminal heparin-binding domain of human plasma fibronectin, Eur. J. Biochem. 201, 71-77 (1991), (Received Feb. 7/Jun. 4, 1991).

Voorter et al., Elastase inhibition by the C-terminal domains of α-crystallin and small heat-shock protein, (Received Apr. 20, 1993) (Revised manuscript received Aug. 17, 1993), Biochemica et Biophysica Acta, 1204 (1994) 43-47 (Received Apr. 20, 199 (Revised manuscript received Aug. 17, 1993).

Zack et al., Identification of Fibronectin Neoepitopes Present in Human Osteoarthritic Cartilage, Arthritis & Rheumatism vol. 54, No. 9, Sep. 2006, pp. 2912-2922.

Graham, et al., Serine Protease HTRA1 Antagonizes Transforming Growth Factor-β Signaling by Cleaving Its Receptor and Loss of HTRA1 In Vivo Enhances Bone Formation, Sep. 2013, vol. 8, Issue 9, www.plosone.org.

Launay et al., HtrA1-dependent proteolysis of TGF-β controls both neuronal maturation and developmental survival, Cell Death and Differentiation (2008) 15, 1408-1416; doi:10.1038/cdd.2008.82; published online Jun. 13, 2008.

Usher et al., Myeloid mineralocorticoid receptor controls macrophage polarization and cardiovascular hypertrophy and remodeling in mice, The Journal of Clinical Investigation http://www.jci.org vol. 120 No. 9 Sep. 2010, http://dx.doi.org/10.1172/JCI41080.

Zhang et al., High Temperature Requirement Factor A1 (HTRA1) Gene Regulates Angiogenesis through Transforming Growth Factor—_Family Member Growth Differentiation Factor 6*, vol. 287•No. 2•Jan. 6, 2012, Journal of Biological Chemistry.

Zhang, et al., High Temperature Requirement Factor A1 (HTRA1) Gene Regulates Angiogenesis through Transforming Growth Factor—_Family Member Growth DifferentiationnFactor 6*, Journal of Biological Chemistry, vol. 287, No. 2, Jan. 6, 2012.

Zeiss, C. J., Review Paper: Animals as Models of Age-Related Macular Degeneration: An Imperfect Measure of the Truth, Veterinary Pathology, vol. 47(3) 396-314 2010.

Zeiss, C. J., Translational models of ocular disease, Veterinary Opthalmology 16, Supplement 1, 15-33, 2013.

Yuan, et al., Genetic Association with Response to Intravitreal Ranibizumab for Neovascular Age-Related Macular Degeneration in the Han Chinese Population, Opthalmologica, DOI: 10.1159/000355068, received Jun. 19, 2013, published online Sep. 25, 2013.

Yuan, et al., Quanitative Proteomics: Comparison of the Macular Bruch Membrane/Choroid Complex from Age-related Macular Degeneration and Normal Eyes*, Molecular & Cellular Proteomics 9.6, American Society for Biochemistry and Molecular Biology, Inc., 1031-1046, 2010.

Yee, et al., Fibrotic-like changes in degenerate human intervertebral dics revealed by quantitative proteonic analysis, Osteoarthritis and Cartilage, DOI: 10.1016/j.joca.2015.09.020, Received Mar. 10, 2015, Revised Date Aug. 13, 2015, Accepted Sep. 19, 2015.

Yang, J., et al., Validation of genome-wide association study (GWAS)-identified disease risk alleles with patient-specific stem cell lines, Human Molecule Genetics, doi:10.1093/hmg/ddu053, 1-11, 2014.

Yan et al., Genome-wide analysis of disease progression in age-related macular degeneration, Human Molecular Genetics, vol. 0, No, 0, DOI: 10.1093/hmg/ddy002, 2018.

Yamashiro, K., et al., Factors Associated With the Response of Age-Related Macular Degeneration to Inravitreal Ranibizumab Treatment, doi:10.1016/j.ajo.2012.01.010, 125-136. Jul. 2012.

Yamashiro, K., et al., A prospective multicenter study on genome wide associations to ranibizumab treatment outcome for age-related macular degeneration, Scientific Reporter, DOI:10.1038/s41598-017-09632-0, 7:9196, Received May 1, 2017, Accepted Jul. 27, 2017, Published online Aug. 23, 2017.

Xie, et al., Suppression and Regression of Choroidal Neovascularization in Mice by a Novel CCR2 Antagonist, INCB3344, PLoS One, www.plosone.org, vol. 6, Issue 12, e28933 Dec. 2011.

Yang, Z., et al., Genetic and Functional Dissection of HTRA1 and LOC387715 in Age-Related Macular Degeneration, PLoS Genetics, vol. 6, Issue 2, e1000836, Feb. 2010.

Yang, Z., et al., A Variant of the HTRA1 Gene Increases Susceptibility to age-Related Macular Degeneration, Science, 314, DOI: 10.1126/science.1133811, 992-993 Nov. 2006.

Yang, et al., A Variant of the HTRA1 Gene Increases Susceptibility to age-Related Macular Degeneration, www.sciencemag.org/cgi/content/full/1133811/DCI, Oct. 19, 2006.

Austin et al., Biologically Active Fibronectin Fragments Stimulate Release of MCP-1 and Catabolic Cytokines from Murine Retinal Pigment Epithelium, Investigative Ophthalmology & Visual Science, Jun. 2009, vol. 50, No. 6.

Cai et al., A frameshift mutation in HTRA1 expands CARASIL syndrome and peripheral small arterial disease to the Chinese population, DOI 10.1007/s10072-015-2121-5, Received Dec. 13, 2014/ Accepted: Feb. 20, 2015.

Cheng et al., Genetic and Functional Dissection of ARMS2 in Age-Related Macular Degeneration and Polypoidal Choroidal Vasculopathy, PLOS, www.plosone.org, Published Jan. 9, 2013, vol. 8, Issue 1.

Didangelos et al., Extracellular Matrix Composition and Remodeling in Human Abdominal Aortic Aneurysms: A Proteomics Approach*, Molecular & Cellular Proteomics 10.8, 2011 by The American Society for Biochemistry and Molecular Biology, WOI: 10.1074/mcp.MI11.008128.

DeWan et al., HTRA1 Promoter Polymorphism in Wet Age-Related Macular Degeneration, www.sciencemag.org vol. 314 Nov. 10, 2006.

Gu et al., Assessing Susceptibility to Age-Related Macular Degeneration with Proteomic and Genomic Biomarkers*, Molecular & Cellular Proteomics 8.6, http://www.mcponline.org, Published, MCP Papers in Press, Feb. 6, 2009, DOI 10.1074/mcp.M800453-MCP200.

Herzlich et al., Peroxisome Proliferator-Activated Receptor and Age-Related Macular Degeneration, Received Oct. 2, 2007; Accepted Nov. 14, 2007, Hindawi Publishing Corporation, PPAR Research, vol. 2008, Article ID 389507, 11 pages, doi:10.1155/2008/389507.

Katschke, et al., Inhibiting Alternative Pathway Complement Activation by Targeting the Exosite of Factor D Supplementary material, 2012.

Karlstetter et al., Retinal microglia: Just bystander or target for therapy?, Progress in Retinal and Eye Research 45 (2015)30-57, http://dx.doi.org/10.1016/j.preteyeres.2014.11.004, http://www.elsevier.com/locate/prer, Available online Dec. 2, 2014.

Kumar et al., Angiographic Features of Transgenic Mice With Increased Expression of Human Serline Protease HTRA1 in Retinal Pigment Epithelium, IOVS, Jun. 2014, vol. 55, No. 6, Downloaded From: http://iovs.arvojournals.org/pdfaccess.ashx?url=/data/Journals/IOVS/932990/ on Aug. 10, 2015.

Liu et al., Subretinal injection of amyloid-β peptide accelerates RPE cell sensescence and retinal degeneration, Received Jul. 2, 2014;

(56) References Cited

OTHER PUBLICATIONS

Accepted Oct. 30, 2014 International Journal of Molecular Medicine 35: 169-176, 2015, DOI: 10.3892/ijmm.2014.1993.

Lin et al., *Association of Single-Nucleotide Polymorphisms in Age-Related Macular Degeneration With Pseudodrusen Secondary Analysis of Data From the Comparison of AMD Treatments Trials*, JAMA Ophthalmology, Brief Report, Downloaded From: by a University of British Columbia User on Jul. 13, 2018, Jun. 2018, vol. 136, No. 6.

Smailhodzic, et al., Risk Alleles in CFH and ARMS2 Are Independently Associated with Systemic Complement Activation in Age-related Macualr Degeneration, *Ophthalmology 2012*; 119;339-346, vol. 119, No. 2, Feb. 2012.

\* cited by examiner

CARBOCYCLIC PROLINAMIDE DERIVATIVES

CROSS-REFERENCE TO RELATED APPLICATIONS

This application is a continuation of U.S. application Ser. No. 16/312,211, filed Dec. 20, 2018, which is the National Stage entry under 35 U.S.C. § 371 of International Application No. PCT/US2017/037766 filed on Jun. 15, 2017, published on Dec. 28, 2017 under Publication Number WO 2017/222914, which claims the benefit of U.S. Provisional Application No. 62/352,959 filed Jun. 21, 2016, the entireties of which are herein incorporated by reference.

BACKGROUND OF THE INVENTION

Field of the Invention

The present disclosure is directed to novel carbocyclic prolinamide derivatives, pharmaceutical compositions containing such novel compounds, as well as methods for preventing and treating age-related macular degeneration (AMD) and related diseases of the eye.

Description of the Related Art

Age-related macular degeneration (AMID) is the leading cause of severe loss of vision in people over the age of 60. Age is the major risk factor for the onset of AMD: the likelihood of developing AMD triples after age 55. Many factors, however, contribute to the likelihood that an individual will develop AMD.

As summarized in WO2001/006262, "environmental" conditions may modulate the rate at which an individual develops AMD or the severity of the disease. Light exposure has been proposed as a possible risk factor, since AMD most severely affects the macula, where light exposure is high. (See Young, R. W. (1988), Surv. Ophthalmol. 32(4), 252-69; Taylor, H. R. et al., (1990), Trans. Amer. Ophthalmol. Soc. 88, 163-73; Schalch W. (1992), Exs, 62, 280-98). The amount of time spent outdoors is associated with increased risk of choroidal neovascularization in men, and wearing hats and/or sunglasses is associated with a decreased incidence of soft drusen (Cruickshanks, K. et al., (1993), Arch. Ophthalmol., 111, 514-518). Accidental exposure to microwave irradiation has also been shown to be associated with the development of numerous drusen (Lim, J. et al., (1993), Retina. 13, 230-3). Cataract removal and light iris pigmentation has also been reported as a risk factor in some studies (Sandberg, M. et al., (1994), Invest. Ophthalmol. Vis. Sci. 35(6), 2734-40). This suggests that: 1) eyes prone to cataracts may be more likely to develop AMD; 2) the surgical stress of cataract removal may result in increased risk of AMD, due to inflammation or other surgically-induced factors; or 3) cataracts prevent excessive light exposure from falling on the macula, and are in some way prophylactic for AMD. While it is possible that dark iris pigmentation may protect the macula from light damage, it is difficult to distinguish between iris pigmentation alone and other, co-segregating genetic factors which may be actual risk factors.

Smoking, gender (women are at greater risk), obesity, and repeated exposure to UV radiation also increase the risk of AMD.

More recently, a number of HTRA1 single nucleotide polymorphs (SNP) have been found to be associated with an increased risk of AMD. See, for example, WO2008/013893A2, WO2008/067040A2 and WO2008/094370A2. These SNP's include rs11200638, rs10490924, rs3750848, rs3793917 and rs932275. In particular, the risk allele rs11200638, was found to be associated with increased HTRA1 mRNA and protein expression, and HTRA1 is present in drusen in patients with AMD. (See Dewan et al., (2006), Science 314:989-992; Yang et al., (2006), Science 314:992-993). These disclosures provide evidence that HTRA1 is an important factor in AMD and the progression thereof.

In broad terms, there are two forms of AMD: dry AMD and wet AMD. The dry form is the more common, and accounts for 85-90% of the patients with AMD, and does not typically result in blindness. In dry AMD, (also called non-neovascular AMD or non-exudative AMD) drusen appear in the macula of the eye, the cells in the macula die, and vision becomes blurry. Dry AMD can progress in three stages: 1) early, 2) intermediate, and 3) advanced dry AMD. Dry AMD can also progress into wet AMD during any of these stages.

Wet AMD (also called neovascular or exudative AMD), is associated with pathologic posterior segment neovascularization. The posterior segment neovascularization (PSNV) found in exudative AMD is characterized as pathologic choroidal neovascularization. Leakage from abnormal blood vessels forming in this process damages the macula and impairs vision, eventually leading to blindness.

The end stage of AMD is characterized by a complete degeneration of the neurosensory retina and of the underlying retinal pigment epithelium in the macular area. Advanced stages of AMD can be subdivided into geographic atrophy (GA) and exudative AMD. Geographic atrophy is characterized by progressive atrophy of the retinal pigment epithelium (RPE). While GA is typically considered less severe than the exudative AMD because its onset is less sudden, to date no treatment has been effective at halting or slowing its progression.

Currently, treatment of dry AMD includes the administration of antioxidant vitamins and/or zinc. For example, one study at the National Eye Institute assessed a composition comprising vitamin C, β-carotene, zinc oxide and cupric oxide.

Treatment of wet AMD is also wanting. Available drug therapies include: bevacizumab (Avastin®, Genentech, Calif.), ranibizumab (Lucentis®, Genentech, Calif.), pegaptanib (Macugen® Bausch & Lomb, NJ), and aflibercept (Eylea®, Regeneron, N.Y.). In each instance, the medication is injected into the eye. Injections may be repeated every four to eight weeks to maintain the beneficial effect of the medication. Those with a positive result may partially recover vision as the blood vessels shrink and the fluid under the retina is absorbed, allowing retinal cells to regain some function.

Pharmacologic therapy for the treatment of macular edema associated with AMD is lacking. The current standard of care is laser photocoagulation, which is used to stabilize or resolve macular edema and retard the progression to later stage disease. Laser photocoagulation may reduce retinal ischemia by destroying healthy tissue and thereby decreasing metabolic demand; it also may modulate the expression and production of various cytokine and trophic factors. There are no current treatments for preventing loss of vision after dry AMD enters an advanced stage. There are also no definitive methods for preventing progression of dry AMD to an advanced stage, other than by avoiding and/or reducing risk factors and using dietary supplements, which cannot guarantee or be relied on to stop AMD progression. Thus, there is a need for therapeutics that can treat dry AMD and prevent progression of dry to wet AMD.

The compound (1-{3-cyclohexyl-2-[naphthalene-2-carbonyl)-amino]-propionyl}-pyrrolidine-2-carboxylic acid [5-(3-cyclohexyl-ureido)-1-dihydroxyboranyl-pentyl]-amide is disclosed in Grau, S. et. al., (2006), J. Biol. Chem., 281(10): 6124-6129 and in WO2012/078540 (identified therein as NVP-LB976) as an inhibitor of HTRA1.

In addition to AMID, a number of publications have described a potential role of HTRA1 and disease, including retinal angiomatous proliferation (Ohkuma, Y., et al., (2014) Clin. Ophthalmol., 8:143-8), foveomacular proliferation (Chowers, I., et al., (2015) Progress in Retinal and Eye Research, 47:64-85), musculoskeletal diseases, including osteoarthritis, spinal disk degeneration rheumatoid arthritis, muscular dystrophy and osteoporosis (Taiden, A. N. and Richards, P. J. (2013) Am. J. Pathology, 182(5):1482-8), and treatment of autologous chondrocytes prior to intraarticular implantation (Ollitrault, D. et al., (2015) Tissue Engineering, Part C Methods, 21(2):133-47). An HTRA1 inhibitor thus may demonstrate a therapeutic benefit in these additional indications.

SUMMARY OF THE INVENTION

The present disclosure is directed to novel carbocyclic prolinamide derivatives of Formula I, and pharmaceutically acceptable salts, solvates, solvates of the salts and prodrugs thereof, pharmaceutical compositions comprising a compound of Formula I, as well as methods for preventing and treating age-related macular degeneration (AMD) and related diseases of the eye comprising administering to a patient in need thereof a therapeutically effective amount of a compound of Formula I. These diseases include, but are not limited to, dry-AMD, wet-AMD, geographic atrophy, diabetic retinopathy, retinopathy of prematurity, polypoidal choroidal vasculopathy, and degeneration of retinal or photoreceptor cells. The compounds of the present disclosure are inhibitors of HTRA1, and are useful in the prevention and treatment of diseases mediated (in whole or in part) by HTRA1. The compounds of the present disclosure are also useful for inhibiting HTRA1 protease activity in an eye or locus of an arthritis or related condition.

DETAILED DESCRIPTION OF THE PREFERRED EMBODIMENT

In a first embodiment the present disclosure provides compounds of Formula

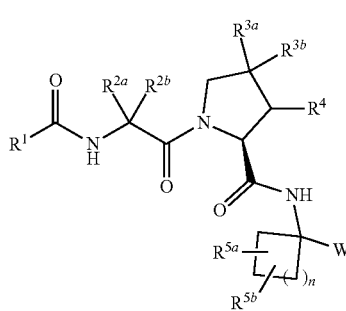

(I)

or a pharmaceutically acceptable salt, solvate, solvate of the salt or prodrug thereof wherein:

W is selected from the group consisting of: —B(OH)$_2$ and —C(O)C(O)NR$^7$R$^8$;

R$^1$ is selected from the group consisting of:
(a) —(CH$_2$)$_{0-6}$-aryl, and
(b) —(CH$_2$)$_{0-6}$-heteroaryl, wherein the aryl and heteroaryl of choices (a) and (b) are each optionally substituted with 1 to 3 substituents independently selected from the group consisting of:
(i) -halogen,
(ii) —CN,
(iii) —C$_{1-6}$alkyl,
(iv) —C$_{0-6}$alkyl-R$^6$,
(v) —C$_{2-6}$alkenyl,
(vi) —C$_{2-6}$alkynyl,
(vii) —C(O)R$^7$,
(viii) —CO$_2$R$^7$,
(ix) —CONR$^7$R$^8$,
(x) —OH,
(xi) —O—C$_{1-6}$alkyl,
(xii) —O—C$_{0-6}$alkyl-R$^6$,
(xiii) —SH,
(xiv) —S(O)$_p$—C$_{1-6}$alkyl,
(xv) —S(O)$_p$—C$_{0-6}$alkyl-R$^6$,
(xvi) —S(O)$_2$NR$^7$R$^8$,
(xvii) —NO$_2$,
(xviii) —NR$^7$R$^8$,
(xix) —NHC(O)R$^7$,
(xx) —NHC(O)OR$^7$,
(xxi) —NHC(O)NR$^7$R$^8$,
(xxii) —NHSO$_2$C$_{1-6}$alkyl, and
(xxiii) —NHSO$_2$C$_{0-6}$alkyl-R$^6$,
(xxiv) —CONH(CH$_2$)$_{2-4}$—[O(CH$_2$)$_{2-4}$]$_m$OC$_{1-4}$alkyl, wherein each of the alkyl group of choices (iii), (iv), (xi), (xii), (xiv), (xv), (xxii), (xxiii) and (xxiv) is optionally substituted with 1 to 5 substituents independently selected from -halogen, -haloC$_{1-4}$alkyl, —COR$^7$, —CO$_2$R$^7$, —CONR$^7$R$^8$, —NR$^7$R$^8$, —OH, —O—C$_{1-4}$alkyl, —SH and —S—C$_{1-4}$alkyl; R$^{2a}$ and R$^{2b}$ are independently selected from the group consisting of:
(a) —H,
(b) —C$_{1-8}$alkyl, and
(c) —C$_{0-6}$alkyl-R$^6$, wherein each of the alkyl group of choices (b) and (c) is optionally substituted with 1 to 5 substituents independently selected from:
(i) -halogen,
(ii) -haloC$_{1-4}$alkyl,
(iii) —NR$^7$R$^8$,
(iv) —OH,
(v) —O—C$_{1-4}$alkyl,
(vi) —SH,
(vii) —S—C$_{1-4}$alkyl,
(viii) —NR$^7$SO$_2$C$_{1-4}$alkyl,
(ix) —NR$^7$C(O)R$^7$, and
(x) —NR$^7$C(O)OR$^7$, with the proviso that R$^{2a}$ and R$^{2b}$ are not both H;
R$^{3a}$ is H, and R$^{3b}$ is selected from the group consisting of:
(a) —H,
(b) —OH,
(c) -heteroaryl,
(d) —O-heteroaryl,
(e) -heterocycle,
(f) -aryl, and
(g) —O-aryl;

wherein each of the heteroaryl of choices (c) and (d), the heterocycle of choice (e) and the aryl of choices (f) and (g)

is optionally substituted with 1 to 3 groups independently selected from the group consisting of:
  (i) -halogen,
  (ii) —OH,
  (iii) —CR$^{10}$R$^{11}$R$^{12}$,
  (iv) —(CH$_2$)$_{0-3}$—NHSO$_2$—C$_{1-4}$alkyl,
  (v) —(CH$_2$)$_{0-3}$—NHSO$_2$—C$_{3-12}$cycloalkyl,
  (vi) —(CH$_2$)$_{0-3}$—SO$_2$—C$_{1-4}$alkyl,
  (vii) —(CH$_2$)$_{0-3}$—C(O)O—R$^7$, and
  (viii) —CN; and
wherein the heterocycle of choice (e) is additionally optionally substituted with 1 to 2 oxo groups; or
R$^{3a}$ and R$^{3b}$ together represent oxo;
R$^4$ is selected from a group consisting of
  (a) —H,
  (b) —C$_{1-4}$alkyl,
  (c) -haloC$_{1-4}$alkyl,
  (d) —O—C$_{1-4}$alkyl, and
  (e) —O-haloC$_{1-4}$alkyl;
R$^{5a}$ and R$^{5b}$ are independently selected from a group consisting of
  (a) —H,
  (b) —C$_{1-4}$alkyl,
  (c) -halogen,
  (d) —OH,
  (e) —O—C$_{1-4}$alkyl,
  (f) —SH, and
  (g) —S—C$_{1-4}$alkyl, or
R$_{5a}$, R$^{5b}$ and the atom(s) to which they are attached together form a 3- to 6-membered cycloalkyl or a 4- to 6-membered heterocycle having a heteroatom selected from O and S(O)$_p$, and wherein said cycloalkyl or heterocycle is optionally substituted with 1 to 2 groups independently selected from halogen, —C$_{1-4}$alkyl, —OH, —O—C$_{1-4}$alkyl, —SH, —S—C$_{1-4}$alkyl;
R$^6$ is selected from the group consisting of:
  (a) —C$_{3-12}$cycloalkyl,
  (b) -aryl,
  (c) -heteroaryl, and
  (d) -heterocyclyl,
wherein each of choices (a) to (d) is optionally substituted with 1 to 3 substituents independently selected from the group consisting of:
  (i) —C$_{1-4}$alkyl,
  (ii) -halogen,
  (iii) —NR$^7$R$^8$,
  (iv) —OH,
  (v) —O—C$_{1-4}$alkyl,
  (vi) —SH, and
  (vii) —S—C$_{1-4}$alkyl;
wherein each of the alkyl group of choices (i), (v) and (vii) is optionally substituted with 1 to 5 substituents independently selected from -halogen, -haloC$_{1-4}$alkyl, —OH, —O—C$_{1-4}$alkyl, —SH and —S—C$_{1-4}$alkyl;
each R$^7$ and each R$^8$ are independently selected from the group consisting of:
  (a) —H,
  (b) —C$_{1-6}$alkyl,
  (c) —C$_{0-6}$alkyl-C$_{3-12}$cycloalkyl,
  (d) —C$_{0-6}$alkyl-heterocyclyl,
  (e) —C$_{0-6}$alkyl-heteroaryl,
  (f) —C$_{0-6}$alkyl-aryl,
  (g) —C$_{2-6}$alkenyl, and
  (h) —C$_{2-6}$alkynyl,
wherein the alkyl group of choices (b)-(f), the alkenyl group of choice (g) and the alkynyl group of (h) are each optionally substituted with 1 to 3 groups independently selected from:
  (i) -halogen,
  (ii) —C(O)C$_{1-4}$alkyl,
  (iii) —C(O)NH$_2$,
  (iv) —C(O)NH(C$_{1-4}$alkyl),
  (v) —C(O)N(C$_{1-4}$alkyl)(C$_{1-4}$alkyl)
  (vi) —OH,
  (vii) —OC$_{1-4}$alkyl,
  (viii) —SH,
  (ix) —S(O)$_p$C$_{1-4}$alkyl,
  (x) —NH$_2$,
  (xi) —NH(C$_{1-4}$alkyl), and
  (xii) —N(C$_{1-4}$alkyl)(C$_{1-4}$alkyl); or
R$^7$, R$^8$ and the nitrogen atom to which they are attached together form a 3- to 7-membered monocyclic or 6- to 11-membered bicyclic heterocycle optionally having an additional heteroatom selected from O, S(O)$_p$, and NR$^9$, and wherein said heterocycle is optionally substituted with 1 to 2 halogen;
R$^9$ is selected from the group consisting of:
  (a) —H,
  (b) —C$_{1-4}$alkyl,
  (c) —C(O)—C$_{1-4}$alkyl,
  (d) —C(O)NH$_2$,
  (e) —C(O)—NH(C$_{1-4}$alkyl),
  (f) —C(O)—N(C$_{1-4}$alkyl)$_2$,
  (g) —C(O)O—C$_{1-4}$alkyl; and
  (h) —C(O)O—C$_{1-4}$alkyl-aryl;
R$^{10}$, R$^{11}$, and R$^{12}$ are independently selected from the group consisting of: H, halogen, —OH and —C$_{1-6}$alkyl; or
R$^{10}$, R$^{11}$ and the atom to which they are attached together form a C$_{3-12}$cycloalkyl or a heterocyclyl group;
n is 0, 1, 2, 3, 4 or 5;
m is 1-25; and
p is 0, 1 or 2.

In a second embodiment, for a compound of the first embodiment, R$^1$ is selected from the group consisting of:
  (a) -aryl, and
  (b) -heteroaryl,
wherein aryl and heteroaryl of choices (a) and (b) are each optionally substituted with 1 to 3 substituents independently selected from the group consisting of:
  (i) -halogen,
  (ii) —CN,
  (iii) —C$_{1-6}$alkyl,
  (iv) —C$_{0-6}$alkyl-R$^6$,
  (v) —C$_{2-6}$alkenyl,
  (vi) —C$_{2-6}$alkynyl,
  (vii) —C(O)R$^7$,
  (viii) —CO$_2$R$^7$,
  (ix) —CONR$^7$R$^8$,
  (x) —OH,
  (xi) —O—C$_{1-6}$alkyl,
  (xii) —O—C$_{0-6}$alkyl-R$^6$,
  (xiii) —SH,
  (xiv) —S(O)$_p$—C$_{1-6}$alkyl,
  (xv) —S(O)$_p$—C$_{0-6}$alkyl-R$^6$,
  (xvi) —S(O)$_2$NR$^7$R$^8$,
  (xvii) —NO$_2$,
  (xviii) —NR$^7$R$^8$,
  (xix) —NHC(O)R$^7$,
  (xx) —NHC(O)OR$^7$,
  (xxi) —NHC(O)NR$^7$R$^8$,
  (xxii) —NHSO$_2$C$_{1-6}$alkyl, and
  (xxiii) —NHSO$_2$C$_{0-6}$alkyl-R$^6$,
  (xxiv) —CONHC$_{2-4}$alkyl-(OC$_{2-4}$alkylene)$_m$OC$_{1-4}$alkyl,
wherein each of the alkyl group of choices (iii), (iv), (xi), (xii), (xiv), (xv), (xxii) and (xxiii) is optionally substituted with 1 to 5 substituents independently selected from -halogen, -haloC$_{1-4}$alkyl, —COR$^7$, —CO$_2$R$^7$, —CONR$^7$R$^8$, —NR$^7$R$^8$, —OH, —O—C$_{1-4}$alkyl, —SH and —S—C$_{1-4}$alkyl.

In a third embodiment, for a compound of any of the preceding embodiments, R$^1$ is selected from the group consisting of:
(a) -aryl, and
(b) -heteroaryl,
wherein the aryl and heteroaryl of choices (a) and (b) are each optionally substituted with 1 to 3 substituents independently selected from the group consisting of:
(i) -halogen,
(ii) —CN,
(iii) —C(O)R$^7$,
(iv) —CONR$^7$R$^8$,
(v) —OH,
(vi) —O—C$_{1-6}$alkyl,
(vii) —S(O)$_p$—C$_{1-6}$alkyl,
(viii) —S(O)$_p$—C$_{0-6}$alkyl-R$^6$,
(ix) —S(O)$_2$NR$^7$R$^8$,
(x) —NHSO$_2$C$_{1-6}$alkyl, and
wherein each of the alkyl group of choices (vi), (vii), (viii) and (x) is optionally substituted with 1 to 5 substituents independently selected from -halogen, -haloC$_{1-4}$alkyl, —COR$^7$, —CO$_2$R$^7$, —CONR$^7$R$^8$, —NR$^7$R$^8$, —OH, —O—C$_{1-4}$alkyl, —SH and —S—C$_{1-4}$alkyl.

In a fourth embodiment, for a compound of any of the preceding embodiments, R$^{2a}$ is H, and R$^{2b}$ is —C$_{1-6}$alkyl-R$^6$, where the alkyl portion of R$^{2b}$ is optionally substituted with 1 to 5 substituents independently selected from:
(i) -halogen,
(ii) -haloC$_{1-4}$alkyl,
(iii) —NR$^7$R$^8$,
(iv) —OH,
(v) —O—C$_{1-4}$alkyl,
(vi) —SH, and
(vii) —S—C$_{1-4}$alkyl.

In a fifth embodiment, for a compound of any of the preceding embodiments,
R$^{2a}$ is H, and R$^{2b}$ is —C$_{1-6}$alkyl-R$^6$, and
R$^6$ is —C$_{3-12}$cycloalkyl, optionally substituted with 1 to 3 substituents independently selected from the group consisting of:
(i) —C$_{1-4}$alkyl,
(ii) -halogen,
(iii) —NR$^7$R$^8$,
(iv) —OH,
(v) —O—C$_{1-4}$alkyl,
(vi) —SH, and
(vii) —S—C$_{1-4}$alkyl.

In a sixth embodiment, for a compound of any of the preceding embodiments, R$^{3a}$ is H, and R$^{3b}$ is selected from the group consisting of:
(a)

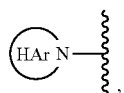

and
(b)

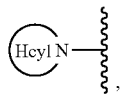

wherein HAr is heteroaryl and Hcyl is heterocycle, wherein HAr and Hcyl are optionally substituted with 1 to 3 groups independently selected from the group consisting of:
(i) -halogen,
(ii) —OH,
(iii) —CR$^{10}$R$^{11}$R$^{12}$,
(iv) —(CH$_2$)$_{0-3}$—NHSO$_2$—C$_{1-4}$alkyl,
(v) —(CH$_2$)$_{0-3}$—NHSO$_2$—C$_{3-12}$cycloalkyl,
(vi) —(CH$_2$)$_{0-3}$—SO$_2$—C$_{1-4}$alkyl,
(vii) —(CH$_2$)$_{0-3}$—C(O)O—R$^7$, and
(viii) —CN; and
wherein Hcyl is additionally optionally substituted with 1 to 2 oxo groups.

In a seventh embodiment, for a compound of the first embodiment is a compound having formula Ia:

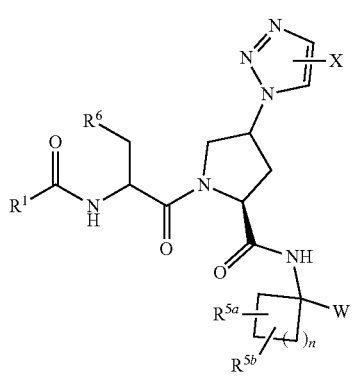

Ia or a pharmaceutically acceptable salt, solvate, solvate of the salt or prodrug thereof wherein:
W is —C(O)C(O)NR$^7$R$^8$,
X is selected from the group consisting of:
(a) —CR$^{10}$R$^{11}$R$^{12}$,
(b) —(CH$_2$)$_{0-3}$—SO$_2$—C$_{1-4}$alkyl,
(c) —(CH$_2$)$_{0-3}$—C(O)O—R$^7$,
(d) —(CH$_2$)$_{0-3}$—NHSO$_2$—C$_{1-4}$alkyl, and
(e) —(CH$_2$)$_{0-3}$—NHSO$_2$—C$_{3-12}$cycloalkyl;
R$^1$ is selected from the group consisting of:
(a) -aryl and
(b) -heteroaryl,
wherein the aryl and heteroaryl of choices (a) and (b) are each optionally substituted with 1 to 3 substituents independently selected from the group consisting of:
(i) -halogen,
(ii) —CN,
(iii) —C(O)R$^7$,
(iv) —CONR$^7$R$^8$,
(v) —OH,
(vi) —O—C$_{1-6}$alkyl,
(vii) —S(O)$_p$—C$_{1-6}$alkyl,
(viii) —S(O)$_p$—C$_{0-6}$alkyl-R$^6$,
(ix) —S(O)$_2$NR$^7$R$^8$, and
(x) —NHSO$_2$C$_{1-6}$alkyl, and
wherein each of the alkyl group of choices (vi), (vii), (viii) and (x) is optionally substituted with 1 to 5 substituents independently selected from -halogen, -haloC$_{1-4}$alkyl, —COR$^7$, —CO$_2$R$^7$, —CONR$^7$R$^8$, —NR$^7$R$^8$, —OH, —O—C$_{1-4}$alkyl, —SH and —S—C$_{1-4}$alkyl;

R$^{5a}$ and R$^{5b}$ are independently selected from a group consisting of
- (a) —H,
- (b) —C$_{1-4}$alkyl,
- (c) -halogen,
- (d) —OH,
- (e) —O—C$_{1-4}$alkyl,
- (f) —SH, and
- (g) —S—C$_{1-4}$alkyl, or R$^{5a}$, R$^{5b}$ and the atom(s) to which they are attached together form a 3- to 6-membered cycloalkyl or a 4- to 6-membered heterocycle having a heteroatom selected from O and S(O)$_p$, and wherein said cycloalkyl or heterocycle is optionally substituted with 1 to 2 groups independently selected from halogen, —C$_{1-4}$alkyl, —OH, —O—C$_{1-4}$alkyl, —SH, —S—C$_{1-4}$alkyl;

R$^6$ is —C$_{3-12}$cycloalkyl, optionally substituted with 1 to 3 substituents independently selected from the group consisting of:
- (i) —C$_{1-4}$alkyl,
- (ii) -halogen,
- (iii) —NR$^7$R$^8$,
- (iv) —OH,
- (v) —O—C$_{1-4}$alkyl,
- (vi) —SH, and
- (vii) —S—C$_{1-4}$alkyl;

each R$^7$ and each R$^8$ are independently selected from the group consisting of:
- (a) —H,
- (b) —C$_{1-6}$alkyl,
- (c) —C$_{0-6}$alkyl-C$_{3-12}$cycloalkyl, and
- (d) —C$_{0-6}$alkyl-heterocyclyl, wherein the alkyl group of choices (b)-(d) are each optionally substituted with 1 to 3 groups independently selected from:
- (i) -halogen,
- (ii) —C(O)C$_{1-4}$alkyl,
- (iii) —C(O)NH$_2$,
- (iv) —C(O)NH(C$_{1-4}$alkyl),
- (v) —C(O)N(C$_{1-4}$alkyl)(C$_{1-4}$alkyl)
- (vi) —S(O)$_p$C$_{1-4}$alkyl, or R$^7$, R$^8$ and the nitrogen atom to which they are attached together form a 3- to 7-membered monocyclic or 6- to 11-membered bicyclic heterocycle optionally having an additional heteroatom selected from O, S(O)$_p$, and NR$^9$, and wherein said heterocycle is optionally substituted with 1 to 2 halogen;

R$^9$ is selected from the group consisting of:
- (a) —H,
- (b) —C$_{1-4}$alkyl,
- (c) —C(O)—C$_{1-4}$alkyl,
- (d) —C(O)NH$_2$,
- (e) —C(O)—NH(C$_{1-4}$alkyl),
- (f) —C(O)—N(C$_{1-4}$alkyl)$_2$,
- (g) —C(O)O—C$_{1-4}$alkyl; and
- (h) —C(O)O—C$_{1-4}$alkyl-aryl;

R$^{10}$, R$^{11}$, and R$^{12}$ are independently selected from the group consisting of: H, halogen, —OH and —C$_{1-6}$ alkyl; or R$^{10}$, R$^1$ and the atom to which they are attached together form a C$_{3-12}$cycloalkyl or a heterocyclyl group;

n is 0, 1, 2, 3, 4 or 5;
m is 1-25; and
p is 0, 1 or 2.

In an eighth embodiment, for a compound of any of the preceding embodiments having the formula Ia, W is —C(O)C(O)NH$_2$.

In a ninth embodiment, for a compound of any of the preceding embodiments having the formula Ia,
X is —CR$^{10}$R$^{11}$R$^{12}$,
R$^{10}$ and R$^{11}$ are each —C$_{1-4}$alkyl, or
R$^{10}$, R$^{11}$ and the atom to which they are attached together form a C$_{3-6}$cycloalkyl or a 4- to 6-membered heterocycle, and
R$^{12}$ is —OH.

In a tenth embodiment, for a compound of any of the preceding embodiments having the formula Ia,
R$^{5a}$ and R$^{5b}$ are independently selected from a group consisting of
- (a) —H, and
- (b) —C$_{1-4}$alkyl, or R$^{5a}$, R$^{5b}$ and the atom(s) to which they are attached together form a 3- to 6-membered cycloalkyl.

In an eleventh embodiment, the compound of the first embodiment is a compound selected from the group consisting of:

(2S,4S)-1-((R)-2-(2-naphthamido)-3-cyclohexylpropanoyl)-N-(1-(2-amino-2-oxoacetyl)-cyclobutyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclopropyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclopentyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclohexyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cycloheptyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclooctyl)-4-(5-(2-hydroxypropan-2-yl)-1H-1,2,3-triazol-1-yl)pyrrolidine-2-carboxamide;

(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)boronic acid;

(2S,4R)-1-((R)-2-(2-naphthamido)-3-cyclohexylpropanoyl)-N-(1-(2-amino-2-oxoacetyl)-cyclohexyl)-4-(piperidin-1-yl)pyrrolidine-2-carboxamide;

(2S,3R,4R)-1-((R)-2-(2-naphthamido)-3-cyclohexylpropanoyl)-N-(1-(2-amino-2-oxoacetyl)cyclohexyl)-4-(5-(2-hydroxypropan-2-yl)-1H-1,2,3-triazol-1-yl)-3-methoxypyrrolidine-2-carboxamide;

(2S,4S)-1-((R)-2-(2-naphthamido)-3-cyclohexylpropanoyl)-N-(1-(2-amino-2-oxoacetyl)-cyclohexyl)-4-(5-((methylsulfonyl)methyl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclohexyl)-4-(5-(3-hydroxyoxetan-3-yl)-1H-1,2,3-triazol-1-yl)pyrrolidine-2-carboxamide;

2-(1-((3S,5S)-1-((R)-2-(2-naphthamido)-3-cyclohexylpropanoyl)-5-((1-(2-amino-2-oxoacetyl)cyclohexyl)carbamoyl)pyrrolidin-3-yl)-1H-1,2,3-triazol-5-yl)acetic acid;

(2S,4S)-1-((R)-2-(2-naphthamido)-3-cyclohexylpropanoyl)-N-(1-(2-amino-2-oxoacetyl)-cyclohexyl)-4-(5-(cyclopropanesulfonamidomethyl)-1H-1,2,3-triazol-1-yl)pyrrolidine-2-carboxamide;

(2S,4S)-N-(1-(2-amino-2-oxoacetyl)cyclohexyl)-1-((R)-3-cyclohexyl-2-(4-(methylsulfonyl)benzamido)propanoyl)-4-(5-((methylsulfonyl)methyl)-1H-1,2,3-triazol-1-yl)pyrrolidine-2-carboxamide;

(2S,4S)-N-(1-(2-amino-2-oxoacetyl)cyclohexyl)-1-((R)-3-cyclohexyl-2-(4-(methylsulfonyl)benzamido)propanoyl)-4-(5-(3-hydroxyoxetan-3-yl)-1H-1,2,3-triazol-1-yl)pyrrolidine-2-carboxamide;

(2S,4S)-N-(1-(2-amino-2-oxoacetyl)cyclohexyl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclohexyl)-4-(4-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclohexyl)-4-(4-(3-hydroxyoxetan-3-yl)-1H-1,2,3-triazol-1-yl)pyrrolidine-2-carboxamide;

(2S,4S)-N-(1-(2-amino-2-oxoacetyl)cyclohexyl)-1-((R)-3-cyclohexyl-2-(4-(methylsulfonyl)benzamido)propanoyl)-4-(4-(2-hydroxypropan-2-yl)-1H-1,2,3-triazol-1-yl)pyrrolidine-2-carboxamide;

(2S,4S)-N-(1-(2-amino-2-oxoacetyl)cyclohexyl)-1-((R)-3-cyclohexyl-2-(4-(methylsulfonyl)benzamido)propanoyl)-4-(4-(3-hydroxyoxetan-3-yl)-1H-1,2,3-triazol-1-yl)pyrrolidine-2-carboxamide;

(2S,4S)-N-(1-(2-amino-2-oxoacetyl)cyclohexyl)-1-((R)-3-cyclohexyl-2-(4-(methylsulfonyl)benzamido)propanoyl)-4-(4-((methylsulfonyl)methyl)-1H-1,2,3-triazol-1-yl)pyrrolidine-2-carboxamide;

N-((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)imidazo[1,2-a]pyridine-6-carboxamide;

(2S,4S)-N-(1-(2-amino-2-oxoacetyl)cyclohexyl)-1-((R)-2-(4-cyanobenzamido)-3-cyclohexylpropanoyl)-4-(5-(2-hydroxypropan-2-yl)-1H-1,2,3-triazol-1-yl)pyrrolidine-2-carboxamide;

N-((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)quinoline-3-carboxamide;

N-((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-1H-indazole-7-carboxamide;

(2S,4S)-N-(1-(2-amino-2-oxoacetyl)cyclohexyl)-1-((R)-3-cyclohexyl-2-(4-((2-methoxyethyl)sulfonyl)benzamido)propanoyl)-4-(5-(2-hydroxypropan-2-yl)-1H-1,2,3-triazol-1-yl)pyrrolidine-2-carboxamide;

(2S,4S)-N-(1-(2-amino-2-oxoacetyl)cyclohexyl)-1-((R)-3-cyclohexyl-2-(4-((difluoromethyl)sulfonyl)benzamido)propanoyl)-4-(5-(2-hydroxypropan-2-yl)-1H-1,2,3-triazol-1-yl)pyrrolidine-2-carboxamide;

(2S,4S)-N-(1-(2-amino-2-oxoacetyl)cyclohexyl)-1-((R)-2-(4-((2-amino-2-oxoethyl)-sulfonyl)benzamido)-3-cyclohexylpropanoyl)-4-(5-(2-hydroxypropan-2-yl)-1H-1,2,3-triazol-1-yl)pyrrolidine-2-carboxamide;

$N^2$-((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-$N^6$-(2,5,8,11-tetraoxatridecan-13-yl)naphthalene-2,6-dicarboxamide;

$N^2$-((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-$N^6$-(tetracosaoxatriheptacontan-73-yl)naphthalene-2,6-dicarboxamide;

(2S,4S)-1-((R)-2-(2-naphthamido)-3-cyclohexylpropanoyl)-N-(1-(2-((2-amino-2-oxoethyl)amino)-2-oxoacetyl)cyclohexyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-4-(5-(2-hydroxypropan-2-yl)-1H-1,2,3-triazol-1-yl)-N-(1-(2-(((methylsulfonyl)methyl)amino)-2-oxoacetyl)-cyclohexyl)pyrrolidine-2-carboxamide;

(2S,4S)-1-((R)-2-(2-naphthamido)-3-cyclohexylpropanoyl)-4-(5-(2-hydroxypropan-2-yl)-1H-1,2,3-triazol-1-yl)-N-(1-(2-oxo-2-((2,2,2-trifluoroethyl)amino)acetyl)cyclohexyl)-pyrrolidine-2-carboxamide;

(2S,4S)-1-((R)-2-(2-naphthamido)-3-cyclohexylpropanoyl)-4-(5-(2-hydroxypropan-2-yl)-1H-1,2,3-triazol-1-yl)-N-(1-(2-(oxetan-3-ylamino)-2-oxoacetyl)cyclohexyl)pyrrolidine-2-carboxamide;

(2S,4S)-1-(2-(2-naphthamido)-3-cyclohexyl-2-methylpropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide;

(2S,4S)-1-(2-(2-naphthamido)-3-(spiro[3.3]heptan-2-yl)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide;

(2S,4S)-1-(2-(2-naphthamido)-3-(bicyclo[2.2.1]heptan-1-yl)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide;

(2S,4S)-N-(1-(2-amino-2-oxoacetyl)cyclohexyl)-1-(3-cyclohexyl-2-methyl-2-(4-(methylsulfonyl)benzamido)propanoyl)-4-(5-(2-hydroxypropan-2-yl)-1H-1,2,3-triazol-1-yl)pyrrolidine-2-carboxamide;

(2S,4S)-N-(1-(2-amino-2-oxoacetyl)cyclohexyl)-4-(5-(2-hydroxypropan-2-yl)-1H-1,2,3-triazol-1-yl)-1-(2-(4-(methylsulfonyl)benzamido)-3-(spiro[3.3]heptan-2-yl)propanoyl)pyrrolidine-2-carboxamide;

(2S,4S)-N-(1-(2-amino-2-oxoacetyl)cyclohexyl)-1-(3-(bicyclo[2.2.1]heptan-1-yl)-2-(4-(methylsulfonyl)benzamido)propanoyl)-4-(5-(2-hydroxypropan-2-yl)-1H-1,2,3-triazol-1-yl)pyrrolidine-2-carboxamide;

benzyl ((R)-2-(2-naphthamido)-3-((2S,4S)-2-((1-(2-amino-2-oxoacetyl)cyclohexyl)-carbamoyl)-4-(5-(2-hydroxypropan-2-yl)-1H-1,2,3-triazol-1-yl)pyrrolidin-1-yl)-3-oxopropyl)carbamate;

(2S,4S)-1-((R)-2-(2-naphthamido)-3-(methylsulfonamido)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide;

(2S,4S)-1-((R)-2-(2-naphthamido)-3-acetamidopropanoyl)-N-(1-(2-amino-2-oxoacetyl)-cyclohexyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(2-(2-amino-2-oxoacetyl)-spiro[3.3]heptan-2-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-4,4-dimethylcyclohexyl)-4-(5-(2-hydroxypropan-2-yl)-1H-1,2,3-triazol-1-yl)pyrrolidine-2-carboxamide;

(2S,4S)-N-(2-(2-amino-2-oxoacetyl)spiro[3.3]heptan-2-yl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide;
(2S,4S)-N-(1-(2-amino-2-oxoacetyl)-4,4-dimethylcyclohexyl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide; and
(2S,4S)-1-((R)-2-(2-naphthamido)-3-cyclohexylpropanoyl)-N-(6-(2-amino-2-oxoacetyl)-spiro[2.5]octan-6-yl)-4-(5-(2-hydroxypropan-2-yl)-1H-1,2,3-triazol-1-yl)pyrrolidine-2-carboxamide; or
a pharmaceutically acceptable salt, solvate, salt of the solvate, or prodrug thereof.

In a twelfth embodiment, the present disclosure provides a pharmaceutical composition comprising a compound of any of the first through the eleventh embodiments, and a pharmaceutically acceptable carrier.

In a thirteenth embodiment, the present disclosure provides a method of preventing, or treating a disease of the eye selected from dry-AMD, wet-AMD, geographic atrophy, diabetic retinopathy, retinopathy of prematurity, polypoidal choroidal vasculopathy, and degeneration of retinal or photoreceptor cells, comprising: administering to a subject in need thereof a therapeutically effective amount of a compound according to any of the first through the eleventh embodiments, or a pharmaceutically acceptable salt, solvate, solvate of the salt or prodrug thereof, or the pharmaceutical composition of the twelfth embodiment.

In a fourteenth embodiment, for the method of the thirteenth embodiment, the method of prevention is selected from delaying the onset of disease and reducing the risk of developing a disease of the eye, wherein the disease of the eye is selected from dry-AMD, wet-AMID, and geographic atrophy, diabetic retinopathy, retinopathy of prematurity, polypoidal choroidal vasculopathy, and degeneration of retinal or photoreceptor cells.

In a fifteenth embodiment, for the method of the thirteenth embodiment the method of treating a disease of the eye is selected from controlling, alleviating, and slowing the progression of, wherein the disease is selected from dry-AMD, wet-AMD, and geographic atrophy, diabetic retinopathy, retinopathy of prematurity, polypoidal choroidal vasculopathy, and degeneration of retinal or photoreceptor cells.

In a sixteenth embodiment, for the method of any one of the thirteenth through the fifteenth embodiments, the disease is geographic atrophy.

In a seventeenth embodiment, the present disclosure provides a method of inhibiting HtrAl protease activity in an eye, comprising administering to a subject in need thereof a therapeutically effective amount of any one of the compounds of the first through the eleventh embodiments or a pharmaceutically acceptable salt, solvate, solvate of the salt or prodrug thereof, or a pharmaceutical composition of the twelfth embodiment.

Any of the features of an embodiment is applicable to all embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other embodiments. Any embodiment of a method can comprise another embodiment of a compound, and any embodiment of a compound can be configured to perform a method of another embodiment.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

The term "patient" includes mammals such as mice, rats, cows, sheep, pigs, rabbits, goats, horses, monkeys, dogs, cats, and humans.

The term "halo" or "halogen" refers to any radical of fluorine, chlorine, bromine or iodine.

The term "alkyl" refers to a saturated hydrocarbon chain that may be a straight chain or branched chain, containing the indicated number of carbon atoms. For example, $C_{1-6}$alkyl indicates that the group may have from 1 to 6 (inclusive) carbon atoms in it. In some embodiments, an alkyl is a $C_{1-6}$alkyl which represents a straight-chain or branched saturated hydrocarbon radical having 1 to 6 carbon atoms. Examples of alkyl include without limitation methyl, ethyl, n-propyl, isopropyl, n-butyl, isobutyl, sec-butyl, and tert-butyl. The notation "$C_{0-n}$alkyl" indicates the absence of an alkyl moiety, or the presence of an alkyl moiety having 1 to n carbon atoms. Thus, for example, the term "$C_{0-6}$alkyl-$R^5$" indicates that the $R^5$ group is attached directly to the parent moiety, or that there is an intervening alkyl group of 1 to 6 carbon atoms between $R^5$ and the parent moiety; such an intervening group may be, for example, —$CH_2$—, —$CH_2CH_2$—, —$CH(CH_3)$— and —$C(CH_3)_2$—.

The term "haloalkyl" refers to an alkyl group in which at least one hydrogen atom is replaced by halo. In some embodiments, more than one hydrogen atom (e.g., 2, 3, 4, 5, 6, 7, 8, 9, 10, 11, 12, 13, or 14) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl).

As referred to herein, the term "alkoxy" refers to a group of formula —O-(alkyl). Alkoxy can be, for example, methoxy, ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S-(alkyl). The terms "haloalkoxy" and "thiohaloalkoxy" refer to —O-(haloalkyl) and —S-(haloalkyl), respectively. The term "sulfhydryl" refers to —SH.

The term "aralkyl" refers to an alkyl moiety in which an alkyl hydrogen atom is replaced by an aryl group. One of the carbons of the alkyl moiety serves as the point of attachment of the aralkyl group to another moiety. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Alkenyl groups can include, e.g., vinyl, allyl, 1-butenyl, and 2-hexenyl. In some embodiments, an alkenyl is a $C_{2-6}$alkenyl.

The term "alkynyl" refers to a straight or branched hydrocarbon chain containing the indicated number of carbon atoms and having one or more carbon-carbon triple bonds. Alkynyl groups can include, e.g., ethynyl, propargyl, 1-butynyl, and 2-hexynyl. In some embodiments, an alkynyl is a $C_{2-6}$alkynyl.

The term "heterocycle", "heterocyclyl" or "heterocyclic" as used herein except where noted, represents a stable 4-, 5-, 6- or 7-membered monocyclic- or a stable 6-, 7-, 8-, 9-, 10-, 11-, or 12-membered bicyclic heterocyclic ring system which comprises at least one non-aromatic (i.e. saturated or partially unsaturated) ring which consists of carbon atoms and from one to four, preferably up to three, heteroatoms selected from the group consisting of N, O and S, wherein the nitrogen and sulfur atoms may optionally be oxidized as N-oxide, sulfoxide or sulfone, and wherein the nitrogen atom may optionally be quaternized. A heterocycle can be bonded via a ring carbon atom or, if available, via a ring nitrogen atom. Bicyclic heterocyclic ring systems may be fused, bridged, or spiro bicyclic heterocyclic ring system(s). In some embodiments, heterocyclyl is monocyclic having 4 to 7, preferably 4 to 6, ring atoms, of which 1 or 2 are heteroatoms independently selected from the group consisting of N, O and S. In some embodiments, a heterocyclyl group is bicyclic, and in which case, the second ring may be an aromatic or a non-aromatic ring which consists of carbon atoms and from one to four, preferably up to three, heteroatoms independently selected from the group consisting of N, O and S, or the second ring may be a benzene ring, or a "cycloalkyl", or a "cycloalkenyl", as defined herein. Examples of such heterocyclic groups include, but are not limited to azetidine, chroman, dihydrofuran, dihydropyran, dioxane, dioxolane, hexahydroazepine, imidazolidine, imidazoline, indoline, isochroman, isoindoline, isothiazoline, isothiazolidine, isoxazoline, isoxazolidine, morpholine, oxazoline, oxazolidine, oxetane, piperazine, piperidine, dihydropyridine, tetrahydropyridine, dihydropyridazine, pyran, pyrazolidine, pyrazoline, pyrrolidine, pyrroline, tetrahydrofuran, tetrahydropyran, thiamorpholine, tetrahydrothiophene, thiazoline, thiazolidine, thiomorpholine, thietane, thiolane, sulfolane, 1,3-dioxolane, 1,3-oxazolidine, 1,3-thiazolidine, tetrahydrothiopyran, tetrahydrotriazine, 1,3-dioxane, 1,4-dioxane, hexahydrotriazine, tetrahydro-oxazine, tetrahydropyrimidine, perhydroazepine, perhydro-1,4-diazepine, perhydro-1,4-oxazepine, 7-azabicyclo[2.2.1]heptane, 3-azabicyclo[3.2.0]heptane, 7-azabicyclo[4.1.0]heptane, 2,5-diazabicyclo[2.2.1]heptane, 2-oxa-5-azabicyclo[2.2.1]heptane, tropane, 2-oxa-6-azaspiro[3.3]heptane, dihydrobenzofuran, diydrobenzimidazolyl, dihydrobenzoxazole, and dihydrobenzothiazolyl, and N-oxides or sulfones or sulfoxides thereof.

The term "cycloalkyl" refers to a fully saturated monocyclic, bicyclic, tricyclic or other polycyclic hydrocarbon group having the indicated number of ring carbon atoms. Multicyclic cycloalkyl may be fused, bridged or spiro ring systems. Cycloalkyl groups include, but are not limited to, cyclopropyl, cyclobutyl, cyclopentyl, cyclohexyl, cycloheptyl, cyclooctyl, norbornyl (bicyclo[2.2.1]heptyl), decalinyl, adamantyl, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, bicyclo[2.2.2]octyl, and spiro[3.5]nonyl. In some embodiments, cycloalkyl is a monocyclic $C_{3-8}$cycloalkyl. In other embodiments, cycloalkyl is a bi- or tricyclic $C_{5-12}$cycloalkyl. In other embodiments, cycloalkyl is a spirocyclic $C_{5-12}$cycloalkyl.

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Cycloalkenyl moieties can include, e.g., cyclopentenyl, cyclohexenyl, cyclohexadienyl, or norbornenyl. In some embodiments, a cycloalkenyl is a $C_{4-10}$cycloalkenyl. In other embodiments, a cycloalkenyl is a $C_{4-6}$cycloalkenyl. In some embodiments, a cycloalkenyl is monocyclic. In some embodiments, a cycloalkenyl is bicyclic.

The term "aryl" as used herein, is intended to mean any stable monocyclic or bicyclic carbon ring of up to 6 members in each ring, wherein at least one ring is aromatic. Examples of aryl include phenyl, naphthyl, tetrahydronaphthyl, indanyl, or biphenyl.

The term "heteroaryl", as used herein except where noted, represents a stable 5-, 6- or 7-membered monocyclic- or stable 9- or 10-membered fused bicyclic ring system which comprises at least one aromatic ring, which consists of carbon atoms and from one to four, preferably up to three, heteroatoms selected from the group consisting of N, O and S wherein the nitrogen and sulfur heteroatoms may optionally be oxidized, and the nitrogen heteroatom may optionally be quaternized. In the case of a "heteroaryl" which is a bicyclic group, the second ring need not be aromatic and need not comprise a heteroatom. Accordingly, bicyclic "heteroaryl" includes, for example, a stable 5- or 6-membered monocyclic aromatic ring consisting of carbon atoms and from one to four, preferably up to three, heteroatoms, as defined immediately above, fused to a benzene ring, or a second monocyclic "heteroaryl", or a "heterocyclyl", a "cycloalkyl", or a "cycloalkenyl", as defined above. Examples of heteroaryl groups include, but are not limited to, benzimidazole, benzopyrazole, benzisothiazole, benzisoxazole, benzofuran, isobenzofuran, benzothiazole, benzothiophene, benzotriazole, benzoxazole, cinnoline, furan, furazan, imidazole, indazole, indole, indolizine, isoquinoline, isothiazole, isoxazole, naphthyridine, oxadiazole, oxazole, phthalazine, pteridine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, benzimidazole, benzothiadiazole, isoindole, pyrrolopyridines, imidazopyridines such as imidazo[1,2-a]pyridine, pyrazolopyridine, pyrrolopyrimidine and N-oxides thereof.

The term "acyl", as used herein, refers to those groups derived from an organic acid by removal of the hydroxy portion of the acid. Accordingly, acyl is meant to include, for example, acetyl, propionyl, butyryl, decanoyl, pivaloyl, benzoyl and the like.

As used herein, the term "fused" refers to a connectivity between two rings in which two adjacent atoms sharing at least one bond (saturated or unsaturated) are common to the rings. For example, in the following structure, rings A and B are fused

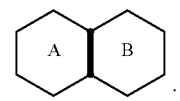

Examples of fused ring structures include, but are not limited to, decahydronaphthalene, 1H-indole, quinolone, chromane, bicyclo[2.1.0]pentane and 6,7,8,9-tetrahydro-5H-benzo[7]annulene.

As used herein, the term "bridged" refers to a connectivity wherein three or more atoms are shared between two rings. The following structures

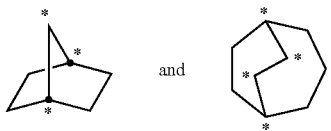 [SMILES: C1C[C@H]2CC[C@H]1C2 ; C1CC2CCC(C1)CC2]

are examples of "bridged" rings because the indicated atoms are shared between at least two rings. Examples of bridged ring structures include, but are not limited to, bicyclo[1.1.1]pentane, 2-oxabicyclo[1.1.1]pentane, 5-azabicyclo[2.1.1]hexane, 6-azabicyclo[3.1.1]heptane, adamantane and norbornane.

As used herein, the term "spiro" refers to a connectivity between two rings wherein the rings have only one atom in common. For example, in the structure

rings C and D are joined by a spiro connection. Examples of spiro connected ring structures include, but are not limited to, spiro[3.3]heptane, 2,6-diazaspiro[3.3]heptane, 2-oxa-6-azaspiro[3.3]heptane, spiro[4.5]decane and 2,6-dioxaspiro[3.3]heptane.

For each of the organic radicals defined above, any atom can be optionally substituted, e.g., by one or more substituents.

Unless otherwise specified, when a bond is depicted in a chemical structure with ᴧᴧᴧ, it is meant that the bond is located at a stereocenter in which the structure may have either the S or R configuration as understood under the Cahn-Ingold System for naming enantiomers. For example, the ᴧᴧᴧ notation can indicate that the bond at the given position can be either a ⫽ or a ⫽. The presence of the ᴧᴧᴧ does not limit the exemplified compound to only a racemate, but can include all possible stereoconfigurations.

The term "treating", "treat", or "treatment" refers generally to controlling, alleviating, ameliorating, slowing the progress of or eliminating a named condition once the condition has been established. In addition to its customary meaning, the term "preventing", "prevent", or "prevention" also refers to delaying the onset of, or reducing the risk of developing a named condition or of a process that can lead to the condition, or the recurrence of symptoms of a condition.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

Compound Forms and Salts

The compounds of this disclosure may contain one or more asymmetric centers and thus occur as racemates and racemic mixtures, enantiomerically enriched mixtures, single enantiomers, individual diastereomers and diastereomeric mixtures. The compounds of the present disclosure may, either by nature of asymmetric centers or by restricted rotation, be present in the form of isomers (e.g., enantiomers, diastereomers).

It will also be appreciated that when two or more asymmetric centers are present in the compounds of the disclosure, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the disclosure.

All isomers, whether separated, pure, partially pure, or in racemic mixture, of the compounds of this disclosure are encompassed within the scope of this disclosure. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

The compounds of the present disclosure include all cis, trans, syn, anti, entgegen (E), and zusammen (Z) isomers as well as mixtures thereof. The compounds of the present disclosure may also be represented in multiple tautomeric forms, in such instances, the present disclosure expressly includes all tautomeric forms of the compounds described herein, even though only a single tautomeric form may be represented. In addition, where a term used in the present disclosure encompasses a group that may tautomerize, all tautomeric forms are expressly included thereunder. For example, hydroxy substituted heteroaryl includes 2-hydroxypyridine as well as 2-pyridone, 1-hydroxyisoquinoline as well as 1-oxo-1,2-dihyroisoquinoline, 4-hydroxyquinazoline as well as 4-oxo-3,4-dihydroquinazoline, and the like. All such isomeric forms of such compounds are expressly included in the present disclosure.

The compounds of the present disclosure include the compounds themselves, as well as their salts, solvate, solvate of the salt and their prodrugs, if applicable. Salts for the purposes of the present disclosure are preferably pharmaceutically acceptable salts of the compounds according to the present disclosure. Salts which are not themselves suitable for pharmaceutical uses but can be used, for example, for isolation or purification of the compounds according to the disclosure are also included. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. When the compound of the present disclosure is basic, pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfonic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, benzenesulfonic, toluenesulfonic, naphthalenedisulfonic, methanesulfonic, ethanesulfonic, ethanedisulfonic, camphorsulfonic, gluconic, mandelic, mucic, pantothenic, oxalic, isethionic, and the like.

When the compound of the present disclosure is acidic, salts may be prepared from pharmaceutically acceptable non-toxic bases, including inorganic and organic bases. Such salts that may be prepared include lithium salt, sodium salt, potassium salt, magnesium salt, calcium salt, dicyclohexylamine salt, N-methyl-D-glucamine salt, tris(hydroxymethyl)methylamine salt, arginine salt, lysine salt, and the like.

Lists of suitable salts may be found in Remington's Pharmaceutical Sciences, 17th ed., Mack Publishing Company, Easton, Pa., 1985, p. 1418; S. M. Berge et al., "Pharmaceutical Salts", J. Pharm. Sci. 1977, 66, 1-19; and "Pharmaceutical Salts: Properties, Selection, and Use. A Handbook"; Wermuth, C. G. and Stahl, P. H. (eds.) Verlag Helvetica Chimica Acta, Zurich, 2002 [ISBN 3-906390-26-8]; each of which is incorporated herein by reference in its entirety.

Solvates in the context of the present disclosure are designated as those forms of the compounds according to the present disclosure which form a complex in the solid or liquid state by stoichiometric coordination with solvent molecules. Hydrates are a specific form of solvates, in which the coordination takes place with water. Hydrates are preferred solvates in the context of the present disclosure. The formation of solvates is described in greater detail in "Solvents and Solvent Effects in Organic Chemistry"; Reichardt, C. and Welton T.; John Wiley & Sons, 2011 [ISBN: 978-3-527-32473-6], the contents of which is incorporated herein by reference in its entirety. A person of ordinary skill in the art would recognize the solvates of the present disclosure.

The present disclosure also encompasses all suitable isotopic variants of the compounds according to the present disclosure, whether radioactive or not. An isotopic variant of a compound according to the present disclosure is understood to mean a compound in which at least one atom within the compound according to the present disclosure has been exchanged for another atom of the same atomic number, but with a different atomic mass than the atomic mass which usually or predominantly occurs in nature. Examples of isotopes which can be incorporated into a compound according to the present disclosure are those of hydrogen, carbon, nitrogen, oxygen, fluorine, chlorine, bromine and iodine, such as $^2$H (deuterium), $^3$H (tritium), $^{13}$C, $^{14}$C, $^{15}$N, $^{17}$O, $^{18}$O, $^{18}$F, $^{36}$Cl, $^{82}$Br, $^{123}$I, $^{124}$I, $^{125}$I, $^{129}$I and $^{131}$I. Particular isotopic variants of a compound according to the present disclosure, especially those in which one or more radioactive isotopes have been incorporated, may be beneficial, for example, for the examination of the mechanism of action or of the active compound distribution in the body. Due to comparatively easy preparability and detectability, especially compounds labelled with $^3$H, $^{14}$C and/or $^{18}$F isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. Such modifications of the compounds according to the present disclosure may therefore in some cases also constitute a preferred embodiment of the present disclosure. In some embodiments, hydrogen atoms of the compounds described herein may be replaced with deuterium atoms. Isotopic variants of the compounds according to the present disclosure can be prepared by processes known to those skilled in the art, for example by the methods described below and the methods described in the working examples, by using corresponding isotopic modifications of the particular reagents and/or starting compounds therein.

The present disclosure includes within its scope prodrugs of the compounds of Formula I. Prodrugs are generally drug precursors that, following administration to a subject are converted to an active, or a more active species via some process, such as conversion by chemical hydrolysis or a metabolic pathway. Thus, in the methods of treatment of the present disclosure, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985 (Amsterdam, NL). Examples of prodrugs include $C_{1-6}$alkyl esters of carboxylic acid groups and esters of boronic acids, which, upon administration to a subject, are capable of providing active compounds.

Esters of boronic acids are illustrated by Formula II:

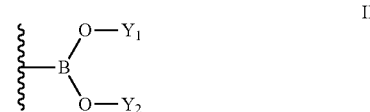

wherein:

$Y_1$ and $Y_2$ are each independently selected from hydrogen, optionally substituted $C_{1-6}$alkyl, $C_{3-10}$cycloalkyl, $C_{1-6}$heterocycle, aryl and heteroaryl, or $Y_1$ and $Y_2$ are joined together to form the group

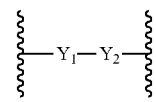

which represents an optionally substituted $C_{2-6}$alkyl in which a carbon atom may be replaced by O, S or —(NCH$_3$)—, optionally substituted $C_{5-12}$cycloalkyl, optionally substituted heterocycle, optionally substituted aryl or optionally substituted heteroaryl. The optional substituents include, for example, hydroxyl, halogen and $C_{1-3}$alkoxy. As will be appreciated by one of skill in the art, for each of the moieties shown herein, a squiggly line describes the point at which the moiety shown is attached to the parent molecule. Illustrating the boronic acid esters are:

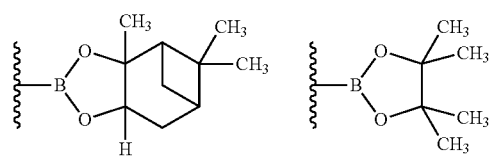

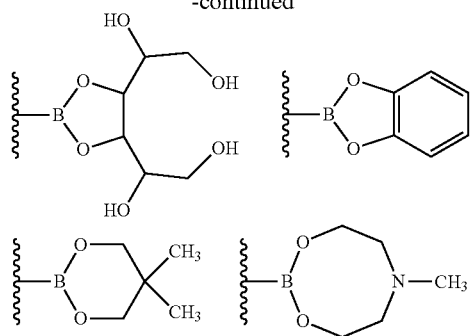

$Y_1$ and $Y_2$ can also represent —B—O—B— to form a 6-membered trioxatriborinane or —B— to form a 4-membered dioxadiboretane.

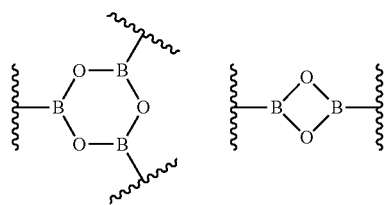 [SMILES: *B1OB(*)OB(*)O1 ; *B1OB(*)O1]

In some embodiments, where W of Formula I is —C(O)C(O)NR$^7$R$^8$ (ketoamides), compounds of Formula I may be prepared as prodrugs. Examples of ketone prodrugs include but are not limited to ketimine, oxime, aminal, ketal, hemiaminal, hemiketal, thioketal, hydrated ketone which, upon administration to a subject, are capable of providing active compounds. Carbonyl derivatives of ketoamides are illustrated by Formula IIIa and IIIb:

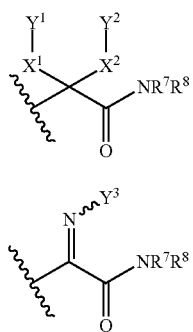

IIIa

IIIb wherein:

$X_1$ and $X_2$ are each independently selected from O, N and S;

$Y_1$ and $Y_2$ are each independently selected from hydrogen, optionally substituted $C_{1-6}$alkyl, $C_{3-10}$cycloalkyl, $C_{1-6}$heterocycle, or $Y_1$ and $Y_2$ are joined together to form the group:

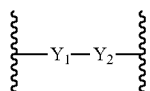

wherein $Y_1$ and $Y_2$ forms an optionally substituted $C_{2-6}$alkyl, or an optionally substituted heterocycle. The optional substituents include, for example, hydroxyl, halogen and $C_{1-3}$alkoxy;

$Y_3$ is H, $C_{1-4}$alkyl, OH or O—$C_{1-4}$alkyl.

Illustrating the ketone prodrugs are:

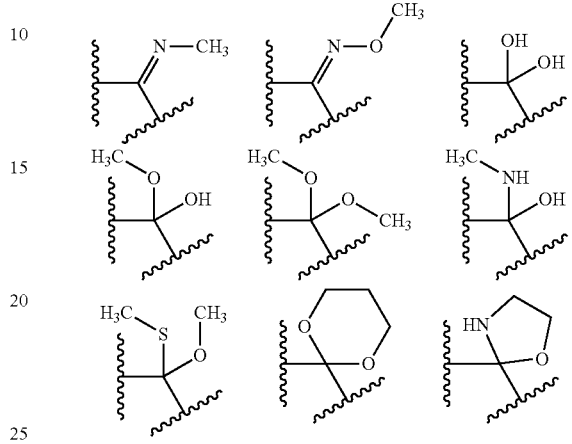

Pharmaceutical Compositions

The term "pharmaceutical composition" as used herein is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure, or a pharmaceutically acceptable salt, or solvate or solvate of the salt thereof, and a pharmaceutically acceptable carrier.

The term "pharmaceutically acceptable carrier" refers to a carrier or an adjuvant that may be administered to a patient, together with a compound of the present disclosure, or a pharmaceutically acceptable salt, solvate, salt of the solvate or prodrug thereof, and which does not destroy the pharmacological activity thereof and is nontoxic when administered in doses sufficient to deliver a therapeutic amount of the compound.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. For convenience, the total daily dosage may be divided and administered in portions during the day if desired.

Pharmaceutical compositions of the present disclosure for injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These pharmaceutical compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin. If desired, and for more effective distribution, the compounds can be incorporated into slow release or targeted delivery systems such as polymer matrices, liposomes, and microspheres.

The pharmaceutical compositions that are injectable formulations can be sterilised, for example, by filtration through a bacterial-retaining filter, or by incorporating sterilising agents in the form of sterile solid pharmaceutical compositions that can be dissolved or dispersed in sterile water or other sterile injectable medium just prior to use.

Solid dosage forms of the instant pharmaceutical compositions for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid pharmaceutical compositions of a similar type may also be employed as fillers in soft and hard-filled gelatin capsules using such excipients as lactose or milk sugar as well as high molecular weight polyethylene glycols and the like.

The solid dosage forms of the instant pharmaceutical compositions of tablets, dragees, capsules, pills, and granules can be prepared with coatings and shells such as enteric coatings and other coatings well known in the pharmaceutical formulating art. They may optionally contain opacifying agents and can also be of a formulation that they release the active ingredient(s) only, or preferentially, in a certain part of the intestinal tract, optionally, in a delayed manner. Examples of embedding pharmaceutical compositions which can be used include polymeric substances and waxes.

The active compounds can also be in microencapsulated form, if appropriate, with one or more of the above-mentioned excipients.

Liquid dosage forms of the instant pharmaceutical compositions for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral pharmaceutical compositions can also include adjuvants such as wetting agents, emulsifying and suspending agents, sweetening, flavouring, and perfuming agents.

Suspensions of the instant compounds, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Pharmaceutical compositions for rectal or vaginal administration are preferably suppositories which can be prepared by mixing the compounds with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound or pharmaceutical composition of the present disclosure include powders, patches, sprays, ointments and inhalants. The active compound is mixed under sterile conditions with a pharmaceutically acceptable carrier and any needed preservatives, buffers, or propellants which may be required.

Dosage forms for application to the eye include solutions, suspensions, ointments, gels, emulsions, strips, inserts such as contact lenses, and implants, which may be administered topically, intravitreally, perioccularly, and the like.

Uses

The present disclosure is directed to novel carbocyclic prolinamide derivatives of Formula I, and pharmaceutically acceptable salts, solvates, salts of solvates and prodrugs thereof, useful in the prevention (e.g., delaying the onset of or reducing the risk of developing) and treatment (e.g., controlling, alleviating, or slowing the progression of) of age-related macular degeneration (AMID) and related diseases of the eye. These diseases include dry-AMID, wet-AMID, geographic atrophy, diabetic retinopathy, retinopathy of prematurity, polypoidal choroidal vasculopathy, diabetic macula edema (DME), other retinopathies such as choroidal neovascularisation (CNV), choroidal neovascular membrane (CNVM), cystoid macular edema (CME), epiretinal membrane (ERM) and macular hole, hypertrophic changes of the retinal pigment epithelium (RPE), atrophic changes of the retinal pigment epithelium, retinal detachment, choroidal vein occlusion, retinal vein occlusion, corneal angiogenesis following, for example, keratitis, cornea transplantation or keratoplasty, corneal angiogenesis due to hypoxia (e.g., induced by extensive contact lens wearing), pterygium conjunctivae, subretinal edema, intraretinal edema, Stargardt disease and degeneration of retinal or photoreceptor cells. The present disclosure disclosed herein is further directed to methods of prevention, slowing the progress of, and treatment of dry-AMD, wet-AMD, and geographic atrophy, diabetic retinopathy, retinopathy of prematurity, polypoidal choroidal vasculopathy, diabetic macula edema (DME), other retinopathies such as choroidal neovascularisation (CNV), choroidal neovascular membrane (CNVM), cystoid macular edema (CME), epi-retinal membrane (ERM) and macular hole, hypertrophic changes of the retinal pigment epithelium (RPE), atrophic changes of the retinal pigment epithelium, retinal detachment, choroidal vein occlusion, retinal vein occlusion, corneal angiogenesis following, for example, keratitis, cornea transplantation or keratoplasty, corneal angiogenesis due to hypoxia (e.g., induced by extensive contact lens wearing), pterygium conjunctivae, subretinal edema, intraretinal edema, Stargardt disease and degeneration of retinal or photoreceptor cells, comprising: administration of a therapeutically effective amount of compound of the present disclosure. The compounds of the present disclosure are inhibitors of HTRA1. Thus, the compounds of the present disclosure are useful in the prevention and treatment of a wide range diseases mediated (in whole or in part) by HTRA1. The compounds of the present disclosure are also useful for inhibiting HTRA1 protease activity in an eye and elsewhere. By virtue of their activity profile, the compounds of the present disclosure are particularly suitable for the treatment and/or prevention of ocular disorders, such as age-related macular degeneration (AMD) like wet-AMD or dry-AMD, geographic atrophy, diabetic retinopathy, Stargardt disease, choroidal neovascularisation (CNV), and diabetic macula edema (DME).

Additionally, compounds of the present disclosure may be useful in the treatment of other diseases in which HTRA1 may be involved, including retinal angiomatous proliferation, foveomacular proliferation, musculoskeletal diseases, including osteoarthritis, spinal disk degeneration rheumatoid arthritis, muscular dystrophy and osteoporosis, and treatment of autologous chondrocytes prior to intraarticular implantation.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug, dosage form, and/or route of administration. The interrelationship of dosages for animals and humans (based on milligrams per meter squared of body surface) is described by Freireich et al., Cancer Chemother. Rep. 50, 219-244 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or by injection. The methods herein contemplate administration of an effective amount of compound or compound composition to achieve the desired or stated effect. Typically, the pharmaceutical compositions of the present disclosure will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, and the judgment of the treating physician.

Dosage forms include from about 0.001 milligrams to about 2,000 milligrams (including, from about 0.001 milligrams to about 1,000 milligrams, from about 0.001 milligrams to about 500 milligrams, from about 0.01 milligrams to about 250 milligrams, from about 0.01 milligrams to about 100 milligrams, from about 0.05-milligrams to about 50 milligrams, and from about 0.1 milligrams to about 25 milligrams) of a compound of Formula I (and/or a compound of any of the other formulae described herein) or a salt (e.g., a pharmaceutically acceptable salt) thereof as defined anywhere herein. The dosage forms can further include a pharmaceutically acceptable carrier and/or an additional therapeutic agent.

With regard to ophthalmic preparation, because AMD and related diseases (including dry-AMD, wet-AMD, geographic atrophy, diabetic retinopathy, retinopathy of prematurity, polypoidal choroidal vasculopathy, and degeneration of retinal or photoreceptor cells) primarily afflict the back of the eye, local administration such as topical administration, trans-scleral drug delivery and intravitreal administration may be preferable over systemic administration. Intravitreal administration can be further divided into intravitreal injection and intravitreal implants. Of these, intravitreal injection appears to be the most widely used. Products utilizing intravitreal injection include Trivaris® (triamcinolone acetonide), Triescence® (triamcinolone acetonide, Alcon Fort Worth, Tex.), Macugen® (pegaptanib sodium, Bausch and Lomb, Rochester, N.Y.), Lucentis® (ranibizumab injection, Genentech, South San Francisco, Calif.), Ozurdex® (dexamethasone, Allergan, Inc., Irvine, Calif.) and Iluvien® (flucinolone acetonide, Alimera Sciences, Alpharetta, Ga.). The preferred dosage range for local administration to the back of the eye ranges from 0.001 mg to 100 mg (including from about 0.01 milligrams to about 500 milligrams, from about 0.05 milligrams to about 250 milligrams, from about 0.05 milligrams to about 100 milligrams, from about 0.1 milligrams to about 50 milligrams, from about 0.1 milligrams to about 25 milligrams, and from about 0.1 milligrams to about 10 milligrams). References on the subject of ophthalmic drug delivery include:

Kompella U. B. et al., Recent Advances in Ophthalmic Drug Delivery, Ther. Deliv. 2010 1(3): 435-456;

Gaudana R. et al., Ocular Drug Delivery, AAPS Journal, Vol. 12, No. 3: 348-360 (2010);

Haghjou N. et al., Sustained Release Intraocular Drug Delivery Devices for Treatment of Uveitis, J. Ophthalmic Vis. Res. 2011; 6 (4): 317-329;

Kuno N. and Fujii S. Recent Advances in Ocular Drug Delivery Systems, Polymers (2011), 3:193-221;

Patel A. et al., Ocular Drug Delivery Systems: An Overview, World J. Pharmacol. (2013) 2:47-64;

Morrison P. W. J. and Khutoryanskiy V. V. Advances in Ophthalmic Drug Delivery, Ther. Deliv. (2014) 5:1297-1315;

Chen H. Recent Developments in Ocular Drug Delivery, J. Drug Target (2015), 23:597-604; all of which are incorporated by reference.

For the treatment and/or prevention of ocular disorders, as described above, the preferred route for administering the compounds of the present disclosure is topically at the eye or by an ocular drug delivery system. Intraocular injections are another way to administer the compounds of the present disclosure that is suitable for such purposes.

Delivery to areas within the eye can be accomplished by injection, employing a cannula or another invasive device designed to introduce precisely metered amounts of a desired formulation to a particular compartment or tissue within the eye (e.g., posterior chamber or retina). An intraocular injection may be into the vitreous (intravitreal), under the conjunctiva (subconjunctival), behind the eye (retrobulbar), into the sclera, or under the Capsule of Tenon (sub-Tenon), and may be in a depot form. Other intraocular routes of administration and injection sites and forms are also contemplated and are within the scope of the present disclosure.

The compounds according to the present disclosure may be formulated in a manner known to those skilled in the art so as to give adequate delivery to the back of the eye, which may be by regular dosing, such as with eye drops, or by using a delivery system to give a controlled release, such as slow release, of the compounds according to the present disclosure.

Preferred ocular formulations for the compounds of the present disclosure include aqueous solutions, suspensions or gels of these compounds in the form of drops of liquid, liquid washes, sprays, ointments or gels, in a mixture with excipients suitable for the manufacture and use of such application forms. Alternatively, the compounds of the present disclosure may be applied to the eye via liposomes or other ocular delivery systems that are known in the art.

Appropriate dosage levels may be determined by any suitable method known to one skilled in the art of treating eye diseases. Preferably, the active substance is administered at a frequency of 1 to 4 times per day for topical administration, or less often if a drug delivery system is used. Typically, an ocular formulation intended for topical application contains the active ingredient in a concentration range of about 0.001% to 10%.

Nevertheless, actual dosage levels and time course of administration of the active ingredients in the pharmaceutical compositions of the present disclosure may be varied so as to obtain an amount of the active ingredient which is effective to achieve the desired therapeutic response for a particular patient, composition and mode of administration, without being toxic to the patient. It may therefore be necessary where appropriate to deviate from the stated amounts, in particular as a function of age, gender, body weight, diet and general health status of the patient, route of administration, individual response to the active ingredient, nature of the preparation, and time or interval over which administration takes place. Thus, it may be satisfactory in some cases to manage with less than the aforementioned minimum amount, whereas in other cases the stated upper limit must be exceeded. It may in the event of administration of larger amounts be advisable to divide these into multiple individual doses spread over the day.

In one aspect the compounds of the present disclosure may be co-administered with one or more additional agents. The additional agents include, but are not limited to Acuvail® (ketorolac tromethamine ophthalmic solution), AK-Con-A®/OcuHist® (pheniramine maleate-naphazoline HCl, ophthalmic solution), Akten® (lidocaine HCl ophthalmic gel), Alamast® (pemirolast potassium ophthalmic solution), Alphagan® (brimonidine tartrate ophthalmic solution), Bepreve® (bepotastine besilate ophthalmic solution), Besivance® (besifloxacin ophthalmic suspension), Betaxon® (levobetaxolol HCl ophthalmic suspension), Cosopt® (dorzolamide HCl—timolol maleate, ophthalmic solution), Cystaran® (cysteamine HCl ophthalmic solution), Durezol® (difluprednate ophthalmic emulsion), Eylea® (aflibercept intravitreal injection), Jetrea® (ocriplasmin intravitreal injection), Lotemax® (loteprednol etabonate ophthalmic suspension), Lucentis® (ranibizumab injection), Lumigan® (bimatoprost ophthalmic solution), Macugen® (pegaptanib intravitreal injection), Ocuflox® (ofloxacin ophthalmic solution), Omidria® (phenylephrine and ketorolac injection), Ozurdex® (dexamethasone intravitreal implant), Quixin® (levofloxacin ophthalmic solution), Rescula® (unoprostone isopropyl ophthalmic solution 0.15%), Restasis® (cyclosporine ophthalmic emulsion), Salagen® (pilocarpine HCl tablets), Travatan® (travoprost ophthalmic solution), Valcyte® (valganciclovir HCl tablets and oral solution), Vistide® (cidofovir tablets), Visudyne® (verteporfin injection), Vitrasert® (ganciclovir implant), Vitravene® (fomivirsen injection), Zioptan® (tafluprost ophthalmic solution), Zirgan® (ganciclovir ophthalmic gel), and Zymaxid® (gatifloxacin ophthalmic solution). Furthermore the compounds of the disclosure may be co-administered with one or more inhibitors of VEGF-mediated angiogenesis, such as, for example, ACTB-1003 (Edding Pharm, CN), apatinib, axitinib, bevacizumab, bevasiranib, BMS-690514 (Bristol-Myers Squibb (BMS), NY), brivanib, cediranib, CT-322 (Adnexus/BMS, MA), dovitinib, lenvatinib, foretinib, KH-902/conbercept (approved in CN for exudative macular degeneration), linifanib, MGCD-265 (Mirati Therapeutics, Calif.), motesanib, elpamotide, pazopanib, pegaptanib, ranibizumab, regorafenib, ruboxystaurin, sorafenib, SU-14813 (Pfizer, CT), sunitinib, telatinib, TG-100801, tivozanib, TSU-68 (Taiho Pharmaceuticals, JP), vandetanib, vargatef, vatalanib and Carbometyx® (cabozantinib tablets, Exelixis, Calif.), or with inhibitors of other signaling pathways, such as disulfiram, fenretinide, mecamylamine, PF-04523655 (Pfizer, CT), sonepcizumab, tandospirone and volociximab.

Additional agents which may be utilized for co-administration include: known vitamins and antioxidants such as AREDS/AREDS2 (supplements used in Age-Related Eye Disease Study/Study 2, National Eye Institute, US), omega-3 fatty acids, lutein, zeaxanthin, vitamin A; visualcycle modulators such as emixustat (ACU-4429, Acucela, Wash.); anti-inflammatory agents such as Illuvien® (fluocinolone acetonide), sirolimus, Triesence®/Trivaris® (triamcinolone acetonide); complement modulators such as lampalizumab, Soliris® (eculizumab, Alexion, CT); amyloid-modulators such as GSK933776 (GlaxosmithKline, Pa.), RN6G (PF-04382923, Pfizer, CT) and platelet-derived growth factor modulators such as, for example, Fovista® (pegpleranib, Ophthotech, N.Y.).

In certain embodiments, the additional agents may be administered separately (e.g., sequentially; on different overlapping schedules), as part of a multiple dose regimen, from the compounds of the present disclosure (e.g., one or more compounds of Formula (I) and/or a compound of any of the other formulae, including any subgenera or specific compounds thereof). In other embodiments, these agents may be part of a single dosage form, mixed together with the compounds of the present disclosure in a single composition. In still another embodiment, these agents can be given as a separate dose that is administered at about the same time as that of one or more compounds of Formula (I) (and/or a compound of any of the other formulae, including any subgenera or specific compounds thereof) are administered (e.g., simultaneously with the administration of one or more compounds of Formula (I) (and/or a compound of any of the other formulae, including any subgenera or specific compounds thereof)). When the compositions of the present disclosure include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of the present disclosure may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions of the present disclosure may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase and then combined with emulsifying and/or suspending agents. If desired, certain sweetening and/or flavoring and/or coloring agents may be added.

Biological Function

The utility of the present disclosure can be demonstrated by one or more of the following methods or other methods known in the art:

Full Length HTRA1 Assay

Serial dilutions (⅓) from 1000 µM down to 0.051 µM of test compounds were prepared in dimethyl sulfoxide (DMSO). Then 2 µL of solution from each dilution were added to 100 µL of 4 nM full-length human His-HTRA1 in assay buffer (50 mM Tris, pH 7.5, 200 mM NaCl and 0.25% 3-[(3-cholamidopropyl)dimethylammonio]-1-propane-sulfonate or CHAPS) in white non-binding 96-well plates. The assay solutions were mixed for 5 seconds on a shaker plate and incubated for 10 minutes at room temperature. Mca-H2OPT (Mca-Ile-Arg-Arg-Val-Ser-Tyr-Ser-Phe-Lys (Dnp)-Lys-OH trifluoroacetate salt) (Mca=7-methoxycoumarin-4-acetic acid; Dnp=dinitrophenyl) (5 M) in 100 µL of assay buffer was added to the assay solutions. The reaction mixture was shaken for 5 seconds on a shaker plate and cleavage of Mca-H2OPT was monitored by spectrofluorometry (SpectraMax M3 by Molecular Devices, Calif.) for 10 minutes (Exλ=330 nm; Emλ=420 nm). Percent inhibition was calculated by fitting values to a standard mathematical model for determining the dose response curve.

| Example | HtrA1 IC$_{50}$ (µM) |
|---|---|
| 1 | 0.261 |
| 2 | 2.91 |
| 3 | 0.0472 |
| 4 | 0.00562 |

-continued

| Example | HtrA1 IC$_{50}$ (µM) |
|---|---|
| 5 | 0.00908 |
| 6 | 0.675 |
| 7 | 0.138 |
| 8 | 0.0125 |
| 9 | 0.199 |
| 10 | 0.0181 |
| 11 | 0.00982 |
| 12 | 0.0811 |
| 13 | 0.0172 |
| 14 | 0.0156 |
| 15 | 0.046 |
| 16 | 0.155 |
| 17 | 0.0201 |
| 18 | 0.0244 |
| 19 | 0.157 |
| 20 | 0.0901 |
| 21 | 0.142 |
| 22 | 0.0403 |
| 23 | 0.0596 |
| 24 | 0.0138 |
| 25 | 0.0368 |
| 26 | 0.0216 |
| 27 | 0.0374 |
| 28 | 0.0553 |
| 29 | 0.0631 |
| 30 | 0.303 |
| 31 | 0.144 |
| 32 | 0.146 |
| 33 | 0.11 |
| 34 | 0.62 |
| 35 | 0.223 |
| 36 | 0.00665 |
| 37 | 0.0104 |
| 38 | 0.523 |
| 39 | 0.0305 |
| 40 | 0.0252 |
| 41 | 0.068 |
| 42 | 0.606 |
| 43 | 1.18 |
| 44 | 0.0223 |
| 45 | 0.0385 |
| 46 | 0.181 |
| 47 | 0.0782 |
| 48 | 0.011 |

Synthesis

The starting materials used for the synthesis are either synthesized or obtained from commercial sources, such as, but not limited to, Sigma-Aldrich, Fluka, Acros Organics, Alfa Aesar, VWR Scientific, Chem-Impex, PharmaBlock, Combi-Blocks, Astatech, Enamine and the like. Nuclear Magnetic Resonance (NMR) analysis was conducted using a Varian Mercury 300 MHz spectrometer with an appropriate deuterated solvent. LCMS analysis was conducted using a Waters Acquity UPLC with a QDA MS detector using a Waters C18 BEH 1.7 µM, 2.1×50 mm column, eluting with 95:5 to 0:100 H$_2$O:MeCN+0.1% formic acid at a flow rate of 0.6 mL/min over 3.5 minutes. The QDA MS detector was set up to scan under both positive and negative mode ions ranging from 100-1200 Daltons. General methods for the preparation of compounds can be modified by the use of appropriate reagents and conditions for the introduction of the various moieties found in the structures as provided herein.

Abbreviations

Boc tert-butyl carbonate
Bn Benzyl
C celcius
CBz carboxybenzyl
m-CPBA meta-chloroperoxybenzoic acid DBU 1,8-Diazabicyclo[5.4.0]undec-7-ene
DCM Dichloromethane
DMP Dess-Martin periodinane
DMF dimethylformamide
DMSO dimethylsulfoxide
EtOAc ethyl acetate
Et ethyl
equiv equivalents
h hours
HATU 1-[bis(dimethylamino)methylene]-1H-1,2,3-triazolo[4,5-b]pyridinium 3-oxid hexafluorophosphate
PyAOP (7-Azabenzotriazol-1-yloxy)tripyrrolidinophosphonium hexafluorophosphate
g grams
L liter
LDA lithium diisopropylamide
LAH lithium aluminum hydride
LCMS liquid chromatography-mass spectrometry
liq. liquid
M molar
Ms methanesulfonyl
Me methyl
MeCN acetonitrile
mg milligrams
mL milliliter
mmol millimoles
mol moles
MS mass spectrometry
Pr (iPr) propyl (isopropyl)
sat. saturated
THF tetrahydrofuran
TLC thin layer chromatography (normally silica gel based)
TEA triethylamine
TFA trifluoroacetic acid
Tf$_2$O triflic anhydride
µL microliter
UHP urea hydrogen peroxide General Synthetic Scheme In some embodiments, compounds described herein are prepared as outlined in the following general synthetic schemes. These compounds may be viewed as consisting of four units as shown in the general structure: A—the $R^1$—C(O) group, B—an α-amino acyl group, C—the prolyl group, and D—an aminocarbocyclic group. All the variables in the general structure and in the synthetic schemes are, unless otherwise specified, as defined in the claims.

General Structure

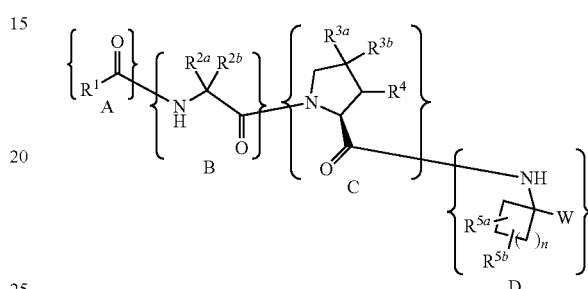

In the schemes, unless otherwise specified, PG is a conventional protecting group (e.g., BOC or CBz for amino group, alkyl ester for carboxylic or boronic acid group); LG is a leaving group (e.g., methanesulfonyloxy); Nuc is a nucleophile (e.g., $N_3$ or piperidine); and R is a protecting group or one or more of optionally protected A, B, C, D units.

Method A: Synthesis of 1-amino 2-hydroxyacetamides

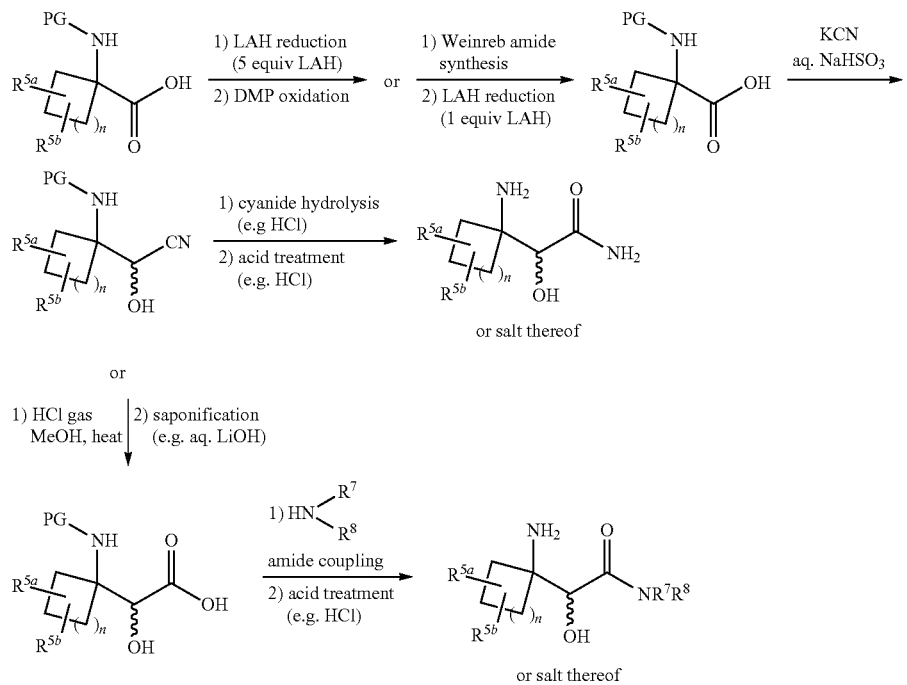

An α-amino acid (commercially available, or otherwise prepared from corresponding ketone using the following literature procedure: Naydenova, E. D., et al. *Eur. J Med. Chem.* 2008, 43, 1199-1205) is reduced to primary alcohol using excess amount of LAH, which is then oxidized to an aldehyde via DMP oxidation. Alternatively, the α-amino acid can be coupled with N,O-dimethylhydroxylamine via amide coupling conditions described in the literature (e.g. Valeur, E., et al. *Chem. Soc. Rev.* 2009, 38, 606-631), yielding a Weinreb amide, which is reacted with 1 equiv LAH to afford the α-amino aldehyde. The resulting α-amino aldehyde is reacted with KCN under aqueous acidic condition (such as aq. $NaHSO_3$) to give 1-amino 2-hydroxycyanide. The cyanide is hydrolyzed to a hydroxyacetamide via oxidative conditions (such as hydrogen peroxide or urea hydrogen peroxide (UHP)). The subsequent N-protected 1-amino 2-hydroxyacetamide is converted to 1-amino 2-hydroxyacetamide or salt thereof by treatment with a strong acid (such as HCl).

Alternatively, the 1-amino 2-hydroxycyanide is treated with excess strong acid (such as HCl gas) in the presence of methanol at elevated temperatures to afford an α-hydroxyl carboxylic ester, which can then be hydrolyzed to the corresponding carboxylic acid under aqueous basic condition (such as aq. 1 M LiOH). The resulting α-hydroxyl carboxylic acid can be coupled with various amines using literature procedures (e.g. Valeur, E., et al. *Chem. Soc. Rev.* 2009, 38, 606-631). Deprotection of the amine under acidic conditions results in 1-amino 2-hydroxyacetamides or salts thereof.

Method B: Synthesis of α-amino Boronates

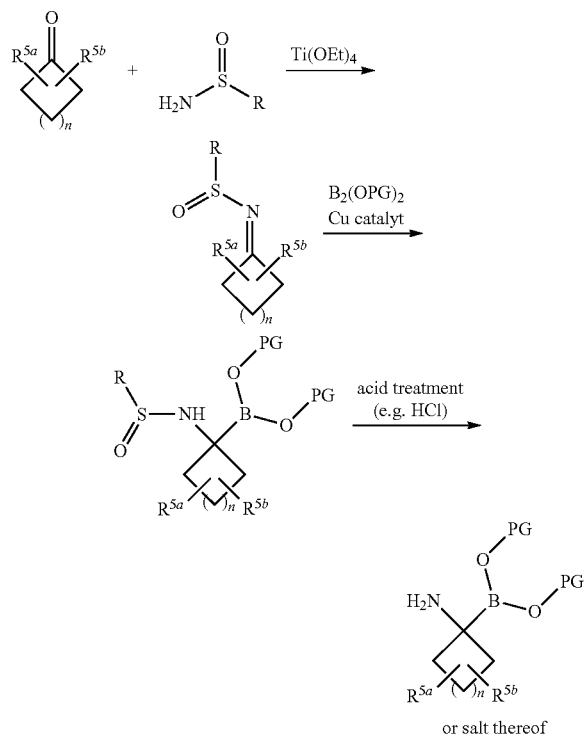

or salt thereof

N-Sulfinylimine is prepared via a titanium-mediated imine formation reaction between ketones and sulfinamides (such as 2-methylpropane-2-sulfinamide) as described in the literature (e.g. Ruano, J. L. G., et al. *Org. Lett.* 2005, 7, 179-182). The resulting N-sulfinylimine is reacted with a bis diboron compound (such as bis(pinacolato)diboron, $B_2pin_2$) through a copper(II)—catalyzed imine borylation reaction following a literature procedure (e.g. Buesking, A. W., et al. *J. Org. Chem.* 2014, 79, 3671-3677). The subsequent N-sulfinyl α-amino boronate is converted to α-amino boronate or salt thereof by treatment with a strong acid (such as HCl).

Method C: Amide Coupling with 1-amino 2-hydroxyacetamides or α-amino Boronates

The prepared 1-amino 2-hydroxyacetamide from Method A or α-amino boronates from Method B can be attached to the proline residue using standard amide coupling conditions described in the literature (e.g. Valeur, E., et a. *Chem. Soc. Rev.* 2009, 38, 606-631). The proline acid may be protected at the nitrogen (e.g. Boc, Cbz) or may be further functionalized with an α-amino acid or derivative.

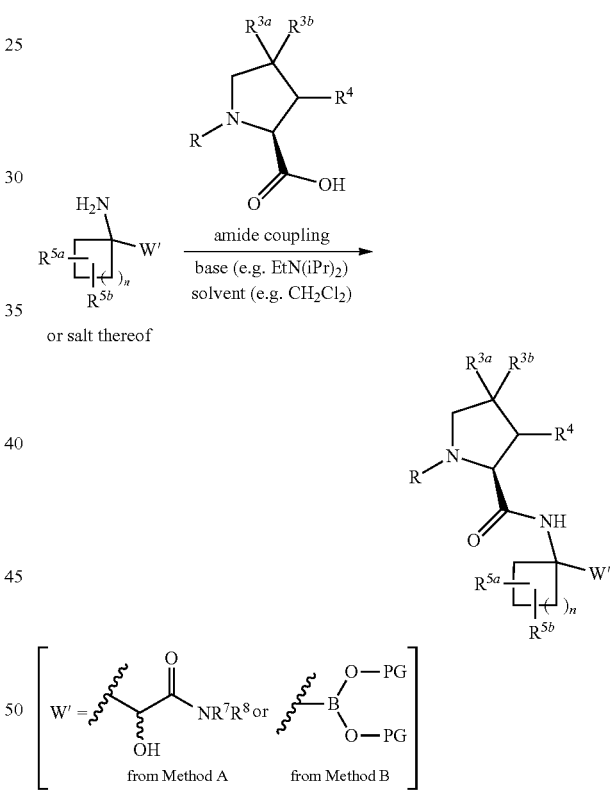

Method D: Synthesis of 4-Substituted Proline Analogs Via Nucleophilic Displacement The alcohol moiety of a 4-hydroxyproline analog can be converted into a suitable leaving group (e.g. mesylate) under standard conditions and then reacted in the presence of a suitable nucleophile (e.g. amine, azide) in the presence of a base (e.g. $Et_3N$ or NaH) to afford a 4-substituted proline derivative. The proline may be protected at the proline nitrogen (e.g. Boc, Cbz) or may be further functionalized with an α-amino acid or derivative.

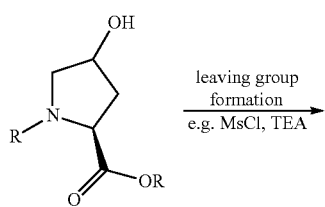

in the 1,5-isomer of the 4-triazole substituted proline analogs. Alternatively, applying another transition metal catalytic system (such as CuSO$_4$/L-ascorbic acid, as described in the literature: Rostovtsev, V. V., et al. *Angew. Chem. Int. Ed.* 2002, 41, 2596-2599), the 1,4-cycloaddition product can be facilitated. The proline may be protected at the proline nitrogen (e.g. Boc, Cbz) or may be further functionalized with an α-amino acid or derivative. The proline may be further functionalized with a 1-amino 2-hydroxyacetamide or α-amino boronates.

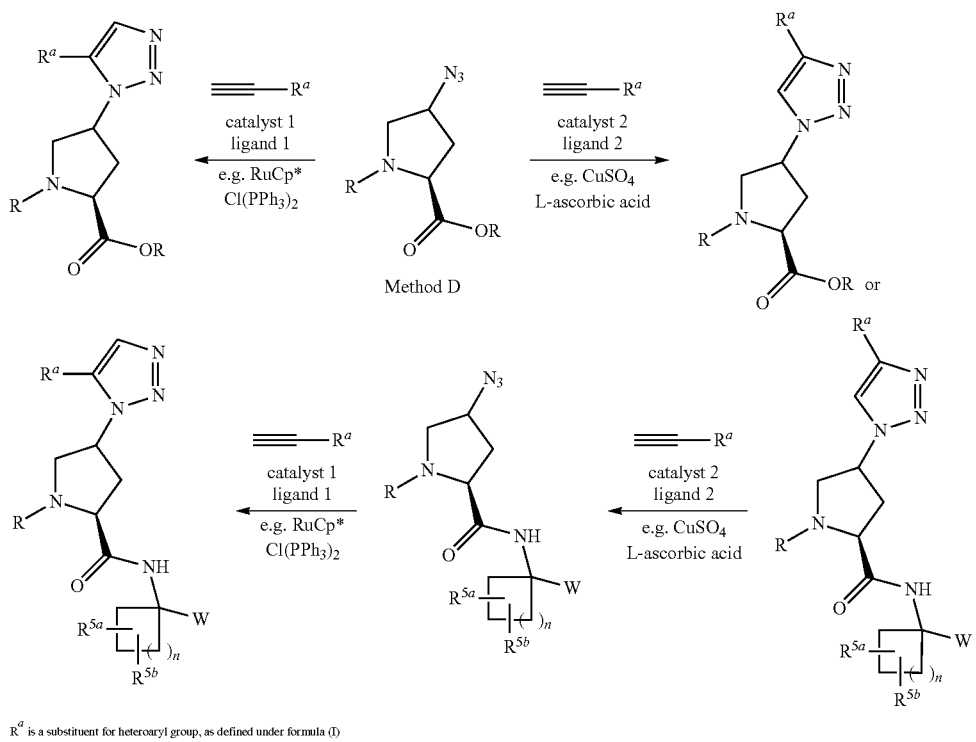

$R^a$ is a substituent for heteroaryl group, as defined under formula (I)

-continued

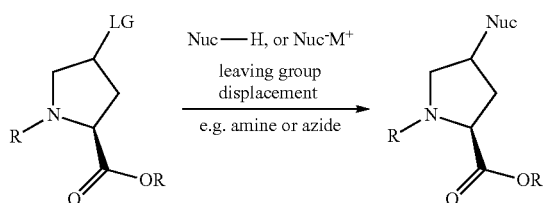

Method E: Synthesis of 4-triazole Substituted Proline Analogs

An appropriate 4-azido proline analog, prepared as in Method D (where LG is N$_3$), is reacted with a terminal alkyne (such as 2-methyl-3-butyn-2-ol) under a transition metal catalyzed 1,5-cycloaddition reaction (such as RuCp*Cl(PPh$_3$)$_2$, as described in the literature: Boren, B. C., et al. *J. Am. Chem. Soc.* 2008, 130, 8923-8930), resulting Method F: Synthesis of 3,4-Disubstituted Proline Analogs The alkene moiety from a 3,4-dehydroproline analog is converted into an epoxide under standard epoxidation conditions (e.g. m-CPBA). The resulting epoxide is then reacted in the presence of a suitable nucleophile (e.g. azide) to afford a 3-hydoxyl 4-substituted proline derivative. The hydroxyl moiety is alkylated using literature alkylation procedures (such as Altmann, E., et al. WO 2012/093101 A1, Jul. 12, 2012). The proline may be protected at the proline nitrogen (e.g. Boc, Cbz) or may be further functionalized with an α-amino acid or derivative. The proline may contain a 2-ester moiety.

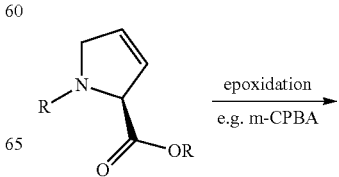

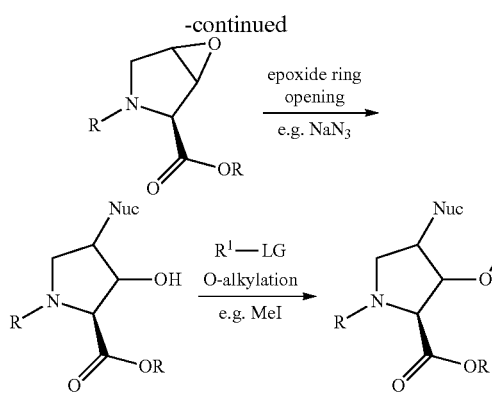

Method G: Synthesis of α-Monosubstituted α-Amino Acid Derivatives

A series of α-monosubstituted α-amino acid derivatives can be obtained via a three-step synthesis from a commercially available primary alcohol. The alcohol is firstly oxidized to an aldehyde under standard alcohol oxidation conditions (e.g. DMP oxidation). The resulting aldehyde can react with commercially available α-phosphoryl-α-amino acid derivatives via a Horner-Wadsworth-Emmons reaction following literature procedures (e.g. St. Jean Jr. D. J., et al. *J. Med. Chem.*, 2014, 57, 309-324). A subsequent olefin hydrogenation of an α,β-unsaturated β-amino ester can be facilitated using conventional heterogeneous catalytic hydrogenation conditions (e.g. cat. Pd/C, $H_2$ balloon), affording α-monosubstituted α-amino acid derivatives.

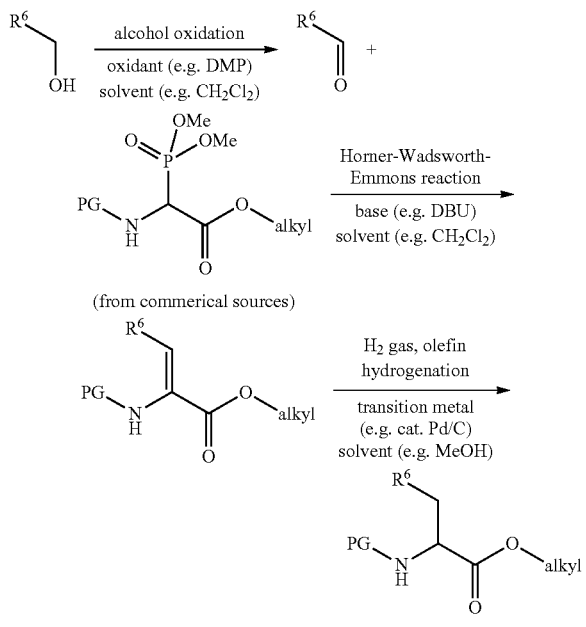

Method H: Synthesis of α,α-Disubstituted α-Amino Acid Derivatives

In certain examples, the α-monosubstituted α-amino acid derivatives can be further functionalized through an α-alkylation process to α,α-disubstituted α-amino acid derivatives. In such cases, an α-monosubstituted α-amino acid derivative is first subjected to α-deprotonation by treatment with a strong base (such as LDA), and the resulting α-nucleophile is reacted with alkyl halides (such as methyl iodide), resulting in an α,α-disubstituted α-amino acid derivative.

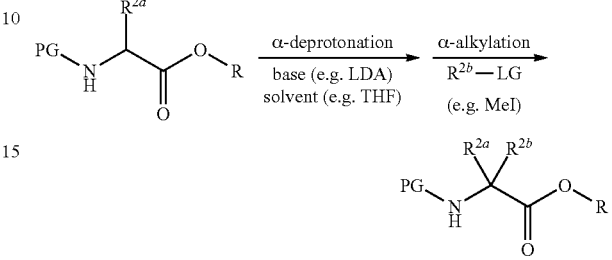

Method I: Amide Coupling of Proline Analogs with α-Amino Acids

A substituted proline analog (or salt thereof) can be linked with an appropriate carboxylic acid to afford the coupled product under standard amide coupling conditions (e.g. HATU, $EtN(iPr)_2$, $CH_2Cl_2$). Typical amide coupling conditions have been described in the literature, including the review article by Valeur, E. et al. *Chem. Soc. Rev.* 2009, 38, 606-631. The α-amino acids may be protected at the nitrogen (e.g. Boc, Cbz) or may be further functionalized with another α-amino acid or derivatives (e.g. $R^1C(O)$—) via another subsequent amide coupling reaction.

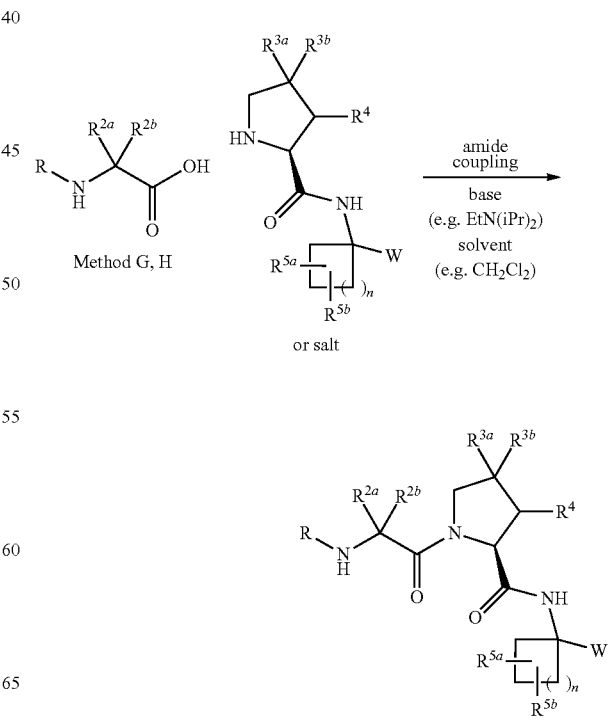

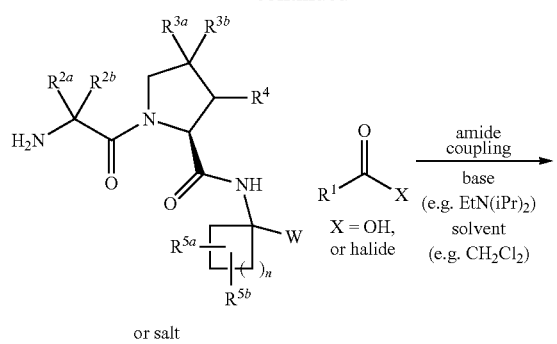

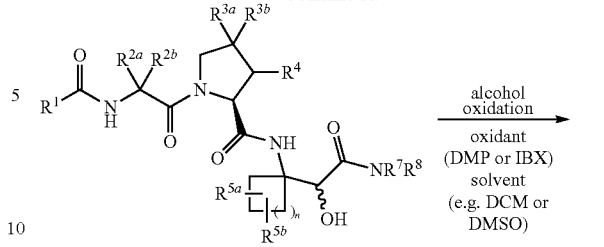

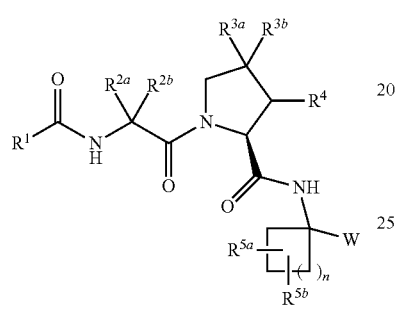

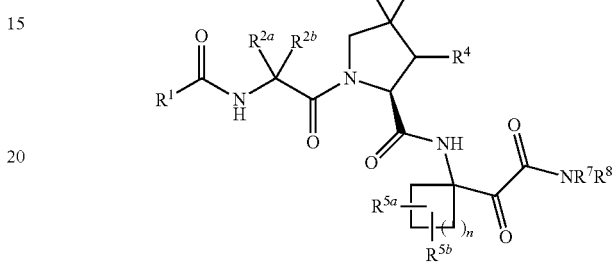

Method J: Oxidation of Hydroxyacetamides to Ketoamides

When W is a hydroxyacetamide moiety, the alcohol can be oxidized to the corresponding ketoamide under standard alcohol oxidation conditions, using oxidizing agents such as DMP or IBX. The proline nitrogen may be protected (e.g. Boc, Cbz) or may be further functionalized with α-amino acids or derivatives.

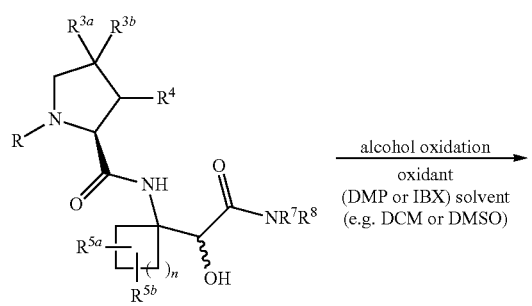

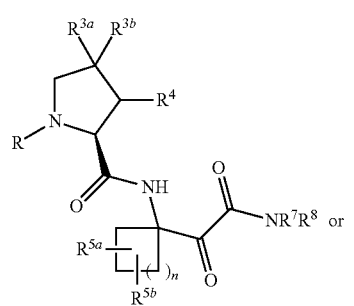

Method K: Deprotection of boronate esters to boronic acids

Boronate esters can be converted to boronic acids using a number of procedures described in the literature, including those described within Boronic Acids: Preparation and Applications in Organic Synthesis, Medicine and Materials, Second Edition; Dennis Hall, Ed.; 2011 John Wiley & Sons. For example, the boronate ester can be reacted with a sacrificial boronic acid (e.g. phenyl boronic acid or isobutyl boronic acid) in an appropriate solvent (e.g. methanol, ethanol, hexanes or octane) with an acid catalyst (e.g. hydrochloric acid or acetic acid).

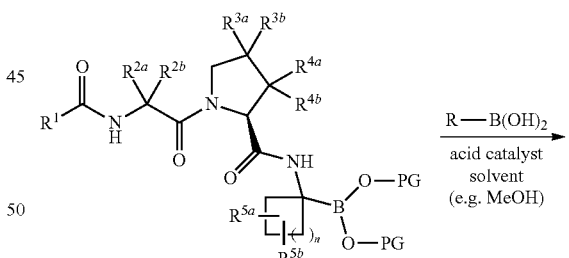

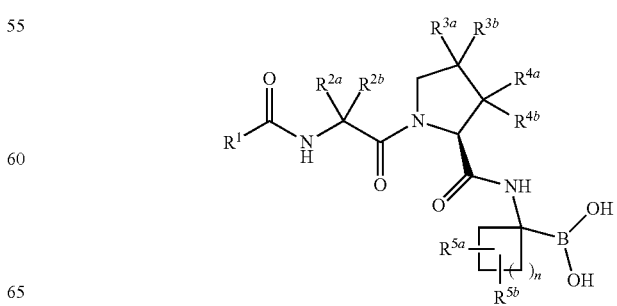

Preparation of Intermediates

Intermediate A:
2-(1-aminocyclobutyl)-2-hydroxyacetamide hydrochloride

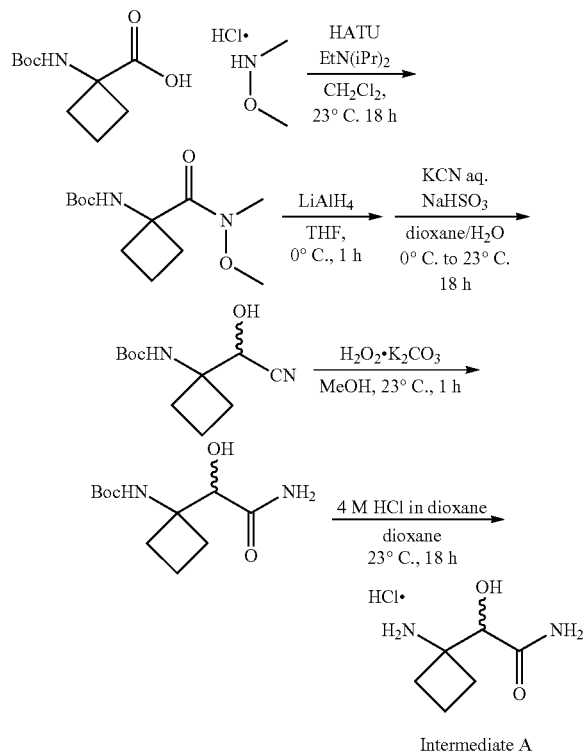

Intermediate A

Step 1: Preparation of tert-butyl (1-(methoxy(methyl)carbamoyl)cyclobutyl)carbamate Into a 100 mL round-bottom flask equipped with a magnetic stir bar and under nitrogen was added the commercially available 1-((tert-butoxycarbonyl)amino)cyclobutanecarboxylic acid (2.0 g, 9.3 mmol, 1.0 equiv), N,O-dimethylhydroxylamine hydrochloride (996 mg, 10.2 mmol, 1.1 equiv), HATU (4.2 g, 11.2 mmol, 1.2 equiv) and dichloromethane (15 mL). EtN(iPr)₂ (3.3 mL, 18.6 mmol, 2.0 equiv) was then added to the reaction mixture. The yellow suspension was stirred at room temperature for 18 h. LCMS analysis revealed conversion to product. The reaction mixture was quenched with sat. aqueous ammonia chloride (50 mL) and extracted with CH₂Cl₂ (3×50 mL) using a 250 mL separatory funnel. The combined organic extracts were washed with brine (50 mL), dried over MgSO₄, filtered and concentrated under reduced pressure. The resulting yellow oil was dried under vacuum and used directly without further purification.

Step 2: Preparation of tert-butyl (1-(cyano(hydroxy)methyl)cyclobutyl)carbamate Into a flamed-dried 100 mL round-bottom flask equipped with a magnetic stir bar and under nitrogen was added LiAlH₄ (706 mg, 18.6 mmol, 1.9 equiv) and THF (anhydrous, 15 mL). The grey suspension was cooled to −10° C. in an ice/brine bath. The mixture was treated with the dropwise addition of tert-butyl (1-(methoxy(methyl)carbamoyl)cyclobutyl)carbamate (9.9 mmol, 1.0 equiv, dissolved in 15 mL THF) over 20 minutes. The resulting reaction mixture was stirred at −10° C. for 1 hour. The reaction mixture was quenched with the dropwise addition of NaHSO₄ in H₂O (~40%, 10 mL). The suspension was warmed up to room temperature and stirred for 1 hour. The mixture was poured into a 125 mL separatory funnel and extracted with Et₂O (3×30 mL). The combined organic extracts were washed with 1 M aq. HCl (30 mL), sat. aqueous NaHCO₃ (30 mL) and brine (30 mL), then dried over MgSO₄, filtered and concentrated under reduced pressure.

Without further purification, the resulting orange-yellow oil was dissolved in 1,4-dioxane (20 mL) under nitrogen in a 100 mL round-bottom flask equipped with a magnetic stir bar. The reaction mixture was cooled to 0° C. in an ice bath. To this mixture was added aq. NaHSO₃ (40% in H₂O, 8.4 mL, 32.2 mmol, 4.0 equiv) over 30 minutes via an additional funnel. KCN (2.1 g, 32.2 mmol, 4.0 equiv) was then added to the reaction mixture. The mixture was stirred at 0° C. for 1 hour and then allowed to warm to room temperature overnight. The reaction mixture was quenched with sat. aq. NaHCO₃ (20 mL) and poured into a 125 mL separatory funnel containing water (25 mL) and extracted with EtOAc (3×30 mL). The combined organic extracts were washed with brine (25 mL), then dried over MgSO₄, filtered and concentrated under reduced pressure. The residue was purified by column chromatography on the ISCO Rf (40 g silica gel column+20 g pre-cartridge) eluting with 100:0 to 60:40 hexanes:EtOAc as a gradient over 30 min. The title product was obtained as a white solid.

Step 3: Preparation of tert-butyl (1-(2-amino-1-hydroxy-2-oxoethyl)cyclobutyl)carbamate Into a 100 mL round-bottom flask equipped with a magnetic stir bar was added tert-butyl (1-(cyano(hydroxy)methyl)cyclobutyl)carbamate (5.2 mmol, 1.0 equiv) and methanol (20 mL). To this solution was added K₂CO₃ (786 mg, 5.7 mmol, 1.1 equiv) and the mixture was treated with the dropwise addition of H₂O₂ (35% in H₂O, 1.5 mL, 15.5 mmol, 3.0 equiv). The suspension was stirred at room temperature for 1 hour. TLC analysis at this time revealed conversion to product. The reaction mixture was poured into a 125 mL separatory funnel containing water (50 mL) and extracted with EtOAc (3×20 mL). The combined organic extracts were washed with brine (20 mL), dried over MgSO₄, filtered and concentrated under reduced pressure. The residue was purified by column chromatography on the ISCO Rf (50 g silica gel column) eluting with 80:20 to 0:100 hexanes:EtOAc as a gradient over 25 min. The title product was obtained as a clear oil.

Step 4: Preparation of 2-(1-aminocyclobutyl)-2-hydroxyacetamide hydrochloride Into a 50 mL round-bottom flask equipped with a magnetic stir bar under nitrogen was added tert-butyl (1-(2-amino-1-hydroxy-2-oxoethyl)cyclobutyl)carbamate (1.9 mmol, 1.0 equiv) and dioxane (2.4 mL). HCl (4 M in dioxane, 2.4 mL, 9.7 mmol, 5.0 equiv) was added and the yellow solution was stirred at room temperature for 18 h. LCMS analysis revealed the complete conversion of starting material. The reaction mixture was concentrated under reduced pressure and was co-evaporated with MeOH to remove any excess HCl. The resulting solid was dried under vacuum for 18 h. Without further purification, the yellowish crude solid was used directly in subsequent steps.

The following hydroxyacetamide hydrochloride salts, intermediates B, C, D and E, were prepared using the same procedures as described above in the synthesis of intermediate A replacing 1-((tert-butoxycarbonyl)amino)cyclobutanecarboxylic acid with 1-((tert-butoxycarbonyl)amino)cyclopropanecarboxylic acid, 1-((tert-butoxycarbonyl)amino)cyclopentanecarboxylic acid, 1-((tert-butoxycarbonyl)amino)cycloheptanecarboxylic acid and 1-((tert-butoxycarbonyl)amino)-cyclooctanecarboxylic acid, respectively.

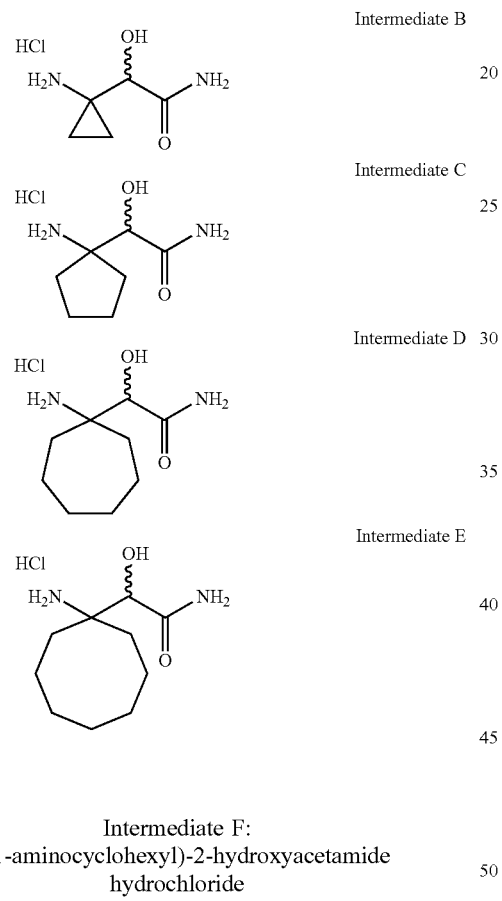

Intermediate B

Intermediate C

Intermediate D

Intermediate E

Intermediate F:
2-(1-aminocyclohexyl)-2-hydroxyacetamide hydrochloride

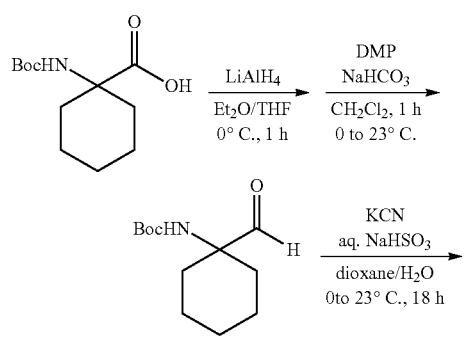

Intermediate F

Step 1: Preparation of tert-butyl (1-formylcyclohexyl)carbamate

Into a flamed-dried 500 mL round-bottom flask equipped with a magnetic stir bar and under nitrogen was added LiAlH$_4$ powder (9.4 g, 246.0 mmol, 4.0 equiv). The solid was diluted with Et$_2$O (anhydrous, 100 mL) and cooled to 0° C. in an ice bath. Into another 250 mL round-bottom flask under nitrogen was added the commercially available 1-((tert-butoxycarbonyl)amino)cyclohexanecarboxylic acid (15.0 g, 61.6 mmol, 1.0 equiv) and THF (anhydrous, 100 mL). The mixture was sonicated to give a solution, which was added dropwise to the LiAlH$_4$/Et$_2$O slurry via an additional funnel over 1 hour. The grey suspension was stirred at 0° C. for 1 hour and then carefully quenched by sequentially dropwise addition of 10 mL H$_2$O, 10 mL of 15% aq. NaOH solution and 25 mL H$_2$O. The resulting grey-white suspension was stirred at 0° C. for 20 minutes and then filtered through a pad of celite on a sintered glass funnel, washing with EtOAc (3×100 mL). The filtrate was dried over MgSO$_4$, filtered and concentrated under reduced pressure. The crude oil was dried under vacuum for 2 hours and used directly without further purification.

Into a 500 mL round-bottom flask equipped with a magnetic stir bar and under nitrogen was added the crude alcohol (61.6 mmol, 1.0 equiv), CH$_2$Cl$_2$ (123 mL, 0.5 M) and NaHCO$_3$ (7.8 g, 92.4 mmol, 1.5 equiv). The suspension was cooled to 0° C. in an ice bath and DMP (31.3 g, 73.9 mmol, 1.2 equiv) was added portionwise over 20 min. The resultant grey-brown reaction mixture was stirred at 0° C. for 40 min. TLC analysis revealed complete conversion of starting material. The reaction mixture was quenched with dropwise addition of 10% aq. sodium thiosulfate solution (50 mL) and poured into a 250 mL separatory funnel containing water (100 mL). The mixture was extracted with CH$_2$Cl$_2$ (3×75 mL). The combined organic extracts were washed with brine (100 mL), dried over MgSO$_4$, filtered and concentrated under reduced pressure. The residue was purified by column chromatography on the ISCO Rf (100 g silica gel column) eluting with 100:0 to 60:40 hexanes:EtOAc as a gradient over 30 min. The title product was obtained as a yellow oil.

Step 2: Preparation of tert-butyl (1-(cyano(hydroxy)methyl)cyclohexyl)carbamate

Into a 250 mL round-bottom flask equipped with a magnetic stir bar and under nitrogen was added tert-butyl (1-formylcyclohexyl)carbamate (24.5 mmol, 1.0 equiv) and dioxane (60 mL). The reaction mixture was cooled to 0° C. in an ice bath. To this mixture was added aq. NaHSO₃ (40% in H₂O, 12.6 mL, 49.0 mmol, 2.0 equiv) over 30 minutes via an additional funnel. KCN (3.2 g, 49.0 mmol, 2.0 equiv) was added last. The mixture was stirred at 0° C. for 1 hour then allowed to warm to room temperature overnight. The reaction mixture was diluted with water (100 mL) and poured into a 250 mL separatory funnel containing water (50 mL) and extracted with EtOAc (3×50 mL). The combined organic extracts were washed with brine (50 mL), then dried over MgSO₄, filtered and concentrated under reduced pressure. The residue was purified by column chromatography on the ISCO Rf (100 g SNAP cartridge) eluting with 100:0 to 60:40 hexanes:EtOAc as a gradient over 30 min. The title product was obtained as a white solid.

Step 3: Preparation of tert-butyl (1-(2-amino-1-hydroxy-2-oxoethyl)cyclohexyl)carbamate Into a 100 mL round-bottom flask equipped with a magnetic stir bar was added tert-butyl (1-(cyano(hydroxy)methyl)cyclohexyl)carbamate (9.56 mmol, 1.0 equiv), DMSO (30 mL) and water (10 mL). The reaction mixture was cooled to 0° C. in an ice bath. To this solution was added K₂CO₃ (660 mg, 4.78 mmol, 0.5 equiv) followed by H₂O₂·urea (4.5 g, 47.8 mmol, 5.0 equiv). The suspension was stirred at 0° C. for 30 min, then slowly warmed up to room temperature overnight in an ice bath. TLC analysis at this time revealed conversion to product. The reaction mixture was cooled to 0° C. in an ice bath, 10% aq. sodium thiosulfate solution (75 mL) was added and the reaction mixture was stirred for 30 min. The mixture was poured into a 250 mL separatory funnel and extracted with EtOAc (3×100 mL). The combined organic extracts were washed with brine (100 mL), dried over MgSO₄, filtered and concentrated under reduced pressure. The residue was purified by column chromatography on the ISCO Rf (40 g silica gel column) eluting with 80:20 to 0:100 hexanes:EtOAc as a gradient over 30 min. The title product was obtained as a yellow oil.

Step 4: Preparation of 2-(1-aminocyclohexyl)-2-hydroxyacetamide hydrochloride

Prepared in the same manner as 2-(1-aminocyclobutyl)-2-hydroxyacetamide hydrochloride (step 4, intermediate A) using tert-butyl (1-(2-amino-1-hydroxy-2-oxoethyl)cyclohexyl)carbamate to provide the title product.

Intermediate G: 2-(2-aminospiro[3.3]heptan-2-yl)-2-hydroxyacetamide hydrochloride

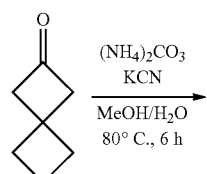

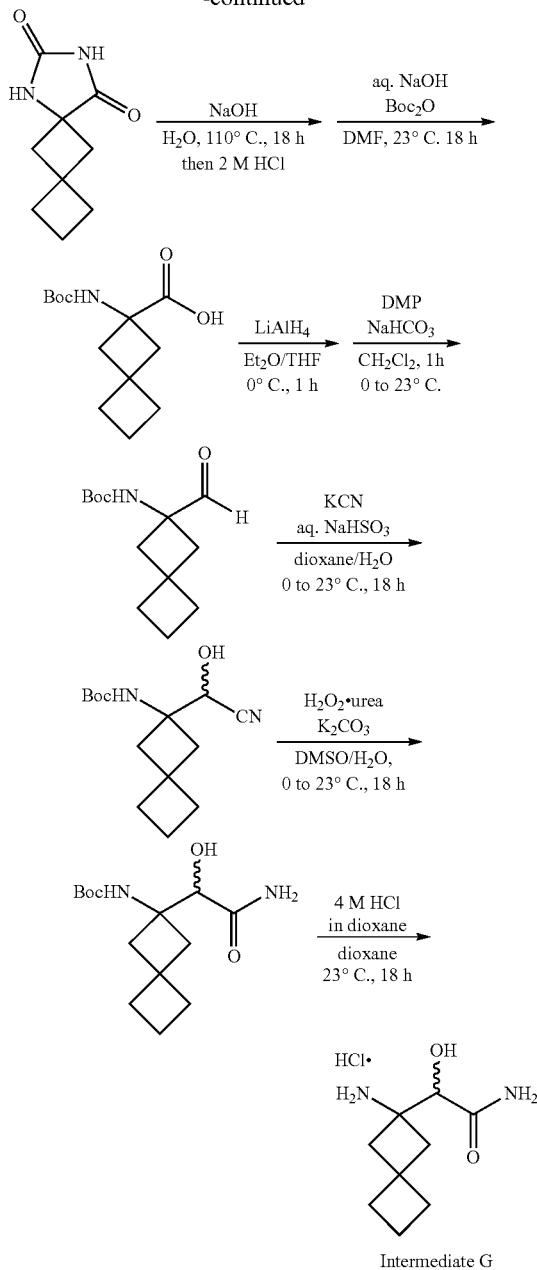

Intermediate G

Step 1: Preparation of 7,9-diazadispiro[3.1.4⁶.1⁴]undecane-8,10-dione

Into a 250 mL round-bottom flask equipped with a magnetic stir bar, reflux condenser and under nitrogen was added spiro[3.3]heptan-2-one (3.3 g, 30 mmol, 1.0 equiv), KCN (5.9 g, 90 mmol, 3.0 equiv), (NH₄)₂CO₃ (8.7 g, 90 mmol, 3.0 equiv), H₂O (45 mL) and methanol (45 mL). The brown solution was refluxed at 80° C. for 6 hours. LCMS analysis revealed the completion of reaction. The reaction mixture was cooled to room temperature and concentrated under reduced pressure to half of its volume. The concentrated solution was cooled in an ice bath for 20 min. The chilled solution was acidified with 2 M HCl (18.8 mL). The resulting precipitate was collected via vacuum filtration and washed with cold water to remove traces of cyanide salt. The solid was dried under vacuum for 18 h to afford the title product as a fine pale yellow solid.

Step 2: Preparation of 2-((tert-butoxycarbonyl)amino)spiro[3.3]heptane-2-carboxylic acid Into a 250 mL round-bottom flask equipped with a magnetic stir bar, reflux condenser and under nitrogen was added 7,9-diazadispiro[3.1.4614]undecane-8,10-dione (3.0 g, 16.8 mmol, 1.0 equiv), NaOH (2.7 g, 67.3 mmol, 4.0 equiv) and H$_2$O (67 mL). The suspension was refluxed at 110° C. for 18 hours, yielding a homogeneous dark brown solution. LCMS revealed the completion of hydrolysis. The reaction mixture was cooled to room temperature and chilled in an ice bath. To the chilled solution was added 34 mL of 2 M HCl (67 mmol, 4.0 equiv). Further dropwise addition of 2 M HCl was conducted until the pH of the solution reached 4-6, as monitored by pH paper. The resultant white precipitate was collected through vacuum filtration and washed with water. The solid was further dried under vacuum for 18 h before subjecting to Boc protection.

Into a 250 mL round-bottom flask equipped with a magnetic stir bar was added the above white solid, 1 M NaOH aqueous solution (33.6 mL, 2.0 equiv), Boc$_2$O (7.2 g, 33.6 mmol, 2.0 equiv) and DMF (5 mL). The reaction mixture was stirred at room temperature for 18 hours. LCMS revealed the completion of reaction. Any excess Boc$_2$O was quenched by adding imidazole (1.1 g, 16.8 mmol, 1.0 equiv). The mixture was stirred for 10 min, diluted with EtOAc (70 mL) and 1 M HCl (70 mL). The biphasic mixture was poured into a 250 mL separatory funnel and extracted with EtOAc (3×100 mL). The organic extracts were combined, washed with brine (100 mL), dried over MgSO$_4$ and concentrated under reduced pressure to yield a white solid, which was further dried under vacuum for 18 h to afford the title product.

Steps 3-6: Preparation of 2-(2-aminospiro[3.3]heptan-2-yl)-2-hydroxyacetamide hydrochloride Steps 3-6 was performed in the same manner as in the steps 1-4 for the synthesis of intermediate F starting with 2-((tert-butoxycarbonyl)amino)spiro[3.3]heptane-2-carboxylic acid.

The following hydroxyacetamide hydrochloride salts, intermediate H and intermediate I, were prepared using the same procedure as described above in the synthesis of intermediate G, starting with 4,4-dimethylcyclohexanone and spiro[2.5]octan-6-one, respectively.

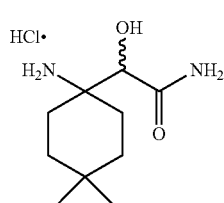

Intermediate H

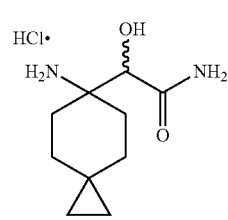

Intermediate I

Intermediate J: methyl 2-(1-aminocyclohexyl)-2-hydroxyacetate hydrochloride

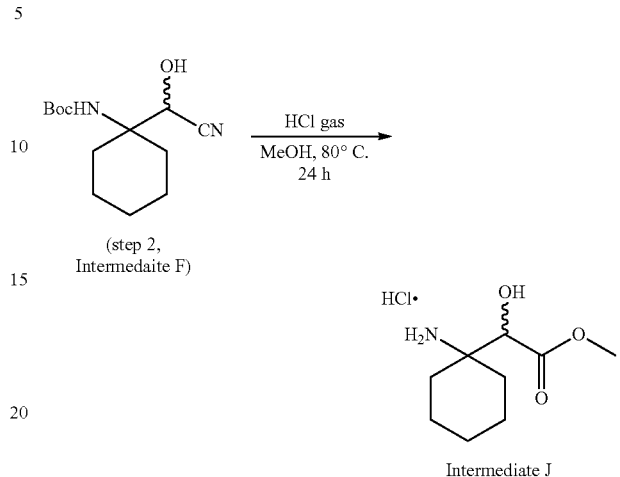

Intermediate J

Into a 200 mL round-bottom flask equipped with a magnetic stir bar, reflux condenser and under nitrogen was added tert-butyl (1-(cyano(hydroxy)methyl)cyclohexyl)carbamate (2.5 g, 9.9 mmol, 1.0 equiv) and methanol (25 mL). The solution was treated with HCl (gas) until saturated (10 min). The resulting mixture was refluxed at 80° C. for 1 hour and additional HCl (gas) was added (1 min). After refluxing at 80° C. for 2 hours, HCl gas was charged again for 1 min. The reaction mixture was refluxed at 80° C. for 18 h. LCMS revealed product and several impurities but no remaining starting material. The reaction mixture was further treated with HCl (gas, 1 min) and refluxed for another 6 hours. The mixture was cooled and concentrated under reduced pressure to give a yellowish oil, which was further dried under vacuum for 18 h to afford the title product.

Intermediate K: 1-(4,4,5,5-tetramethyl-1,3,2-dioxaborolan-2-yl)cyclohexan-1-amine hydrochloride

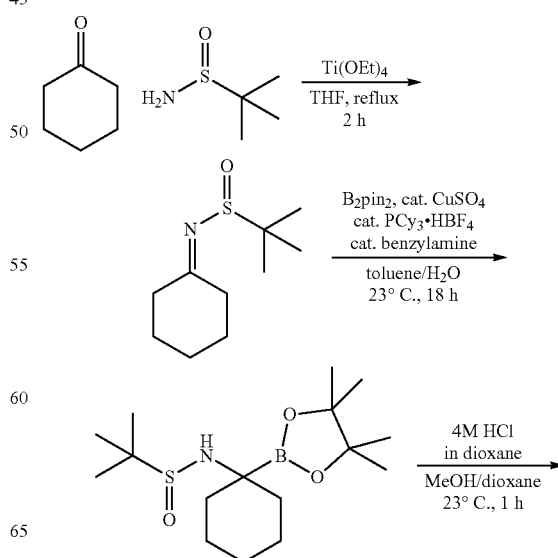

-continued

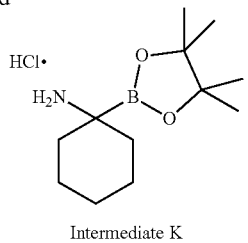

Intermediate K

Step 1: Preparation of N-cyclohexylidene-2-methylpropane-2-sulfinamide

Into a 100 mL round-bottom flask equipped with a magnetic stir bar and under nitrogen was added cyclohexanone (2.0 g, 18.4 mmol, 1.0 equiv), 2-methyl-2-propanesulfinamide (2.3 g, 18.4 mmol, 1.0 equiv), Ti(OEt)$_4$ (8.1 mL, 37.0 mmol, 2.0 equiv) and THF (anhydrous, 25 mL). The mixture was refluxed for 2 hours. TLC analysis revealed completion of reaction. The mixture was cooled to room temperature and poured into 10 mL of sat. aq. NaHCO$_3$ and filtered through a pad of celite on a sintered plastic funnel and washed with CH$_2$Cl$_2$. The combined organic extracts were concentrated under reduced pressure. The residue was purified by column chromatography through silica gel (8 cm×4 cm), eluting with 50:50 hexanes:EtOAc. The title product was obtained as a light yellow oil.

Step 2: Preparation of 2-methyl-N-(1-(4,4,5,5-tetramethyl-1,3,2-dioxaborolan-2-yl)cyclohexyl)propane-2-sulfinamide Into a 4 mL vial equipped with a magnetic stir bar and under nitrogen was added tricyclohexylphosphine tetrafluoroborate (PCy$_3$.HBF$_4$) (11 mg, 0.03 mmol, 0.02 equiv), toluene (300 µL), and an aq. solution of CuSO$_4$ (100 mM, 300 µL, 0.03 mmol, 0.02 equiv). The blue suspension was treated with benzylamine and the reaction mixture was stirred at room temperature for 10 min. The mixture was treated with N-cyclohexylidene-2-methylpropane-2-sulfinamide (300 mg, 1.49 mmol, 1.0 equiv) as a solution in 1.2 mL toluene and bis(pinacolate)diboron (762 mg, 3.0 mmol, 1.0 equiv). The resulting light brown solution was stirred at room temperature for 23 hours. LCMS analysis revealed product formation. The reaction mixture was filtered through a plug of Fluorosil (5 cm×3 cm diameter), eluting with EtOAc (30 mL). The yellow filtrate was concentrated under reduced pressure. The residue was purified by column chromatography through Fluorosil (12 cm×4 cm), eluting with 75:25 hexanes:EtOAc. The title product was obtained as a yellow oily solid.

Step 3: Preparation of 1-(4,4,5,5-tetramethyl-1,3,2-dioxaborolan-2-yl)cyclohexan-1-amine hydrochloride Into a 100 mL round-bottom flask equipped with a magnetic stir bar and under nitrogen was added 2-methyl-N-(1-(4,4,5,5-tetramethyl-1,3,2-dioxaborolan-2-yl)cyclohexyl)propane-2-sulfinamide, methanol (1 mL) and dioxane (3 mL). The solution was treated with 4 M HCl in dioxane (900 µL, 3.7 mmol, 2.0 equiv) and the reaction mixture was stirred at room temperature for 1 hour. LCMS analysis revealed complete conversion of starting material. The reaction mixture was concentrated under reduced pressure, resuspended in Et$_2$O (3 mL) and stirred for 20 min, resulting in a beige suspension. After 30 min, the suspension was filtered through Nylon 0.45 m filter paper and the beige solid was dried under vacuum for 18 h to afford the title product.

Intermediate L: (2S,4S)-1-((R)-2-(2-naphthamido)-3-cyclohexylpropanoyl)-4-azidopyrrolidine-2-carboxylic acid

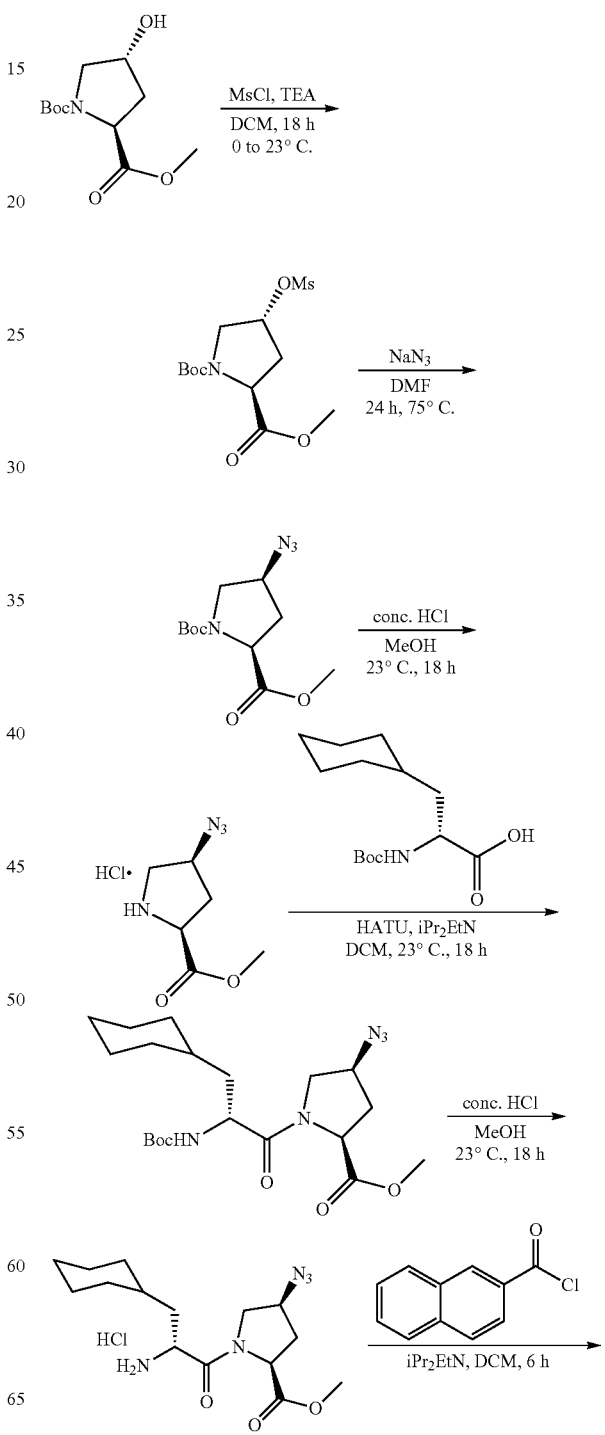

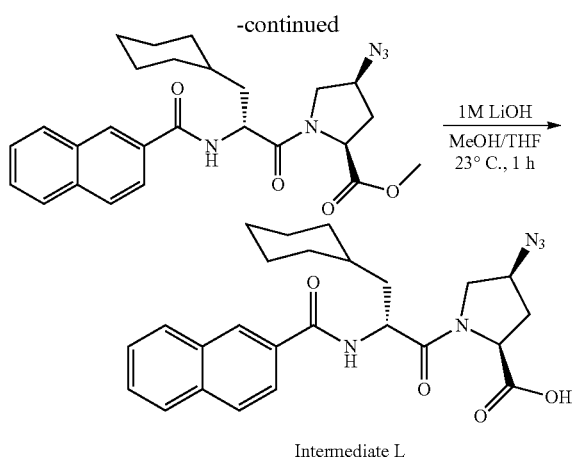

Intermediate L

Step 1: Preparation of 1-(tert-butyl) 2-methyl (2S,4R)-4-((methylsulfonyl)oxy)pyrrolidine-1,2-dicarboxylate To a solution of 1-(tert-butyl) 2-methyl (2S,4R)-4-hydroxypyrrolidine-1,2-dicarboxylate (13.2 g, 53.8 mmol, 1.0 equiv) in DCM (110 mL) cooled to 0° C. in an ice bath was added TEA (17 mL, 236.8 mmol, 4.4 equiv) and MsCl (9.2 mL, 118.4 mmol, 2.2 equiv). The reaction mixture was allowed to warm to 23° C. and stirred for 18 hours. After this time, the reaction mixture was diluted with DCM and washed with sat. aq. NaHCO₃, water and then brine. The organic layer was dried over MgSO4, filtered and concentrated under reduced pressure to provide the title compound.

Step 2: Preparation 1-(tert-butyl) 2-methyl (2S,4S)-4-azidopyrrolidine-1,2-dicarboxylate A suspension of 1-(tert-butyl) 2-methyl (2S,4R)-4-((methylsulfonyl)oxy) pyrrolidine-1,2-dicarboxylate (20.0 g, 53.8 mmol, 1.0 equiv) and NaN$_3$ (7.0 g, 107.6 mmol, 2.0 equiv) in DMF (110 mL) was stirred at 75° C. After 24 hours, the mixture was allowed to cool to 23° C. and was diluted with water and extracted with EtOAc (3×). The combined organic extracts were washed with brine, dried over MgSO$_4$, filtered and concentrated under reduced pressure. This residue was purified by column chromatography using a RediSep cartridge (80 g) eluting with a 0:100 to 20:80 EtOAc:hexanes gradient. The desired fractions were concentrated under reduced pressure to provide the title compound.

Step 3: Preparation of methyl (2S,4S)-4-azidopyrrolidine-2-carboxylate hydrochloride To a solution of 1-(tert-butyl) 2-methyl (2S,4S)-4-azidopyrrolidine-1,2-dicarboxylate (14.5 g, 53.8 mmol, 1.0 equiv) in MeOH (135 mL) was added 36% aq. HCl (19 mL, 188.3 mmol, 3.5 equiv) and the reaction mixture was stirred at 23° C. After 18 hours, the reaction mixture was concentrated under reduced pressure and the residue was azeotroped with MeOH (3×) to provide the title compound.

Step 4: Preparation of methyl (2S,4S)-4-azido-1-((R)-2-(((ler-butoxycarbonyl)amino)-3-cyclohexylpropanoyl)pyrrolidine-2-carboxylate A suspension of (R)-2-((tert-butoxycarbonyl)amino)-3-cyclohexylpropanoic acid (12.8 g, 47 mmol, 1.0 equiv) and HATU (17.9 g, 47 mmol, 1.0 equiv) in DCM (110 mL) was stirred for 10 minutes and then methyl (2S,4S)-4-azidopyrrolidine-2-carboxylate hydrochloride (9.7 g, 47 mmol, 1.0 equiv) and iPr$_2$EtN (20.5 mL, 118 mmol, 2.5 equiv) were added and the reaction mixture was stirred at 23° C. After 18 hours, the mixture was partitioned with 1 M HCl (200 mL). The aqueous layer was extracted with DCM (3×). The combined organic extracts were washed with brine, dried over MgSO$_4$, filtered and concentrated under reduced pressure. This residue was purified by column chromatography using a RediSep cartridge (120 g) eluting with a 0:100 to 50:50 EtOAc:hexanes gradient. The fractions were monitored by TLC (EtOAc/hexanes (⅜), visualized by ninhydrin staining). The desired fractions were concentrated under reduced pressure to provide the title compound.

Step 5: Preparation of methyl (2S,4S)-1-((R)-2-amino-3-cyclohexylpropanoyl)-4-azidopyrrolidine-2-carboxylate hydrochloride Prepared in a similar manner as methyl (2S,4S)-4-azidopyrrolidine-2-carboxylate hydrochloride (step 3, intermediate L) using methyl (2S,4S)-4-azido-1-((R)-2-((tert-butoxycarbonyl)amino)-3-cyclohexylpropanoyl)pyrrolidine-2-carboxylate to provide the title compound.

Step 6: Preparation of methyl (2S,4S)-1-((R)-2-(2-naphthamido)-3-cyclohexylpropanoyl)-4-azidopyrrolidine-2-carboxylate To a suspension of methyl (2S,4S)-1-((R)-2-amino-3-cyclohexylpropanoyl)-4-azidopyrrolidine-2-carboxylate hydrochloride (10.4 g, 29 mmol, 1.0 equiv) and 2-naphthoyl chloride (6.1 g, 31.9 mmol, 1.1 equiv) in DCM (150 mL) was added iPr$_2$EtN (12.6 mL, 72.5 mmol, 2.5 equiv) and the reaction mixture was stirred at 23° C. After 6 hours, the mixture was partitioned between 1 M HCl (100 mL) and DCM (3×). The combined organic extracts were washed with water, dried over MgSO$_4$, filtered and concentrated under reduced pressure. This residue was purified by column chromatography using a RediSep cartridge (330 g) eluting with a 0:100 to 50:50 EtOAc:hexanes gradient. The desired fractions were concentrated under reduced pressure to provide the title compound.

Step 7: Preparation of (2S,4S)-1-((R)-2-(2-naphthamido)-3-cyclohexylpropanoyl)-4-azidopyrrolidine-2-carboxylicacid To a solution of methyl (2S,4S)-1-((R)-2-(2-naphthamido)-3-cyclohexylpropanoyl)-4-azido pyrrolidine-2-carboxylate (2.9 g, 5.3 mmol, 1.0 equiv) in MeOH (25 mL) and THF (25 mL) was added 1 M aq. LiOH (26 mL, 26 mmol, 5.0 equiv) and the mixture was stirred at 23° C. After 1 hour, the reaction mixture was concentrated under reduced pressure and the resulting residue was dissolved in THF (30 mL) and 1 M aq. HCl was added until the pH of the solution reached 1. This mixture was further diluted with water and extracted with EtOAc (3×20 mL). The combined organic extracts were dried over MgSO$_4$, filtered and concentrated under reduced pressure to provide the title compound.

Intermediate M: (2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxylicacid

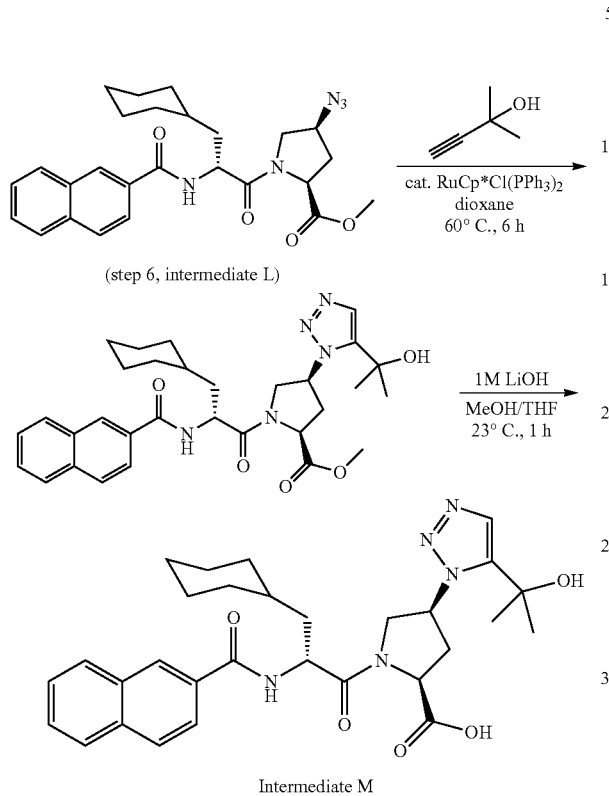

Intermediate M

Step 1: Preparation of methyl (2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxylate To a 40 mL scintillation vial was added methyl (2S,4S)-1-((R)-2-(2-naphthamido)-3-cyclohexylpropanoyl)-4-azidopyrrolidine-2-carboxylate (2.5 g, 5.2 mmol, 1.0 equiv), 2-methylbut-3-yn-2-ol (1.7 g, 20.8 mmol, 4.0 equiv), pentamethylcyclopentadienylbis(triphenylphosphine)ruthenium (II) chloride (199 mg, 0.26 mmol, 0.05 equiv) and dioxane (26 mL). The dark brown solution was purged with a stream of nitrogen for 30 min. The bubbler was removed and this mixture was stirred at 60° C. under nitrogen for 6 h. After this time, the mixture was purified by column chromatography using a RediSep cartridge (40 g) eluting with 100% EtOAc. The desired fractions were concentrated under reduced pressure to provide the title compound.

Step 2: Preparation of (2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxylic acid Prepared in a similar manner as (2S,4S)-1-((R)-2-(2-naphthamido)-3-cyclohexylpropanoyl)-4-azido pyrrolidine-2-carboxylic acid (step 7, intermediate L) to provide the title compound.

Intermediate N: (R)-2-(2-naphthamido)-3-cyclohexylpropanoic acid

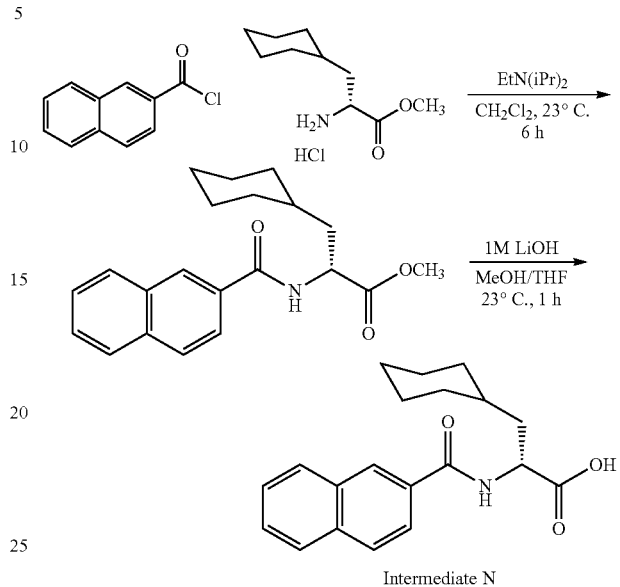

Intermediate N

Step 1: Preparation of methyl (R)-2-(2-naphthamido)-3-cyclohexylpropanoate

Prepared in a similar manner as methyl (2S,4S)-1-((R)-2-(2-naphthamido)-3-cyclohexylpropanoyl)-4-azidopyrrolidine-2-carboxylate (step 6, intermediate L) using (R)-methyl 2-amino-3-cyclohexylpropanoate hydrochloride and 2-naphthoyl chloride to provide the title compound.

Step 2: Preparation of (R)-2-(2-naphthamido)-3-cyclohexylpropanoic acid

Prepared in a similar manner as (2S,4S)-1-((R)-2-(2-naphthamido)-3-cyclohexylpropanoyl)-4-azido pyrrolidine-2-carboxylic acid (step 7, intermediate L) using (R)-methyl 2-(2-naphthamido)-3-cyclohexylpropanoate to provide the title compound.

Intermediate O: Benzyl(2S,3R,4R)-4-(5-(2-hydroxypropan-2-yl)-1H-1,2,3-triazol-1-yl)-3-methoxypyrrolidine-2-carboxylate hydrochloride

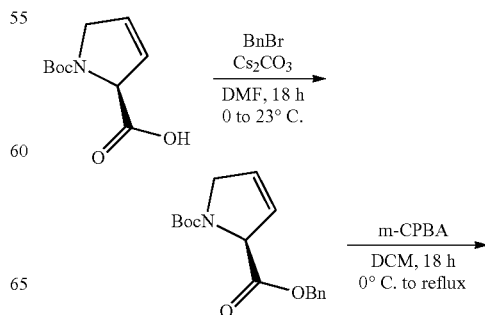

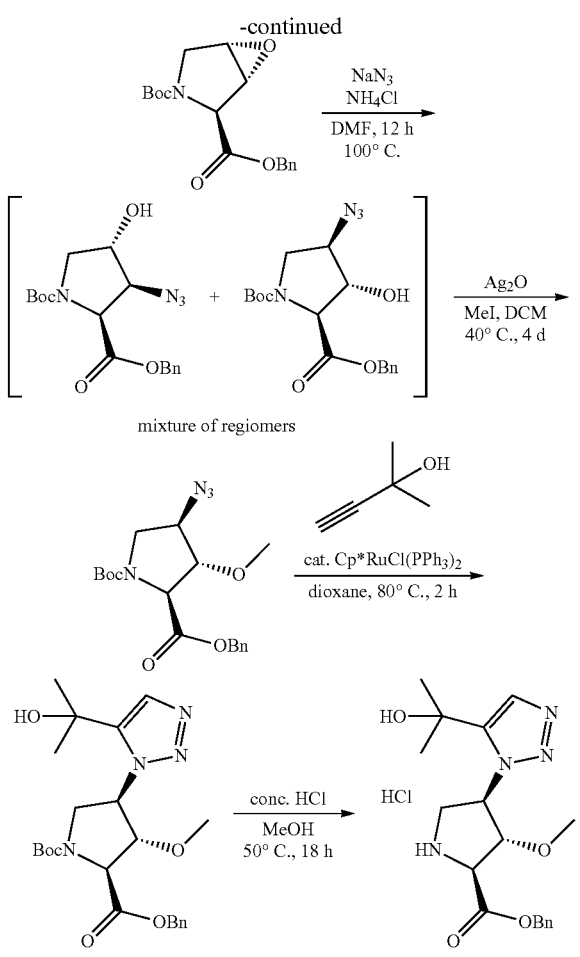

mixture of regiomers

Intermediate O

Step 1: Preparation of (S)-2-benzyl 1-tert-butyl 1H-pyrrole-1,2(2H,5H)-dicarboxylate Into a 250 mL round bottom flask equipped with a magnetic stir bar and under nitrogen was added Boc-3,4-dihydro-Pro-OH (5.0 g, 23.4 mmol, 1.0 equiv), $Cs_2CO_3$ (8.4 g, 25.7 mmol, 1.1 equiv) and DMF (75 mL). The suspension was cooled to 0° C. and benzyl bromide (3.3 mL, 28.1 mmol, 1.2 equiv) was added. The grey-tan suspension was stirred at 0° C. for 1 hour, then allowed to warm to room temperature overnight. LCMS revealed product formation. The reaction mixture was quenched with water (200 mL) and poured into a 500 mL separatory funnel containing water (50 mL) and extracted with EtOAc (3×50 mL). The combined organic extracts were washed with brine, dried over $MgSO_4$, filtered and concentrated under reduced pressure. The residue was purified by column chromatography on the ISCO Rf (100 g SNAP cartridge) eluting with 100:0 to 60:40 hexanes:EtOAc as a gradient over 30 min. The resulting yellow oil was further dried under vacuum to yield the title product.

Step 2: Preparation of 2-benzyl 3-(tert-butyl) (1R,2S,5S)-6-oxa-3-azabicyclo[3.1.0]hexane-2,3-dicarboxylate Into a 250 mL round bottom flask equipped with magnetic stir bar, reflux condenser and under nitrogen was added (S)-2-benzyl 1-tert-butyl 1H-pyrrole-1,2(2H,5H)-dicarboxylate (4.5 g, 14.9 mmol, 1.0 equiv) and DCM (35 mL). The solution was cooled to 0° C. in an ice bath and treated with m-CPBA (6.7 g, 29.7 mmol, 2.0 equiv). After warming to room temperature, the reaction mixture was refluxed for 18 h. LCMS analysis revealed complete conversion of starting material. The reaction mixture was cooled to room temperature and quenched with 10% aq. $Na_2S_2O_3$ (100 mL). The mixture was stirred at room temperature for 1 hour and poured into a 250 mL separatory funnel and extracted with DCM (3×75 mL). The combined organic extracts were washed with sat. aq. $NaHCO_3$ (2×75 mL), brine (75 mL), dried over $MgSO_4$, filtered and concentrated under reduced pressure. The residue was purified by column chromatography on the ISCO Rf (80 g silica gel Gold column+20 g pre-cartridge) eluting with 100:0 to 60:40 hexanes:EtOAc as a gradient over 30 min. Both diastereomers were collected and further dried under vacuum. The resulting mixture of two diastereomers was subject to further purification by column chromatography on the ISCO Rf (80 g silica gel Gold column+20 g pre-cartridge) eluting with 100:0 to 60:40 hexanes:EtOAc as a gradient over 30 min. The desired diastereomer (first eluting peak) was isolated as a clear oil.

Step 3: Preparation of 2-benzyl 1-(tert-butyl) (2S,3S,4S)-3-azido-4-hydroxypyrrolidine-1,2-dicarboxylate and 2-benzyl 1-(tert-butyl) (2S,3R,4R)-4-azido-3-hydroxypyrrolidine-1,2-dicarboxylate (Mixture of Two Regioisomers)

Into a 100 mL microwave vial equipped with magnetic stir bar under nitrogen was added 2-benzyl 3-(tert-butyl) (1R,2S,5S)-6-oxa-3-azabicyclo[3.1.0]hexane-2,3-dicarboxylate (1.8 g, 5.6 mmol, 1.0 equiv), sodium azide (1.8 g, 28.2 mmol, 5.0 equiv), $NH_4Cl$ (603 mg, 11.3 mmol, 2.0 equiv) and DMF (15 mL). The vial was sealed, kept under nitrogen and heated to 100° C. in an oil bath for 2 hours. LCMS analysis revealed complete conversion of starting material and formation of two regioisomers. Both LCMS and TLC indicated that the two regioisomers would be difficult to separate. The reaction mixture was cooled to room temperature and poured into a 250 mL separatory funnel containing water (100 mL) and extracted with EtOAc (3×30 mL). The combined organic extracts were washed with brine, dried over $MgSO_4$, filtered and concentrated under reduced pressure. The residue was purified by column chromatography on the ISCO Rf (80 g silica gel column+20 g pre-cartridge) eluting with 80:20 to 20:80 hexanes:EtOAc as a gradient over 30 min. The mixture of two regioisomers were collected, further dried under vacuum to afford a clear oil.

Step 4: Preparation of 2-benzyl 1-(tert-butyl) (2S,3R,4R)-4-azido-3-methoxypyrrolidine-1,2-dicarboxylate Into a 75 mL bomb (high pressure, thick-walled reaction flask) equipped with magnetic stir bar was added the mixture of regioisomers obtained in step 3 (1.6 g, 4.3 mmol, 1.0 equiv), silver oxide (5.0 g, 21.5 mmol, 5.0 equiv) and DCM (10 mL). Iodomethane (1.3 mL, 21.5 mmol, 5.0 equiv) was then added. The black suspension was sealed in the flask, wrapped with aluminum foil and heated in an oil bath at 40° C. for 4 days. LCMS analysis revealed complete conversion of one regioisomer and formation of the desired methylation product, while the other regioisomer remained inactive under above reaction conditions. The reaction mixture was cooled to room temperature and filtered through a pad of celite on a sintered glass funnel, washing with DCM (3×10 mL). The combined organic extracts were concentrated under reduced pressure and dried under vacuum to afford the title product as a clear oil.

Step 5: Preparation of 2-benzyl 1-(tert-butyl) (2S,3R,4R)-4-(5-(2-hydroxypropan-2-yl)-1H-1,2,3-triazol-1-yl)-3-methoxypyrrolidine-1,2-dicarboxylate To a 40 mL scintillation vial was added 2-benzyl 1-(tert-butyl) (2S,3R,4R)-4-azido-3-methoxypyrrolidine-1,2-dicarboxylate (4.3 mmol, 1.0 equiv), 2-methylbut-3-yn-2-ol (855 μL, 8.6 mmol, 2 equiv), pentamethylcyclopentadienylbis(triphenylphosphine)ruthenium(II) chloride (169 mg, 0.22 mmol, 0.05 equiv) and dioxane (15 mL). This mixture was stirred at 80° C. under nitrogen for 2 hours. This reaction mixture was concentrated under reduced pressure and loaded onto an 80 g Gold silica gel column. The residue was purified by column chromatography on the ISCO Rf eluting with 80:20 to 20:80 hexanes:EtOAc as a gradient over 25 min. The desired fractions were concentrated under reduced pressure and further dried under vacuum to afford a brownish oil as the title product.

Step 6: Preparation of benzyl (2S,3R,4R)-4-(5-(2-hydroxypropan-2-yl)-1H-1,2,3-triazol-1-yl)-3-methoxypyrrolidine-2-carboxylate hydrochloride Into a 100 mL round bottom flask equipped with magnetic stir bar and under nitrogen was added 2-benzyl 1-(tert-butyl) (2S,3R,4R)-4-(5-(2-hydroxypropan-2-yl)-1H-1,2,3-triazol-1-yl)-3-methoxy pyrrolidine-1,2-dicarboxylate (1.7 g, 3.7 mmol, 1.0 equiv) and methanol (25 mL). Concentrated aq. HCl (12 M, 2 mL, 24 mmol, 6.5 equiv) was added and the brown solution was heated to 50° C. in an oil bath for 18 h. LCMS revealed conversion of starting material to product. The reaction mixture was cooled to room temperature and concentrated under reduced pressure. The crude mixture was co-evaporated with methanol (2×30 mL) to remove any trace amounts of HCl and water, yielding the title product.

Intermediate P: 2-((tert-butoxycarbonyl)amino)-3-cyclohexyl-2-methylpropanoic acid

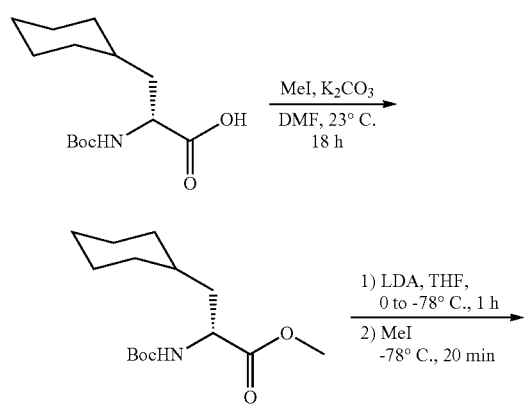

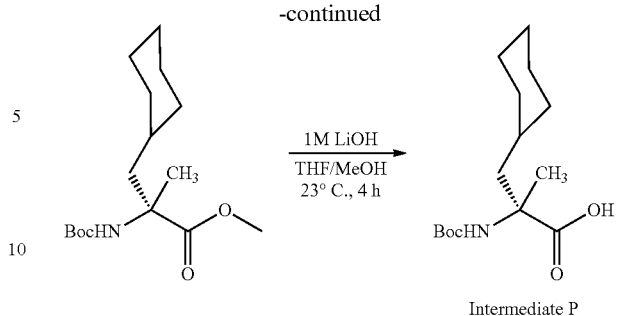

Intermediate P

Step 1: Preparation of methyl (R)-2-((tert-butoxycarbonyl)amino)-3-cyclohexylpropanoate Into a 100 mL round bottom flask equipped with a magnetic stir bar and under nitrogen was added Boc-3-cyclohexyl-D-alanine (3.0 g, 11.1 mmol, 1.0 equiv), K₂CO₃ (8.4 g, 11.1 mmol, 1.0 equiv) and DMF (20 mL). The solution was treated with methyl iodide (753 μL, 12.1 mmol, 1.1 equiv) and the reaction mixture was stirred at room temperature for 18 h. To the reaction mixture was added EtOAc (100 mL) and the mixture was washed with water (3×100 mL). The organic layer was dried over MgSO₄, filtered and concentrated under reduced pressure to give the title compound as an oil.

Step 2: Preparation of methyl 2-((tert-butoxycarbonyl)amino)-3-cyclohexyl-2-methylpropanoate Into a 100 mL flame-dried round bottom flask equipped with magnetic stir bar under nitrogen was added diisopropylamine (3.7 mL, 26.4 mmol, 2.4 equiv) and anhydrous THF (25 mL). The solution was cooled to −78° C. in an acetone/dry ice bath. n-Butyllithium (2.5 M in hexanes, 10.6 mL, 2.4 equiv) was added dropwise and the mixture was stirred at −78° C. for 30 min. Into another 100 mL flame-dried round bottom flask under nitrogen was added (R)-2-((tert-butoxycarbonyl)amino)-3-cyclohexylpropanoate (11.0 mmol, 1.0 equiv) and anhydrous THE (25 mL). The mixture was added to the lithium diisopropylamide solution dropwise. The reaction mixture was stirred at −78° C. for 30 min, followed by the addition of methyl iodide (691 μL, 11.0 mmol, 1.1 equiv). The mixture was allowed to warm up to room temperature and stirred for 20 min. LCMS analysis revealed the formation of product. The reaction mixture was quenched with sat. aq. NaHCO₃ (100 mL) and poured into a 250 mL separatory funnel and extracted with DCM (3×100 mL). The combined organic extracts were washed with brine (75 mL), dried over MgSO₄, filtered and concentrated under reduced pressure. The residue was purified by column chromatography on the ISCO Rf (40 g silica gel Gold column+20 g pre-cartridge) eluting with 100:0 to 90:10 DCM:MeOH as a gradient over 17 min. The desired peaks were concentrated under reduced pressure and dried under vacuum to afford the title compound.

Step 3: Preparation of 2-((tert-butoxycarbonyl)amino)-3-cyclohexyl-2-methylpropanoic acid Prepared in a similar manner as (2S,4S)-1-((R)-2-(2-naphthamido)-3-cyclohexylpropanoyl)-4-azido pyrrolidine-2-carboxylic acid (step 7, intermediate L) using methyl 2-((tert-butoxycarbonyl)amino)-3-cyclohexyl-2-methylpropanoate to provide the title compound.

Intermediate O: 2-((tert-butoxycarbonyl)amino)-3-(spiro[3.3]heptan-2-yl)propanoic acid

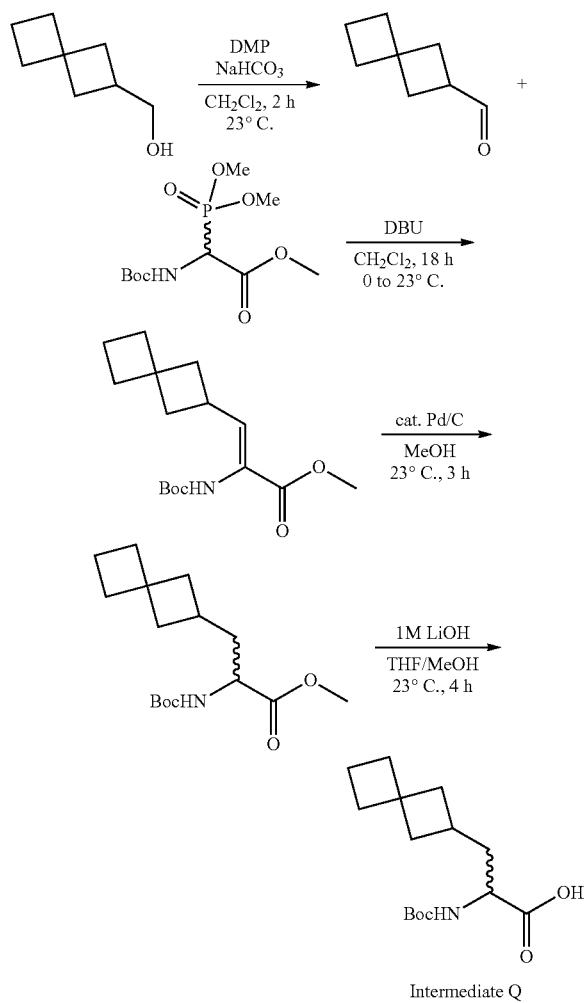

Intermediate Q

Step 1: Preparation of spiro[3.3]heptane-2-carbaldehyde

Into a 50 mL round-bottom flask equipped with a magnetic stir bar and under nitrogen was added spiro[3.3]heptan-2-ylmethanol (150 mg, 1.2 mmol, 1.0 equiv), NaHCO₃ (150 mg, 1.8 mmol, 1.5 equiv) and DCM (3 mL). The suspension was treated with DMP (605 mg, 1.4 mmol, 1.2 equiv) and the mixture was stirred for 2 hours at room temperature. TLC analysis (10:90 EtOAC:hexanes v/v) revealed complete conversion of the starting alcohol. The reaction mixture was quenched with 10 mL of 10% aq. Na₂S₂O₃ and stirred at room temperature for 30 min. The mixture was extracted with DCM (3×10 mL) using a Cl-phase separator cartridge. The combined organic extracts were concentrated under reduced pressure and loaded onto a 5 g C18 pre-cartridge. Purification was conducted by reverse-phase chromatography on the ISCO Rf (12 g Gold C18 column) eluting with 0:100 to 20:80 MeOH:DCM as a gradient over 20 min. The desired peaks were concentrated under reduced pressure and dried under vacuum to afford the title compound as a clear oil.

Step 2: Preparation of methyl (Z)-2-((tert-butoxycarbonyl)amino)-3-(spiro[3.3]heptan-2-yl) acrylate Into a 100 mL flame-dried round bottom flask equipped with magnetic stir bar under nitrogen was added methyl 2-((tert-butoxycarbonyl)amino)-2-(dimethoxyphosphoryl) acetate (169 mg, 0.57 mmol, 1.0 equiv) and anhydrous DCM (2 mL). The solution was cooled to 0° C. in an ice bath. To this mixture was slowly added DBU (86 L, 0.57 mmol, 1.0 equiv). The mixture was stirred at 0° C. for 20 min and then treated with a solution of spiro[3.3]heptane-2-carbaldehyde (86 mg, 0.69 mmol, 1.2 equiv) in DCM (2 mL). The reaction mixture was allowed to warm to room temperature slowly overnight. LCMS analysis revealed the formation of product. The reaction mixture was quenched with sat. aq. NH₄Cl (20 mL) and poured into a 125 mL separatory funnel and extracted with DCM (3×15 mL). The combined organic extracts were washed with brine (25 mL), dried over MgSO₄, filtered and concentrated under reduced pressure. The residue was purified by column chromatography on the ISCO Rf (12 g silica gel column+5 g pre-cartridge) eluting with 0:100 to 30:70 EtOAc:hexanes as a gradient over 19 min. The desired peaks were concentrated under reduced pressure and dried under vacuum to afford the title compound.

Step 3: Preparation of methyl 2-((tert-butoxycarbonyl)amino)-3-(spiro[3.3]heptan-2-yl)propanoate Into a 25 mL round bottom flask equipped with a magnetic stir bar and under nitrogen was added methyl (Z)-2-((tert-butoxycarbonyl)amino)-3-(spiro[3.3]heptan-2-yl) acrylate (358 mg, 0.57 mmol, 1.0 equiv) and MeOH (3 mL). The solution was sparged with nitrogen for 30 min. Pd/C (10% wt., 25 mg) was added. The nitrogen source was then replaced with a hydrogen balloon. The reaction mixture was sparged with 1 balloon of hydrogen and the reaction mixture was stirred at room temperature under an atmosphere of hydrogen for 3 h. LCMS analysis revealed completion of reaction. The reaction mixture was filtered through a pad of celite on a plastic sintered funnel, washed with DCM (3×5 mL). The clear filtrate was concentrated under reduced pressure and used directly in the next step without further purification.

Step 4: Preparation of 2-((tert-butoxycarbonyl)amino)-3-(spiro[3.3]heptan-2-yl)propanoic acid Prepared in a similar manner as (2S,4S)-1-((R)-2-(2-naphthamido)-3-cyclohexylpropanoyl)-4-azido pyrrolidine-2-carboxylic acid (step 7, intermediate L) using methyl 2-((tert-butoxycarbonyl)amino)-3-(spiro[3.3]heptan-2-yl) propanoate to provide the title compound.

Intermediate R: 3-(bicyclo[2.2.1]heptan-1-yl)-2-((tert-butoxycarbonyl)amino)propanoic acid

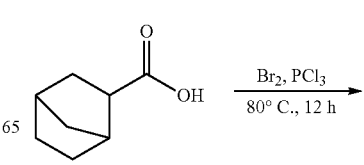

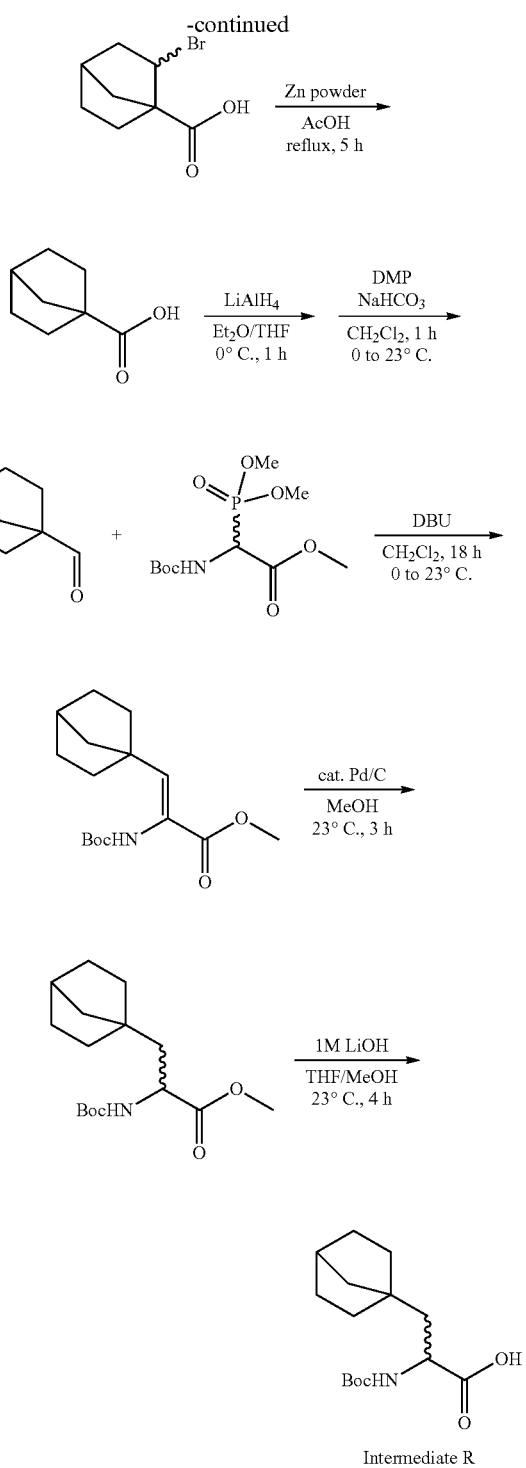

Step 1: Preparation of 2-bromobicyclo[2.2.1]heptane-1-carboxylic acid

To a 50 mL round bottom flask equipped with magnetic stir bar was added norbornane-2-carboxylic acid (4.7 g, 35.7 mmol, 1.0 equiv) and bromine (1.9 mL, 40.8 mmol, 1.1 equiv). The suspension was stirred at room temperature until a solution was obtained. $PCl_3$ (141 µL, 1.7 mmol, 0.05 equiv) was then added slowly and dropwise (significant exotherm observed). A reflux condenser was fitted to the flask with a nitrogen gas inlet and gas outlet (Tygon tubing) running into a scrubber solution of sodium sulfite (1 M, 200 mL). After the addition was complete, the reaction mixture was heated in an oil bath at 80° C. for 4 h. After this time, the reaction mixture was cooled to 10° C. and $PCl_3$ (2 ml, 24.2 mmol, 0.68 equiv) was added dropwise. The reaction mixture was again heated to 80° C. for 8 h. The resulting dark orange mixture was then cooled to room temperature and diluted with ether (500 mL). The ethereal solution was transferred to a 1 L separation funnel and washed with 1 M sodium sulfite (2×300 mL), water (1×200 mL), and brine (1×200 mL). The organic layer was dried over $MgSO_4$, filtered, and concentrated under reduced pressure to afford an oil. Ice cold pentane (30 mL) was then added to the crude product and the mixture was stirred vigorously. After 20 min, a fine white precipitate formed, which was filtered and washed with pentane (10 mL) and then air dried under a gentle vacuum to afford the title product as a white solid material.

Step 2: Preparation of bicyclo[2.2.1]heptane-1-carboxylic acid

To a 50 mL round bottom flask equipped with magnetic stir bar and refluxing condenser was added zinc powder (<10 micron, 4.8 g, 73 mmol, 10 equiv) and acetic acid (6.7 mL). While vigorously stirring the heterogeneous mixture, 2-bromobicyclo[2.2.1]heptane-1-carboxylic acid (1.6 g, 7.3 mmol, 1.0 equiv) was added. A second portion of acetic acid (6.7 mL) was applied to rinse the walls of the flask. The reaction mixture was brought to a gentle reflux in an oil bath for 5 h. The reaction mixture was cooled to room temperature, filtered through a pad of Celite on a plastic sintered funnel, and washed with acetic acid (10 mL) and ethyl acetate (15 mL). The filtrate was concentrated under reduced pressure, water (10 mL) was added, and then the mixture was stirred vigorously to induce precipitation. The precipitate was collected by filtration, washed with water, and dried under vacuum for 18 h. Pentane (10 mL) was then added, and the mixture was stirred vigorously for 20 min during which time a fine white precipitate formed. The resulting precipitate was filtered, washed with pentane (5 mL), and air dried to afford the title product as a white solid.

Step 3: Preparation of bicyclo[2.2.1]heptane-1-carbaldehyde

Prepared in a similar manner as tert-butyl (1-formylcyclohexyl)carbamate (step 1, intermediate F) using bicyclo[2.2.1]heptane-1-carboxylic acid to provide the title compound.

Steps 4-6: Preparation of 3-(bicyclo[2.2.1]heptan-1-yl)-2-((tert-butoxycarbonyl)amino)propanoic acid Steps 4-6 were performed in the same manner as in steps 2-4 for the synthesis of intermediate Q starting with bicyclo[2.2.1]heptane-1-carbaldehyde.

PREPARATION OF EXAMPLES

Example 1: (2S,4S)-1-((R)-2-(2-naphthamido)-3-cyclohexylpropanoyl)-N-(1-(2-amino-2-oxoacetyl)cyclobutyl)-4-(5-(2-hydroxypropan-2-yl)-1H-1,2,3-triazol-1-yl)pyrrolidine-2-carboxamide

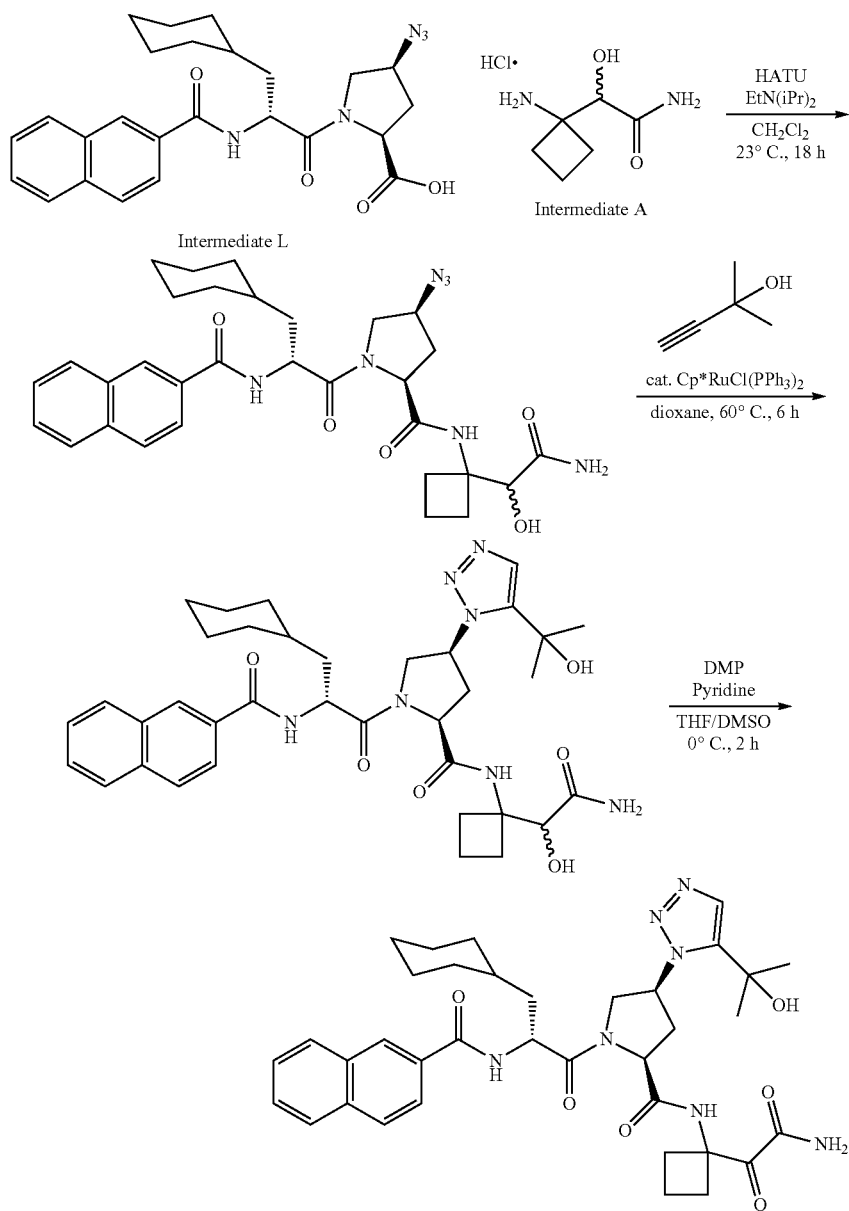

Example 1

Step 1: Preparation of (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide Into a 100 mL round-bottom flask, equipped with a magnetic stir bar and under nitrogen was added intermediate L (816 mg, 1.8 mmol, 1.0 equiv), intermediate A (350 mg, 1.9 mmol, 1.1 equiv) and HATU (737 mg, 1.9 mmol, 1.1 equiv). The solids were suspended in CH$_2$Cl$_2$ (anhydrous, 5 mL), treated with EtN(iPr)$_2$ (615 µL, 3.5 mmol, 2.0 equiv) and the reaction mixture was stirred at room temperature for 1 hour. LCMS analysis revealed conversion to product. The reaction mixture was quenched with 1 M HCl (30 mL) and extracted with CH$_2$Cl$_2$ (3×30 mL) using a Cl-phase separator cartridge. The combined organic extracts were concentrated under reduced pressure. The residue was purified by column chromatography on the ISCO Rf (40 g silica gel column+20 g pre-cartridge), eluting with 100:0 to 90:10 CH$_2$Cl$_2$:MeOH as a gradient over 20 min. The title product was obtained as a solid.

Step 2: Preparation of (2S,4S)-1-((R)-2-(2-naphthamido)-3-cyclohexylpropanoyl)-N-(1-(2-amino-1-hydroxy-2-oxoethyl)cyclobutyl)-4-(5-(2-hydroxypropan-2-yl)-1H-1,2,3-triazol-1-yl)pyrrolidine-2-carboxamide Prepared in a similar manner as methyl (2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxylate (step 1, intermediate M) using (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide to provide the title compound.

Step 3: Preparation of (2S,4S)-1-((R)-2-(2-naphthamido)-3-cyclohexylpropanoyl)-N-(1-(2-amino-2-oxoacetyl)cyclobutyl)-4-(5-(2-hydroxypropan-2-yl)-1H-1,2,3-triazol-1-yl)pyrrolidine-2-carboxamide Into a 25 mL round-bottom flask equipped with a magnetic stir bar and under nitrogen was added (2S,4S)-1-((R)-2-(2-naphthamido)-3-cyclohexylpropanoyl)-N-(1-(2-amino-1-hydroxy-2-oxoethyl)cyclobutyl)-4-(5-(2-hydroxypropan-2-yl)-1H-1,2,3-triazol-1-yl)pyrrolidine-2-carboxamide (180 mg, 0.27 mmol, 1.0 equiv), THE (2 mL), DMSO (0.5 mL) and pyridine (3 drops). The solution was cooled to 0° C. and DMP (907 mg, 2.14 mmol, 8.0 equiv) was added in two portions over 15 min. The mixture was stirred for 2 hours at 0° C. LCMS revealed approximately 60% conversion. In order to prevent further formation of impurities, the reaction mixture was quenched at this point by adding 2 mL of 10% aq. Na$_2$S203 and the mixture was stirred at room temperature for 30 min. The mixture was extracted with DCM (3×10 mL) using a Cl-phase separator cartridge. The combined organic extracts were concentrated under reduced pressure and loaded onto a 5 g C18 pre-cartridge. Purification was conducted by reverse-phase chromatography on the ISCO Rf (C18 column 26 g) eluting with 70:30 to 0:100 H$_2$O:MeCN+0.1% HCOOH as a gradient over 25 min. The desired peaks were concentrated under reduced pressure and dried under vacuum to afford the title compound as a white solid. MS (ESI+) 672 (M+1)$^{\oplus}$ The following compounds, examples 2 and 3, were prepared in a similar manner as example 1, from intermediates B and C, respectively.

| Example | Structure | MW | MS (ESI+) |
|---|---|---|---|
| 2 | (2S,4S)-1-((R)-2-(2-naphthamido)-3-cyclohexylpropanoyl)-N-(1-(2-amino-2-oxoacetyl)cyclopropyl)-4-(5-(2-hydroxypropan-2-yl)-1H-1,2,3-triazol-1-yl)pyrrolidine-2-carboxamide | 657.77 | 658 (M + 1)$^{\oplus}$ |
| 3 | (2S,4S)-1-((R)-2-(2-naphthamido)-3-cyclohexylpropanoyl)-N-(1-(2-amino-2-oxoacetyl)cyclopentyl)-4-(5-(2-hydroxypropan-2-yl)-1H-1,2,3-triazol-1-yl)pyrrolidine-2-carboxamide | 685.83 | 686 (M + 1)$^{\oplus}$ |

Example 4: (2S,4S)-1-((R)-2-(2-naphthamido)-3-cyclohexylpropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide

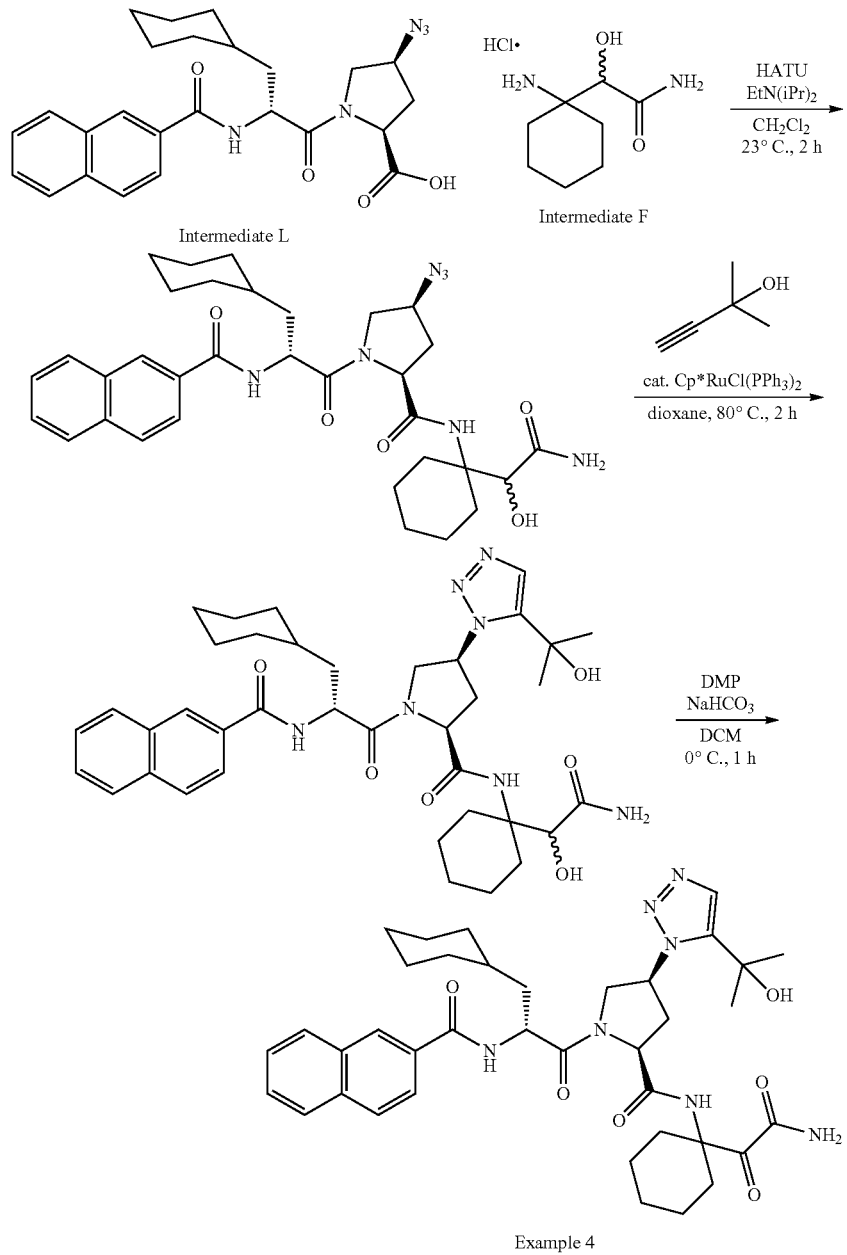

Example 4

Step 1: Preparation of (2S,4S)-1-((R)-2-(2-naphthamido)-3-cyclohexylpropanoyl)-N-(1-(2-amino-1-hydroxy-2-oxoethyl)cyclohexyl)-4-azidopyrrolidine-2-carboxamide Into a 50 mL round-bottom flask, equipped with a magnetic stir bar and under nitrogen was added intermediate L (326 mg, 0.70 mmol, 1.0 equiv), intermediate F (0.85 mmol, 1.2 equiv) and HATU (294 mg, 0.77 mmol, 1.1 equiv). The solids were suspended in $CH_2Cl_2$ (anhydrous, 2 mL), treated with $EtN(iPr)_2$ (367 µL, 2.1 mmol, 3.0 equiv) and the reaction mixture was stirred at room temperature for 2 h. LCMS analysis revealed conversion to product. The reaction mixture was quenched with 1 M HCl (15 mL) and extracted with $CH_2Cl_2$ (3×10 mL) using a Cl-phase separator cartridge. The combined organic extracts were concentrated under reduced pressure. The residue was purified by column chromatography on the ISCO Rf (24 g Gold silica gel column+5 g pre-cartridge), eluting with 100:0 to 90:10 $CH_2Cl_2$:MeOH as a gradient over 25 min. The desired fractions were concentrated under reduced pressure and dried under vacuum to provide the title compound.

Step 2: Preparation of (2S,4S)-1-((R)-2-(2-naph-thamido)-3-cyclohexylpropanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide Into a 25 mL round-bottom flask equipped with a magnetic stir bar, refluxing condenser and under nitrogen was added (2S,4S)-1-((R)-2-(2-naphthamido)-3-cyclohexylpropanoyl)-N-(1-(2-amino-1-hydroxy-2-oxoethyl)cyclohexyl)-4-azidopyrrolidine-2-carboxamide (350 mg, 0.57 mmol, 1.0 equiv), 2-methylbut-3-yn-2-ol (113 µL, 1.14 mmol, 2.0 equiv), pentamethylcyclopentadienylbis(triphenylphosphine)ruthenium (II) chloride (48 mg, 0.06 mmol, 0.1 equiv) and dioxane (3 mL). This red solution was sparged with nitrogen for 15 min, capped and heated in an oil bath at 80° C. under nitrogen for 2 h. After this time, the mixture was cooled to room temperature and loaded onto a 12 g silica gel pre-cartridge and dried. Purification was conducted by column chromatography on the ISCO Rf (24 g Gold silica gel column) eluting with 100:0 to 90:10 DCM:MeOH as a gradient over 25 min. The desired fractions were concentrated under reduced pressure and dried under vacuum to provide the title compound.

Step 3: Preparation of (2S,4S)-1-((R)-2-(2-naphthamido)-3-cyclohexylpropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide Into a 50 mL round-bottom flask equipped with a magnetic stir bar and under nitrogen was added (2S,4S)-1-((R)-2-(2-naphthamido)-3-cyclohexylpropanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide (150 mg, 0.21 mmol, 1.0 equiv), NaHCO$_3$ (36 mg, 0.43 mmol, 2.0 equiv) and DCM (2 mL). The suspension was cooled to 0° C. in an ice bath and DMP (109 mg, 0.26 mmol, 1.2 equiv) was added. The mixture was stirred for 1 hour at 0° C. LCMS revealed approximately 70% conversion. Another 0.25 equiv of DMP (23 mg) was added and the reaction mixture was stirred for 30 min. LCMS revealed over 90% conversion. The reaction mixture was quenched with 10 mL of 10% aq. Na$_2$S$_2$O$_3$ and was stirred at room temperature for 30 min. The mixture was extracted with DCM (3×10 mL) using a Cl-phase separator cartridge. The combined organic extracts were concentrated under reduced pressure and loaded onto a 5 g C18 pre-cartridge. Purification was conducted by reverse-phase chromatography on the ISCO Rf (13 g Gold C18 column) eluting with 90:10 to 20:80 H$_2$O:MeCN+0.1% HCOOH as a gradient over 20 min. The desired peaks were concentrated under reduced pressure and dried under vacuum to afford the title compound as a white solid. MS (ESI+): 700 (M+1)$^\oplus$; $^1$H NMR (300 MHz, DMSO-d$_6$) δ 8.86-8.72 (m, 1H), 8.58-8.44 (m, 1H), 8.19-8.06 (m, 1H), 8.06-7.86 (m, 4H), 7.70-7.46 (m, 3H), 7.44-7.32 (m, 1H), 7.32-7.23 (m, 1H), 5.79-5.52 (m, 2H), 5.03-4.80 (m, 1H), 4.56-4.38 (m, 1H), 4.38-4.16 (m, 1H), 4.16-3.95 (m, 1H), 2.85-2.55 (m, 2H), 2.26-1.95 (m, 2H), 1.94-1.44 (m, 15H), 1.44-1.20 (m, 6H), 1.20-0.72 (m, 6H) ppm.

The following compounds, examples 5 and 6, were prepared in a similar manner as example 1, from intermediates D and E, respectively.

| Example | Structure | MW | MS (ESI+) |
|---|---|---|---|
| 5 | 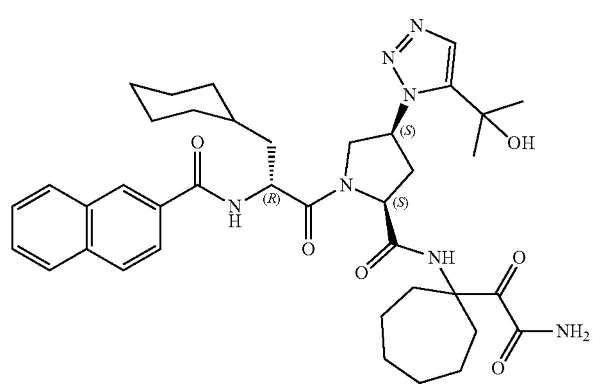 | 713.88 | 714 (M + 1)$^\oplus$ |

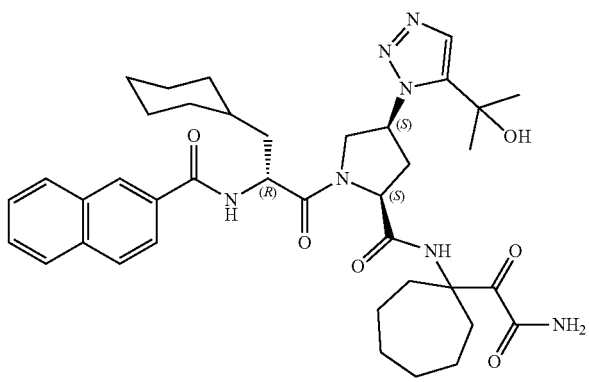

(2S,4S)-1-((R)-2-(2-naphthamido)-3-cyclohexylpropanoyl)-N-(1-(2-amino-2-oxoacetyl)cycloheptyl)-4-(5-(2-hydroxypropan-2-yl)-1H-1,2,3-triazol-1-yl)pyrrolidine-2-carboxamide

| Example | Structure | MW | MS (ESI+) |
|---|---|---|---|
| 6 | 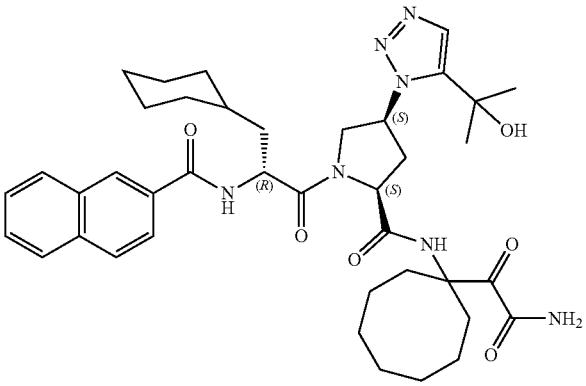 (2S,4S)-1-((R)-2-(naphthamido)-3-cyclohexylpropanoyl)-N-(1-(2-amino-2-oxoacetyl)cyclooctyl)-4-(5-(2-hydroxypropan-2-yl)-1H-1,2,3-triazol-1-yl)pyrrolidine-2-carboxamide | 727.91 | 728 $(M + 1)^{\oplus}$ |
Example 7: (1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)boronic acid
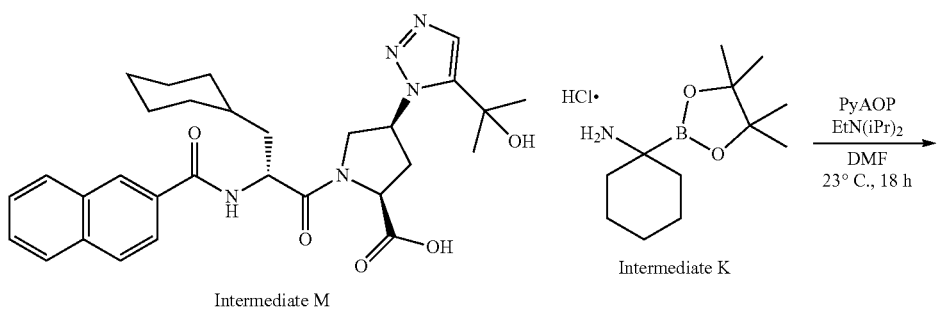
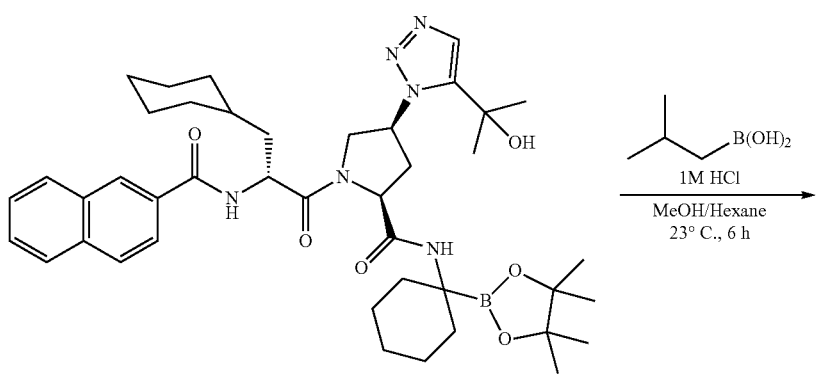

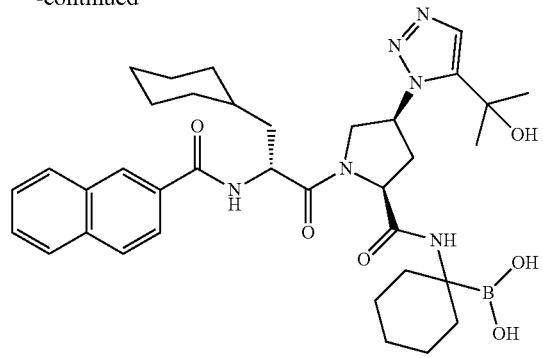

Example 7

Step 1: Preparation of (2S,4S)-1-((R)-2-(2-naphthamido)-3-cyclohexylpropanoyl)-4-(5-(2-hydroxypropan-2-yl)-1H-1,2,3-triazol-1-yl)-N-(1-(4,4,5,5-tetramethyl-1,3,2-dioxaborolan-2-yl)cyclohexyl)pyrrolidine-2-carboxamide Into a 4 mL sample vial equipped with a magnetic stir bar and under nitrogen was added intermediate M (103 mg, 0.19 mmol, 1.0 equiv), intermediate K (60 mg, 0.23 mmol, 1.2 equiv), PyAOP (120 mg, 0.23 mmol, 1.2 equiv), DMF (1 mL) and EtN(iPr)$_2$ (66 µL, 0.38 mmol, 2.0 equiv). The yellow solution was stirred at room temperature for 18 hours. LCMS revealed approximately 40% product formation. The reaction mixture was quenched with water (5 mL) and extracted with DCM (3×5 mL) using a Cl-phase separatory cartridge. The combined organic extracts were concentrated under reduced pressure. The residue was purified by column chromatography on Fluorosil (3 cm×8 cm), eluting with 95:5 DCM:MeOH. The desired fractions were concentrated under reduced pressure and dried under vacuum for 18 h to afford the title compound as a white solid.

Step 2: Preparation of (1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)boronic acid Into an 8 mL sample vial equipped with a magnetic stir bar and under nitrogen was added (2S,4S)-1-((R)-2-(2-naphthamido)-3-cyclohexylpropanoyl)-4-(5-(2-hydroxypropan-2-yl)-1H-1,2,3-triazol-1-yl)-N-(1-(4,4,5,5-tetramethyl-1,3,2-dioxaborolan-2-yl)cyclohexyl)pyrrolidine-2-carboxamide (30 mg, 0.04 mmol, 1.0 equiv), isobutyl boronic acid (20 mg, 0.20 mmol, 5.0 equiv) in methanol (0.5 mL) and hexanes (0.5 mL). The reaction mixture was treated with 1 M HCl in water (160 µL, 0.16 mmol, 4.0 equiv) and the biphasic suspension was stirred rigorously at room temperature for 6 h. LCMS analysis revealed complete conversion of starting material to desired product. The bottom methanol layer was removed and washed with hexanes (2×2 mL). The top hexane layer was further extracted with methanol (1 mL), and the combined methanol layers were concentrated under reduced pressure. Without further purification, the crude was further dried under vacuum for 18 h to afford the title compound. MS (ESI+) 656 (M-17)$^\oplus$

Example 8: (2S,4R)-1-((R)-2-(2-naphthamido)-3-cyclohexylpropanoyl)-N-(1-(2-amino-2-oxoacetyl)cyclohexyl)-4-(piperidin-1-yl)pyrrolidine-2-carboxamide

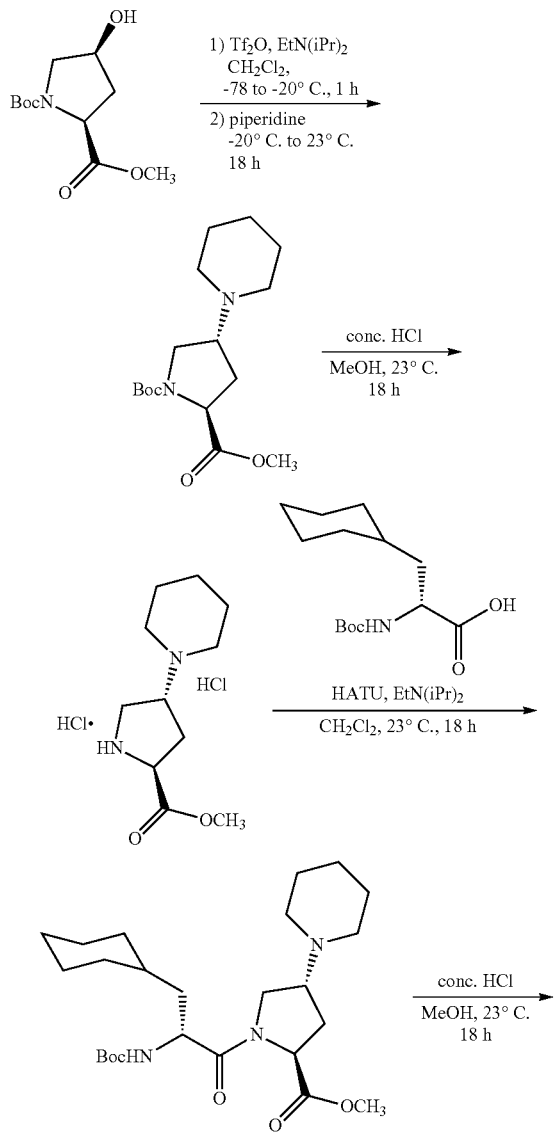

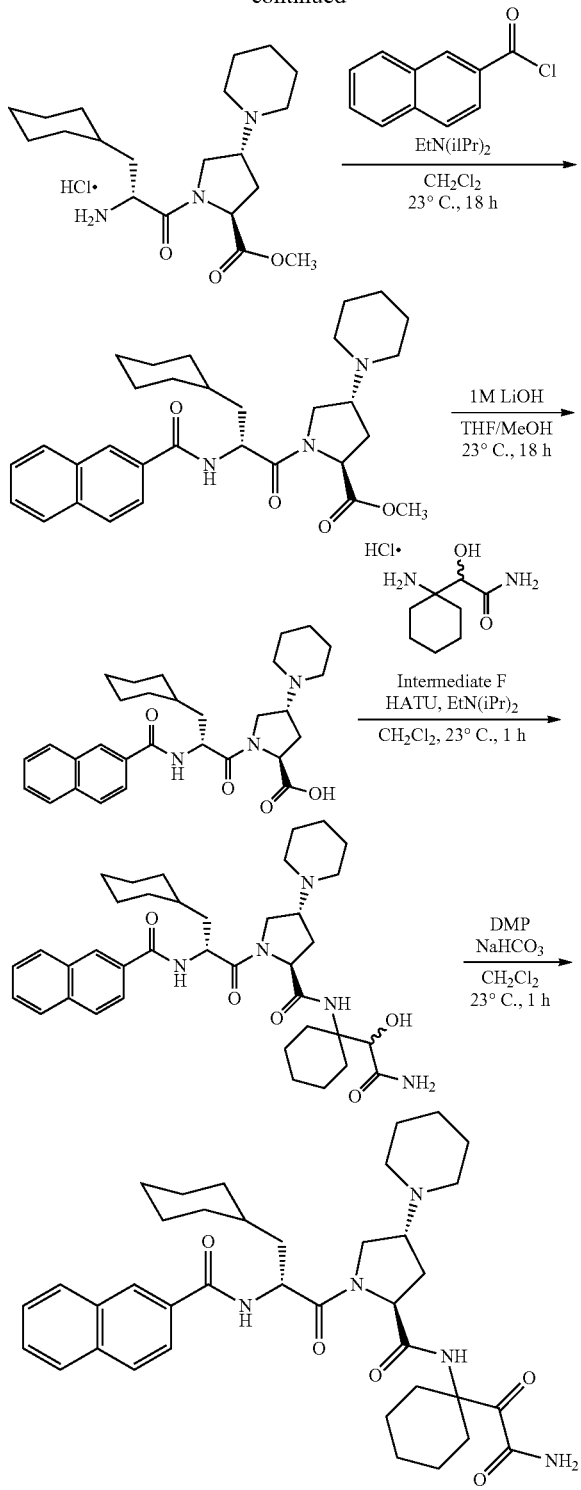

Example 8

Step 1: Preparation of 1-(tert-butyl) 2-methyl (2S, 4R)-4-(piperidin-1-yl)pyrrolidine-1,2-dicarboxylate Into a 1 L round-bottom flask equipped with a magnetic stir bar and under nitrogen was weighted 1-(tert-butyl) 2-methyl (2S,4S)-4-hydroxypyrrolidine-1,2-dicarboxylate (19.8 g, 80.7 mmol, 1.0 equiv). The solid was dissolved in CH$_2$Cl$_2$ (330 mL) and cooled to −78° C. in a dry ice/acetone Dewar. The cold solution was treated with EtN(iPr)$_2$ (17.0 mL, 96.9 mmol, 1.2 equiv) and then triflic anhydride (14.7 mL, 88.8 mmol, 1.1 equiv) was added dropwise over 5 minutes. After stirring at −78° C. for 20 min, the mixture was warmed to −10° C. and piperidine (15.9 mL, 161.4 mmol, 2.0 equiv) was added dropwise over 15 minutes. The reaction mixture was allowed to warm to room temperature with stirring for 18 h. LCMS analysis revealed product formation. The reaction mixture was quenched with 200 mL sat. aq. NaHCO$_3$ and the aqueous layer was extracted with DCM (3×). The combined organic extracts were washed with brine (1×), dried over MgSO$_4$, filtered and concentrated under reduced pressure. The residue was purified by column chromatography through silica gel (2×120 g), eluting with 20:80 to 80:20 EtOAc:Hexanes as a gradient over 34 min to afford the title compound.

Step 2: Preparation of methyl (2S,4R)-4-(piperidin-1-yl)pyrrolidine-2-carboxylate dihydrochloride Prepared in a similar manner as methyl (2S,4S)-4-azidopyrrolidine-2-carboxylate hydrochloride (step 3, intermediate L) using 1-(tert-butyl) 2-methyl (2S,4R)-4-(piperidin-1-yl)pyrrolidine-1,2-dicarboxylate to provide the title compound.

Step 3: Preparation of methyl (2S,4R)-1-((R)-2-((tert-butoxycarbonyl)amino)-3-cyclohexylpropanoyl)-4-(piperidin-1-yl)pyrrolidine-2-carboxylate Prepared in a similar manner as methyl (2S,4S)-4-azido-1-((R)-2-((tert-butoxycarbonyl)amino)-3-cyclohexylpropanoyl)pyrrolidine-2-carboxylate (step 4, intermediate L) using methyl (2S,4R)-4-(piperidin-1-yl)pyrrolidine-2-carboxylate dihydrochloride to provide the title compound.

Step 4: Preparation of methyl (2S,4R)-1-((R)-2-amino-3-cyclohexylpropanoyl)-4-(piperidin-1-yl)pyrrolidine-2-carboxylate hydrochloride Prepared in a similar manner as methyl (2S,4S)-4-azidopyrrolidine-2-carboxylate hydrochloride (step 3, intermediate L) using methyl (2S,4R)-1-((R)-2-((tert-butoxycarbonyl)amino)-3-cyclohexyl propanoyl)-4-(piperidin-1-yl)pyrrolidine-2-carboxylate to provide the title compound.

Step 5: Preparation of methyl (2S,4R)-1-((R)-2-(2-naphthamido)-3-cyclohexylpropanoyl)-4-(piperidin-1-yl)pyrrolidine-2-carboxylate To a stirred solution of methyl (2S,4R)-1-((R)-2-amino-3-cyclohexylpropanoyl)-4-(piperidin-1-yl)pyrrolidine-2-carboxylate hydrochloride (47.7 mmol, 1.0 equiv) and 2-naphthoyl chloride (10.9 g, 57.2 mmol, 1.2 equiv) in DCM (160 mL) was added iPr$_2$EtN (26.5 mL, 152.6 mmol, 3.2 equiv) and the reaction mixture was stirred at 23° C. for 18 hours. The reaction was quenched with 250 mL of water and the aqueous layer was extracted with DCM (3×). The combined organic extracts were washed with brine (1×), dried over MgSO$_4$, filtered and concentrated under reduced pressure. The residue was purified by column chromatography through silica gel (2×120 g), eluting with 30:70 to 100:0 EtOAc:Hexanes as a gradient over 47 min to afford the title compound.

Step 6: Preparation of (2S,4R)-1-((R)-2-(2-naph-thamido)-3-cyclohexylpropanoyl)-4-(piperidin-1-yl) pyrrolidine-2-carboxylicacid A solution of methyl (2S,4R)-1-((R)-2-(2-naphthamido)-3-cyclohexylpropanoyl)-4-(piperidin-1-yl)pyrrolidine-2-carboxylate (12.7 g, 24.6 mmol, 1.0 equiv) in MeOH (35 mL) and THF (35 mL). The resulting solution was treated with 1 M aqueous LiOH (36.8 mL, 36.8 mmol, 1.5 equiv). The solution was stirred at room temperature for 18 hours. The reaction mixture was quenched with acetic acid (2.1 mL, glacial, 17.5 M, 1.5 equiv), yielding a thick white precipitate. The organic solvents were removed under reduced pressure. The resulting aqueous suspension was stirred vigorously overnight. The precipitate was collected by vacuum filtration, washed with water and further dried under high vacuum to afford the title compound as a white solid.

Step 7: Preparation of (2S,4R)-1-((R)-2-(2-naph-thamido)-3-cyclohexylpropanoyl)-N-(1-(2-amino-1-hydroxy-2-oxoethyl)cyclohexyl)-4-(piperidin-1-yl) pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4R)-1-((R)-2-(2-naphthamido)-3-cyclohexylpropanoyl)-4-(piperidin-1-yl) pyrrolidine-2-carboxylic acid and intermediate F to provide the title compound.

Step 8: Preparation of (2S,4R)-1-((R)-2-(2-naph-thamido)-3-cyclohexylpropanoyl)-N-(1-(2-amino-2-oxoacetyl)cyclohexyl)-4-(piperidin-1-yl)pyrrolidine-2-carboxamide Prepared in a similar manner as (2S,4S)-1-((R)-2-(2-naphthamido)-3-cyclohexylpropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide (step 3, example 4) using (2S,4R)-1-((R)-2-(2-naphthamido)-3-cyclohexyl-propanoyl)-N-(1-(2-amino-1-hydroxy-2-oxoethyl)cyclo-hexyl)-4-(piperidin-1-yl)pyrrolidine-2-carboxamide to provide the title compound. MS (ESI+) 658 (M+1)⊕

Example 9: (2S,3R,4R)-1-((R)-2-(2-naphthamido)-3-cyclohexylpropanoyl)-N-(1-(2-amino-2-oxoacetyl) cyclohexyl)-4-(5-(2-hydroxypropan-2-yl)-1H-1,2,3-triazol-1-yl)-3-methoxypyrrolidine-2-carboxamide

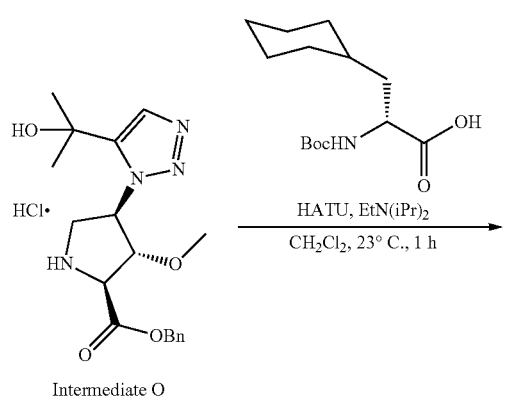

Intermediate O

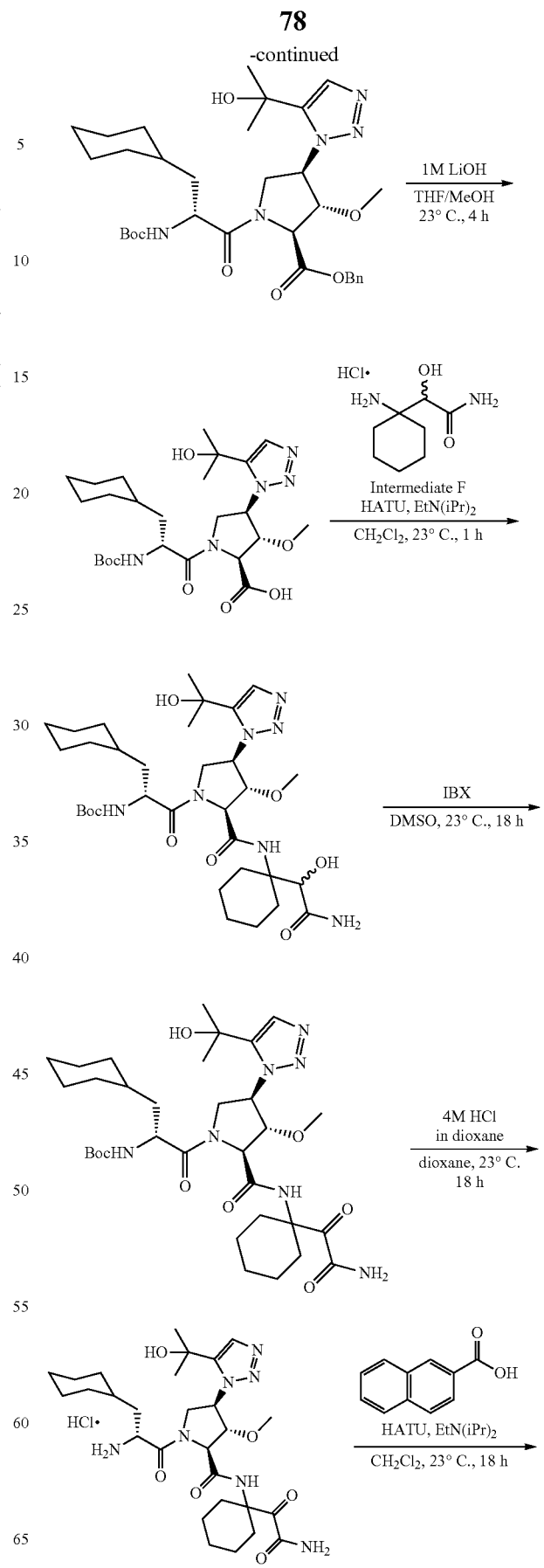

-continued

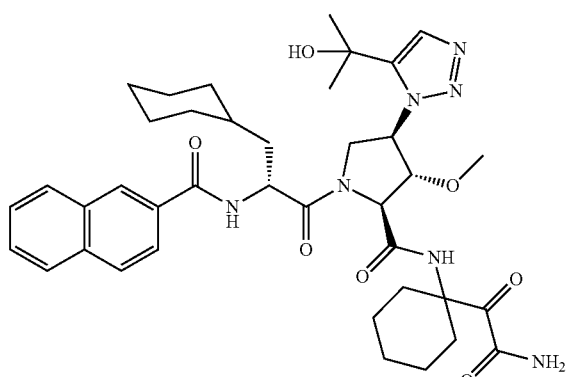

Example 9

Step 1: Preparation of benzyl (2S,3R,4R)-1-((R)-2-((tert-butoxycarbonyl)amino)-3-cyclohexylpropanoyl)-4-(5-(2-hydroxypropan-2-yl)-1H-1,2,3-triazol-1-yl)-3-methoxypyrrolidine-2-carboxylate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using intermediate O and (R)-2-((tert-butoxycarbonyl)amino)-3-cyclohexylpropanoic acid to provide the title compound.

Step 2: Preparation of (2S,3R,4R)-1-((R)-2-((tert-butoxycarbonyl)amino)-3-cyclohexylpropanoyl)-4-(5-(2-hydroxypropan-2-yl)-1H-1,2,3-triazol-1-yl)-3-methoxypyrrolidine-2-carboxylic acid Prepared in a similar manner as (2S,4S)-1-((R)-2-(2-naphthamido)-3-cyclohexylpropanoyl)-4-azido pyrrolidine-2-carboxylic acid (step 7, intermediate L) using benzyl (2S,3R,4R)-1-((R)-2-((tert-butoxycarbonyl)amino)-3-cyclohexylpropanoyl)-4-(5-(2-hydroxypropan-2-yl)-1H-1,2,3-triazol-1-yl)-3-methoxypyrrolidine-2-carboxylate to provide the title compound.

Step 3: Preparation of tert-butyl ((2R)-1-((2S,3R,4R)-2-((1-(2-amino-1-hydroxy-2-oxoethyl)cyclohexyl)carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl)carbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,3R,4R)-1-((R)-2-((tert-butoxycarbonyl)amino)-3-cyclohexylpropanoyl)-4-(5-(2-hydroxypropan-2-yl)-1H-1,2,3-triazol-1-yl)-3-methoxypyrrolidine-2-carboxylic acid and intermediate F to provide the title compound.

Step 4: Preparation of tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl)carbamate Into a 50 mL round bottom flask equipped with a magnetic stir bar and under nitrogen was added tert-butyl ((2R)-1-((2S,3R,4R)-2-((1-(2-amino-1-hydroxy-2-oxoethyl)cyclohexyl)carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl)carbamate (370 mg, 0.55 mmol, 1.0 equiv) and DMSO (2 mL). The solution was treated with IBX (679 mg, 1.1 mmol, 2.0 equiv) and the reaction mixture was stirred at room temperature for 18 h. LCMS revealed complete conversion of starting material and product formation. The reaction mixture was directly loaded onto a reverse-phase 5 g pre-cartridge and dried. Purification was conducted by reverse-phase column chromatography on the ISCO Rf (C18 Gold 15.5 g column) eluting with 80:20 to 20:80 $H_2O$:MeCN+0.1% HCOOH as a gradient over 20 min. The desired material was concentrated under reduced pressure and dried under vacuum to afford the title product as a white solid.

Step 5: Preparation of (2S,3R,4R)-N-(1-(2-amino-2-oxoacetyl)cyclohexyl)-1-((R)-2-amino-3-cyclohexylpropanoyl)-4-(5-(2-hydroxypropan-2-yl)-1H-1,2,3-triazol-1-yl)-3-methoxypyrrolidine-2-carboxamide hydrochloride Prepared in the same manner as 2-(1-aminocyclobutyl)-2-hydroxyacetamide hydrochloride (step 4, intermediate A). using tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl)carbamate to provide the title compound.

Step 6: Preparation of (2S,3R,4R)-1-((R)-2-(2-naphthamido)-3-cyclohexylpropanoyl)-N-(1-(2-amino-2-oxoacetyl)cyclohexyl)-4-(5-(2-hydroxypropan-2-yl)-1H-1,2,3-triazol-1-yl)-3-methoxypyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,3R,4R)-N-(1-(2-amino-2-oxoacetyl)cyclohexyl)-1-((R)-2-amino-3-cyclohexylpropanoyl)-4-(5-(2-hydroxypropan-2-yl)-1H-1,2,3-triazol-1-yl)-3-methoxypyrrolidine-2-carboxamide hydrochloride and 2-naphthoic acid to provide the title compound. MS (ESI+) 730 (M+1)$^\oplus$ Example 10: (2S,4S)-1-((R)-2-(2-naphthamido)-3-cyclohexylpropanoyl)-N-(1-(2-amino-2-oxoacetyl)cyclohexyl)-4-(5-((methylsulfonyl)methyl)-1H-1,2,3-triazol-1-yl)pyrrolidine-2-carboxamide

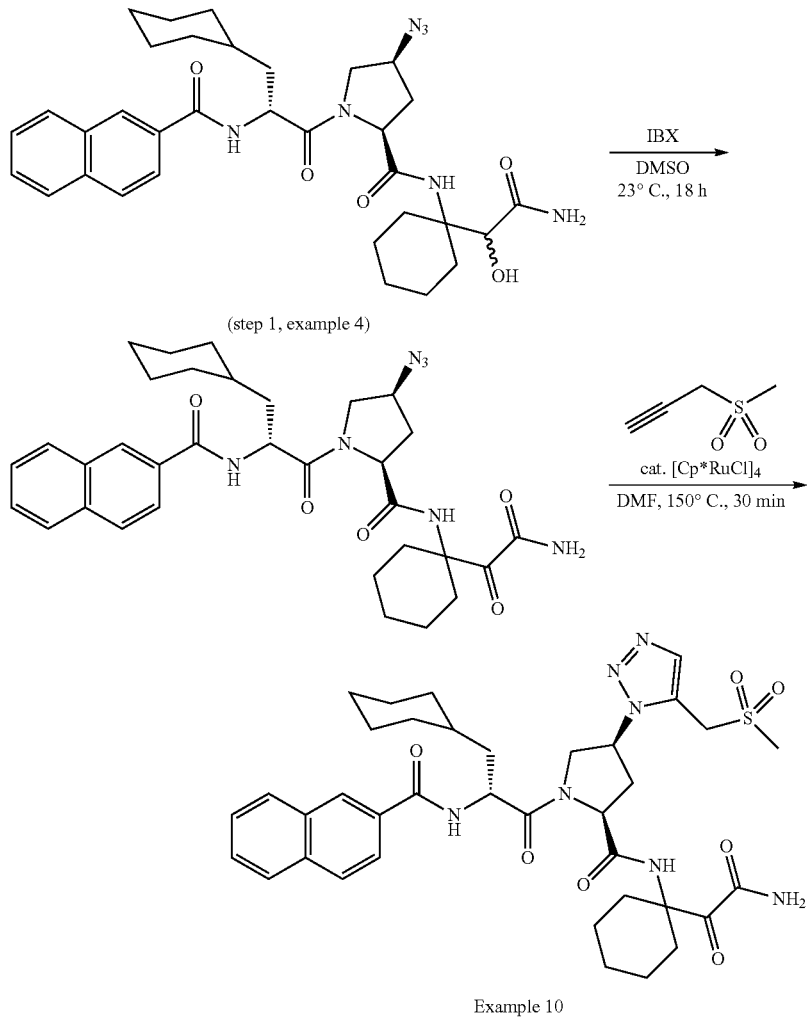

Example 10

Step 1: Preparation of (2S,4S)-1-((R)-2-(2-naphthamido)-3-cyclohexylpropanoyl)-N-(1-(2-amino-2-oxoacetyl)cyclohexyl)-4-azidopyrrolidine-2-carboxamide Prepared in a similar manner as tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) (2S,4S)-1-((R)-2-(2-naphthamido)-3-cyclohexylpropanoyl)-N-(1-(2-amino-1-hydroxy-2-oxoethyl)cyclohexyl)-4-azidopyrrolidine-2-carboxamide to provide the title compound.

Step 2: Preparation of (2S,4S)-1-((R)-2-(2-naphthamido)-3-cyclohexylpropanoyl)-N-(1-(2-amino-2-oxoacetyl)cyclohexyl)-4-(5-((methylsulfonyl)methyl)-1H-1,2,3-triazol-1-yl)pyrrolidine-2-carboxamide Into a 2.5 mL microwave vial with a magnetic stir bar was added (2S,4S)-1-((R)-2-(2-naphthamido)-3-cyclohexylpropanoyl)-N-(1-(2-amino-2-oxoacetyl)cyclohexyl)-4-azidopyrrolidine-2-carboxamide (25 mg, 0.04 mmol, 1.0 equiv), 3-methylsulfonyl-1-propyne (16 µL, 0.16 mmol, 4 equiv), [Cp*RuCl]$_4$ (4.5 mg, 0.004, 0.1 equiv) and DMF (anhydrous, 1 mL). The vial was sealed and heated to 150° C. for 30 min to yield a brown solution. LCMS revealed product formation. The mixture was loaded directly onto a 5 g C18 pre-cartridge and dried. Purification was conducted by reverse phase column chromatography on the ISCO Rf (15.5 g C18 Gold column) eluting with 80:20 to 0:100 H$_2$O:MeCN+0.1% HCOOH as a gradient over 20 min. The desired product was isolated as a beige solid, which was further dried under vacuum to afford the title product. MS (ESI+) 734 (M+1)$^\oplus$ The following compounds, examples 11, 12 and 13, were prepared in a similar manner as example 10 using 3-ethynyloxetan-3-ol, but-3-ynoic acid and N-(prop-2-yn-1-yl)cyclopropanesulfonamide, respectively, in step 2.

| Example | Structure | MW | MS (ESI+) |
|---|---|---|---|
| 11 | (2S,4S)-1-((R)-2-(2-naphthamido)-3-cyclohexylpropanoyl)-N-(1-(2-amino-2-oxoacetyl)cyclohexyl)-4-(5-(3-hydroxyoxetan-3-yl)-1H-1,2,3-triazol-1-yl)pyrrolidine-2-carboxamide | 713.84 | 714 (M + 1)$^{\oplus}$ |
| 12 | 2-(1-((3S,5S)-1-((R)-2-(2-naphthamido)-3-cyclohexylpropanoyl)-5-((1-(2-amino-2-oxoacetyl)cyclohexyl)carbamoyl)pyrrolidin-3-yl)-1H-1,2,3-triazol-5-yl)acetic acid | 699.81 | 700 (M + 1)$^{\oplus}$ |
| 13 | (2S,4S)-1-((R)-2-(2-naphthamido)-3-cyclohexylpropanoyl)-N-(1-(2-amino-2-oxoacetyl)cyclohexyl)-4-(5-(cyclopropanesulfonamidomethyl)-1H-1,2,3-triazol-1-yl)pyrrolidine-2-carboxamide | 774.94 | 775 (M + 1)$^{\oplus}$ |

Example 14: (2S,4S)-N-(1-(2-amino-2-oxoacetyl)cyclohexyl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide
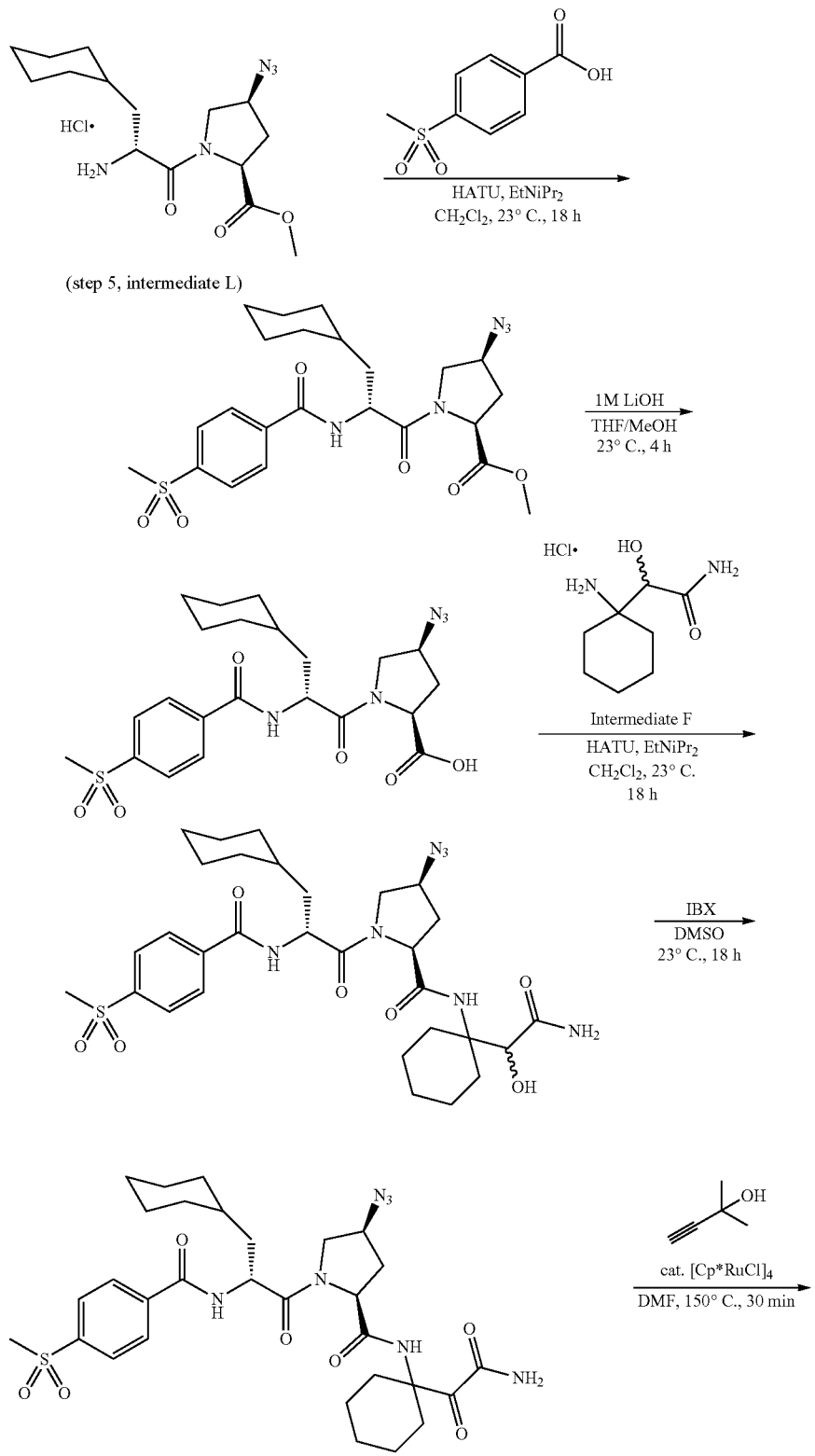

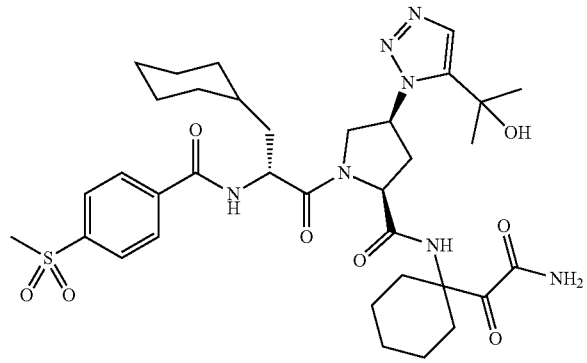 [SMILES: CC(C)(O)c1cnnn1[C@H]1C[C@@H](C(=O)NC2(C(=O)C(N)=O)CCCCC2)N(C(=O)[C@@H](CC2CCCCC2)NC(=O)c2ccc(S(C)(=O)=O)cc2)C1]

Step 1: Preparation of (2S,4S)-methyl 4-azido-1-((R)-3-cyclohexyl-2-(4-(methylsulfonyl)benzamido)propanoyl)pyrrolidine-2-carboxylate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-methyl 1-((R)-2-amino-3-cyclohexylpropanoyl)-4-azidopyrrolidine-2-carboxylate hydrochloride and 4-(methylsulfonyl)benzoic acid to provide the title compound.

Step 2: Preparation of (2S,4S)-4-azido-1-((R)-3-cyclohexyl-2-(4-(methylsulfonyl)benzamido)propanoyl)pyrrolidine-2-carboxylicacid Prepared in a similar manner as (2S,4S)-1-((R)-2-(2-naphthamido)-3-cyclohexylpropanoyl)-4-azido pyrrolidine-2-carboxylic acid (step 7, intermediate L) using (2S,4S)-methyl 4-azido-1-((R)-3-cyclohexyl-2-(4-(methylsulfonyl)benzamido)propanoyl)pyrrolidine-2-carboxylate to provide the title compound.

Step 3: Preparation of (2S,4S)-N-(1-(2-amino-1-hydroxy-2-oxoethyl)cyclohexyl)-4-azido-1-((R)-3-cyclohexyl-2-(4-(methylsulfonyl)benzamido)propanoyl)pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-4-azido-1-((R)-3-cyclohexyl-2-(4-(methylsulfonyl)benzamido) propanoyl)pyrrolidine-2-carboxylic acid and intermediate F to provide the title compound.

Step 4: Preparation of (2S,4S)-N-(1-(2-amino-2-oxoacetyl)cyclohexyl)-4-azido-1-((R)-3-cyclohexyl-2-(4-(methylsulfonyl)benzamido)propanoyl)pyrrolidine-2-carboxamide Prepared in a similar manner as tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using (2S,4S)-N-(1-(2-amino-1-hydroxy-2-oxoethyl)cyclohexyl)-4-azido-1-((R)-3-cyclohexyl-2-(4-(methylsulfonyl)benzamido)propanoyl)pyrrolidine-2-carboxamide to provide the title compound.

Step 5: Preparation of (2S,4S)-N-(1-(2-amino-2-oxoacetyl)cyclohexyl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide Prepared in a similar manner as (2S,4S)-1-((R)-2-(2-naphthamido)-3-cyclohexylpropanoyl)-N-(1-(2-amino-2-oxoacetyl)cyclohexyl)-4-(5-((methylsulfonyl)methyl)-1H-1,2,3-triazol-1-yl)pyrrolidine-2-carboxamide (step 2, example 10) using (2S,4S)-N-(1-(2-amino-2-oxoacetyl)cyclohexyl)-4-azido-1-((R)-3-cyclohexyl-2-(4-(methylsulfonyl)benzamido)propanoyl)pyrrolidine-2-carboxamide and 2-methylbut-3-yn-2-ol to provide the title compound. MS (ESI+) 728 (M+1)$^{\oplus}$; $^1$H NMR (300 MHz, CDCl$_3$) δ 8.80-7.75 (m, 6H), 7.75-6.62 (m, 4H), 6.12-5.50 (m, 2H), 5.40-4.75 (m, 2H), 4.75-4.0 (m, 4H), 3.80-2.80 (m, 2H), 2.75-0.45 (m, 29H) ppm.

The following compound examples 15 and 16 was prepared in a similar manner as example 14 using 3-ethynyloxetan-3-ol and prop-2-yne-1-sulfonic acid, respectively, in step 5

| Example | Structure | MW | MS (ESI+) |
|---|---|---|---|
| 15 | (2S,4S)-N-(1-(2-amino-2-oxoacetyl)cyclohexyl)-1-((R)-3-cyclohexyl-2-(4-(methylsulfonyl)benzamido)propanoyl)-4-(5-(3-hydroxyoxetan-3-yl)-1H-1,2,3-triazol-1-yl)pyrrolidine-2-carboxamide | 741.86 | 742 (M + 1)⊕ |
| 16 | (2S,4S)-N-(1-(2-amino-2-oxoacetyl)cyclohexyl)-1-((R)-3-cyclohexyl-2-(4-(methylsulfonyl)benzamido)propanoyl)-4-(5-((methylsulfonyl)methyl)-1H-1,2,3-triazol-1-yl)pyrrolidine-2-carboxamide | 761.91 | 762 (M + 1)⊕ |

Example 17: (2S,4S)-1-((R)-2-(2-naphthamido)-3-cyclohexylpropanoyl)-N-(1-(2-amino-2-oxoacetyl)cyclohexyl)-4-(4-(2-hydroxypropan-2-yl)-1H-1,2,3-triazol-1-yl)pyrrolidine-2-carboxamide

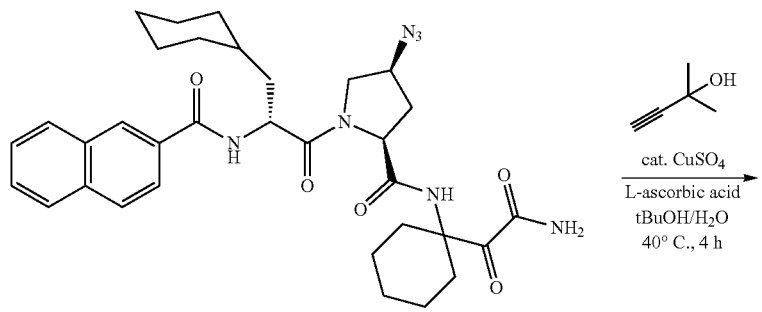

(step 1, example 10)

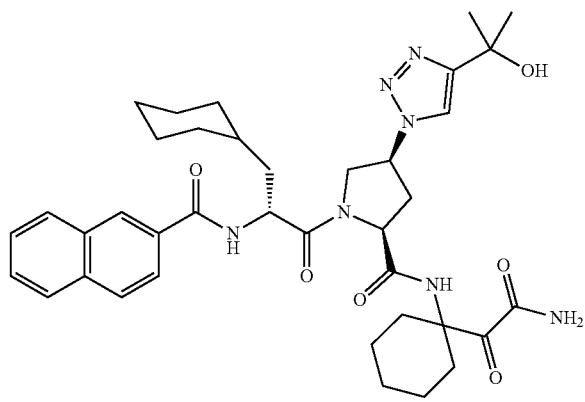

Example 17

Into an 8 mL sample vial equipped with a magnetic stir bar was added (2S,4S)-1-((R)-2-(2-naphthamido)-3-cyclohexylpropanoyl)-N-(1-(2-amino-2-oxoacetyl)cyclohexyl)-4-azidopyrrolidine-2-carboxamide (100 mg, 0.16 mmol, 1.0 equiv), 2-methylbut-3-yn-2-ol (40 µL, 0.41 mmol, 2.5 equiv), CuSO$_4$ (5 mg, 0.03 mmol, 0.2 equiv), L-ascorbic acid (29 mg, 0.16 mmol, 1.0 equiv) and tBuOH:H$_2$O (1:1 v/v, 2 mL). The mixture was heated to 40° C. for 4 h. LCMS analysis revealed product formation. The reaction mixture was loaded onto a C18 5 g pre-cartridge and dried. Purification was conducted by reverse phase column chromatography on the ISCO Rf (15.5 g C18 Gold column) eluting with 80:20 to 10:90 H$_2$O:MeCN+0.1% HCOOH as a gradient over 20 min. The desired product was isolated as a beige solid, which was further dried under vacuum to afford the title product. MS (ESI+) 722 (M+23)$^⊕$ The following compound, examples 18, was prepared in a similar manner as example 17 using 3-ethynyloxetan-3-ol.

| Example | Structure | MW | MS (ESI+) |
|---|---|---|---|
| 18 | 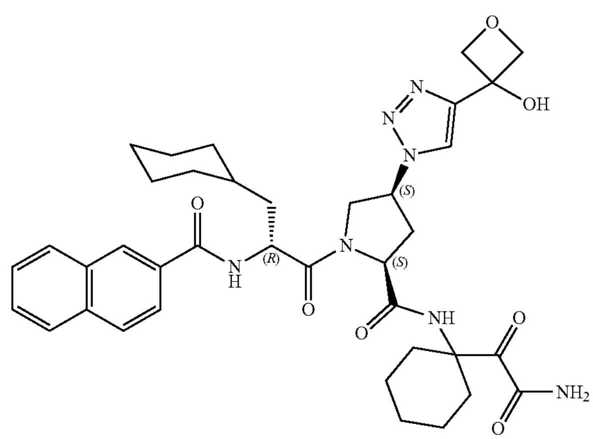 | 713.84 | 714 (M + 1)$^⊕$ |

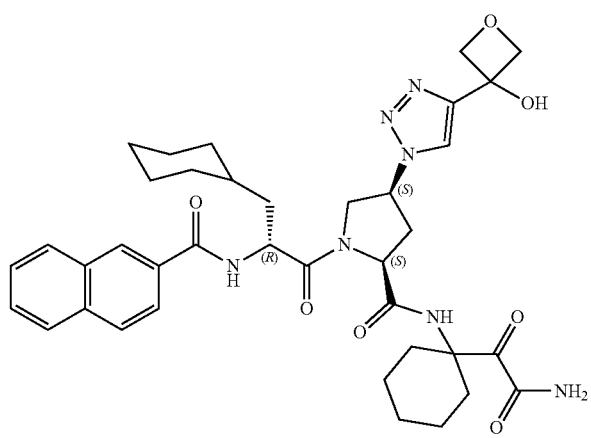

(2S,4S)-1-((R)-2-(2-naphthamido)-3-cyclohexylpropanoyl)-N-(1-(2-amino-2-oxoacetyl)cyclohexyl)-4-(4-(3-hydroxyoxetan-3-yl)-1H-1,2,3-triazol-1-yl)pyrrolidine-2-carboxamide Example 19: (2S,4S)-N-(1-(2-amino-2-oxoacetyl)cyclohexyl)-1-((R)-3-cyclohexyl-2-(4-(methylsulfonyl)benzamido)propanoyl)-4-(4-(2-hydroxypropan-2-yl)-1H-1,2,3-triazol-1-yl)pyrrolidine-2-carboxamide

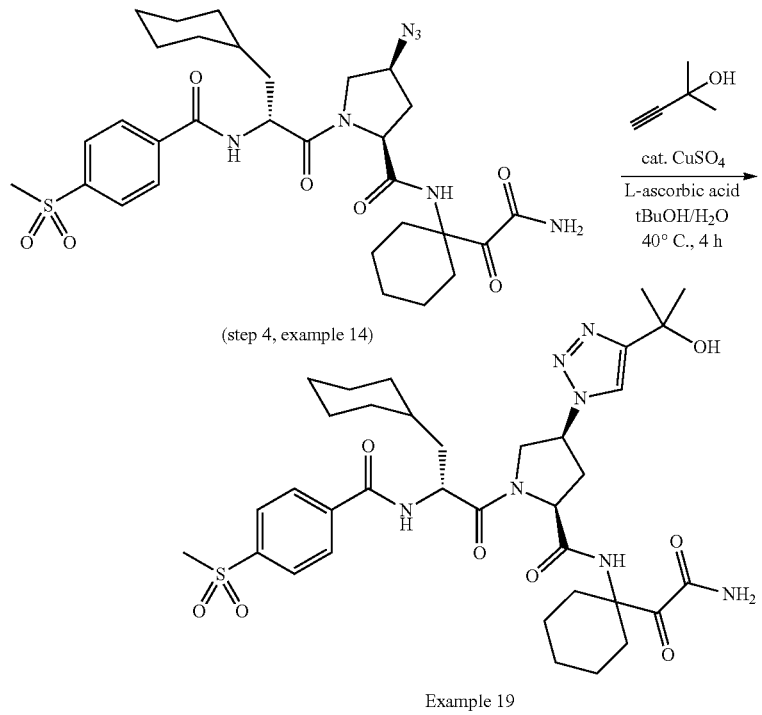

Prepared in a similar manner as (2S,4S)-1-((R)-2-(2-naphthamido)-3-cyclohexylpropanoyl)-N-(1-(2-amino-2-oxoacetyl)cyclohexyl)-4-(4-(2-hydroxypropan-2-yl)-1H-1,2,3-triazol-1-yl)pyrrolidine-2-carboxamide (example 17) using (2S,4S)-N-(1-(2-amino-2-oxoacetyl)cyclohexyl)-4-azido-1-((R)-3-cyclohexyl-2-(4-(methylsulfonyl)benzamido)propanoyl)pyrrolidine-2-carboxamide to provide the title compound. MS (ESI+) 728 (M+1)$^{\oplus}$ The following compounds, examples 20 and 21, were prepared in a similar manner as example 19 using 3-ethynyloxetan-3-ol and 3-(methylsulfonyl)prop-1-yne, respectively.

| Example | Structure | MW | MS (ESI+) |
|---|---|---|---|
| 20 | (2S,4S)-N-(1-(2-amino-2-oxoacetyl)cyclohexyl)-1-((R)-3-cyclohexyl-2-(4-(methylsulfonyl)benzamido)propanoyl)-4-(4-(3-hydroxyoxetan-3-yl)-1H-1,2,3-triazol-1-yl)pyrrolidine-2-carboxamide | 741.86 | 742 (M + 1)$^{\oplus}$ |

| Example | Structure | MW | MS (ESI+) |
|---|---|---|---|
| 21 | (2S,4S)-N-(1-(2-amino-2-oxoacetyl)cyclohexyl)-1-((R)-3-cyclohexyl-2-(4-(methylsulfonyl)benzamido)propanoyl)-4-(4-((methylsulfonyl)methyl)-1H-1,2,3-triazol-1-yl)pyrrolidine-2-carboxamide | 761.91 | 762 (M + 1)⁺ |
Example 22: N-((R)-1-((2S,4S)-2-((1-(2-amino-2-oxoacetyl)cyclohexyl)carbamoyl)-4-(5-(2-hydroxy-propan-2-yl)-1H-1,2,3-triazol-1-yl)pyrrolidin-1-yl)-3-cyclohexyl-1-oxopropan-2-yl)imidazo[1,2-a]pyridine-6-carboxamide
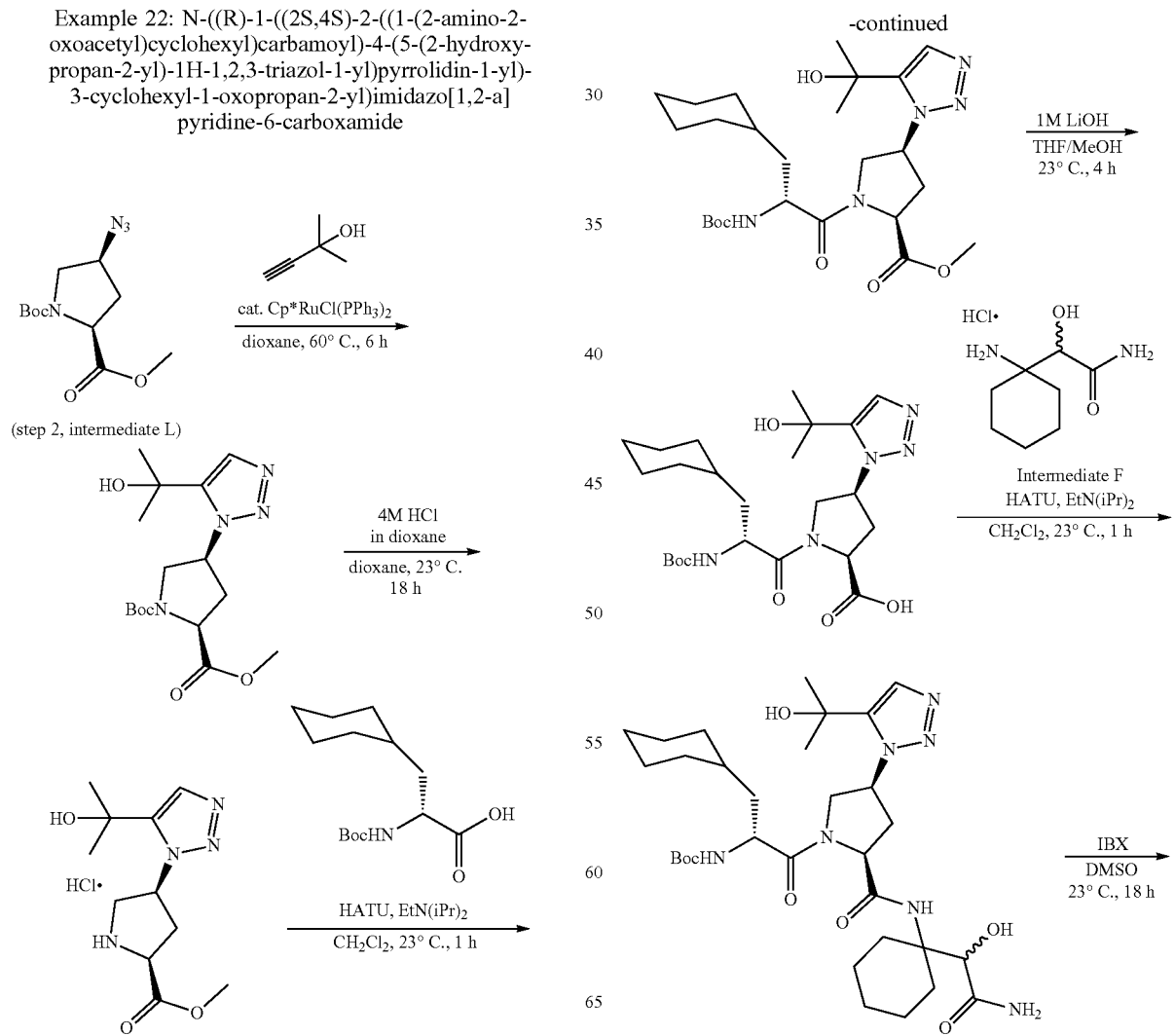

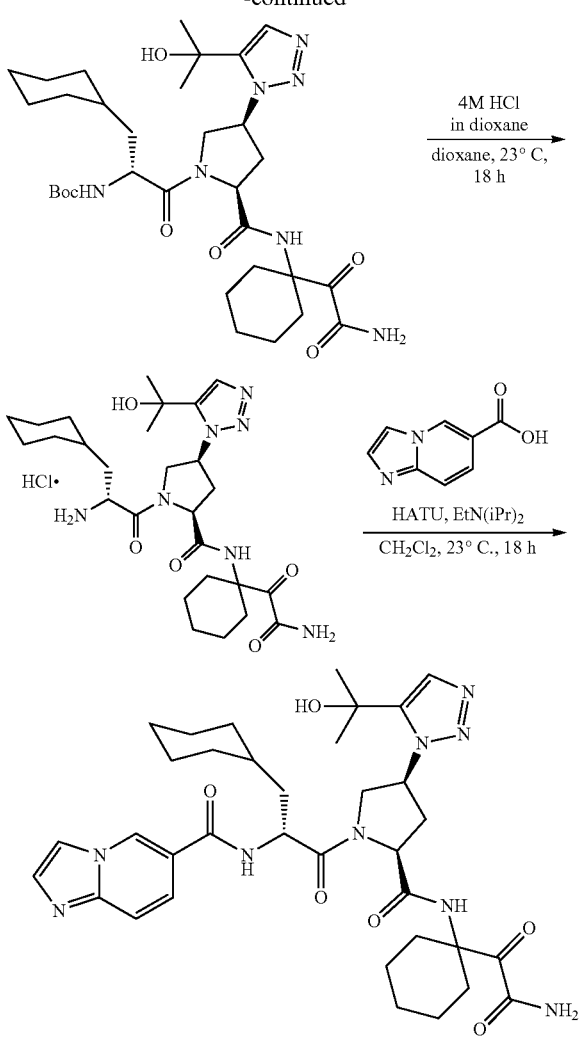

Example 22

Step 1: Preparation of 1-(tert-butyl) 2-methyl (2S, 4S)-4-(5-(2-hydroxypropan-2-yl)-1H-1,2,3-triazol-1-yl)pyrrolidine-1,2-dicarboxylate Prepared in a similar manner as methyl (2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxylate (step 1, intermediate M) using (2S,4S)-1-tert-butyl 2-methyl 4-azidopyrrolidine-1,2-dicarboxylate to provide the title compound.

Step 2: Preparation of methyl (2S,4S)-4-(5-(2-hydroxypropan-2-yl)-1H-1,2,3-triazol-1-yl) pyrrolidine-2-carboxylate hydrochloride Prepared in the same manner as 2-(1-aminocyclobutyl)-2-hydroxyacetamide hydrochloride (step 4, intermediate A) using 1-(tert-butyl) 2-methyl (2S,4S)-4-(5-(2-hydroxypropan-2-yl)-1H-1,2,3-triazol-1-yl)pyrrolidine-1,2-dicarboxylate to provide the title compound.

Step 3: Preparation of methyl (2S,4S)-1-((R)-2-((tert-butoxycarbonyl)amino)-3-cyclohexyl propanoyl)-4-(5-(2-hydroxypropan-2-yl)-1H-1,2,3-triazol-1-yl)pyrrolidine-2-carboxylate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using methyl (2S,4S)-4-(5-(2-hydroxypropan-2-yl)-1H-1,2,3-triazol-1-yl) pyrrolidine-2-carboxylate hydrochloride and (R)-2-((tert-butoxycarbonyl)amino)-3-cyclohexylpropanoic acid to provide the title compound.

Step 4: Preparation of (2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxylic acid Prepared in a similar manner as (2S,4S)-1-((R)-2-(2-naphthamido)-3-cyclohexylpropanoyl)-4-azido pyrrolidine-2-carboxylic acid (step 7, intermediate L) using (2S,4S)-1-((R)-2-((tert-butoxycarbonyl)amino)-3-cyclohexyl propanoyl)-4-(5-(2-hydroxypropan-2-yl)-1H-1,2,3-triazol-1-yl)pyrrolidine-2-carboxylate to provide the title compound.

Step 5: Preparation of tert-butyl ((2R)-1-((2S,4S)-2-((1-(2-amino-1-hydroxy-2-oxoethyl)cyclohexyl) carbamoyl)-4-(5-(2-hydroxypropan-2-yl)-1H-1,2,3-triazol-1-yl)pyrrolidin-1-yl)-3-cyclohexyl-1-oxopropan-2-yl)carbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxylic acid and intermediate F to provide the title compound.

Step 6: Preparation of tert-butyl ((R)-1-((2S,4S)-2-((1-(2-amino-2-oxoacetyl)cyclohexyl) carbamoyl)-4-(5-(2-hydroxypropan-2-yl)-1H-1,2,3-triazol-1-yl) pyrrolidin-1-yl)-3-cyclohexyl-1-oxopropan-2-yl) carbamate Prepared in a similar manner as tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using tert-butyl ((2R)-1-((2S,4S)-2-((1-(2-amino-1-hydroxy-2-oxoethyl)cyclohexyl) carbamoyl)-4-(5-(2-hydroxypropan-2-yl)-1H-1,2,3-triazol-1-yl)pyrrolidin-1-yl)-3-cyclohexyl-1-oxopropan-2-yl)carbamate to provide the title compound.

Step 7: Preparation of (2S,4S)-N-(1-(2-amino-2-oxoacetyl)cyclohexyl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride Prepared in the same manner as 2-(1-aminocyclobutyl)-2-hydroxyacetamide hydrochloride (step 4, intermediate A) using tert-butyl ((R)-1-((2S,4S)-2-((1-(2-amino-2- oxoacetyl)cyclohexyl) carbamoyl)-4-(5-(2-hydroxypropan-2-yl)-1H-1,2,3-triazol-1-yl)pyrrolidin-1-yl)-3-cyclohexyl-1-oxopropan-2-yl)carbamate.

Step 8: Preparation of N-((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)imidazo[1,2-a]pyridine-6-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-N-(1-(2-amino-2-oxoacetyl)cyclohexyl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride and imidazo[1,2-a]pyridine-6-carboxylic acid to provide the title compound. MS (ESI+) 690 (M+1)⊕

The following compounds, examples 23, 24, 25, 26, 27 and 28, were prepared in a similar manner as example 22 using commercially available acids.

| Example | Structure | MW | MS (ESI+) |
|---------|-----------|-----|-----------|
| 23 | 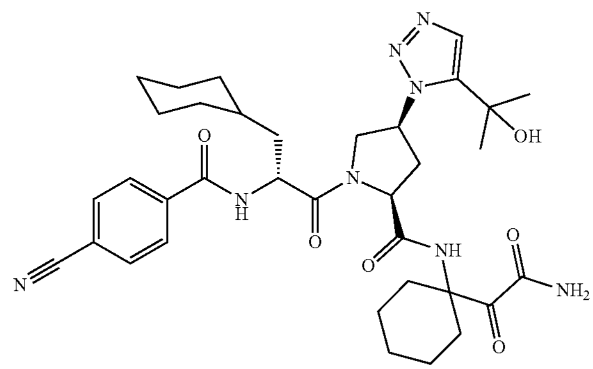 | 674.79 | 676 (M + 1)⊕ |

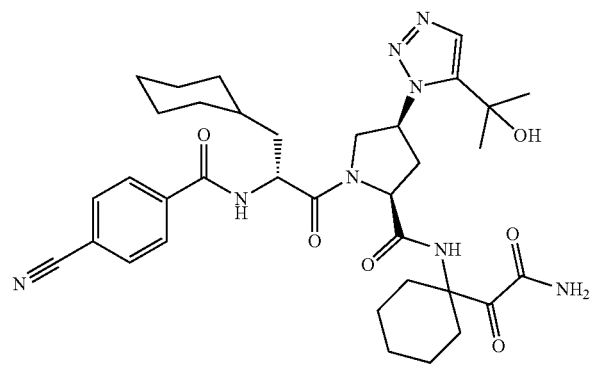

(2S,4S)-N-(1-(2-amino-2-oxoacetyl)cyclohexyl)-1-((R)-2-(4-cyanobenzamido)-3-cyclohexylpropanoyl)-4-(5-(2-hydroxypropan-2-yl)-1H-1,2,3-triazol-1-yl)pyrrolidine-2-carboxamide

| 24 | | 746.86 | 745 (M − 1)⊖ |

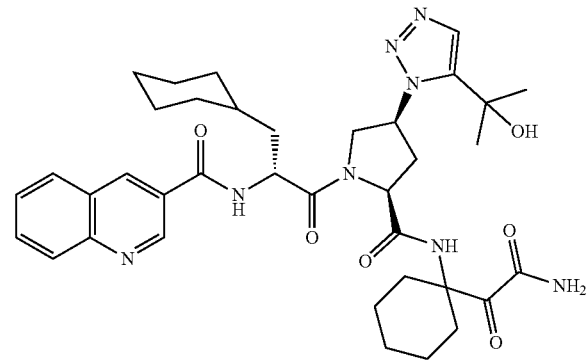

N-((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)quinoline-3-carboxamide -continued

| Example | Structure | MW | MS (ESI+) |
|---|---|---|---|
| 25 | N-((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-1H-indazole-7-carboxamide | 689.82 | 690 (M + 1)⊕ |
| 26 | (2S,4S)-N-(1-(2-amino-2-oxoacetyl)cyclohexyl)-1-((R)-3-cyclohexyl-2-(4-((2-methoxyethyl)sulfonyl)benzamido)propanoyl)-4-(5-(2-hydroxypropan-2-yl)-1H-1,2,3-triazol-1-yl)pyrrolidine-2-carboxamide | 771.92 | 772 (M + 1)⊕ |
| 27 | (2S,4S)-N-(1-(2-amino-2-oxoacetyl)cyclohexyl)-1-((R)-3-cyclohexyl-2-(4-((difluoromethyl)sulfonyl)benzamido)propanoyl)-4-(5-(2-hydroxypropan-2-yl)-1H-1,2,3-triazol-1-yl)pyrrolidine-2-carboxamide | 763.85 | 765 (M + 1)⊕ |

| Example | Structure | MW | MS (ESI+) |
|---|---|---|---|
| 28 | (2S,4S)-N-(1-(2-amino-2-oxoacetyl)cyclohexyl)-1-((R)-2-(4-((2-amino-2-oxoethyl)sulfonyl)benzamido)-3-cyclohexylpropanoyl)-4-(5-(2-hydroxypropan-2-yl)-1H-1,2,3-triazol-1-yl)pyrrolidine-2-carboxamide | 770.90 | 772 (M + 1)⊕ |

Example 29: $N^2$-((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-$N^6$-(2,5,8,11-tetraoxatridecan-13-yl)naphthalene-2,6-dicarboxamide

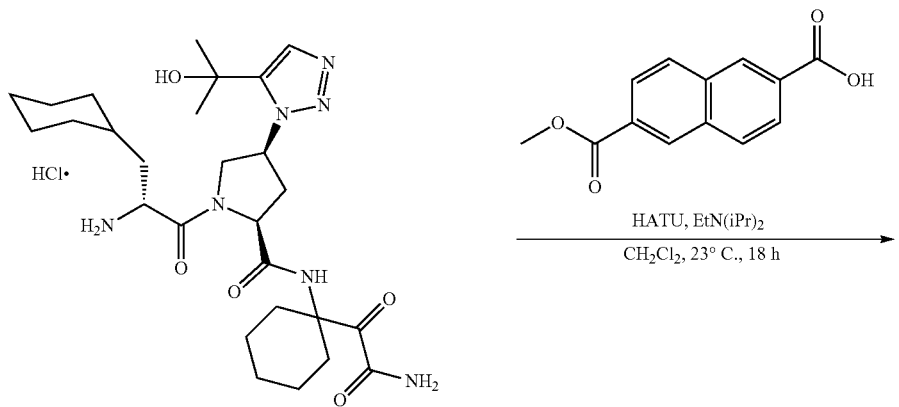

(step 7, example 22)

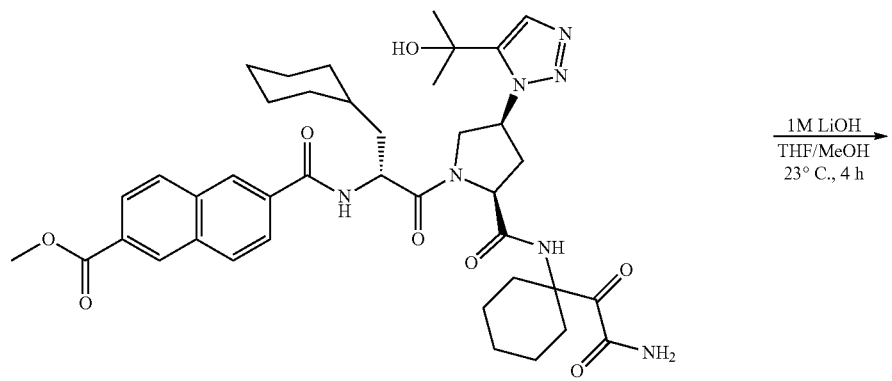

-continued

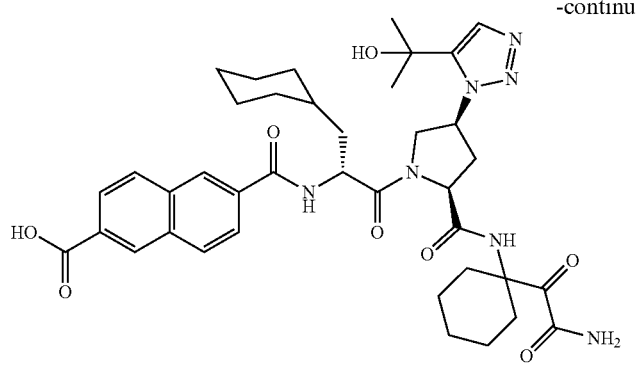 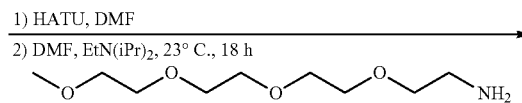

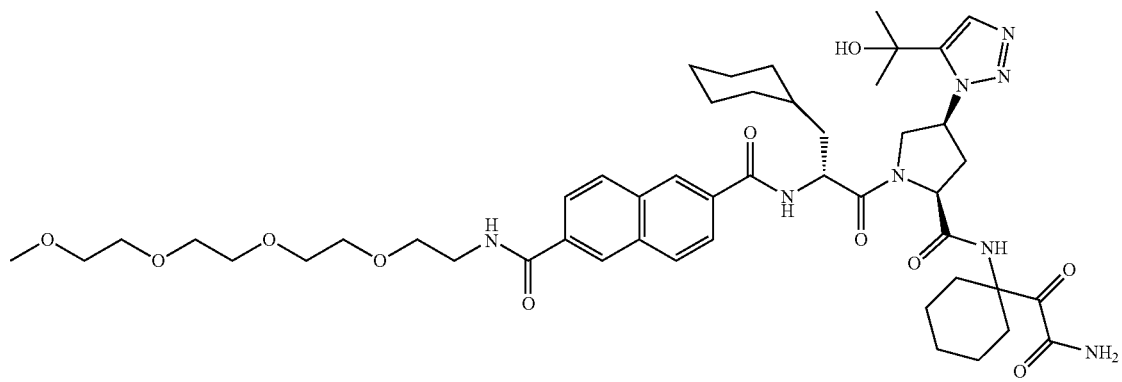

Example 29

Step 1: Preparation of methyl 6-(((R)-1-((2S,4S)-2-((1-(2-amino-2-oxoacetyl)cyclohexyl) carbamoyl)-4-(5-(2-hydroxypropan-2-yl)-1H-1,2,3-triazol-1-yl) pyrrolidin-1-yl)-3-cyclohexyl-1-oxopropan-2-yl) carbamoyl)-2-naphthoate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-N-(1-(2-amino-2-oxoacetyl)cyclohexyl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride and 6-(methoxycarbonyl)-2-naphthoic acid to provide the title compound.

Step 2: Preparation of 6-(((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl) carbamoyl)-2-naphthoic acid Prepared in a similar manner as (2S,4S)-1-((R)-2-(2-naphthamido)-3-cyclohexylpropanoyl)-4-azido pyrrolidine-2-carboxylic acid (step 7, intermediate L) using methyl 6-(((R)-1-((2S,4S)-2-((1-(2-amino-2-oxoacetyl)cyclohexyl) carbamoyl)-4-(5-(2-hydroxypropan-2-yl)-1H-1,2,3-triazol-1-yl)pyrrolidin-1-yl)-3-cyclohexyl-1-oxopropan-2-yl)carbamoyl)-2-naphthoate to provide the title compound.

Step 3: Preparation of $N^2$-((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-$N^6$-(2,5,8,11-tetraoxatridecan-13-yl)naphthalene-2,6-dicarboxamide Into a 4 mL sample vial equipped with a magnetic stir bar was added 6-(((R)-1-((2S,4S)-2-((1-(2-amino-2-oxoacetyl) cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamoyl)-2-naphthoic acid (42.6 mg, 0.057 mmol, 1.0 equiv), HATU (25 mg, 0.066 mmol, 1.2 equiv) and DMF (300 µL). The resulting solution was stirred at room temperature for 10 min. A DMF (200 µL) solution of 2,5,8,11-tetraoxatridecan-13-amine (24 mg, 0.114 mmol, 2.0 equiv) was added. Another 200 µL DMF was used to wash and transfer the remaining 2,5,8,11-tetraoxatridecan-13-amine. EtNiPr$_2$ (25 µL, 0.143 mmol, 2.5 equiv) was then added and the mixture was stirred at room temperature for 18 h. LCMS analysis revealed product formation. The reaction mixture was loaded onto a C18 5 g pre-cartridge and dried. Purification was conducted by reverse phase column chromatography on the ISCO Rf (30 g C18 Gold column) eluting with 100:0 to 0:100 H$_2$O:MeCN+0.1% HCOOH as a gradient over 30 min. The desired product was isolated and further dried under vacuum to afford the title product. MS (ESI+) 933 (M+1)$^{\oplus}$ The following compound, example 30, was prepared in a similar manner as example 29 using 2,5,8,11,14,17,20,23,26,29,32,35,38,41,44,47,50,53,56,59,62,65,68,71-tetracosaoxatriheptacontan-73-amine in step 3.

| Example | Structure | MW | MS (ESI+) |
|---|---|---|---|
| 30 | 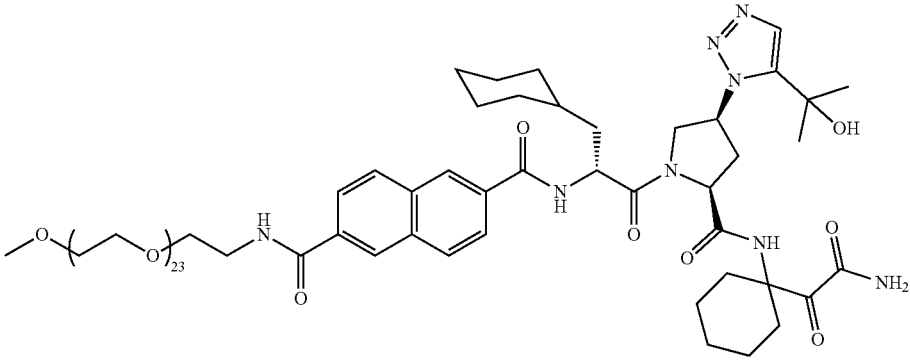 N²-((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-N⁶-(tetracosaoxatriheptacontan-73-yl)naphthalene-2,6-dicarboxamide | 1813.0 | 908 [(M + 2)/2]⊕ |

Example 31: (2S,4S)-1-((R)-2-(2-naphthamido)-3-cyclohexylpropanoyl)-N-(1-(2-((2-amino-2-oxoethyl)amino)-2-oxoacetyl)cyclohexyl)-4-(5-(2-hydroxypropan-2-yl)-1H-1,2,3-triazol-1-yl)pyrrolidine-2-carboxamide

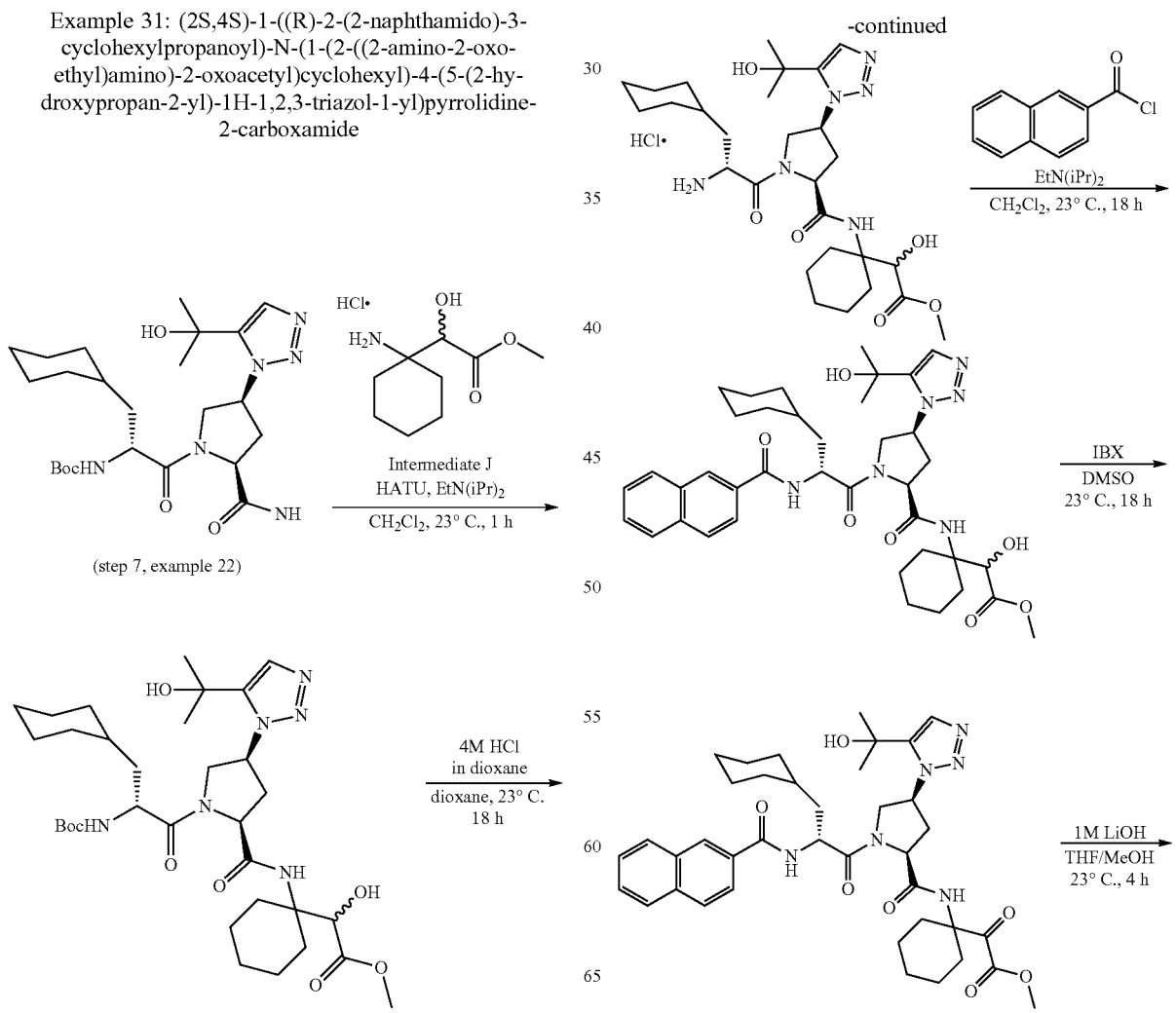

-continued

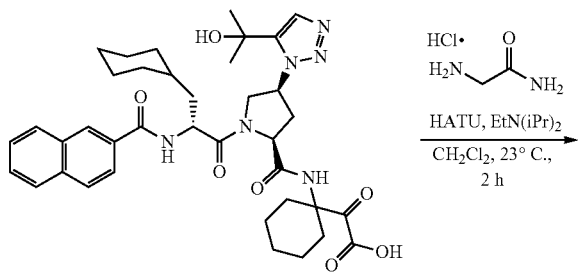

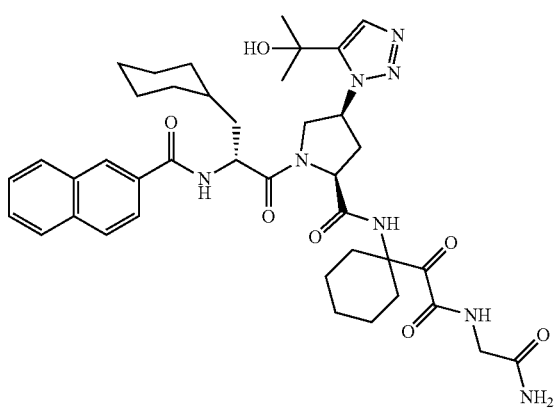

Example 31

Step 1: Preparation of methyl 2-(1-((2S,4S)-1-((R)-2-((tert-butoxycarbonyl)amino)-3-cyclohexyl propanoyl)-4-(5-(2-hydroxypropan-2-yl)-1H-1,2,3-triazol-1-yl)pyrrolidine-2-carboxamido)cyclohexyl)-2-hydroxyacetate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxylic acid and intermediate J to provide the title compound.

Step 2: Preparation of methyl 2-(1-((2S,4S)-1-((R)-2-amino-3-cyclohexylpropanoyl)-4-(5-(2-hydroxypropan-2-yl)-1H-1,2,3-triazol-1-yl)pyrrolidine-2-carboxamido)cyclohexyl)-2-hydroxyacetate hydrochloride Prepared in the same manner as 2-(1-aminocyclobutyl)-2-hydroxyacetamide hydrochloride (step 4, intermediate A) using methyl 2-(1-((2S,4S)-1-((R)-2-((tert-butoxycarbonyl)amino)-3-cyclohexyl propanoyl)-4-(5-(2-hydroxypropan-2-yl)-1H-1,2,3-triazol-1-yl)pyrrolidine-2-carboxamido)cyclohexyl)-2-hydroxyacetate.

Step 3: Preparation of methyl 2-(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)-2-hydroxyacetate Prepared in a similar manner as methyl (2S,4S)-1-((R)-2-(2-naphthamido)-3-cyclohexylpropanoyl)-4-azidopyrrolidine-2-carboxylate (step 6, intermediate L) using methyl 2-(1-((2S,4S)-1-((R)-2-amino-3-cyclohexylpropanoyl)-4-(5-(2-hydroxypropan-2-yl)-1H-1,2,3-triazol-1-yl)pyrrolidine-2-carboxamido)cyclohexyl)-2-hydroxyacetate hydrochloride and 2-naphthoyl chloride to provide the title compound.

Step 4: Preparation of methyl 2-(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)-2-oxoacetate Prepared in a similar manner as tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using methyl 2-(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)-2-hydroxyacetate to provide the title compound.

Step 5: Preparation of 2-(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)-2-oxoacetic acid Prepared in a similar manner as (2S,4S)-1-((R)-2-(2-naphthamido)-3-cyclohexylpropanoyl)-4-azido pyrrolidine-2-carboxylic acid (step 7, intermediate L) using methyl 2-(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)-2-oxoacetate to provide the title compound.

Step 6: Preparation of (2S,4S)-1-((R)-2-(2-naphthamido)-3-cyclohexylpropanoyl)-N-(1-(2-((2-amino-2-oxoethyl)amino)-2-oxoacetyl)cyclohexyl)-4-(5-(2-hydroxypropan-2-yl)-1H-1,2,3-triazol-1-yl)pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using 2-(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)-2-oxoacetic acid and 2-aminoacetamide hydrochloride to provide the title compound. MS (ESI+) 758 (M+1)$^{\oplus}$ The following compounds, examples 32, 33 and 34, were prepared in a similar manner as example 31 using commercially available amines in step 6.

| Example | Structure | MW | MS (ESI+) |
|---|---|---|---|
| 32 | 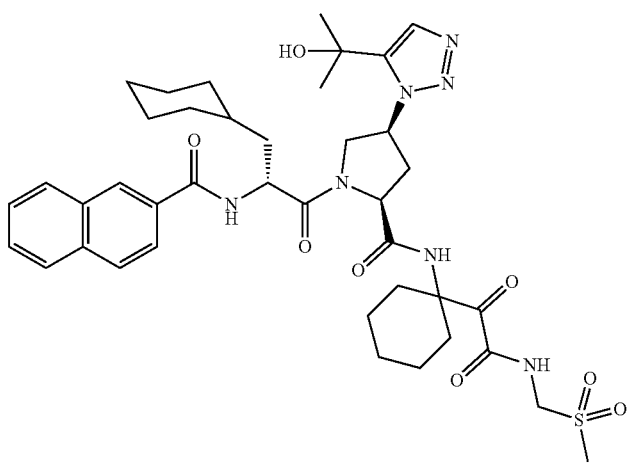 (2S,4S)-1-((R)-2-(2-naphthamido)-3-cyclohexylpropanoyl)-4-(5-(2-hydroxypropan-2-yl)-1H-1,2,3-triazol-1-yl)-N-(1-(2-(((methylsulfonyl)methyl)amino)-2-oxoacetyl)cyclohexyl)pyrrolidine-2-carboxamide | 805.98 | 806 (M + 1)⊕ |
| 33 | 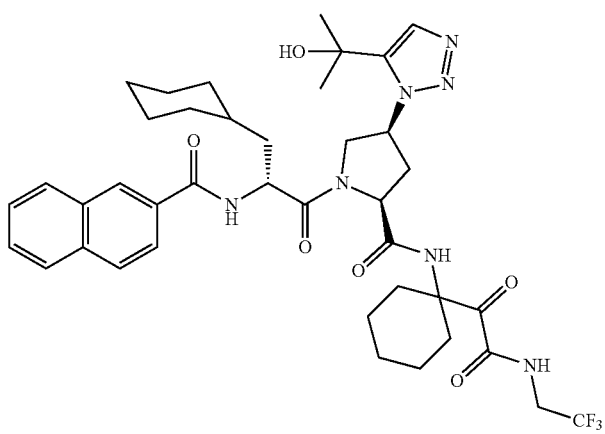 (2S,4S)-1-((R)-2-(2-naphthamido)-3-cyclohexylpropanoyl)-4-(5-(2-hydroxypropan-2-yl)-1H-1,2,3-triazol-1-yl)-N-(1-(2-oxo-2-((2,2,2-trifluoroethyl)amino)acetyl)cyclohexyl)pyrrolidine-2-carboxamide | 781.86 | 783 (M + 1)⊕ |

| Example | Structure | MW | MS (ESI+) |
|---|---|---|---|
| 34 | 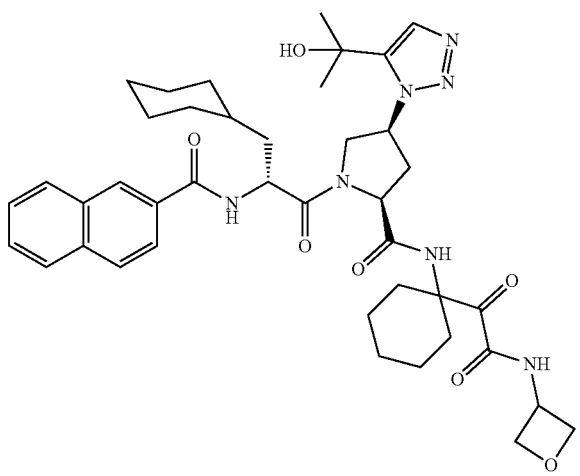 (2S,4S)-1-((R)-2-(2-naphthamido)-3-cyclohexylpropanoyl)-4-(5-(2-hydroxypropan-2-yl)-1H-1,2,3-triazol-1-yl)-N-(1-(2-(oxetan-3-ylamino)-2-oxoacetyl)cyclohexyl)pyrrolidine-2-carboxamide | 755.90 | 757 (M + 1)⊕ |
Example 35: (2S,4S)-1-(2-(2-naphthamido)-3-cyclohexyl-2-methylpropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide
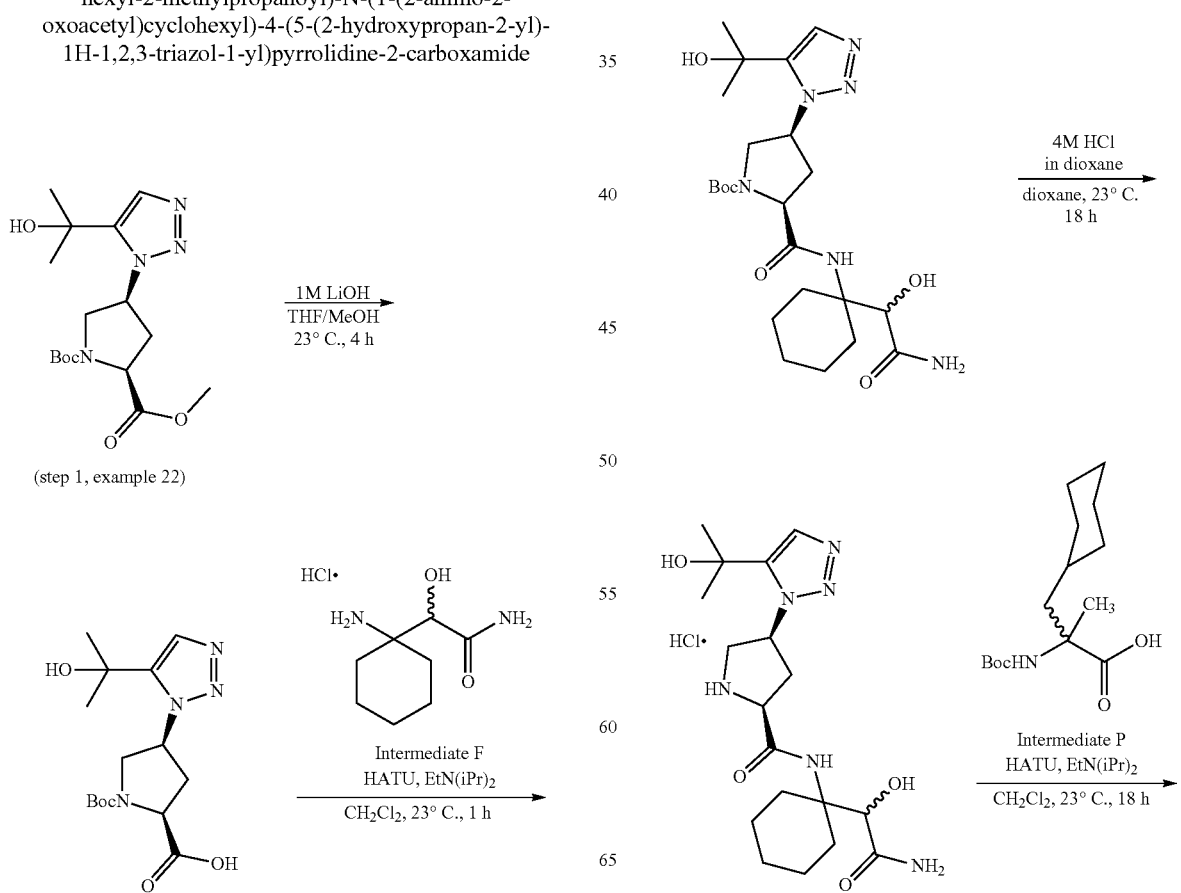

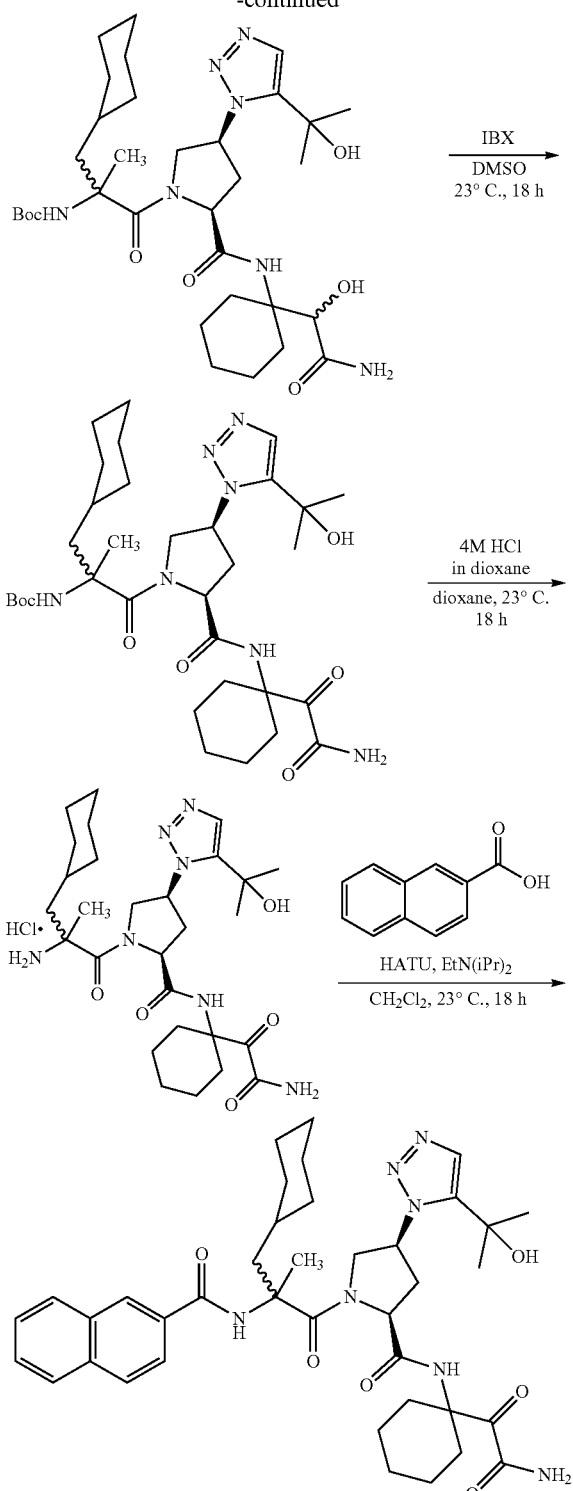

Example 35

Step 1: Preparation of (2S,4S)-1-(tert-butoxycarbonyl)-4-(5-(2-hydroxypropan-2-yl)-1H-1,2,3-triazol-1-yl)pyrrolidine-2-carboxylic acid Prepared in a similar manner as (2S,4S)-1-((R)-2-(2-naphthamido)-3-cyclohexylpropanoyl)-4-azido pyrrolidine-2-carboxylic acid (step 7, intermediate L) using (2S,4S)-1-tert-butyl 2-methyl 4-(5-(2-hydroxypropan-2-yl)-1H-1,2,3-triazol-1-yl)pyrrolidine-1,2-dicarboxylate to provide the title compound.

Step 2: Preparation of tert-butyl (2S,4S)-2-((1-(2-amino-1-hydroxy-2-oxoethyl)cyclohexyl) carbamoyl)-4-(5-(2-hydroxypropan-2-yl)-1H-1,2,3-triazol-1-yl)pyrrolidine-1-carboxylate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-1-(tert-butoxycarbonyl)-4-(5-(2-hydroxypropan-2-yl)-1H-1,2,3-triazol-1-yl)pyrrolidine-2-carboxylic acid and intermediate F to provide the title compound.

Step 3: Preparation of (2S,4S)-N-(1-(2-amino-1-hydroxy-2-oxoethyl)cyclohexyl)-4-(5-(2-hydroxy propan-2-yl)-1H-1,2,3-triazol-1-yl)pyrrolidine-2-carboxamide hydrochloride Prepared in the same manner as 2-(1-aminocyclobutyl)-2-hydroxyacetamide hydrochloride (step 4, intermediate A) using tert-butyl (2S,4S)-2-((1-(2-amino-1-hydroxy-2-oxoethyl)cyclohexyl) carbamoyl)-4-(5-(2-hydroxypropan-2-yl)-1H-1,2,3-triazol-1-yl)pyrrolidine-1-carboxylate to provide the title compound.

Step 4: Preparation of tert-butyl (1-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-cyclohexyl-2-methyl-1-oxopropan-2-yl)carbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-N-(1-(2-amino-1-hydroxy-2-oxoethyl)cyclohexyl)-4-(5-(2-hydroxy propan-2-yl)-1H-1,2,3-triazol-1-yl)pyrrolidine-2-carboxamide hydrochloride and intermediate P to provide the title compound.

Step 5: Preparation of tert-butyl (1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-2-methyl-1-oxopropan-2-yl)carbamate Prepared in a similar manner as tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using tert-butyl (1-((2S,4S)-2-((1-(2-amino-1-hydroxy-2-oxoethyl) cyclohexyl) carbamoyl)-4-(5-(2-hydroxypropan-2-yl)-1H-1,2,3-triazol-1-yl)pyrrolidin-1-yl)-3-cyclohexyl-2-methyl-1-oxopropan-2-yl)carbamate to provide the title compound.

Step 6: Preparation of (2S,4S)-N-(1-(2-amino-2-oxoacetyl)cyclohexyl)-1-(2-amino-3-cyclohexyl-2-methylpropanoyl)-4-(5-(2-hydroxypropan-2-yl)-1H-1,2,3-triazol-1-yl)pyrrolidine-2-carboxamide hydrochloride Prepared in the same manner as 2-(1-aminocyclobutyl)-2-hydroxyacetamide hydrochloride (step 4, intermediate A)

using tert-butyl (1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-2-methyl-1-oxopropan-2-yl)carbamate to provide the title product.

Step 7: Preparation of (2S,4S)-1-(2-(2-naphthamido)-3-cyclohexyl-2-methylpropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-N-(1-(2-amino-2-oxoacetyl)cyclohexyl)-1-(2-amino-3-cyclohexyl-2-methylpropanoyl)-4-(5-(2-hydroxypropan-2-yl)-1H-1,2,3-triazol-1-yl)pyrrolidine-2-carboxamide hydrochloride and 2-naphthoic acid to provide the title compound. MS (ESI+) 736 (M+23)⊕

Example 36: (2S,4S)-1-(2-(2-naphthamido)-3-(bicyclo[2.2.1]heptan-1-yl)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide

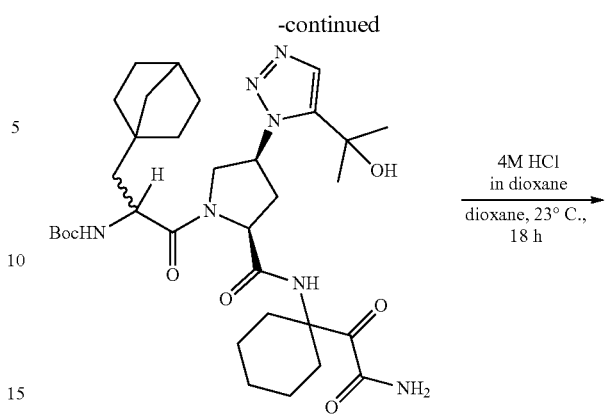

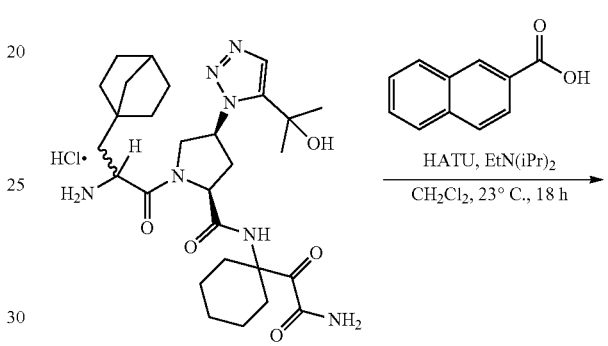

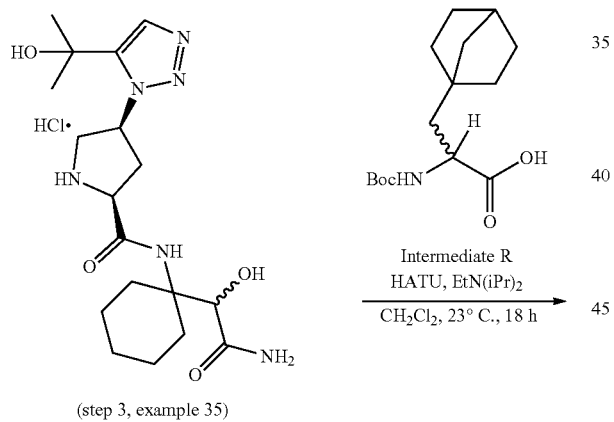

(step 3, example 35)

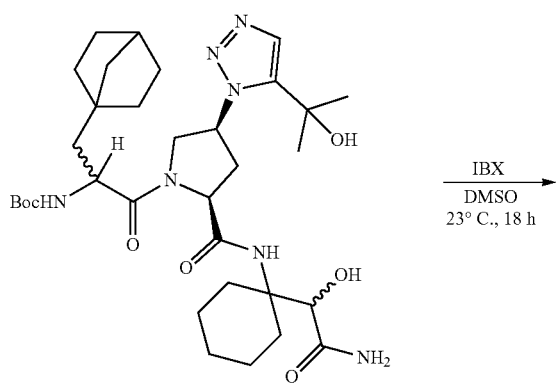

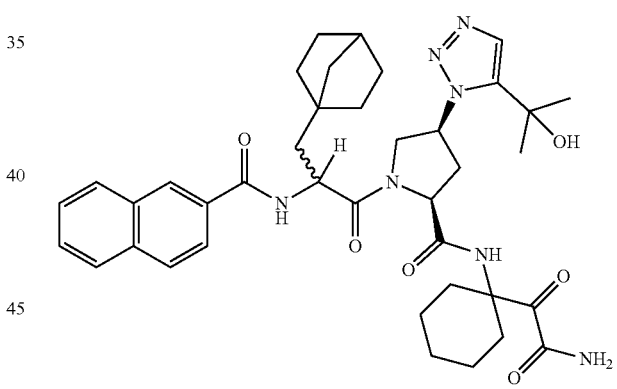

Example 36

Step 1: Preparation of tert-butyl (1-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-(bicyclo[2.2.1]heptan-1-yl)-1-oxopropan-2-yl)carbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide hydrochloride (step 4, example 35) and intermediate R to provide the title compound.

Step 2: Preparation of tert-butyl (1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-(bicyclo[2.2.1]heptan-1-yl)-1-oxopropan-2-yl)carbamate Prepared in a similar manner as tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using tert-butyl (1-((2S,4S)-2-((1-(2-amino-1-hydroxy-2-oxoethyl)cyclohexyl) carbamoyl)-4-(5-(2-hydroxypropan-2-yl)-1H-1,2,3-triazol-1-yl)pyrrolidin-1-yl)-3-(bicyclo[2.2.1]heptan-1-yl)-1-oxopropan-2-yl)carbamate to provide the title compound.

Step 3: Preparation of (2S,4S)-N-(1-(2-amino-2-oxoacetyl)cyclohexyl)-1-(2-amino-3-(bicyclo[2.2.1]heptan-1-yl)propanoyl)-4-(5-(2-hydroxypropan-2-yl)-1H-1,2,3-triazol-1-yl)pyrrolidine-2-carboxamide hydrochloride Prepared in the same manner as 2-(1-aminocyclobutyl)-2-hydroxyacetamide hydrochloride (step 4, intermediate A) using tert-butyl (1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-(bicyclo[2.2.1]heptan-1-yl)-1-oxopropan-2-yl)carbamate to provide the title product.

Step 4: Preparation of (2S,4S)-1-(2-(2-naphthamido)-3-(bicyclo[2.2.1]heptan-1-yl)propanoyl)-N-(1-(2-amino-2-oxoacetyl)cyclohexyl)-4-(5-(2-hydroxypropan-2-yl)-1H-1,2,3-triazol-1-yl) pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-N-(1-(2-amino-2-oxoacetyl)cyclohexyl)-1-(2-amino-3-(bicyclo[2.2.1]heptan-1-yl)propanoyl)-4-(5-(2-hydroxypropan-2-yl)-1H-1,2,3-triazol-1-yl)pyrrolidine-2-carboxamide hydrochloride and 2-naphthoic acid to provide the title compound. MS (ESI+) 728 (M+1)$^⊕$; $^1$H NMR (300 MHz, CDCl$_3$) δ 8.50-8.25 (m, 1H), 8.23-7.77 (m, 5H), 7.77-7.47 (m, 3H), 7.43-7.30 (m, 1H), 7.25-6.95 (m, 1H), 6.90-6.30 (m, 1H), 6.06 (br s, 1H), 5.80-5.50 (m, 1H), 5.25-4.75 (m, 2H), 4.75-4.15 (m, 2H), 2.72-2.25 (m, 7H), 2.25-1.94 (m, 3H), 1.94-1.02 (m, 19H), 1.02-0.65 (m, 2H).

The following compound, example 37, was prepared in a similar manner as example 36, from intermediate O in step 1.

| Example | Structure | MW | MS (ESI+) |
|---|---|---|---|
| 37 | 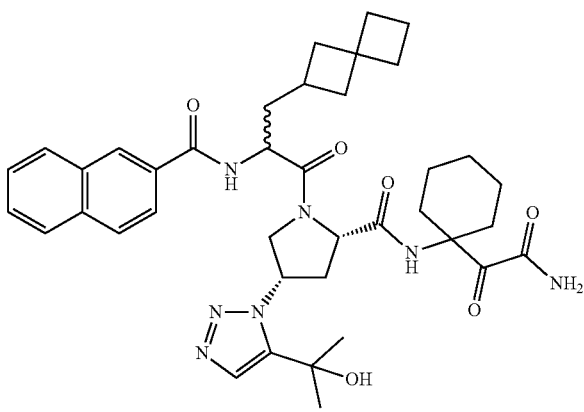 | 711.85 | 712 (M + 1)$^⊕$ |

(2S,4S)-1-(2-(2-naphthamido)-3-(spiro[3.3]heptan-2-yl)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide

Example 38: (2S,4S)-N-(1-(2-amino-2-oxoacetyl)cyclohexyl)-1-(3-cyclohexyl-2-methyl-2-(4-(methylsulfonyl)benzamido)propanoyl)-4-(5-(2-hydroxypropan-2-yl)-1H-1,2,3-triazol-1-yl)pyrrolidine-2-carboxamide

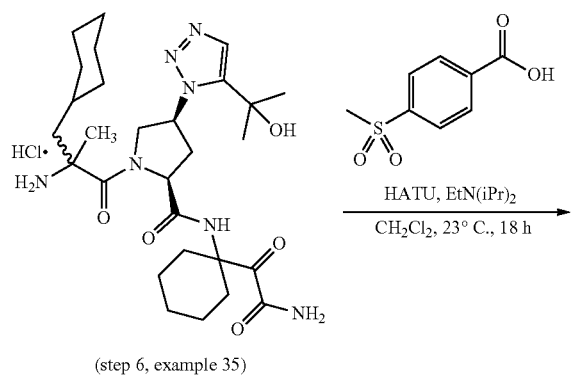

(step 6, example 35)

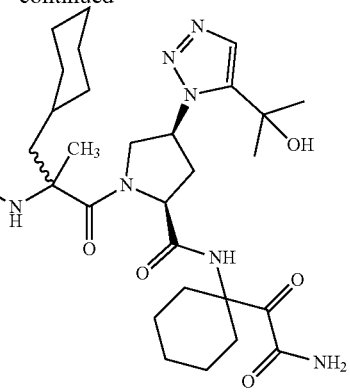

Example 38

Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-N-(1-(2-amino-2-oxoacetyl)cyclohexyl)-1-(2-amino-3-cyclohexyl-2-methylpropanoyl)-4-(5-(2-hydroxypropan-2-yl)-1H-1,2,3-triazol-1-yl)pyrrolidine-2-carboxamide hydrochloride and 4-(methylsulfonyl)benzoic acid to provide the title compound. MS (ESI+) 742 (M+1)$^{\oplus}$ The following compounds, examples 39 and 40, were prepared in a similar manner as example 38 using intermediate Q and intermediate R, respectively.

| Example | Structure | MW | MS (ESI+) |
|---|---|---|---|
| 39 | 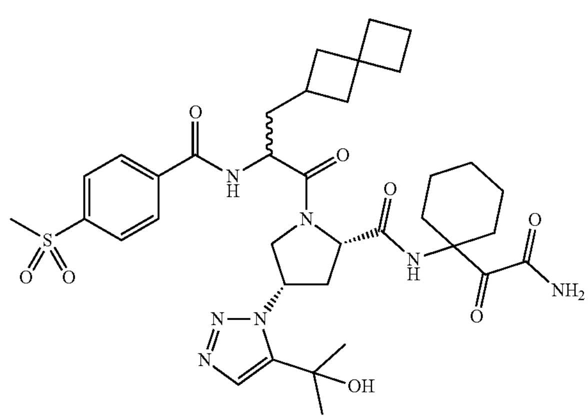 | 739.88 | 740 (M + 1)$^{\oplus}$ |

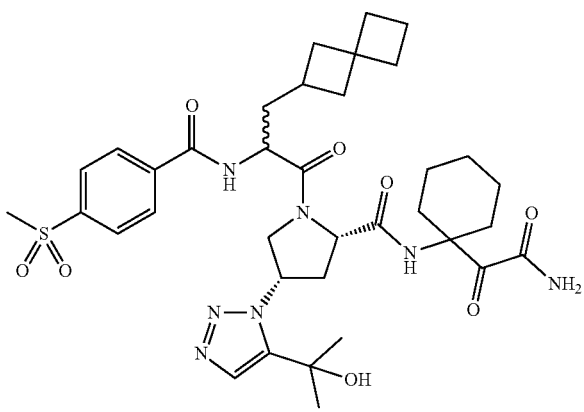

(2S,4S)-N-(1-(2-amino-2-oxoacetyl)cyclohexyl)-4-(5-(2-hydroxypropan-2-yl)-1H-1,2,3-triazol-1-yl)-1-(2-(4-(methylsulfonyl)benzamido)-3-(spiro[3.3]heptan-2-yl)propanoyl)pyrrolidine-2-carboxamide -continued
| Example | Structure | MW | MS (ESI+) |
|---|---|---|---|
| 40 | (2S,4S)-N-(1-(2-amino-2-oxoacetyl)cyclohexyl)-1-(3-(bicyclo[2.2.1]heptan-1-yl)-2-(4-(methylsulfonyl)benzamido)propanoyl)-4-(5-(2-hydroxypropan-2-yl)-1H-1,2,3-triazol-1-yl)pyrrolidine-2-carboxamide | 739.88 | 740 (M + 1)⊕ |
Example 41: benzyl ((R)-2-(2-naphthamido)-3-((2S,4S)-2-((1-(2-amino-2-oxoacetyl)cyclohexyl) carbamoyl)-4-(5-(2-hydroxypropan-2-yl)-1H-1,2,3-triazol-1-yl)pyrrolidin-1-yl)-3-oxopropyl)carbamate
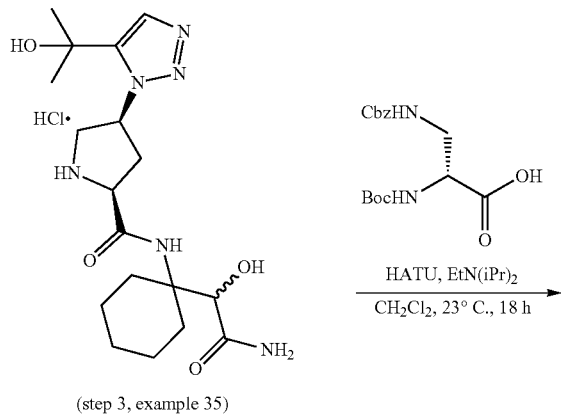
(step 3, example 35)
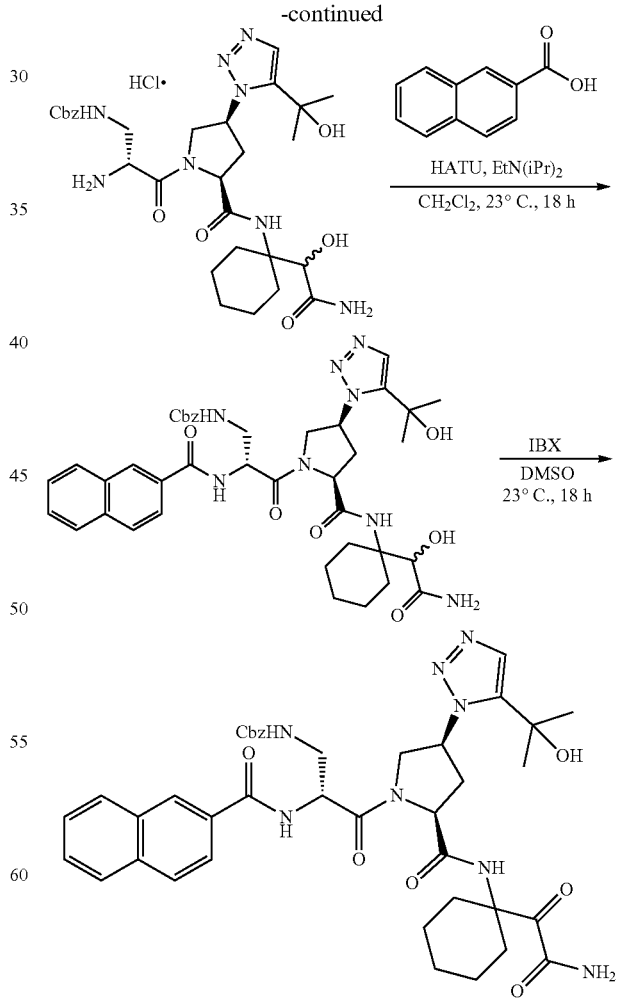
Example 41

Step 1: Preparation of benzyl tert-butyl ((2R)-3-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-oxopropane-1,2-diyl)dicarbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide hydrochloride and (R)-3-(((benzyloxy)carbonyl)amino)-2-((tert-butoxycarbonyl)amino)propanoic acid to provide the title compound.

Step 2: Preparation of benzyl ((2R)-2-amino-3-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-oxopropyl)carbamate hydrochloride Prepared in the same manner as 2-(1-aminocyclobutyl)-2-hydroxyacetamide hydrochloride (step 4, intermediate A) using benzyl tert-butyl ((2R)-3-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-oxopropane-1,2-diyl)dicarbamate to provide the title compound.

Step 3: Preparation of benzyl ((2R)-2-(2-naphthamido)-3-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-oxopropyl)carbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using benzyl ((2R)-2-amino-3-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-oxopropyl)carbamate hydrochloride and 2-naphthoic acid to provide the title compound.

Step 4: Preparation of benzyl ((R)-2-(2-naphthamido)-3-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-oxopropyl)carbamate Prepared in a similar manner as tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using benzyl ((2R)-2-(2-naphthamido)-3-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-oxopropyl) carbamate to provide the title compound. MS (ESI+) 767 (M+1)⊕

Example 42: (2S,4S)-1-((R)-2-(2-naphthamido)-3-(methylsulfonamido)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide

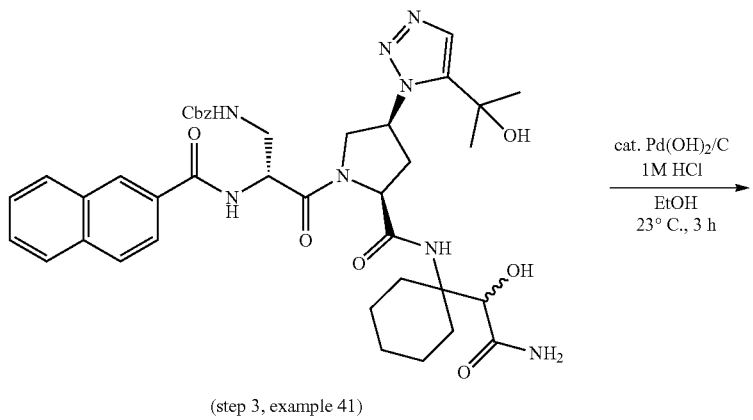

(step 3, example 41)

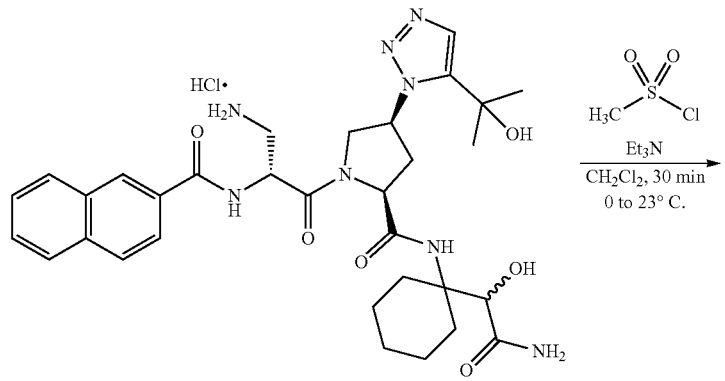

-continued

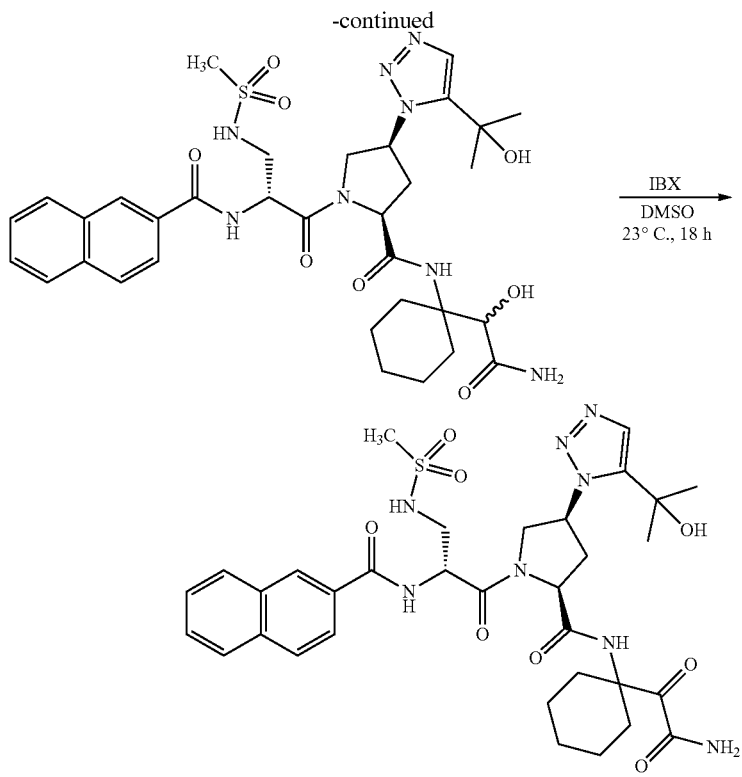

Example 42

Step 1: Preparation of (2S,4S)-1-((R)-2-(2-naphthamido)-3-aminopropanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide hydrochloride Into a 25 mL round bottom flask equipped with a magnetic stir bar and under nitrogen was added ((2R)-2-(2-naphthamido)-3-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-oxopropyl) carbamate (114 mg, 0.15 mmol, 1.0 equiv), EtOH (2.5 mL) and aq. HCl (1 M, 190 µL, 0.19 mmol, 1.3 equiv). The solution was sparged with nitrogen for 30 min. Pd(OH)$_2$/C (20% wt., 20 mg) was added and the nitrogen source was then replaced with a hydrogen balloon. The reaction mixture was sparged with 1 balloon of hydrogen, followed by removing the bubbler. The reaction mixture was stirred at room temperature for 3 h under an atmosphere of hydrogen. LCMS analysis revealed completion of reaction. The reaction mixture was filtered through a pad of celite on a plastic sintered funnel and washed with DCM (3×5 mL). The clear filtrate was concentrated under reduced pressure and used directly in the next step without further purification.

Step 2: Preparation of (2S,4S)-1-((R)-2-(2-naphthamido)-3-(methylsulfonamido)propanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide Into a 4 mL sample vial equipped with magnetic stir bar and under nitrogen was added (2S,4S)-1-((R)-2-(2-naphthamido)-3-aminopropanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide hydrochloride (24.2 mg, 0.036 mmol, 1.0 equiv), methylsulfonyl chloride (2.8 µL, 0.036 mmol, 1.0 equiv) and DCM (360 µL). The suspension was cooled to 0° C. in an ice bath and then treated with Et$_3$N (16.5 µL, 0.120 mmol, 3.3 equiv). The mixture was warmed up to room temperature and stirred for 30 min. LCMS analysis revealed the formation of product. The reaction mixture was loaded onto a C18 5 g pre-cartridge and dried. Purification was conducted by reverse phase column chromatography on the ISCO Rf (15.5 g C18 Gold column) eluting with 100:0 to 30:70 H$_2$O:MeCN+ 0.1% HCOOH as a gradient over 14 min. The desired product was isolated and further dried under vacuum to afford the title product.

Step 3: Preparation of (2S,4S)-1-((R)-2-(2-naphthamido)-3-(methylsulfonamido)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide Prepared in a similar manner as tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using (2S,4S)-1-((R)-2-(2-naphthamido)-3-(methylsulfonamido)propanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide to provide the title compound. MS (ESI+) 711 (M+1)$^⊕$ Example 43: (2S,4S)-1-((R)-2-(2-naphthamido)-3-acetamidopropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide

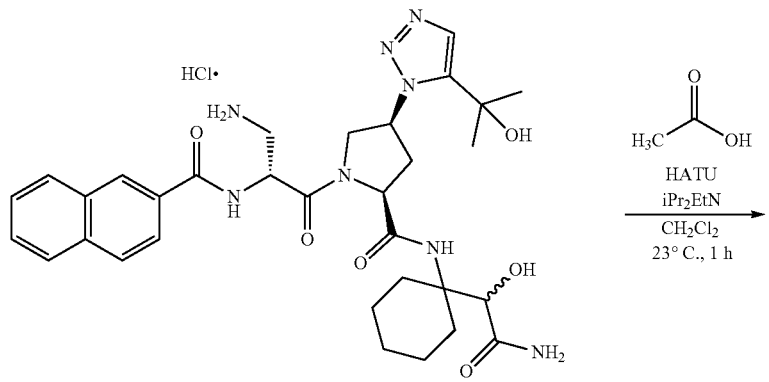

(step 1, example 42)

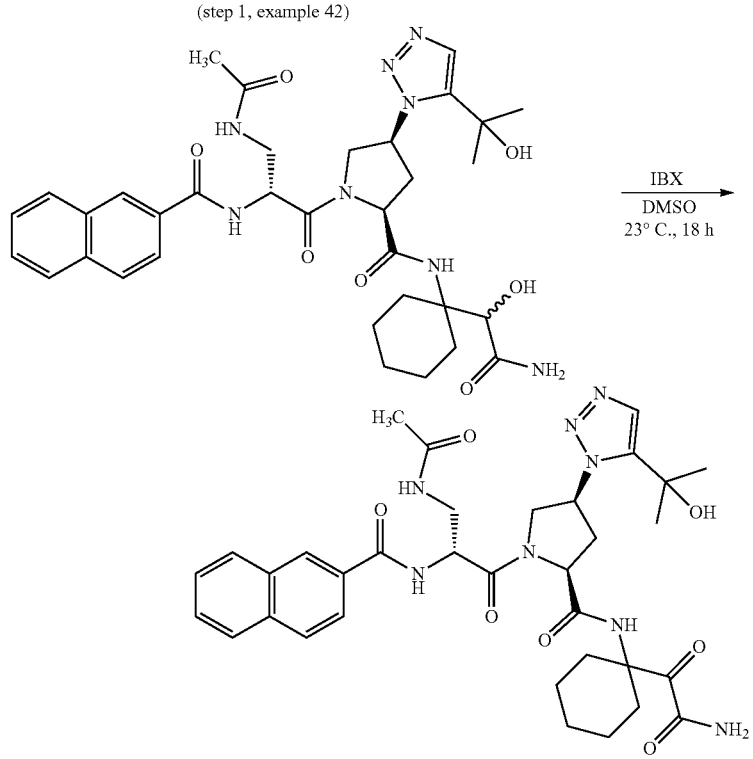

Example 43

Step 1: Preparation of (2S,4S)-1-((R)-2-(2-naphthamido)-3-acetamidopropanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-1-((R)-2-(2-naphthamido)-3-aminopropanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide hydrochloride and acetic acid to provide the title compound.

Step 2: Preparation of (2S,4S)-1-((R)-2-(2-naphthamido)-3-acetamidopropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide Prepared in a similar manner as tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using (2S,4S)-1-((R)-2-(2-naphthamido)-3-acetamidopropanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide to provide the title compound. MS (ESI+) 675 (M+1)$^{\oplus}$ Example 44: (2S,4S)-1-((R)-2-(2-naphthamido)-3-cyclohexylpropanoyl)-N-(2-(2-amino-2-oxoacetyl)spiro[3.3]heptan-2-yl)-4-(5-(2-hydroxypropan-2-yl)-1H-1,2,3-triazol-1-yl)pyrrolidine-2-carboxamide
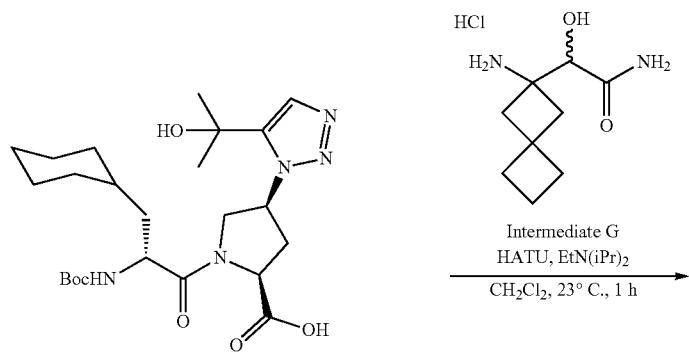
(step 4, example 22)
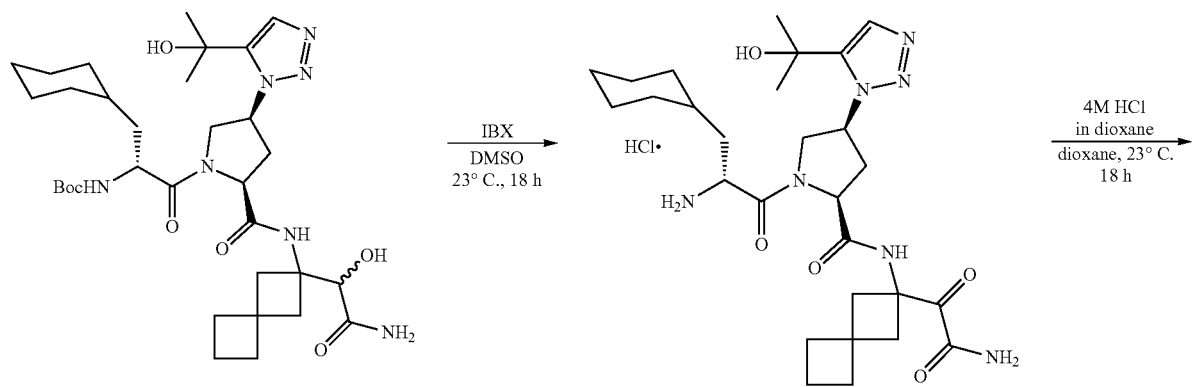
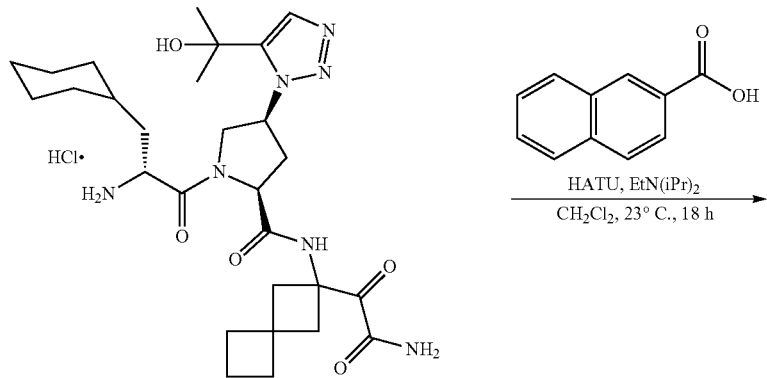

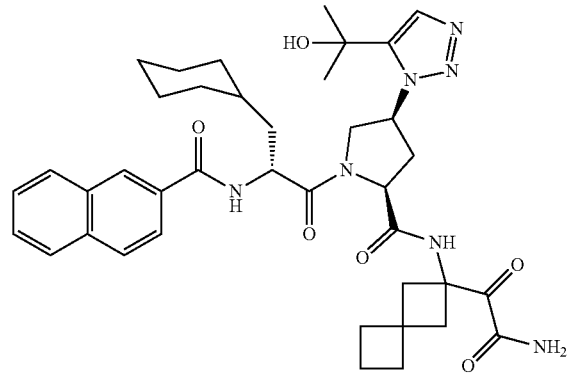

Example 44

Step 1: Preparation of tert-butyl ((2R)-1-((2S,4S)-2-((2-(2-amino-1-hydroxy-2-oxoethyl)spiro[3.3]heptan-2-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxylic acid and intermediate G to provide the title compound.

Step 2: Preparation of tert-butyl ((R)-1-((2S,4S)-2-((2-(2-amino-2-oxoacetyl)spiro[3.3]heptan-2-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate Prepared in a similar manner as tert-butyl ((R)-1-((2S,3R,4R)-2-((1-(2-amino-2-oxoacetyl)cyclohexyl)carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl)carbamate (step 4, example 9) using tert-butyl ((2R)-1-((2S,4S)-2-((2-(2-amino-1-hydroxy-2-oxoethyl)spiro[3.3]heptan-2-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate to provide the title compound.

Step 3: Preparation of (2S,4S)-N-(2-(2-amino-2-oxoacetyl)spiro[3.3]heptan-2-yl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride Prepared in the same manner as 2-(1-aminocyclobutyl)-2-hydroxyacetamide hydrochloride (step 4, intermediate A) using tert-butyl ((R)-1-((2S,4S)-2-((2-(2-amino-2-oxoacetyl)spiro[3.3]heptan-2-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate to provide the title compound.

Step 4: Preparation of (2S,4S)-1-((R)-2-(2-naphthamido)-3-cyclohexylpropanoyl)-N-(2-(2-amino-2-oxoacetyl)spiro[3.3]heptan-2-yl)-4-(5-(2-hydroxypropan-2-yl)-1H-1,2,3-triazol-1-yl)pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-N-(2-(2-amino-2-oxoacetyl)spiro[3.3]heptan-2-yl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride and 2-naphthoic acid to provide the title compound. MS (ESI+): 712 (M+1); $^1$H NMR (300 MHz, CD$_3$OD) δ 8.45 (s, 1H), 8.04-7.85 (m, 4H), 7.65-7.55 (m, 2H), 7.53 (s, 1H), 5.90-5.71 (m, 1H), 5.08-4.94 (m, 1H), 4.65-4.45 (m, 1H), 4.45-4.25 (m, 1H), 4.25-4.10 (m, 1H), 2.98-2.48 (m, 4H), 2.50-2.20 (m, 2H), 2.19-2.03 (m, 1H), 2.03-1.82 (m, 4H), 1.82-1.53 (m, 15H), 1.54-1.37 (m, 1H), 1.36-1.15 (m, 3H), 1.15-0.85 (s, 1H) ppm.

The following compound, example 45, was prepared in a similar manner as example 44 using intermediate H in step 1.

| Example | Structure | MW | MS (ESI+) |
|---|---|---|---|
| 45 | 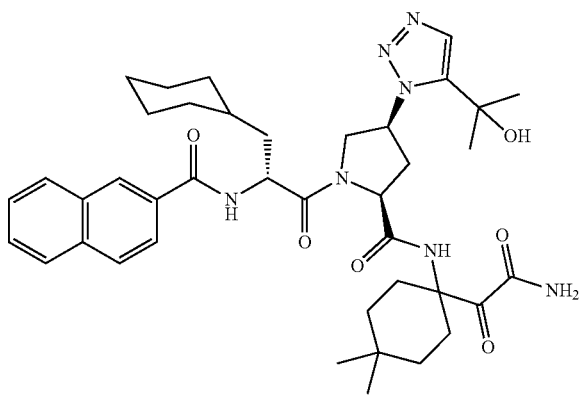<br>(2S,4S)-1-((R)-2-(2-naphthamido)-3-cyclohexylpropanoyl)-N-(1-(2-amino-2-oxoacetyl)-4,4-dimethylcyclohexyl)-4-(5-(2-hydroxypropan-2-yl)-1H-1,2,3-triazol-1-yl)pyrrolidine-2-carboxamide | 727.89 | 728 (M + 1)⊕ |
Example 46: (2S,4S)-N-(2-(2-amino-2-oxoacetyl)spiro[3.3]heptan-2-yl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide
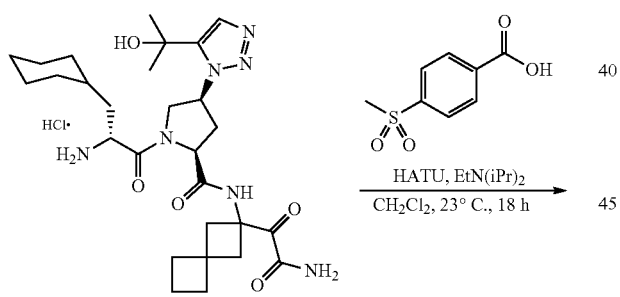
(step 3, example 44)
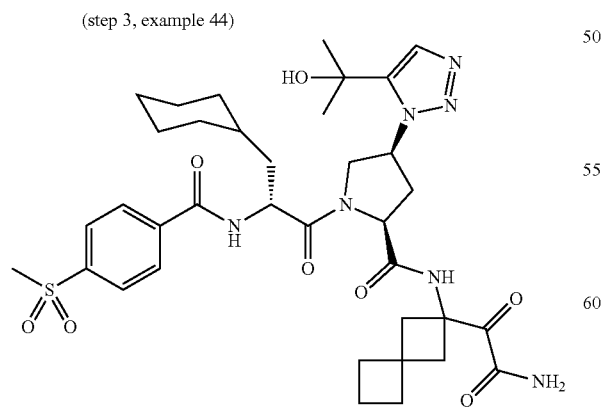
Example 46

Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-N-(2-(2-amino-2-oxoacetyl)spiro[3.3]heptan-2-yl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride and 4-(methylsulfonyl)benzoic acid to provide the title compound. MS (ESI+) 740 (M+1)$^\oplus$ The following compound, example 47, was prepared in a similar manner as example 46 using intermediate H.

| Example | Structure | MW | MS (ESI+) |
|---|---|---|---|
| 47 | (2S,4S)-N-(1-(2-amino-2-oxoacetyl)-4,4-dimethylcyclohexyl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide | 755.92 | 756 (M + 1)$^\oplus$ |

Example 48: (2S,4S)-1-((R)-2-(2-naphthamido)-3-cyclohexylpropanoyl)-N-(6-(2-amino-2-oxoacetyl)spiro[2.5]octan-6-yl)-4-(5-(2-hydroxypropan-2-yl)-1H-1,2,3-triazol-1-yl)pyrrolidine-2-carboxamide

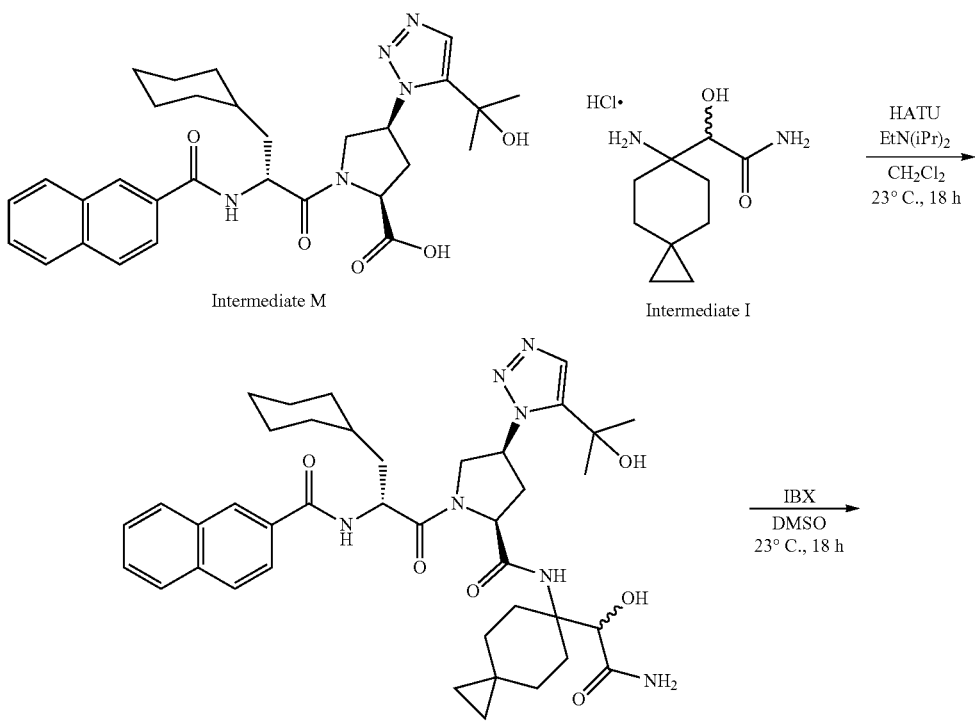

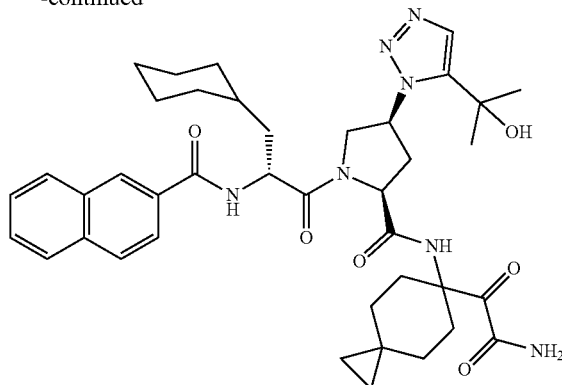

Example 48

Step 1: Preparation of (2S,4S)-1-((R)-2-(2-naphthamido)-3-cyclohexylpropanoyl)-N-(6-(2-amino-1-hydroxy-2-oxoethyl)spiro[2.5]octan-6-yl)-4-(5-(2-hydroxypropan-2-yl)-1H-1,2,3-triazol-1-yl)pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using intermediate M and intermediate I to provide the title compound.

Step 2: Preparation of (2S,4S)-1-((R)-2-(2-naphthamido)-3-cyclohexylpropanoyl)-N-(6-(2-amino-2-oxoacetyl)spiro[2.5]octan-6-yl)-4-(5-(2-hydroxypropan-2-yl)-1H-1,2,3-triazol-1-yl)pyrrolidine-2-carboxamide Prepared in a similar manner as tert-butyl ((R)-1-((2S,3R,4R)-2-((1-(2-amino-2-oxoacetyl)cyclohexyl)carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl)carbamate (step 4, example 9) using (2S,4S)-1-((R)-2-(2-naphthamido)-3-cyclohexylpropanoyl)-N-(6-(2-amino-1-hydroxy-2-oxoethyl)spiro[2.5]octan-6-yl)-4-(5-(2-hydroxypropan-2-yl)-1H-1,2,3-triazol-1-yl)pyrrolidine-2-carboxamide to provide the title compound. MS (ESI+) 726 (M+1)$^{\oplus}$ While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the present disclosure. It is intended that the following claims define the scope of the present disclosure and that methods and structures within the scope of these claims and their equivalents be covered thereby.

What is claimed is:

1. A pharmaceutical composition comprising a compound of Formula I

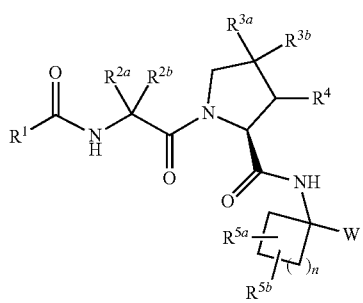

or a pharmaceutically acceptable salt, solvate, solvate of the salt, or prodrug thereof; and a pharmaceutically acceptable carrier.

2. The pharmaceutical composition of claim 1, comprising a dosage form appropriate for injection.

3. The pharmaceutical composition of claim 2, comprising a dosage form selected from a solution, dispersion, suspension, emulsion, or powder for reconstitution.

4. The pharmaceutical composition of claim 2, wherein the dosage form comprises one or more adjuvants.

5. The pharmaceutical composition of claim 4, wherein the one or more adjuvants are selected from one or more preservatives, one or more wetting agents, one or more emulsifying agents, one or more dispersing agents, and a combination thereof.

6. The pharmaceutical composition of claim 1, comprising a dosage form appropriate for oral administration.

7. The pharmaceutical composition of claim 6, comprising a dosage form selected from a capsule, tablet, pill, powder, and granules.

8. The pharmaceutical composition of claim 7, wherein the dosage form comprises one or more fillers, one or more binders, one or more humectants, one or more disintegrating agents, one or more solution-retarding agents, one or more absorption accelerators, one or more wetting agents, one or more absorbents, one or more lubricants, or a combination thereof.

9. The pharmaceutical composition of claim 6, comprising a liquid dosage form.

10. The pharmaceutical composition of claim 9, comprising a liquid dosage form selected from an emulsion, solution, suspension, syrup, and elixir.

11. The pharmaceutical composition of claim 1, comprising a dosage form appropriate for rectal or vaginal administration.

12. The pharmaceutical composition of claim 1, comprising a dosage form appropriate for topical administration.

13. The pharmaceutical composition of claim 12, comprising a dosage form selected from a powder, patch, spray, ointment, and inhalant.

14. The pharmaceutical composition of claim 1, comprising a dosage form appropriate for application to the eye.

15. The pharmaceutical composition of claim 14, comprising a dosage form selected from a solution, suspension, ointment, gel, emulsion, strip, insert, and implant.

16. A method of treating a disease of the eye selected from dry-AMD, wet-AMD, geographic atrophy, diabetic retinopathy, retinopathy of prematurity, polypoidal choroidal vasculopathy, and degeneration of retinal or photoreceptor cells, comprising:
    administering to a subject in need thereof a therapeutically effective amount of a pharmaceutical composition, wherein the pharmaceutical composition comprises a compound of Formula I

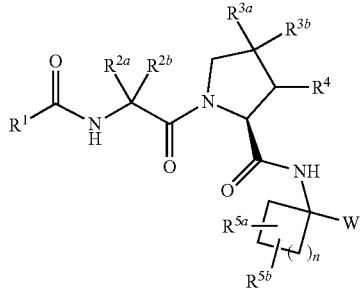

(I)

or a pharmaceutically acceptable salt, solvate, solvate of the salt, or prodrug thereof; and a pharmaceutically acceptable carrier.

17. The method of treating a disease of the eye according to claim 16, wherein the method is selected from controlling, alleviating, and slowing the progression of the disease of the eye;
    wherein the disease is selected from dry-AMD, wet-AMD, and geographic atrophy, diabetic retinopathy, retinopathy of prematurity, polypoidal choroidal vasculopathy, and degeneration of retinal or photoreceptor cells.

18. The method according to claim 16, wherein the disease is geographic atrophy.

19. A method of inhibiting HTRA1 protease activity in an eye comprising:
    administering to a subject in need thereof a therapeutically effective amount of a pharmaceutical composition, wherein the pharmaceutical composition comprises a compound of Formula I

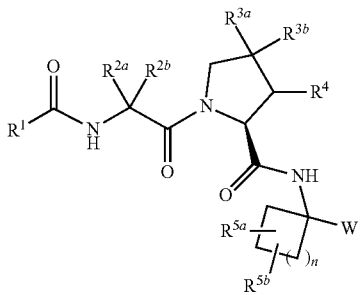

(I)

or a pharmaceutically acceptable salt, solvate, solvate of the salt, or prodrug thereof; and a pharmaceutically acceptable carrier.

* * * * *